United States Patent
Kee et al.

(10) Patent No.: US 9,920,300 B2
(45) Date of Patent: Mar. 20, 2018

(54) INDUCTION OF GERM CELLS FROM PLURIPOTENT CELLS

(75) Inventors: Keh Kooi Kee, Beijing (CN); Renee A. Reijo Pera, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1121 days.

(21) Appl. No.: 13/501,998

(22) PCT Filed: Oct. 22, 2010

(86) PCT No.: PCT/US2010/053708
§ 371 (c)(1),
(2), (4) Date: May 25, 2012

(87) PCT Pub. No.: WO2011/050251
PCT Pub. Date: Apr. 28, 2011

(65) Prior Publication Data
US 2012/0231451 A1   Sep. 13, 2012

Related U.S. Application Data

(60) Provisional application No. 61/279,608, filed on Oct. 23, 2009.

(51) Int. Cl.
*C12N 5/00* (2006.01)
*C12N 5/076* (2010.01)
*C12N 5/075* (2010.01)
*G01N 33/50* (2006.01)

(52) U.S. Cl.
CPC ........... *C12N 5/061* (2013.01); *C12N 5/0609* (2013.01); *G01N 33/5073* (2013.01); *C12N 2501/155* (2013.01); *C12N 2501/65* (2013.01); *C12N 2506/02* (2013.01); *C12N 2506/45* (2013.01)

(58) Field of Classification Search
USPC ................................. 435/455, 325
See application file for complete search history.

(56) References Cited

U.S. PATENT DOCUMENTS

| | | | |
|---|---|---|---|
| 6,878,542 B1 * | 4/2005 | Smith et al. | 435/325 |
| 7,459,600 B2 * | 12/2008 | Smith et al. | 800/8 |
| 2006/0206952 A1 * | 9/2006 | Van de Lavoir et al. | 800/19 |
| 2009/0075877 A1 * | 3/2009 | Tang | 514/12 |

FOREIGN PATENT DOCUMENTS

| | | | |
|---|---|---|---|
| EP | 1911842 A1 * | 4/2008 | |
| JP | 2002/065261 * | 3/2002 | |
| WO | WO 2002/29064 A2 * | 4/2002 | |
| WO | WO 2006/129696 A1 * | 12/2006 | |

OTHER PUBLICATIONS

Toyooka (PNAS, 2003, vol. 100, No. 20, p. 11457-11462).*
Kee (Stem Cells Develop., 2006, vol. 15, p. 831-837.*
Toyooka (PNAS, Sep. 30, 2003, vol. 100, No. 20, p. 11457-11462).*
Geijsen (Nature, Jan. 8, 2004, vol. 427, p. 148-154).*
Kee (Stem Cells and Develop., 2006, vol. 15, p. 831-837).*
Takahashi (Cell, Nov. 30, 2007, vol. 131, p. 861-872).*
Yuasa (Expert Rev. Cardiovasc. Therapy, 2008, 6(6)803-810).*
Hanna (Science, 2007, vol. 318, p. 1920-1923), Nakauchi (U.S. Pat. No. 8,546,141.*
Senju (Stem Cells 2009, vol. 27, p. 1021-1031.*
Reijo (Biol. Reproduction, 2000, vol. 63, p. 1490-1496).*
Kee; et al., Bone Morphogenetic Proteins Induce Germ Cell Differentiation from Human Embryonic Stem Cells, Stem Cells and Development (Dec. 2006), 15(6):831-837.
Kee; et al., "Human DAZL, DAZ and BOULE genes modulate primordial germ-cell and haploid gamete formation", Nature (Nov. 2009) 462(7270):222-5.
Kee; et al., "Human Primordial Germ Cell Formation Is Diminished by Exposure to Environmental Toxicants Acting through the AHR Signaling Pathway", Toxicological Sciences (Sep. 2010), 117(1):218-224.
Reijo; et al., "DAZ Family Proteins Exist Throughout Male Germ Cell Development and Transit from Nucleus to Cytoplasm at Meiosis in Humans and Mice", Biology of Reproduction (Nov. 2000), 63(5):1490-11496.
Reijo; et al., "Diverse spermatogenic defects in humans caused by Y chromosome deletions encompassing a novel RNA-binding protein gene", Nature Genetics (Aug. 1995), 10(4):383-93.
Reijo; et al., "Severe oligozoospermia resulting from deletions of azoospermia factor gene on Y chromosome", The Lancet (May 1996), 347(9011):1290-3.
Xu; et al., "A gene family required for human germ cell development evolved from an ancient meiotic gene conserved in metazoans", PNAS (Jun. 2001), 98(13):7414-7419.
Xu; et al., "Human BOULE gene rescues meiotic defects in infertile flies", Human Molecular Genetics (Jan. 2003), 12 (2):169-75.

* cited by examiner

*Primary Examiner* — Michael C Wilson
(74) *Attorney, Agent, or Firm* — Pamela J. Sherwood; Bozicevic, Field & Francis LLP

(57) ABSTRACT

Methods and compositions are provided for promoting germ cell differentiation from pluripotent cells, and for identifying agents that modulate germ cell differentiation.

7 Claims, 43 Drawing Sheets

H9, XX, Day 7

| | P. | E. | N.S. |
|---|---|---|---|
| Control | 0 | 0 | 100 |
| DAZL | 9 | 5 | 86 |
| BOULE | 13 | 9 | 78 |
| DAZL+BOULE | 10 | 10 | 80 |

H9, XX, Day 14

| | P. | E. | N.S. |
|---|---|---|---|
| Control | 3 | 0 | 97 |
| DAZL | 4 | 1 | 93 |
| BOULE | 2 | 3 | 98 |
| DAZL+BOULE | 8 | 0 | 92 |

HSF1, XY, Day 7

| | P. | E. | N.S. |
|---|---|---|---|
| Control | 0 | 0 | 100 |
| DAZ | 22 | 0 | 78 |
| DAZL | 8 | 9 | 92 |
| BOULE | 7 | 1 | 92 |
| DAZ+DAZL | 3 | 7 | 90 |
| DAZ+BOULE | 11 | 6 | 83 |
| DAZL+BOULE | 6 | 3 | 91 |
| DAZ+DAZL+BOULE | 27 | 6 | 67 |

HSF1, XY, Day 14

| | P. | E. | N.S. |
|---|---|---|---|
| Control | 2 | 0 | 98 |
| DAZ | 29 | 4 | 67 |
| DAZL | 3 | 1 | 96 |
| BOULE | 5 | 1 | 94 |
| DAZ+DAZL | 16 | 6 | 78 |
| DAZ+BOULE | 5 | 3 | 92 |
| DAZL+BOULE | 5 | 10 | 87 |
| DAZ+DAZL+BOULE | 11 | 11 | 80 |

FIG. 19

SEQUENCE LISTING

```
<160> NUMBER OF SEQ ID NOS: 42

<210> SEQ ID NO 1
<211> LENGTH: 4419
<212> TYPE: DNA
<213> ORGANISM: homo sapiens

<400> SEQUENCE: 1
tgccacccat tggctcaggc cgataccacg cgccccgata cccggcacag gagccacctc      60
ccagagcccc gcagtccatg cctcagtcgg cctgcgctcc tcagcctggc ggttctacct     120
ccgagggttc gcccgccctt ggttttcctt acaccttagc ctttggctcc tttgaccact     180
cgaagcccca cagcgtgttc cagcggactt caccagcaga cccagaagtg gtgggtgaaa     240
cactgcctct gttcctcctt gagcctgtcg ggagctgctg cctgccacca ccatgtctgc     300
tgcaaatcct gagactccaa actcaaccat ctccagagag gccagcaccc agtcttcatc     360
agctgcagct agccaaggct gggtgttacc agaaggcaaa atcgtgccaa acactgtttt     420
tgttggtgga attgatgcta ggatggatga aactgagatt ggaagctgct ttggtagata     480
cggttcagtg aaagaagtga agataatcac gaatcgaact ggtgtgtcca aaggctatgg     540
atttgtttcg tttgttaatg acgtggatgt ccagaagata gtaggatcac agatacattt     600
ccatggtaaa aagctgaagc tgggccctgc aatcaggaaa caaaagttat gtgctcgtca     660
tgtgcagcca cgtcctttgg tagttaatcc tcctcctcca ccacagtttc agaacgtctg     720
gcggaatcca aacactgaaa cctacctgca gccccaaatc acgccgaatc ctgtaactca     780
gcacgttcag tctgctgcaa atcctgagac tccaaactca accatctcca gagaggccag     840
cacccagtct tcatcagctg cagctagcca aggctgggtg ttaccagaag gcaaaatcgt     900
gccaaacact gttttgttg gtggaattga tgctaggatg atgaaactg agattggaag     960 ctgctttggt agatacggtt cagtgaaaga agtgaagata atcacgaatc gaactggtgt    1020
gtccaaaggc tatggatttg tttcgtttgt taatgacgtg gatgtccaga agatagtagg    1080
atcacagata catttccatg gtaaaaagct gaagctgggc cctgcaatca ggaaacaaaa    1140
gttatgtgct cgtcatgtgc agccacgtcc tttggtagtt aatcctcctc ctccaccaca    1200
gtttcagaac gtctggcgga atccaaacac tgaaacctac ctgcagcccc aaatcacgcc    1260
gaatcctgta actcagcacg ttcagtctgc tgcaaatcct gagactccaa actcaaccat    1320
ctccagagag gccagcaccc agtcttcatc agctgcagct agccaaggct gggtgttacc    1380
agaaggcaaa atcgtgccaa acactgtttt tgttggtgga attgatgcta ggatggatga    1440
aactgagatt ggaagctgct ttggtagata cggttcagtg aaagaagtga agataatcac    1500
gaatcgaact ggtgtgtcca aaggctatgg atttgtttcg tttgttaatg acgtggatgt    1560
```

```
ccagaagata gtaggatcac agatacattt ccatggtaaa aagctgaagc tgggccctgc    1620
aatcaggaaa caaaagttat gtgctcgtca tgtgcagcca cgtcctttgg tagttaatcc    1680
tcctcctcca ccacagtttc agaacgtctg gcggaatcca aacactgaaa cctacctgca    1740
gccccaaatc acgccgaatc ctgtaactca gcacgttcag gcttactctg cttatccaca    1800
ttcaccaggt caggtcatca ctggatgtca gttgcttgta tataattatc aggaatatcc    1860
tacttatccc gattcagcat ttcaggtcac cactggatat cagttgcctg tatataatta    1920
tcagccattt cctgcttatc aagatcacc atttcaggtc actgctggat atcagttgcc    1980
tgtatataat tatcaggcat ttcctgctta tccaaattca ccatttcaag tcgccactgg    2040
atatcagttc cctgtataca attatcagcc atttcctgct tatccaagtt caccatttca    2100
ggtcactgct ggatatcagt tgcctgtata taattatcag gcatttcctg cttatccaaa    2160
ttcaccattt caagtcgcca ctggatatca gttccctgta taaattatc aggcatttcc    2220 tgcttatcca aattcaccag ttcaggtcac cactggatat cagttgcctg tatacaatta    2280
tcaggcattt cctgcttatc aagttcacc atttcaggtc accactggat atcagttgcc    2340
tgtatataat tatcaggcat ttcctgctta tccaaattca gcagttcagg tcaccactgg    2400
atatcagttc catgtataca attaccagat gccaccgcga tgccctgttg gggagcaaag    2460
gagaaatctg tggaccgaag catacaaatg gtggtatctt gtctgtttaa tccagagaag    2520
agactgataa attccgttgt tactcaagat gactgcttca agggtaaaag agtgcatcgc    2580
tttagaagaa gtttggcagt atttaaatct gttggatcct ctcagctatc tagtttcatg    2640
ggaagttgct ggttttgaat attaagctaa aagttttcca ctattacaga aattctgaat    2700
tttggtaaat cacactgaaa ctttctgtat aacttgtatt attagactct ctagttttat    2760
cttaacactg aaactgttct tcattagatg tttatttaga acctggttct gtgtttaata    2820
tatagtttaa agtaacaaat aatcgagact gaaagaatgt taagatttat ctgcaaggat    2880 tttttaaaaaa ttgaaacttg cattttaagt gtttaaaagc aaatactgac tttcaaaaaa    2940 gttttttaaaa cctgatttga aagctaacaa ttttgatagt ctgaacacaa gcatttcact    3000
tctccaagaa gtacctgtga acagtacaat atttcagtat tgagctttgc atttatgatt    3060
tatctagaaa tttacctcaa aagcagaatt tttaaaactg catttttaat cagtggaact    3120
caatgtatag ttagctttat tgaagtctta tccaaaccca gtaaaacaga ttctaagcaa    3180
acagtccaat cagtgagtca taatgtttat tcaaagtatt ttatctttta tctagaatcc    3240
acatatgtat gtccaatttg attgggatag tagttaggat aactaaaatt ctgggcctaa    3300 tttttttaaag aatccaagac aaactaaact ttactgggta tataaccttc tcaatgagtt    3360
accattcttt tttataaaaa aaattgttcc ttgaaatgct aaacttaatg gctgtatgtg    3420
aaatttgcaa atactggta ttaaagaacg ctgcagcttt tttatgtcac tcaaaggtta    3480
atcggagtat ctgaaaggaa ttgttttat aaaaacattg aagtattagt tacttgctat    3540
aaatagattt ttatttttgt tttttagcct gttatatttc cttctgtaaa ataaaatatg    3600
tccagaagag gcatgttgtt tctagattag gtagtgtcct cattttatat tgtgaccaca    3660
cagctagagc accagagccc ttttgctata ctcacagtct tgttttccca gcctctttta    3720
ctagtctttc aggaggtttg ctcttagaac tggtgatgta aagaatggaa gtagctgtat    3780
gagcagttca aaggccaagc cgtggaatgg tagcaatggg atataatacc tttctaaggg    3840
aaacatttgt atcagtatca tttgatctgc catggacatg tgtttaaagt ggctttctgg    3900
cccttctttc aatggcttct tccctaaaac gtggagactc taagttaatg tcgttactat    3960
```

-continued

```
gggccatatt actaatgccc actggggtct atgatttctc aaaattttca ttcggaatcc   4020
gaaggataca gtctttaaac tttagaattc ccaagaaggc tttattacac ctcagaaatt   4080
gaaagcacca tgactttgtc cattaaaaaa ttatccatag ttttttttagt gcttttaaca   4140 ttccgacata catcattctg tgattaaatc tccagatttc tgtaaatgat acctacattc   4200
taaagagtta attctaatta ttccgatatg accttaagga aaagtaaagg aataaatttt   4260
tgtctttgtt gaagtattta atagagtaag gtaaagaaga tattaagtcc ctttcaaaat   4320
ggaaaattaa ttctaaactg agaaaaatgt tcctactacc tattgctgat actgtctttg   4380
cataaatgaa taaaaataaa cttttttttct tcaaatgtg                          4419
```

<210> SEQ ID NO 2
<211> LENGTH: 744
<212> TYPE: PRT
<213> ORGANISM: homo sapiens

<400> SEQUENCE: 2

```
Met Ser Ala Ala Asn Pro Glu Thr Pro Asn Ser Thr Ile Ser Arg Glu
1               5                   10                  15

Ala Ser Thr Gln Ser Ser Ser Ala Ala Ser Gln Gly Trp Val Leu
            20                  25                  30

Pro Glu Gly Lys Ile Val Pro Asn Thr Val Phe Val Gly Gly Ile Asp
        35                  40                  45

Ala Arg Met Asp Glu Thr Glu Ile Gly Ser Cys Phe Gly Arg Tyr Gly
    50                  55                  60

Ser Val Lys Glu Val Lys Ile Ile Thr Asn Arg Thr Gly Val Ser Lys
65                  70                  75                  80

Gly Tyr Gly Phe Val Ser Phe Val Asn Asp Val Asp Val Gln Lys Ile
                85                  90                  95

Val Gly Ser Gln Ile His Phe His Gly Lys Lys Leu Lys Leu Gly Pro
            100                 105                 110

Ala Ile Arg Lys Gln Lys Leu Cys Ala Arg His Val Gln Pro Arg Pro
        115                 120                 125

Leu Val Val Asn Pro Pro Pro Pro Gln Phe Gln Asn Val Trp Arg
    130                 135                 140

Asn Pro Asn Thr Glu Thr Tyr Leu Gln Pro Gln Ile Thr Pro Asn Pro
145                 150                 155                 160

Val Thr Gln His Val Gln Ser Ala Ala Asn Pro Glu Thr Pro Asn Ser
                165                 170                 175

Thr Ile Ser Arg Glu Ala Ser Thr Gln Ser Ser Ser Ala Ala Ala Ser
            180                 185                 190

Gln Gly Trp Val Leu Pro Glu Gly Lys Ile Val Pro Asn Thr Val Phe
        195                 200                 205

Val Gly Gly Ile Asp Ala Arg Met Asp Glu Thr Glu Ile Gly Ser Cys
    210                 215                 220

Phe Gly Arg Tyr Gly Ser Val Lys Glu Val Lys Ile Ile Thr Asn Arg
225                 230                 235                 240

Thr Gly Val Ser Lys Gly Tyr Gly Phe Val Ser Phe Val Asn Asp Val
                245                 250                 255

Asp Val Gln Lys Ile Val Gly Ser Gln Ile His Phe His Gly Lys Lys
            260                 265                 270

Leu Lys Leu Gly Pro Ala Ile Arg Lys Gln Lys Leu Cys Ala Arg His
        275                 280                 285
```

```
Val Gln Pro Arg Pro Leu Val Val Asn Pro Pro Pro Gln Phe
    290                 295             300
Gln Asn Val Trp Arg Asn Pro Asn Thr Glu Thr Tyr Leu Gln Pro Gln
305                 310                 315                 320
Ile Thr Pro Asn Pro Val Thr Gln His Val Gln Ser Ala Ala Asn Pro
                325                 330                 335
Glu Thr Pro Asn Ser Thr Ile Ser Arg Glu Ala Ser Thr Gln Ser Ser
                340                 345                 350
Ser Ala Ala Ser Gln Gly Trp Val Leu Pro Glu Gly Lys Ile Val
            355                 360                 365
Pro Asn Thr Val Phe Val Gly Ile Asp Ala Arg Met Asp Glu Thr
370                 375                 380
Glu Ile Gly Ser Cys Phe Gly Arg Tyr Gly Ser Val Lys Glu Val Lys
385                 390                 395                 400
Ile Ile Thr Asn Arg Thr Gly Val Ser Lys Gly Tyr Gly Phe Val Ser
                405                 410                 415
Phe Val Asn Asp Val Asp Val Gln Lys Ile Val Gly Ser Gln Ile His
                420                 425                 430
Phe His Gly Lys Lys Leu Lys Leu Gly Pro Ala Ile Arg Lys Gln Lys
            435                 440                 445
Leu Cys Ala Arg His Val Gln Pro Arg Pro Leu Val Val Asn Pro Pro
450                 455                 460
Pro Pro Pro Gln Phe Gln Asn Val Trp Arg Asn Pro Asn Thr Glu Thr
465                 470                 475                 480
Tyr Leu Gln Pro Gln Ile Thr Pro Asn Pro Val Thr Gln His Val Gln
                485                 490                 495
Ala Tyr Ser Ala Tyr Pro His Ser Pro Gly Gln Val Ile Thr Gly Cys
            500                 505                 510
Gln Leu Leu Val Tyr Asn Tyr Gln Glu Tyr Pro Thr Tyr Pro Asp Ser
            515                 520                 525
Ala Phe Gln Val Thr Thr Gly Tyr Gln Leu Pro Val Tyr Asn Tyr Gln
            530                 535                 540
Pro Phe Pro Ala Tyr Pro Arg Ser Pro Phe Gln Val Thr Ala Gly Tyr
545                 550                 555                 560
Gln Leu Pro Val Tyr Asn Tyr Gln Ala Phe Pro Ala Tyr Pro Asn Ser
                565                 570                 575
Pro Phe Gln Val Ala Thr Gly Tyr Gln Phe Pro Val Tyr Asn Tyr Gln
            580                 585                 590
Pro Phe Pro Ala Tyr Pro Ser Ser Pro Phe Gln Val Thr Ala Gly Tyr
            595                 600                 605
Gln Leu Pro Val Tyr Asn Tyr Gln Ala Phe Pro Ala Tyr Pro Asn Ser
            610                 615                 620
Pro Phe Gln Val Ala Thr Gly Tyr Gln Phe Pro Val Tyr Asn Tyr Gln
625                 630                 635                 640
Ala Phe Pro Ala Tyr Pro Asn Ser Pro Val Gln Val Thr Thr Gly Tyr
                645                 650                 655
Gln Leu Pro Val Tyr Asn Tyr Gln Ala Phe Pro Ala Tyr Pro Ser Ser
            660                 665                 670
Pro Phe Gln Val Thr Thr Gly Tyr Gln Leu Pro Val Tyr Asn Tyr Gln
            675                 680                 685
Ala Phe Pro Ala Tyr Pro Asn Ser Ala Val Gln Val Thr Thr Gly Tyr
690                 695                 700
Gln Phe His Val Tyr Asn Tyr Gln Met Pro Pro Gln Cys Pro Val Gly
```

```
705                 710                 715                 720
Glu Gln Arg Arg Asn Leu Trp Thr Glu Ala Tyr Lys Trp Trp Tyr Leu
                725                 730                 735

Val Cys Leu Ile Gln Arg Arg Asp
            740

<210> SEQ ID NO 3
<211> LENGTH: 3759
<212> TYPE: DNA
<213> ORGANISM: homo sapiens

<400> SEQUENCE: 3
gcgctcagcc tggcggttct acctccgagg gttcgcccgc ccttggtttt ccttacacct     60
tagcctttgg ctcctttgac cactcgaagc cccacagcgt gttccagcgg acttcaccag    120
cagacccaga agtggtgggt gaaacactgc ctctgttcct ccttgagcct gtcgggagct    180
gctgcctgcc accaccatgt ctgctgcaaa tcctgagact ccaaactcaa ccatctccag    240
agaggccagc acccagtctt catcagctgc agctagccaa ggctgggtgt taccagaagg    300
caaaatcgtg ccaaacactg tttttgttgg tggaattgat gctaggatgg atgaaactga    360
gattggaagc tgctttggta gatacggttc agtgaaagaa gtgaagataa tcacgaatcg    420
aactggtgtg tccaaaggct atggatttgt ttcgtttgtt aatgacgtgg atgtccagaa    480
gatagtagga tcacagatac atttccatgg taaaaagctg aagctgggcc ctgcaatcag    540
gaaacaaaag ttatgtgctc gtcatgtgca gccacgtcct ttggtagtta atcctcctcc    600
tccaccacag tttcagaacg tctggcggaa tccaaacact gaaacctacc tgcagcccca    660
aatcacgccg aatcctgtaa ctcagcacgt tcaggcttat tctgcttatc cacattcacc    720
aggtcaggtc atcactggat gtcagttgct tgtatataat tatcaggaat atcctactta    780
tcccgattca gcatttcagg tcaccactgg atatcagttg cctgtatata attatcagcc    840
atttcctgct tatccaagat caccatttca ggtcactgct ggatatcagt tgcctgtata    900
taattatcag gcattccctg cttatccaaa ttcaccattt caagtcgcca ctggatatca    960
gttccctgta tacaattatc agccatttcc tgcttatcca agttcaccat ttcaggtcac   1020
tgctggatat cagttgcctg tatataatta tcaggcattt cctgcttatc caaattcacc   1080
atttcaagtc gccactggat atcagttccc tgtatacaat tatcaggcat ttcctgctta   1140
tccaaattca ccagttcagg tcaccactgg atatcagttg cctgtataca attatcaggc   1200
atttcctgct tatccaagtt caccatttca ggtcaccact ggatatcagt tgcctgtata   1260
taattatcag gcattccctg cttatccaag ttcaccattt caggtcacca ctggatatca   1320
gttgcctgta taattatc aggcatttcc tgcttatcca agttcaccat ttcaggtcac   1380
cactggatat cagttgcctg tatataatta tcaggcattt cctgcttatc caagttcacc   1440
atttcaggtc accactggat atcagttgcc tgtatataat tatcaggcat ttcctgctta   1500
tccaagttca ccatttcagg tcaccactgg atatcagttg cctgtatata attatcaggc   1560
atttcctgct tatccaagtt caccatttca ggtcaccact ggatatcagt tgcctgtata   1620
taattatcag gcattcctg cttatccaag ttcaccattt caggtcacca ctggatatca   1680
gttgcctgta tataattatc aggcatttcc tgcttatcca aattcagcag ttcaggtcac   1740
cactggatat cagttccatg tatacaatta ccagatgcca ccgcagtgcc ctgttgggga   1800
gcaaaggaga atctgtggaa ccgaagcata caaatggtgg tatcttgtct gtttaatcca   1860
gagaagagac tgataaaatt ccgttgttact caagatgact gcttcaaggg taaaagagtg   1920
```

```
catcgcttta gaagaagttt ggcagtattt aaatctgttg gatcctctca gctatctagt    1980
ttcatgggaa gttgctggtt ttgaatatta agctaaaagt tttccactat tacagaaatt    2040
ctgaattttg gtaaatcaca ctgaaacttt ctgtataact tgtattatta gactctctag    2100
ttttatctta acactgaaac tgttcttcat tagatgttta tttagaacct ggttctgtgt    2160
ttaatatata gtttaaagta acaaataatc gagactgaaa gaatgttaag atttatctgc    2220
aaggattttt aaaaaattga aacttgcatt ttaagtgttt aaaagcaaat actgactttc    2280
aaaaaagttt ttaaaacctg atttgaaagc taacaatttt gatagtctga acacaagcat    2340
ttcacttctc caagaagtac ctgtgaacag tacaatattt cagtattgag ctttgcattt    2400
atgatttatc tagaaattta cctcaaaagc agaatttta aaactgcatt tttaatcagt     2460
ggaactcaat gtatagttag ctttattgaa gtcttatcca aacccagtaa aacagattct    2520
aagcaaacag tccaatcagt gagtcataat gtttattcaa agtatttat cttttatcta     2580 gaatccacat atgtatgtcc aatttgattg ggatagtagt taggataact aaaattctgg    2640
gcctaatttt ttaaagaatc aagacaaac taaactttac tgggtatata accttctcaa     2700
tgagttacca ttcttttta taaaaaaat tgttccttga aatgctaaac ttaatggctg      2760
tatgtgaaat ttgcaaaata ctggtattaa agaacgctgc agcttttta tgtcactcaa     2820 aggtaatcg gagtatctga aaggaattgt ttttataaaa acattgaagt attagttact     2880
tgctataaat agatttttat ttttgttttt tagcctgtta tatttccttc tgtaaaataa    2940
aatatgtcca gaagaggcat gttgtttcta gattaggtag tgtcctcatt ttatattgtg    3000
accacacagc tagagcacca gagcccttttt gctatactca cagtcttgtt ttcccagcct   3060 ctttttactag tctttcagga ggtttgctct tagaactggt gatgtaaaga atggaagtag   3120
ctgtatgagc agttcaaagg ccaagccgtg gaatggtagc aatgggatat aataccttc    3180 taagggaaac atttgtatca gtatcatttg atctgccatg gacatgtgtt taaagtggct    3240 ttctggcct tctttcaatg gcttcttccc taaaacgtgg agactctaag ttaatgtcgt     3300
tactatgggc catattacta atgcccactg gggtctatga tttctcaaaa ttttcattcg    3360
gaatccgaag gatacagtct ttaaacttta gaattcccaa gaaggcttta ttacacctca    3420
gaaattgaaa gcaccatgac tttgtccatt aaaaaattat ccatagtttt tttagtgctt    3480
ttaacattcc gacatacatc attctgtgat taaatctcca gatttctgta aatgatacct    3540
acattctaaa gagttaattc taattattcc gatatgacct taaggaaaag taaaggaata    3600 aattttttgtc tttgttgaag tatttaatag agtaaggtaa agaagatatt aagtcccttt   3660
caaaatggaa aattaattct aaactgagaa aaatgttcct actacctatt gctgatactg    3720
tctttgcata aatgaataaa aataaacttt ttttcttca                            3759
```

<210> SEQ ID NO 4
<211> LENGTH: 558
<212> TYPE: PRT
<213> ORGANISM: homo sapiens

<400> SEQUENCE: 4

Met Ser Ala Ala Asn Pro Glu Thr Pro Asn Ser Thr Ile Ser Arg Glu
1               5                   10                  15

Ala Ser Thr Gln Ser Ser Ser Ala Ala Ala Ser Gln Gly Trp Val Leu
            20                  25                  30

Pro Glu Gly Lys Ile Val Pro Asn Thr Val Phe Val Gly Gly Ile Asp
        35                  40                  45

```
Ala Arg Met Asp Glu Thr Glu Ile Gly Ser Cys Phe Gly Arg Tyr Gly
         50                  55                  60

Ser Val Lys Glu Val Lys Ile Ile Thr Asn Arg Thr Gly Val Ser Lys
 65                  70                  75                  80

Gly Tyr Gly Phe Val Ser Phe Val Asn Asp Val Asp Val Gln Lys Ile
                     85                  90                  95

Val Gly Ser Gln Ile His Phe His Gly Lys Lys Leu Lys Leu Gly Pro
             100                 105                 110

Ala Ile Arg Lys Gln Lys Leu Cys Ala Arg His Val Gln Pro Arg Pro
             115                 120                 125

Leu Val Val Asn Pro Pro Pro Gln Phe Gln Asn Val Trp Arg
             130                 135                 140

Asn Pro Asn Thr Glu Thr Tyr Leu Gln Pro Gln Ile Thr Pro Asn Pro
145                 150                 155                 160

Val Thr Gln His Val Gln Ala Tyr Ser Ala Tyr Pro His Ser Pro Gly
                 165                 170                 175

Gln Val Ile Thr Gly Cys Gln Leu Leu Val Tyr Asn Tyr Gln Glu Tyr
                 180                 185                 190

Pro Thr Tyr Pro Asp Ser Ala Phe Gln Val Thr Gly Tyr Gln Leu
             195                 200                 205

Pro Val Tyr Asn Tyr Gln Pro Phe Pro Ala Tyr Pro Arg Ser Pro Phe
210                 215                 220

Gln Val Thr Ala Gly Tyr Gln Leu Pro Val Tyr Asn Tyr Gln Ala Phe
225                 230                 235                 240

Pro Ala Tyr Pro Asn Ser Pro Phe Gln Val Ala Thr Gly Tyr Gln Phe
             245                 250                 255

Pro Val Tyr Asn Tyr Gln Pro Phe Pro Ala Tyr Pro Ser Ser Pro Phe
             260                 265                 270

Gln Val Thr Ala Gly Tyr Gln Leu Pro Val Tyr Asn Tyr Gln Ala Phe
             275                 280                 285

Pro Ala Tyr Pro Asn Ser Pro Phe Gln Val Ala Thr Gly Tyr Gln Phe
             290                 295                 300

Pro Val Tyr Asn Tyr Gln Ala Phe Pro Ala Tyr Pro Asn Ser Pro Val
305                 310                 315                 320

Gln Val Thr Thr Gly Tyr Gln Leu Pro Val Tyr Asn Tyr Gln Ala Phe
                 325                 330                 335

Pro Ala Tyr Pro Ser Ser Pro Phe Gln Val Thr Thr Gly Tyr Gln Leu
             340                 345                 350

Pro Val Tyr Asn Tyr Gln Ala Phe Pro Ala Tyr Pro Ser Ser Pro Phe
             355                 360                 365

Gln Val Thr Thr Gly Tyr Gln Leu Pro Val Tyr Asn Tyr Gln Ala Phe
             370                 375                 380

Pro Ala Tyr Pro Ser Ser Pro Phe Gln Val Thr Thr Gly Tyr Gln Leu
385                 390                 395                 400

Pro Val Tyr Asn Tyr Gln Ala Phe Pro Ala Tyr Pro Ser Ser Pro Phe
             405                 410                 415

Gln Val Thr Thr Gly Tyr Gln Leu Pro Val Tyr Asn Tyr Gln Ala Phe
             420                 425                 430

Pro Ala Tyr Pro Ser Ser Pro Phe Gln Val Thr Thr Gly Tyr Gln Leu
             435                 440                 445

Pro Val Tyr Asn Tyr Gln Ala Phe Pro Ala Tyr Pro Ser Ser Pro Phe
             450                 455                 460
```

```
Gln Val Thr Thr Gly Tyr Gln Leu Pro Val Tyr Asn Tyr Gln Ala Phe
465                 470                 475                 480

Pro Ala Tyr Pro Ser Ser Pro Phe Gln Val Thr Thr Gly Tyr Gln Leu
                485                 490                 495

Pro Val Tyr Asn Tyr Gln Ala Phe Pro Ala Tyr Pro Asn Ser Ala Val
                500                 505                 510

Gln Val Thr Thr Gly Tyr Gln Phe His Val Tyr Asn Tyr Gln Met Pro
                515                 520                 525

Pro Gln Cys Pro Val Gly Glu Gln Arg Arg Asn Leu Trp Thr Glu Ala
                530                 535                 540

Tyr Lys Trp Trp Tyr Leu Val Cys Leu Ile Gln Arg Arg Asp
545                 550                 555
```

<210> SEQ ID NO 5
<211> LENGTH: 3756
<212> TYPE: DNA
<213> ORGANISM: homo sapiens

<400> SEQUENCE: 5

```
cacgcgcccc gatacccggc acaggagcca cctcccagag cccgcagtc catgcctcag      60 tcggcctgcg ctcctcagcc tggcggttct acctccgagg gttcgcccgc ccttggtttt    120
ccttacacct tagcctttgg ctcctttgac cactcgaagc cccacagcgt gttccagcgg    180
acttcaccag cagacccaga agtggtgggt gaaacactgc tctgttcct ccttgagcct     240 gtcgggagct gctgcctgcc accaccatgt ctgctgcaaa tcctgagact ccaaactcaa    300
ccatctccag agaggccagc acccagtctt catcagctgc agctagccaa ggctgggtgt    360
taccagaagg caaaatcgtg ccaaacactg ttttgttgg tggaattgat gctaggatgg     420
atgaaactga gattggaagc tgctttggta gatacggttc agtgaaagaa gtgaagataa    480
tcacgaatcg aactggtgtg tccaaaggct atggatttgt ttcgtttgtt aatgacgtgg    540
atgtccagaa gatagtagga tcacagatac atttccatgg taaaaagctg aagctgggcc    600
ctgcaatcag gaaacaaaag ttatgtgctc gtcatgtgca gccacgtcct ttggtagtta    660
atcctcctcc tccaccacag tttcagaacg tctggcggaa tccaaacact gaaacctacc    720
tgcagcccca aatcacgccg aatcctgtaa ctcagcacgt tcaggcttat tctgcttatc    780
cacattcacc aggtcaggtc atcactggat gtcagttgct tgtatataat tatcaggaat    840
atcctactta tcccgattca gcatttcagg tcaccactgg atatcagttg cctgtatata    900
attatcagcc atttcctgct tatccaagat caccatttca ggtcactgct ggatatcagt    960
tgcctgtata taattatcag gcatttcctg cttatccaaa ttcaccatt caagtcgcca   1020 ctggatatca gttccctgta tacaattatc agccatttcc tgcttatcca agttcaccat   1080
ttcaggtcac tgctggatat cagttgcctg tatataatta tcaggcattt cctgcttatc   1140
caaattcacc atttcaagtc gccactggat atcagttccc tgtatacaat tatcaggcat   1200 tcctgctta tccaaattca ccagttcagg tcaccactgg atatcagttg cctgtataca   1260
attatcaggc atttcctgct tatccaagtt caccatttca ggtcaccact ggatatcagt   1320
tgcctgtata taattatcag gcatttcctg cttatccaag ttcaccattt caggtcacca   1380
ctggatatca gttgcctgta tataattatc aggcatttcc tgcttatcca agttcaccat   1440
ttcaggtcac cactggatat cagttgcctg tataattac aggcatttt cctgcttatc     1500 caagttcacc atttcaggtc accactggat atcagttgcc tgtatataat tatcaggcat   1560
ttcctgctta tccaagttca ccatttcagg tcaccactgg atatcagttg cctgtatata   1620
```

-continued

```
attatcaggc atttcctgct tatccaagtt caccatttca ggtcaccact ggatatcagt    1680
tgcctgtata taattatcag gcatttcctg cttatccaaa ttcagcagtt caggtcacca    1740
ctggatatca gttccatgta tacaattacc agatgccacc gcagtgccct gttggggagc    1800
aaaggagaaa tctgtggacc gaagcataca aatggtggta tcttgtctgt ttaatccaga    1860
gaagagactg ataaattccg ttgttactca agatgactgc ttcaagggta aaagagtgca    1920
tcgctttaga agaagtttgg cagtatttaa atctgttgga tcctctcagc tatctagttt    1980
catgggaagt tgctggtttt gaatattaag ctaaaagttt tccactatta cagaaattct    2040
gaattttggt aaatcacact gaaactttct gtataacttg tattattaga ctctctagtt    2100
ttatcttaac actgaaactg ttcttcatta gatgtttatt tagaacctgg ttctgtgttt    2160
aatatatagt ttaaagtaac aaataatcga gactgaaaga atgttaagat ttatctgcaa    2220
ggatttttaa aaaattgaaa cttgcatttt aagtgtttaa aagcaaatac tgactttcaa    2280
aaaagttttt aaaacctgat ttgaaagcta acaattttga tagtctgaac acaagcattt    2340
cacttctcca agaagtacct gtgaacagta caatatttca gtattgagct ttgcatttat    2400
gatttatcta gaaatttacc tcaaaagcag aatttttaaa actgcatttt taatcagtgg    2460
aactcaatgt atagttagct ttattgaagt cttatccaaa cccagtaaaa cagattctaa    2520
gcaaacagtc caatcagtga gtcataatgt ttattcaaag tattttatct tttatctaga    2580
atccacatat gtatgtccaa tttgattggg atagtagtta ggataactaa aattctgggc    2640
ctaatttttt aaagaatcca agacaaacta aactttactg ggtatataac cttctcaatg    2700
agttaccatt cttttttata aaaaaaattg ttccttgaaa tgctaaactt aatggctgta    2760
tgtgaaattt gcaaaatact ggtattaaag aacgctgcag cttttttatg tcactcaaag    2820
gttaatcgga gtatctgaaa ggaattgttt ttataaaaac attgaagtat tagttacttg    2880
ctataaatag attttttattt ttgttttttta gcctgttata tttccttctg taaaataaaa    2940
tatgtccaga agaggcatgt tgtttctaga ttaggtagtg tcctcatttt atattgtgac    3000
cacacagcta gagcaccaga gccctttgc tatactcaca gtcttgtttt cccagcctct    3060
tttactagtc tttcaggagg tttgctctta gaactggtga tgtaaagaat ggaagtagct    3120
gtatgagcag ttcaaaggcc aagccgtgga atggtagcaa tgggatataa tacctttcta    3180
agggaaacat ttgtatcagt atcatttgat ctgccatgga catgtgttta aagtggcttt    3240
ctggcccttc tttcaatggc ttcttcccta aaacgtggag actctaagtt aatgtcgtta    3300
ctatgggcca tattactaat gcccactggg gtctatgatt tctcaaaatt ttcattcgga    3360
atccgaagga tacagtcttt aaactttaga attcccaaga aggctttatt acacctcaga    3420
aattgaaagc accatgactt tgtccattaa aaaattatcc atagtttttt tagtgctttt    3480
aacattccga catacatcat tctgtgatta aatctccaga tttctgtaaa tgatacctac    3540
attctaaaga gttaattcta attattccga tatgaccttta aggaaaagta aaggaataaa    3600
tttttgtctt tgttgaagta tttaatagag taaggtaaag aagatattaa gtccctttca    3660
aaatggaaaa ttaattctaa actgagaaaa atgttcctac tacctattgc tgatactgtc    3720
tttgcataaa tgaataaaaa taaacttttt ttcttc                                3756
```

<210> SEQ ID NO 6
<211> LENGTH: 534
<212> TYPE: PRT
<213> ORGANISM: homo sapiens

<400> SEQUENCE: 6

```
Met Ser Ala Ala Asn Pro Glu Thr Pro Asn Ser Thr Ile Ser Arg Glu
1               5                   10                  15

Ala Ser Thr Gln Ser Ser Ala Ala Ser Gln Gly Trp Val Leu
            20                  25                  30

Pro Glu Gly Lys Ile Val Pro Asn Thr Val Phe Val Gly Ile Asp
        35                  40                  45

Ala Arg Met Asp Glu Thr Glu Ile Gly Ser Cys Phe Gly Arg Tyr Gly
    50                  55                  60

Ser Val Lys Glu Val Lys Ile Ile Thr Asn Arg Thr Gly Val Ser Lys
65                  70                  75                  80

Gly Tyr Gly Phe Val Ser Phe Val Asn Asp Val Asp Val Gln Lys Ile
                85                  90                  95

Val Gly Ser Gln Ile His Phe His Gly Lys Lys Leu Lys Leu Gly Pro
            100                 105                 110

Ala Ile Arg Lys Gln Lys Leu Cys Ala Arg His Val Gln Pro Arg Pro
        115                 120                 125

Leu Val Val Asn Pro Pro Pro Gln Phe Gln Asn Val Trp Arg
    130                 135                 140

Asn Pro Asn Thr Glu Thr Tyr Leu Gln Pro Gln Ile Thr Pro Asn Pro
145                 150                 155                 160

Val Thr Gln His Val Gln Ala Tyr Ser Ala Tyr Pro His Ser Pro Gly
                165                 170                 175

Gln Val Ile Thr Gly Cys Gln Leu Leu Val Tyr Asn Tyr Gln Glu Tyr
            180                 185                 190

Pro Thr Tyr Pro Asp Ser Ala Phe Gln Val Thr Thr Gly Tyr Gln Leu
        195                 200                 205

Pro Val Tyr Asn Tyr Gln Pro Phe Pro Ala Tyr Pro Arg Ser Pro Phe
    210                 215                 220

Gln Val Thr Ala Gly Tyr Gln Leu Pro Val Tyr Asn Tyr Gln Ala Phe
225                 230                 235                 240

Pro Ala Tyr Pro Asn Ser Pro Phe Gln Val Ala Thr Gly Tyr Gln Phe
                245                 250                 255

Pro Val Tyr Asn Tyr Gln Pro Phe Pro Ala Tyr Pro Ser Ser Pro Phe
            260                 265                 270

Gln Val Thr Ala Gly Tyr Gln Leu Pro Val Tyr Asn Tyr Gln Ala Phe
        275                 280                 285

Pro Ala Tyr Pro Asn Ser Pro Phe Gln Val Ala Thr Gly Tyr Gln Phe
    290                 295                 300

Pro Val Tyr Asn Tyr Gln Ala Phe Pro Ala Tyr Pro Asn Ser Pro Val
305                 310                 315                 320

Gln Val Thr Thr Gly Tyr Gln Leu Pro Val Tyr Asn Tyr Gln Ala Phe
                325                 330                 335

Pro Ala Tyr Pro Ser Ser Pro Phe Gln Val Thr Thr Gly Tyr Gln Leu
            340                 345                 350

Pro Val Tyr Asn Tyr Gln Ala Phe Pro Ala Tyr Pro Ser Ser Pro Phe
        355                 360                 365

Gln Val Thr Thr Gly Tyr Gln Leu Pro Val Tyr Asn Tyr Gln Ala Phe
    370                 375                 380

Pro Ala Tyr Pro Ser Ser Pro Phe Gln Val Thr Thr Gly Tyr Gln Leu
385                 390                 395                 400

Pro Val Tyr Asn Tyr Gln Ala Phe Pro Ala Tyr Pro Ser Ser Pro Phe
                405                 410                 415
```

```
Gln Val Thr Thr Gly Tyr Gln Leu Pro Val Tyr Asn Tyr Gln Ala Phe
            420                 425                 430
Pro Ala Tyr Pro Ser Ser Pro Phe Gln Val Thr Thr Gly Tyr Gln Leu
            435                 440                 445
Pro Val Tyr Asn Tyr Gln Ala Phe Pro Ala Tyr Pro Ser Ser Pro Phe
450                 455                 460
Gln Val Thr Thr Gly Tyr Gln Leu Pro Val Tyr Asn Tyr Gln Ala Phe
465                 470                 475                 480
Pro Ala Tyr Pro Asn Ser Ala Val Gln Val Thr Thr Gly Tyr Gln Phe
            485                 490                 495
His Val Tyr Asn Tyr Gln Met Pro Pro Gln Cys Pro Val Gly Glu Gln
            500                 505                 510
Arg Arg Asn Leu Trp Thr Glu Ala Tyr Lys Trp Trp Tyr Leu Val Cys
            515                 520                 525
Leu Ile Gln Arg Arg Asp
    530

<210> SEQ ID NO 7
<211> LENGTH: 3198
<212> TYPE: DNA
<213> ORGANISM: homo sapiens

<400> SEQUENCE: 7
```

| | | |
|---|---|---|
| agtcggcctg cgctcctcag cctggcggtt ctacctccga gggttcgccc gcccttggtt | 60 |
| ttccttacac cttagccttt ggctcctttg accactcgaa gccccacagc gtgttccagc | 120 |
| ggacttcacc agcagaccca gaagtggtgg gtgaaacact gcctctgttc ctccttgagc | 180 |
| ctgtcgggag ctgctgcctg ccaccaccat gtctgctgca aatcctgaga ctccaaactc | 240 |
| aaccatctcc agagaggcca gcacccagtc ttcatcagct gcagctagcc aaggctgggt | 300 |
| gttaccagaa ggcaaaatcg tgccaaaaca ctgttttgtt ggtggaattg atgctaggat | 360 |
| ggatgaaact gagattggaa gctgctttgg tagatacggt tcagtgaaag aagtgaagat | 420 |
| aatcacgaat cgaactggtg tgtccaaagg ctatggattt gtttcgtttg ttaatgacgt | 480 |
| ggatgtccag aagatagtag gatcacagat acatttccat ggtaaaaagc tgaagctggg | 540 |
| ccctgcaatc aggaaacaaa agttatgtgc tcgtcatgtg cagccacgtc ctttggtagt | 600 |
| taatcctcct cctccaccac agtttcagaa cgtctggcgg aatccaaaca ctgaaaccta | 660 |
| cctgcagccc caaatcacgc cgaatcctgt aactcagcac gttcaggctt attctgctta | 720 |
| tccacattca ccaggtcagg tcatcactgg atgtcagttg cttgtatata attatcagga | 780 |
| atatcctact tatcccgatt caccatttca ggtcaccact ggatatcagt tgcctgtata | 840 |
| taattatcag ccatttcctg cttatccaag ttcaccattt caggtcactg ctggatatca | 900 |
| gttgcctgta tataattatc aggcatttcc tgcttatcca agttcaccat ttcaggtcac | 960 |
| cactggatat cagttgcctg tatataatta tcaggcattt cctgcttatc caagttcacc | 1020 |
| atttcaggtc accactggat atcagttgcc tgtatataat tatcaggcat tcctgctta | 1080 |
| tccaagttca ccatttcagg tcaccactgg atatcagttg cctgtatata attatcaggc | 1140 |
| atttcctgct tatccaaatt cagcagttca ggtcaccact ggatatcagt tccatgtata | 1200 |
| caattaccag atgccaccgc agtgccctgt tggggagcaa aggagaaatc tgtggaccga | 1260 |
| agcatacaaa tggtggtatc ttgtctgttt aatccagaga agagactgat aaattccgtt | 1320 |
| gttactcaag atgactgctt caagggtaaa agagtgcatc gctttagaag aagttttggca | 1380 |

```
gtatttaaat ctgttggatc ctctcagcta tctagtttca tgggaagttg ctggttttga   1440
atattaagct aaaagttttc cactattaca gaaattctga attttggtaa atcacactga   1500
aactttctgt ataacttgta ttattagact ctctagtttt atcttaacac tgaaactgtt   1560
cttcattaga tgtttattta gaacctggtt ctgtgtttaa tatatagttt aaagtaacaa   1620
ataatcgaga ctgaaagaat gttaagattt atctgcaagg attttaaaa aattgaaact    1680 tgcattttaa agtgtttaaa agcaaattac tgactttcaa aaagttttt aaacctgat     1740 ttgaaagcta acaattttgg atagtctgaa cacaagcatt tcacttctcc aagaagtacc   1800
tgtgaacagt acaatatttc agtattgagc tttgcattta tgatttatct agaaatttac   1860
ctcaaaagca gaattttta aactgcattt ttaatcagtg aactcaatg tatagttagc     1920 tttattgaag tcttatccaa acccagtaaa acagattcta agcaaacagt ccaatcagtg   1980
agtcataatg tttattcaaa gtattttatc ttttatctag aatccacata tgtatgtcca   2040
atttgattgg gatagtagtt aggataacta aaattctggg cctaattttt taaagaatcc   2100
aagacaaact aaactttact gggtatataa ccttctcaat gagttaccat tctttttat    2160 aaaaaaatt gttccttgaa atgctaaact taatggctgt atgtgaaatt tgcaaaatac    2220
tggtattaaa gaacgctgca gctttttat gtcactcaaa ggttaatcgg agtatctgaa    2280
aggaattgtt tttataaaaa cattgaagta ttagttactt gctataaata gatttttatt   2340 tttgttttt agcctgttat atttccttct gtaaaataaa atatgtccag aagaggcatg    2400
ttgtttctag attaggtagt gtcctcattt tatattgtga ccacacagct agagcaccag   2460
agcccttttg ctatactcac agtcttgttt tcccagcctc ttttactagt ctttcaggag   2520
gtttgctctt agaactggtg atgtaaagaa tggaagtagc tgtatgagca gttcaaaggc   2580
caagccgtgg aatggtagca atgggatata ataccttct aagggaaaca tttgtatcag    2640
tatcatttga tctgccatgg acatgtgttt aaagtggctt tctggcccct ctttcaatgg   2700
cttcttccct aaaacgtgga gactctaagt taatgtcgtt actatgggcc atattactaa   2760
tgcccactgg ggtctatgat ttctcaaaat tttcattcgg aatccgaagg atacagtctt   2820
taaactttag aattcccaag aaggctttat tacacctcag aaattgaaag caccatgact   2880
ttgtccatta aaaaattatc catagttttt ttagtgcttt taacattccg acatacatca   2940
ttctgtgatt aaatctccag atttctgtaa atgataccta cattctaaag agttaattct   3000
aattattccg atatgacctt aaggaaaagt aaaggaataa attttgtct tgttgaagt     3060 atttaataga gtaaggtaaa gaagatatta agtccctttc aaaatggaaa attaattcta   3120
aactgagaaa aatgttccta ctacctattg ctgatactgt ctttgcataa atgaataaaa   3180
ataaactttt tttcttca                                                  3198
```

<210> SEQ ID NO 8
<211> LENGTH: 366
<212> TYPE: PRT
<213> ORGANISM: homo sapiens

<400> SEQUENCE: 8

```
Met Ser Ala Ala Asn Pro Glu Thr Pro Asn Ser Thr Ile Ser Arg Glu
1               5                   10                  15

Ala Ser Thr Gln Ser Ser Ser Ala Ala Ala Ser Gln Gly Trp Val Leu
            20                  25                  30

Pro Glu Gly Lys Ile Val Pro Asn Thr Val Phe Val Gly Gly Ile Asp
        35                  40                  45
```

```
Ala Arg Met Asp Glu Thr Glu Ile Gly Ser Cys Phe Gly Arg Tyr Gly
 50                  55                  60
Ser Val Lys Glu Val Lys Ile Ile Thr Asn Arg Thr Gly Val Ser Lys
 65                  70                  75                  80
Gly Tyr Gly Phe Val Ser Phe Val Asn Asp Val Asp Val Gln Lys Ile
                 85                  90                  95
Val Gly Ser Gln Ile His Phe His Gly Lys Lys Leu Lys Leu Gly Pro
            100                 105                 110
Ala Ile Arg Lys Gln Lys Leu Cys Ala Arg His Val Gln Pro Arg Pro
            115                 120                 125
Leu Val Val Asn Pro Pro Pro Pro Gln Phe Gln Asn Val Trp Arg
130                 135                 140
Asn Pro Asn Thr Glu Thr Tyr Leu Gln Pro Gln Ile Thr Pro Asn Pro
145                 150                 155                 160
Val Thr Gln His Val Gln Ala Tyr Ser Ala Tyr Pro His Ser Pro Gly
                165                 170                 175
Gln Val Ile Thr Gly Cys Gln Leu Leu Val Tyr Asn Tyr Gln Glu Tyr
            180                 185                 190
Pro Thr Tyr Pro Asp Ser Pro Phe Gln Val Thr Thr Gly Tyr Gln Leu
            195                 200                 205
Pro Val Tyr Asn Tyr Gln Pro Phe Pro Ala Tyr Pro Ser Ser Pro Phe
            210                 215                 220
Gln Val Thr Ala Gly Tyr Gln Leu Pro Val Tyr Asn Tyr Gln Ala Phe
225                 230                 235                 240
Pro Ala Tyr Pro Ser Ser Pro Phe Gln Val Thr Thr Gly Tyr Gln Leu
            245                 250                 255
Pro Val Tyr Asn Tyr Gln Ala Phe Pro Ala Tyr Pro Ser Ser Pro Phe
            260                 265                 270
Gln Val Thr Thr Gly Tyr Gln Leu Pro Val Tyr Asn Tyr Gln Ala Phe
            275                 280                 285
Pro Ala Tyr Pro Ser Ser Pro Phe Gln Val Thr Thr Gly Tyr Gln Leu
            290                 295                 300
Pro Val Tyr Asn Tyr Gln Ala Phe Pro Ala Tyr Pro Asn Ser Ala Val
305                 310                 315                 320
Gln Val Thr Thr Gly Tyr Gln Phe His Val Tyr Asn Tyr Gln Met Pro
                325                 330                 335
Pro Gln Cys Pro Val Gly Glu Gln Arg Arg Asn Leu Trp Thr Glu Ala
            340                 345                 350
Tyr Lys Trp Trp Tyr Leu Val Cys Leu Ile Gln Arg Arg Asp
            355                 360                 365

<210> SEQ ID NO 9
<211> LENGTH: 3391
<212> TYPE: DNA
<213> ORGANISM: homo sapiens

<400> SEQUENCE: 9
gcgggcggtt ctacctccga gggttcgccc gcccttggtt ttccttacac cttagccttt     60
ggctcctttg accactcgaa gccccacagc gtgttccagc ggacttcacc agcagaccca    120
gaagtggtgg gtgaaacact gcctctgttc ctccttgagc ctgtcgggag ctgctgcctg    180
ccaccaccat gtctgctgca aatcctgaga ctccaaactc aaccatctcc agagaggcca    240
gcacccagtc ttcatcagct gcagctagcc aaggctgggt gttaccagaa ggcaaaatcg    300
tgccaaacac tgttttttgtt ggtggaattg atgctaggat ggatgaaact gagattggaa    360
```

```
gctgctttgg tagatacggt tcagtgaaag aagtgaagat aatcacgaat cgaactggtg    420
tgtccaaagg ctatggattt gtttcgtttg ttaatgacgt ggatgtccag aagatagtag    480
gatcacagat acatttccat ggtaaaaagc tgaagctggg ccctgcaatc aggaaacaaa    540
agttatgtgc tcgtcatgtg cagccacgtc ctttggtagt taatcctcct cctccaccac    600
agtttcagaa cgtctggcgg aatccaaaca ctgaaaccta cctgcagccc caaatcacgc    660
cgaatcctgt aactcagcac gttcaggctt actctgctta ccacattca ccaggtcagg    720 tcatcactgg atgtcagttg cttgtatata attatcagga atatcctact tatcccgatt    780
cagcatttca ggtcaccact ggatatcagt tgcctgtata taattatcag ccatttcctg    840
cttatccaag atcaccattt caggtcactg ctggatatca gttgcctgta tataattatc    900
aggcatttcc tgcttatcca aattcaccat ttcaagtcgc cactggatat cagttccctg    960
tatacaatta tcaggcattt cctgcttatc caaattcacc agttcaggtc accactggat   1020
atcagttgcc tgtatacaat tatcaggcat ttcctgctta tccaaattca ccatttcaag   1080
tcgccactgg atatcagttc cctgtataca attatcaggc atttcctgct tatccaaatt   1140
caccagttca ggtcaccact ggatatcagt tgcctgtata caattatcag gcatttcctg   1200
cttatccaaa ttcaccattt caagtcgcca ctggatatca gttccctgta caattatc    1260 aggcatttcc tgcttatcca aattcaccag ttcaggtcac cactggatat cagttgcctg   1320
tatacaatta tcaggcattt cctgcttatc caaattcagc agttcaggtc accactggat   1380
atcagttcca tgtatacaat taccagatgc caccgcagtg ccctgttggg gagcaaagga   1440
gaaatctgtg gaccgaagca tacaaatggt ggtatcttgt ctgtttaatc cagagaagag   1500
actgataaat tccgttgtta ctcaagatga ctgcttcaag ggtaaaagag tgcatcgctt   1560
tagaagaagt ttggcagtat ttaaatctgt tggatcctct cagctatcta gtttcatggg   1620
aagttgctgg ttttgaatat taagctaaaa gttttccact attacagaaa ttctgaattt   1680
tggtaaatca cactgaaact ttctgtataa cttgtattat tagactctct agttttatct   1740
taacactgaa actgttcttc attagatgtt tatttagaac ctggttctgt gtttaatata   1800
tagtttaaag taacaaataa tcgagactga agaatgtta agatttatct gcaaggattt    1860
ttaaaaaatt gaaacttgca ttttaagtgt ttaaaagcaa atactgactt tcaaaaaagt   1920
ttttaaaacc tgatttgaaa gctaacaatt ttgatagtct gaacacaagc atttcacttc   1980
tccaagaagt acctgtgaac agtacaatat ttcagtattg agctttgcat ttatgattta   2040
tctagaaatt tacctcaaaa gcagaatttt taaaactgca tttttaatca gtggaactca   2100
atgtatagtt agctttattg aagtcttatc caaacccagt aaaacagatt ctaagcaaac   2160
agtccaatca gtgagtcata atgtttattc aaagtatttt atcttttatc tagaatccac   2220
atatgtatgt ccaatttgat tgggatagta gttaggataa ctaaaattct gggcctaatt   2280
ttttaaagaa tccaagacaa actaaacttt actgggtata taaccttctc aatgagttac   2340
cattcttttt tataaaaaaa attgttcctt gaaatgctaa acttaatggc tgtatgtgaa   2400
atttgcaaaa tactggtatt aaagaacgct gcagcttttt tatgtcactc aaaggttaat   2460
cggagtatct gaaaggaatt gttttttataa aaacattgaa gtattagtta cttgctataa   2520
atagattttt atttttgttt tttagcctgt tatatttcct tctgtaaaat aaaatatgtc   2580
cagaagaggc atgttgtttc tagattaggt agtgtcctca tttatattg tgaccacaca    2640 gctagagcac cagagcccctt ttgctatact cacagtcttg ttttcccagc ctcttttact   2700
```

```
agtctttcag gaggtttgct cttagaactg gtgatgtaaa gaatggaagt agctgtatga    2760
gcagttcaaa ggccaagccg tggaatggta gcaatgggat ataataccct tctaagggaa    2820
acatttgtat cagtatcatt tgatctgcca tggacatgtg tttaaagtgg ctttctggcc    2880
cttctttcaa tggcttcttc cctaaaacgt ggagactcta agttaatgtc gttactatgg    2940
gccatattac taatgcccac tggggtctat gatttctcaa aattttcatt cggaatccga    3000
aggatacagt ctttaaactt tagaattccc aagaaggctt tattacacct cagaaattga    3060
aagcaccatg actttgtcca ttaaaaaatt atccatagtt ttttagtgc ttttaacatt     3120 ccgacataca tcattctgtg attaaatctc cagatttctg taaatgatac ctacattcta    3180
aagagttaat tctaattatt ccgatatgac cttaaggaaa agtaaggaa taaattttg      3240 tctttgttga agtatttaat agagtaaggt aagaagata ttaagtccct ttcaaaatgg     3300
aaaattaatt ctaaactgag aaaaatgttc ctactaccta ttgctgatac tgtctttgca    3360
taaatgaata aaaataaact tttttcttc a                                    3391
```

<210> SEQ ID NO 10
<211> LENGTH: 438
<212> TYPE: PRT
<213> ORGANISM: homo sapiens

<400> SEQUENCE: 10

```
Met Ser Ala Ala Asn Pro Glu Thr Pro Asn Ser Thr Ile Ser Arg Glu
1               5                   10                  15

Ala Ser Thr Gln Ser Ser Ala Ala Ala Ser Gln Gly Trp Val Leu
            20                  25                  30

Pro Glu Gly Lys Ile Val Pro Asn Thr Val Phe Val Gly Gly Ile Asp
        35                  40                  45

Ala Arg Met Asp Glu Thr Glu Ile Gly Ser Cys Phe Gly Arg Tyr Gly
    50                  55                  60

Ser Val Lys Glu Val Lys Ile Ile Thr Asn Arg Thr Gly Val Ser Lys
65                  70                  75                  80

Gly Tyr Gly Phe Val Ser Phe Val Asn Asp Val Asp Val Gln Lys Ile
                85                  90                  95

Val Gly Ser Gln Ile His Phe His Gly Lys Lys Leu Lys Leu Gly Pro
            100                 105                 110

Ala Ile Arg Lys Gln Lys Leu Cys Ala Arg His Val Gln Pro Arg Pro
        115                 120                 125

Leu Val Val Asn Pro Pro Pro Pro Gln Phe Gln Asn Val Trp Arg
    130                 135                 140

Asn Pro Asn Thr Glu Thr Tyr Leu Gln Pro Gln Ile Thr Pro Asn Pro
145                 150                 155                 160

Val Thr Gln His Val Gln Ala Tyr Ser Ala Tyr Pro His Ser Pro Gly
                165                 170                 175

Gln Val Ile Thr Gly Cys Gln Leu Leu Val Tyr Asn Tyr Gln Glu Tyr
            180                 185                 190

Pro Thr Tyr Pro Asp Ser Ala Phe Gln Val Thr Thr Gly Tyr Gln Leu
        195                 200                 205

Pro Val Tyr Asn Tyr Gln Pro Phe Pro Ala Tyr Arg Ser Pro Phe
    210                 215                 220

Gln Val Thr Ala Gly Tyr Gln Leu Pro Val Tyr Asn Tyr Gln Ala Phe
225                 230                 235                 240

Pro Ala Tyr Pro Asn Ser Pro Phe Gln Val Ala Thr Gly Tyr Gln Phe
                245                 250                 255
```

```
Pro Val Tyr Asn Tyr Gln Ala Phe Pro Ala Tyr Pro Asn Ser Pro Val
            260                 265                 270

Gln Val Thr Thr Gly Tyr Gln Leu Pro Val Tyr Asn Tyr Gln Ala Phe
        275                 280                 285

Pro Ala Tyr Pro Asn Ser Pro Phe Gln Val Ala Thr Gly Tyr Gln Phe
        290                 295                 300

Pro Val Tyr Asn Tyr Gln Ala Phe Pro Ala Tyr Pro Asn Ser Pro Val
305                 310                 315                 320

Gln Val Thr Thr Gly Tyr Gln Leu Pro Val Tyr Asn Tyr Gln Ala Phe
                325                 330                 335

Pro Ala Tyr Pro Asn Ser Pro Phe Gln Val Ala Thr Gly Tyr Gln Phe
            340                 345                 350

Pro Val Tyr Asn Tyr Gln Ala Phe Pro Ala Tyr Pro Asn Ser Pro Val
            355                 360                 365

Gln Val Thr Thr Gly Tyr Gln Leu Pro Val Tyr Asn Tyr Gln Ala Phe
        370                 375                 380

Pro Ala Tyr Pro Asn Ser Ala Val Gln Val Thr Thr Gly Tyr Gln Phe
385                 390                 395                 400

His Val Tyr Asn Tyr Gln Met Pro Pro Gln Cys Pro Val Gly Glu Gln
                405                 410                 415

Arg Arg Asn Leu Trp Thr Glu Ala Tyr Lys Trp Trp Tyr Leu Val Cys
            420                 425                 430

Leu Ile Gln Arg Arg Asp
        435
```

<210> SEQ ID NO 11
<211> LENGTH: 3821
<212> TYPE: DNA
<213> ORGANISM: homo sapiens

<400> SEQUENCE: 11

```
ctcagcctgg cggttctacc tccgagggtt cgcccgccct tggttttcct tacaccttag     60
cctttggctc ctttgaccac tcgaagcccc acagcgtgtt ccagcggact tcaccagcag    120
acccagaagt ggtgggtgaa acactgcctc tgttcctcct tgagcctgtc gggagctgct    180
gcctgccacc accatgtctg ctgcaaatcc tgagactcca aactcaacca tctccagaga    240
ggccagcacc cagtcttcat cagctgcagc tagccaaggc tgggtgttac agaaggcaa     300 aatcgtgcca acactgtttt tgttggtgg aattgatgct aggatggatg aaactgagat    360
tggaagctgc tttggtagat acggttcagt gaaagaagtg aagataatca cgaatcgaac    420
tggtgtgtcc aaaggctatg gatttgtttc gtttgttaat gacgtggatg tccagaagat    480
agtaggatca cagatacatt ccatggtaa aaagctgaag ctgggccctg caatcaggaa    540
acaaaagtta tgtgctcgtc atgtgcagcc acgtcctttg gtagttaatc ctcctcctcc    600
accacagttt cagaacgtct ggcggaatcc aaacactgaa acctacctgc agccccaaat    660
cacgccgaat cctgtaactc agcacgttca gtctgctgca atcctgaga ctccaaactc     720 aaccatctcc agagaggcca gcacccagtc ttcatcagct gcagctagcc aaggctgggt    780
gttaccagaa ggcaaaatcg tgccaaacac tgttttgtt ggtggaattg atgctaggat     840
ggatgaaact gagattggaa ctgctttgg tagatacggt tcagtgaaag aagtgaagat     900
aatcacgaat cgaactggtg tgtccaaagg ctatggattt gtttcgtttg ttaatgacgt    960
ggatgtccag aagatagtag gatcacagat acatttccat ggtaaaaagc tgaagctggg   1020
```

```
ccctgcaatc aggaaacaaa agttatgtgc tcgtcatgtg cagccacgtc ctttggtagt    1080
taatcctcct cctccaccac agtttcagaa cgtctggcgg aatccaaaca ctgaaaccta    1140
cctgcagccc caaatcacgc cgaatcctgt aactcagcac gttcaggctt actctgctta    1200
tccacattca ccaggtcagg tcatcactgg atgtcagttg cttgtatata attatcagga    1260
atatcctact tatcccgatt cagcatttca ggtcaccact ggatatcagt tgcctgtata    1320
taattatcag ccatttcctg cttatccaag atcaccattt caggtcactg ctggatatca    1380
gttgcctgta tataattatc aggcatttcc tgcttatcca aattcaccat ttcaagtcgc    1440
cactggatat cagttccctg tatacaatta tcagccattt cctgcttatc caagttcacc    1500
atttcaggtc actgctggat atcagttgcc tgtatataat tatcaggcat ttcctgctta    1560
tccaaattca ccatttcaag tcgccactgg atatcagttc cctgtataca attatcaggc    1620
atttcctgct tatccaaatt caccagttca ggtcaccact ggatatcagt tgcctgtata    1680
caattatcag gcatttcctg cttatccaag ttcaccattt caggtcacca ctggatatca    1740
gttgcctgta tataattatc aggcatttcc tgcttatcca aattcagcag ttcaggtcac    1800
cactggatat cagttccatg tatacaatta ccagatgcca ccgcagtgcc ctgttgggga    1860
gcaaggagaa atctgtggac cgaagcataa caaatggtgg tatcttgtct gtttaatcca    1920
gagaagagac tgataaaattc cgttgttact caagatgact gcttcaaggg taaaagagtg    1980
catcgcttta gaagaagttt ggcagtattt aaatctgttg gatcctctca gctatctagt    2040
ttcatgggaa gttgctggtt ttgaatatta agctaaaagt tttccactat tacagaaatt    2100
ctgaattttg gtaaatcaca ctgaaacttt ctgtataact tgtattatta gactctctag    2160
ttttatctta acactgaaac tgttcttcat tagatgttta tttagaacct ggttctgtgt    2220
ttaatatata gtttaaagta acaaataatc gagactgaaa gaatgttaag atttatctgc    2280
aaggattttt aaaaaattga aacttgcatt ttaagtgttt aaaagcaaat actgactttc    2340
aaaaaagttt ttaaaacctg atttgaaagc taacaatttt gatagtctga acacaagcat    2400
ttcacttctc caagaagtac ctgtgaacag tacaatattt cagtattgag ctttgcattt    2460
atgatttatc tagaaatttta cctcaaaagc agaatttta aaactgcatt tttaatcagt    2520
ggaactcaat gtatagttag ctttattgaa gtcttatcca aacccagtaa aacagattct    2580
aagcaaacag tccaatcagt gagtcataat gtttattcaa agtatttttat cttttatcta    2640 gaatccacat atgtatgtcc aatttgattg ggatagtagt taggataact aaaattctgg    2700
gcctaatttt ttaaagaatc caagacaaac taaactttac tgggtatata accttctcaa    2760
tgagttacca ttcttttttta taaaaaaaat tgttccttga aatgctaaac ttaatggctg    2820
tatgtgaaat ttgcaaaata ctggtattaa agaacgctgc agctttttta tgtcactcaa    2880
aggttaatcg gagtatctga aaggaattgt ttttataaaa acattgaagt attagttact    2940
tgctataaat agatttttat ttttgttttt tagcctgtta tatttccttc tgtaaaataa    3000
aatatgtcca gaagaggcat gttgtttcta gattaggtag tgtcctcatt ttatattgtg    3060
accacacagc tagagcacca gagcccttt tgctatactca cagtcttgtt ttcccagcct    3120
cttttactag tctttcagga ggtttgctct tagaactggt gatgtaaaga atggaagtag    3180
ctgtatgagc agttcaaagg ccaagccgtg gaatggtagc aatgggatat aatacctttc    3240
taagggaaac atttgtatca gtatcatttg atctgccatg gacatgtgtt taaagtggct    3300 ttctggcccct tctttcaatg gcttcttccc taaaacgtgg agactctaag ttaatgtcgt    3360
tactatgggc catattacta atgcccactg gggtctatga tttctcaaaa ttttcattcg    3420
```

```
gaatccgaag gatacagtct ttaaacttta gaattcccaa gaaggcttta ttacacctca    3480
gaaattgaaa gcaccatgac tttgtccatt aaaaaattat ccatagtttt tttagtgctt    3540
ttaacattcc gacatacatc attctgtgat taaatctcca gatttctgta aatgatacct    3600
acattctaaa gagttaattc taattattcc gatatgacct taaggaaaag taaggaata     3660 aatttttgtc tttgttgaag tatttaatag agtaaggtaa agaagatatt aagtcccttt    3720
caaaatggaa aattaattct aaactgagaa aaatgttcct actacctatt gctgatactg    3780
tctttgcata aatgaataaa aataaacttt ttttcttcaa a                        3821
```

<210> SEQ ID NO 12
<211> LENGTH: 579
<212> TYPE: PRT
<213> ORGANISM: homo sapiens

<400> SEQUENCE: 12

```
Met Ser Ala Ala Asn Pro Glu Thr Pro Asn Ser Thr Ile Ser Arg Glu
1               5                   10                  15

Ala Ser Thr Gln Ser Ser Ala Ala Ala Ser Gln Gly Trp Val Leu
            20                  25                  30

Pro Glu Gly Lys Ile Val Pro Asn Thr Val Phe Val Gly Ile Asp
        35                  40                  45

Ala Arg Met Asp Glu Thr Glu Ile Gly Ser Cys Phe Gly Arg Tyr Gly
50                  55                  60

Ser Val Lys Glu Val Lys Ile Ile Thr Asn Arg Thr Gly Val Ser Lys
65                  70                  75                  80

Gly Tyr Gly Phe Val Ser Phe Val Asn Asp Val Asp Val Gln Lys Ile
                85                  90                  95

Val Gly Ser Gln Ile His Phe His Gly Lys Lys Leu Lys Leu Gly Pro
            100                 105                 110

Ala Ile Arg Lys Gln Lys Leu Cys Ala Arg His Val Gln Pro Arg Pro
        115                 120                 125

Leu Val Val Asn Pro Pro Pro Pro Gln Phe Gln Asn Val Trp Arg
130                 135                 140

Asn Pro Asn Thr Glu Thr Tyr Leu Gln Pro Gln Ile Thr Pro Asn Pro
145                 150                 155                 160

Val Thr Gln His Val Gln Ser Ala Ala Asn Pro Glu Thr Pro Asn Ser
                165                 170                 175

Thr Ile Ser Arg Glu Ala Ser Thr Gln Ser Ser Ser Ala Ala Ala Ser
            180                 185                 190

Gln Gly Trp Val Leu Pro Glu Gly Lys Ile Val Pro Asn Thr Val Phe
        195                 200                 205

Val Gly Gly Ile Asp Ala Arg Met Asp Glu Thr Glu Ile Gly Ser Cys
    210                 215                 220

Phe Gly Arg Tyr Gly Ser Val Lys Glu Val Lys Ile Ile Thr Asn Arg
225                 230                 235                 240

Thr Gly Val Ser Lys Gly Tyr Gly Phe Val Ser Phe Val Asn Asp Val
                245                 250                 255

Asp Val Gln Lys Ile Val Gly Ser Gln Ile His Phe His Gly Lys Lys
            260                 265                 270

Leu Lys Leu Gly Pro Ala Ile Arg Lys Gln Lys Leu Cys Ala Arg His
        275                 280                 285

Val Gln Pro Arg Pro Leu Val Val Asn Pro Pro Pro Pro Gln Phe
    290                 295                 300
```

```
Gln Asn Val Trp Arg Asn Pro Asn Thr Glu Thr Tyr Leu Gln Pro Gln
305                 310                 315                 320

Ile Thr Pro Asn Pro Val Thr Gln His Val Gln Ala Tyr Ser Ala Tyr
                325                 330                 335

Pro His Ser Pro Gly Gln Val Ile Thr Gly Cys Gln Leu Leu Val Tyr
            340                 345                 350

Asn Tyr Gln Glu Tyr Pro Thr Tyr Pro Asp Ser Ala Phe Gln Val Thr
        355                 360                 365

Thr Gly Tyr Gln Leu Pro Val Tyr Asn Tyr Gln Pro Phe Pro Ala Tyr
370                 375                 380

Pro Arg Ser Pro Phe Gln Val Thr Ala Gly Tyr Gln Leu Pro Val Tyr
385                 390                 395                 400

Asn Tyr Gln Ala Phe Pro Ala Tyr Pro Asn Ser Pro Phe Gln Val Ala
                405                 410                 415

Thr Gly Tyr Gln Phe Pro Val Tyr Asn Tyr Gln Pro Phe Pro Ala Tyr
            420                 425                 430

Pro Ser Ser Pro Phe Gln Val Thr Ala Gly Tyr Gln Leu Pro Val Tyr
        435                 440                 445

Asn Tyr Gln Ala Phe Pro Ala Tyr Pro Asn Ser Pro Phe Gln Val Ala
    450                 455                 460

Thr Gly Tyr Gln Phe Pro Val Tyr Asn Tyr Gln Ala Phe Pro Ala Tyr
465                 470                 475                 480

Pro Asn Ser Pro Val Gln Val Thr Thr Gly Tyr Gln Leu Pro Val Tyr
                485                 490                 495

Asn Tyr Gln Ala Phe Pro Ala Tyr Pro Ser Ser Pro Phe Gln Val Thr
            500                 505                 510

Thr Gly Tyr Gln Leu Pro Val Tyr Asn Tyr Gln Ala Phe Pro Ala Tyr
        515                 520                 525

Pro Asn Ser Ala Val Gln Val Thr Thr Gly Tyr Gln Phe His Val Tyr
    530                 535                 540

Asn Tyr Gln Met Pro Pro Gln Cys Pro Val Gly Glu Gln Arg Arg Asn
545                 550                 555                 560

Leu Trp Thr Glu Ala Tyr Lys Trp Trp Tyr Leu Val Cys Leu Ile Gln
                565                 570                 575

Arg Arg Asp

<210> SEQ ID NO 13
<211> LENGTH: 3271
<212> TYPE: DNA
<213> ORGANISM: homo sapiens

<400> SEQUENCE: 13
tcagtcggcc tgcgctcctc agcctggcgg ttctacctcc gagggttcgc ccgcccttgg       60
ttttccttac accttagcct ttggctcctt tgaccactcg aagccccaca gcgtgttcca      120
gcggacttca ccagcagacc cagaagtggt gggtgaaaca ctgcctctgt tcctccttga      180
gcctgtcggg agctgctgcc tgccaccacc atgtctgctg caaatcctga gactccaaac      240
tcaaccatct ccagagaggc cagcacccag tcttcatcag ctgcagctag caaggctgg       300 gtgttaccag aaggcaaaat cgtgccaaac actgttttg ttggtggaat tgatgctagg      360
atggatgaaa ctgagattgg aagctgcttt ggtagatacg gttcagtgaa agaagtgaag      420
ataatcacga atcgaactgg tgtgtccaaa ggctatggat ttgtttcgtt tgttaatgac      480
gtggatgtcc agaagatagt aggatcacag atacatttcc atggtaaaaa gctgaagctg      540
```

-continued

```
ggccctgcaa tcaggaaaca aaagttatgt gctcgtcatg tgcagccacg tcctttggta    600
gttaatcctc ctcctccacc acagtttcag aacgtctggc ggaatccaaa cactgaaacc    660
tacctgcagc cccaaatcac gccgaatcct gtaactcagc acgttcaggc ttactctgct    720
tatccacatt caccaggtca ggtcatcact ggatgtcagt tgcttgtata taattatcag    780
gaatatccta cttatcccga ttcagcattt caggtcacca ctggatatca gttgcctgta    840
tataattatc agccatttcc tgcttatcca agatcaccat ttcaggtcac tgctggatat    900
cagttgcctg tatataatta tcaggcattt cctgcttatc caaattcacc atttcaagtc    960
gccactggat atcagttccc tgtatacaat tatcagccat ttcctgctta tccaagttca   1020
ccatttcagg tcactgctgg atatcagttg cctgtatata attatcaggc atttcctgct   1080
tatccaaatt caccatttca gtcgccact ggatatcagt tccctgtata caattatcag   1140
gcatttcctg cttatccaaa ttcaccagtt caggtcacca ctggatatca gttgcctgta   1200
tacaattatc aggcatttcc tgcttatcca aattcagcag ttcaggtcac cactggatat   1260
cagttccatg tatacaatta ccagatgcca ccgcagtgcc ctgttgggga caaaggaga    1320
aatctgtgga ccgaagcata caaatggtgg tatcttgtct gtttaatcca gagaagagac   1380
tgataaaattc cgttgttact caagatgact gcttcaaggg taaaagagtg catcacttta   1440
gaagaagttt ggcagtattt aaatctgttg atcctctca gctatctagt ttcatgggaa    1500
gttgctggtt ttgaatatta agctaaaagt tttccactat tacagaaatt ctgaattttg   1560
gtaaatcaca ctgaaactt ctgtataact tgtattatta gactctctag ttttatctta    1620
acactgaaac tgttcttcat tagatgttta tttagaacct ggttctgtgt ttaatatata   1680
gtttaaagta acaaataatc gagactgaaa gaatgttaag atttatctgc aaggattttt   1740
aaaaaattga aacttgcatt ttaagtgttt aaaagcaaat actgactttc aaaaaagttt   1800
ttaaaacctg atttgaaagc taacaatttt gatagtctga acacaagcat ttcacttctc   1860
caagaagtac ctgtgaacag tacaatattt cagtattgag ctttgcattt atgatttatc   1920
tagaaattta cctcaaaagc agaatttta aaactgcatt tttaatcagt ggaactcaat    1980
gtatagttag ctttattgaa gtcttatcca aacccagtaa aacagattct aagcaaacag   2040
tccaatcagt gagtcataat gtttattcaa agtattttat cttttatcta gaatccacat   2100
atgtatgtcc aatttgattg ggatagtagt taggataact aaaattctgg gcctaatttt   2160
ttaaagaatc caagacaaac taaactttac tgggtatata accttctcaa tgagttacca   2220
ttcttttta taaaaaaaat tgttccttga atgctaaac ttaatggctg tatgtgaaat    2280
ttgcaaaata ctggtattaa agaacgctgc agcttttta tgtcactcaa aggttaatcg    2340
gagtatctga aggaattgt ttttataaaa acattgaagt attagttact tgctataaat    2400
agatttttat ttttgttttt tagcctgtta tatttccttc tgtaaaataa aatatgtcca   2460
gaagaggcat gttgtttcta gattaggtag tgtcctcatt ttatattgtg accacacagc   2520
tagagcacca gagcccttt gctatactca cagtcttgtt ttcccagcct cttttactag    2580
tctttcagga ggttttgctct tagaactggt gatgtaaaga atggaagtag ctgtatgagc   2640
agttcaaagg ccaagccgtg aatggtagc aatgggatat aatacctttc taagggaaac    2700
atttgtatca gtatcatttg atctgccatg acatgtgtt taaagtggct ttctggccct    2760
tctttcaatg gcttcttccc taaaacgtgg agactctaag ttaatgtcgt tactatgggc   2820
catattacta atgcccactg gggtctatga tttctcaaaa ttttcattcg gaatccgaag   2880
```

```
gatacagtct ttaaacttta gaattcccaa gaaggcttta ttacacctca gaaattgaaa    2940
gcaccatgac tttgtccatt aaaaaattat ccatagtttt tttagtgctt ttaacattcc    3000
gacatacatc attctgtgat taaatctcca gatttctgta aatgatacct acattctaaa    3060
gagttaattc taattattcc gatatgacct taaggaaaag taaggaata aattttgtc     3120 tttgttgaag tatttaatag agtaaggtaa agaagatatt aagtcccttt caaaatggaa    3180
aattaattct aaactgagaa aaatgttcct actacctatt gctgatactg tctttgcata    3240
aatgaataaa aataaacttt ttttcttcaa a                                    3271
```

<210> SEQ ID NO 14
<211> LENGTH: 390
<212> TYPE: PRT
<213> ORGANISM: homo sapiens

<400> SEQUENCE: 14

```
Met Ser Ala Ala Asn Pro Glu Thr Pro Asn Ser Thr Ile Ser Arg Glu
1               5                   10                  15

Ala Ser Thr Gln Ser Ser Ala Ala Ser Gln Gly Trp Val Leu
                20                  25                  30

Pro Glu Gly Lys Ile Val Pro Asn Thr Val Phe Val Gly Gly Ile Asp
                35                  40                  45

Ala Arg Met Asp Glu Thr Glu Ile Gly Ser Cys Phe Gly Arg Tyr Gly
    50                  55                  60

Ser Val Lys Glu Val Lys Ile Ile Thr Asn Arg Thr Gly Val Ser Lys
65                  70                  75                  80

Gly Tyr Gly Phe Val Ser Phe Val Asn Asp Val Asp Val Gln Lys Ile
                85                  90                  95

Val Gly Ser Gln Ile His Phe His Gly Lys Lys Leu Lys Leu Gly Pro
            100                 105                 110

Ala Ile Arg Lys Gln Lys Leu Cys Ala Arg His Val Gln Pro Arg Pro
        115                 120                 125

Leu Val Val Asn Pro Pro Pro Pro Gln Phe Gln Asn Val Trp Arg
130                 135                 140

Asn Pro Asn Thr Glu Thr Tyr Leu Gln Pro Gln Ile Thr Pro Asn Pro
145                 150                 155                 160

Val Thr Gln His Val Gln Ala Tyr Ser Ala Tyr Pro His Ser Pro Gly
                165                 170                 175

Gln Val Ile Thr Gly Cys Gln Leu Leu Val Tyr Asn Tyr Gln Glu Tyr
            180                 185                 190

Pro Thr Tyr Pro Asp Ser Ala Phe Gln Val Thr Thr Gly Tyr Gln Leu
        195                 200                 205

Pro Val Tyr Asn Tyr Gln Pro Phe Pro Ala Tyr Pro Arg Ser Pro Phe
    210                 215                 220

Gln Val Thr Ala Gly Tyr Gln Leu Pro Val Tyr Asn Tyr Gln Ala Phe
225                 230                 235                 240

Pro Ala Tyr Pro Asn Ser Pro Phe Gln Val Ala Thr Gly Tyr Gln Phe
                245                 250                 255

Pro Val Tyr Asn Tyr Gln Pro Phe Pro Ala Tyr Pro Ser Ser Pro Phe
            260                 265                 270

Gln Val Thr Ala Gly Tyr Gln Leu Pro Val Tyr Asn Tyr Gln Ala Phe
        275                 280                 285

Pro Ala Tyr Pro Asn Ser Pro Phe Gln Val Ala Thr Gly Tyr Gln Phe
    290                 295                 300
```

```
Pro Val Tyr Asn Tyr Gln Ala Phe Pro Ala Tyr Pro Asn Ser Pro Val
305                 310                 315                 320

Gln Val Thr Thr Gly Tyr Gln Leu Pro Val Tyr Asn Tyr Gln Ala Phe
            325                 330                 335

Pro Ala Tyr Pro Asn Ser Ala Val Gln Val Thr Thr Gly Tyr Gln Phe
        340                 345                 350

His Val Tyr Asn Tyr Gln Met Pro Pro Gln Cys Pro Val Gly Glu Gln
        355                 360                 365

Arg Arg Asn Leu Trp Thr Glu Ala Tyr Lys Trp Trp Tyr Leu Val Cys
    370                 375                 380

Leu Ile Gln Arg Arg Asp
385                 390

<210> SEQ ID NO 15
<211> LENGTH: 3108
<212> TYPE: DNA
<213> ORGANISM: homo sapiens

<400> SEQUENCE: 15
```

| | | | | | |
|---|---|---|---|---|---|
| actcccacgc | gcctccgccc | cgccagcctc | atttctggcg | cgctctcccc | gtggctccgc | 60 |
| aagatggcgc | cgggcctgct | gagggacttg | ccttcttaaa | cttcgagggc | cggagcttcc | 120 |
| ttaggaagtg | gttccctcct | ggtccctgta | cttggtgggg | tgggcggggt | tcgtgggggc | 180 |
| ctcagcgtgg | ggtgtggggc | gtcctgaagg | catggccctg | tagctgaggg | ggctgggccg | 240 |
| gaagtgcctc | tggtcccctc | gcgcctgtca | gctgcggggg | acttgctgat | ggcggctccc | 300 |
| tcgtgtggcg | gcgacagaaa | agctcgcctg | acgccatctt | tgccgcacga | gtctactgca | 360 |
| aatcctgaaa | ctccaaactc | aaccatctcc | agagaggcca | gcacccagtc | ctcatcagct | 420 |
| gcaaccagcc | aaggctatat | tttaccagaa | ggcaaaatca | tgccaaacac | tgttttttgtt | 480 |
| ggaggaattg | atgttaggat | ggatgaaact | gagattagaa | gcttctttgc | tagatatggt | 540 |
| tcagtgaaag | aagtgaagat | aatcactgat | cgaactggtg | tgtccaaagg | ctatggattt | 600 |
| gtttcatttt | taatgacgt | ggatgtgcag | aagatagtag | aatcacagat | aaatttccat | 660 |
| ggtaaaaagc | tgaagctggg | ccctgcaatc | aggaaacaaa | atttatgtgc | ttatcatgtg | 720 |
| cagccacgtc | ctttggtttt | taatcatcct | cctccaccac | agtttcagaa | tgtctggact | 780 |
| aatccaaaca | ctgaaactta | tatgcagccc | acaaccacga | tgaatcctat | aactcagtat | 840 |
| gttcaggcat | atcctactta | cccaaattca | ccagttcagg | tcatcactgg | atatcagttg | 900 |
| cctgtatata | attatcagat | gccaccacag | tggcctgttg | gggagcaaag | gagctatgtt | 960 |
| gtacctccgg | cttattcagc | tgttaactac | cactgtaatg | aagttgatcc | aggagctgaa | 1020 |
| gttgtgccaa | atgaatgttc | agttcatgaa | gctactccac | cctctggaaa | tggcccacaa | 1080 |
| aagaaatctg | tggaccgaag | catacaaacg | gtggtatctt | gtctgtttaa | tccagagaac | 1140 |
| agactgagaa | actctgttgt | tactcaagat | gactacttca | aggataaaag | agtgcatcac | 1200 |
| tttagaagaa | gtcgggcaat | gcttaaatct | gtttgatcct | cctggcttat | ctagttacat | 1260 |
| gggaagttgc | tggttttgaa | tattaagcta | aaaggtttcc | actattatag | aaattctgaa | 1320 |
| ttttggtaaa | tcacactcaa | actttgtgta | taagttgtat | tattagactc | tctagtttta | 1380 |
| tcttaaactg | ttcttcatta | gatgtttatt | tagaaactgg | ttctgtgttg | aaatatagtt | 1440 |
| gaaagtaaaa | aaataattga | gactgaaaga | aactaagatt | tatctgcaag | gattttttaa | 1500 |
| aaattggcat | tttaagtgtt | taaaagcaaa | tactgatttt | caaaaaaatg | ttttttaaaaa | 1560 |
| cctatttgga | aaggtcagaa | ttttgttggt | ctgaatacaa | acatttcact | tctccaacaa | 1620 |

-continued

```
gtacctgtga acagtacagt atttacagta ttgagctttg catttatgat ttctccagaa      1680
atttaccaca aaagcaaaat ttttaaaact gcattttaa tcagtggaac tcaatatata      1740
gttagcttta ttgaagtctt cttatctaaa cccagcaaaa cagattcaaa gcgaacagtc      1800
caatcagtgg gtcatatgtt tattcaaaat attttatctt ttagctagaa tccacacata      1860
tatatcctat ttgattaggg tagtaattag gataactaaa attctgggcc taattttta       1920 aagaatccaa gacaaactaa actttactag gtacataagc ttctcaatga gtcaccattc      1980
ttcttttttg taaaaacttt tttctttgaa atgctaaact tggctgtatg tcaaattgtg      2040
caaaatattg gtattaaaga atgctgcaac ttttttatgt ctcttagagg ttaatcagag      2100
tatctgaagg gaattgtttt tataaaaaca ttgaaatatt agttacttgc tataaataga      2160
tttagtctgt tatatttcct tttgtaaagt aaaatatgtc cagaagagtc aaagtagtta      2220
gttttggtta tttctaaacc acaaaagttg tttaataagt atatcttaag aatgtgctag      2280
agttaaaagt tagcattgtt tctagattag ctggtgtctt cattttacat tgtgacaaac      2340
agctagagca tcagagccct tttgctatac cacagtcttt cgtttccagc ctttgtcact      2400 agtcttgag gaggttttgct cctagaactg gtgatataaa gaatgaaagt agctgtatga     2460
gcagagcagt tcaagggcca aaccctggaa cggtagcaat gggatataat acctttctaa      2520
gggaaaaagt tgtatcagta ccatttgatc tgccatggac atgagtttaa agcggctttc      2580
tggcccttct ttcagtgact tcttccctaa aatgtagaaa ttctaactta atgtagttac      2640
tgtgagccat attactagtg cccctaggg tctataattc cttaaaattt tcattctgaa       2700
tctgaaggag agagtctttt aactttagaa ttcccaagag ggctttatta cacctcagaa      2760
attgaaagca ctatgaattt gtccatttaa aaatgatctg tagtttttt ggtgctataa       2820 cattctgaca catatcattc tgtgattaaa tctccagctt actataaatg atatctatat      2880
tctaaagagc tacttctaat tattccaata tgaccttaag gaaagtaag ggaataaatt       2940 tttgtctttg ttggagtgaa gcatttaaaa gagtaagggt aaaaaagata aagtcctgaa      3000
cctttcaaaa tggaaaatta attctaaact tagaaatatg cttctgccta ttgctgatac      3060
tgtctttgca tacatgaata aaaataaagt ttttttcttc aaaaaaaa                   3108
```

<210> SEQ ID NO 16
<211> LENGTH: 315
<212> TYPE: PRT
<213> ORGANISM: homo sapiens

<400> SEQUENCE: 16

```
Met Ala Ala Pro Ser Cys Gly Gly Asp Arg Lys Ala Arg Leu Thr Pro
1               5                   10                  15

Ser Leu Pro His Glu Ser Thr Ala Asn Pro Glu Thr Pro Asn Ser Thr
            20                  25                  30

Ile Ser Arg Glu Ala Ser Thr Gln Ser Ser Ser Ala Ala Thr Ser Gln
        35                  40                  45

Gly Tyr Ile Leu Pro Glu Gly Lys Ile Met Pro Asn Thr Val Phe Val
    50                  55                  60

Gly Gly Ile Asp Val Arg Met Asp Glu Thr Glu Ile Arg Ser Phe Phe
65                  70                  75                  80

Ala Arg Tyr Gly Ser Val Lys Glu Val Lys Ile Ile Thr Asp Arg Thr
                85                  90                  95

Gly Val Ser Lys Gly Tyr Gly Phe Val Ser Phe Phe Asn Asp Val Asp
            100                 105                 110
```

Val Gln Lys Ile Val Glu Ser Gln Ile Asn Phe His Gly Lys Lys Leu
            115                 120                 125

Lys Leu Gly Pro Ala Ile Arg Lys Gln Asn Leu Cys Ala Tyr His Val
        130                 135                 140

Gln Pro Arg Pro Leu Val Phe Asn His Pro Pro Pro Gln Phe Gln
145                 150                 155                 160

Asn Val Trp Thr Asn Pro Asn Thr Glu Thr Tyr Met Gln Pro Thr Thr
                165                 170                 175

Thr Met Asn Pro Ile Thr Gln Tyr Val Gln Ala Tyr Pro Thr Tyr Pro
            180                 185                 190

Asn Ser Pro Val Gln Val Ile Thr Gly Tyr Gln Leu Pro Val Tyr Asn
        195                 200                 205

Tyr Gln Met Pro Pro Gln Trp Pro Val Gly Glu Gln Arg Ser Tyr Val
    210                 215                 220

Val Pro Pro Ala Tyr Ser Ala Val Asn Tyr His Cys Asn Glu Val Asp
225                 230                 235                 240

Pro Gly Ala Glu Val Val Pro Asn Glu Cys Ser Val His Glu Ala Thr
                245                 250                 255

Pro Pro Ser Gly Asn Gly Pro Lys Lys Ser Val Asp Arg Ser Ile
            260                 265                 270

Gln Thr Val Val Ser Cys Leu Phe Asn Pro Glu Asn Arg Leu Arg Asn
        275                 280                 285

Ser Val Val Thr Gln Asp Asp Tyr Phe Lys Asp Lys Arg Val His His
    290                 295                 300

Phe Arg Arg Ser Arg Ala Met Leu Lys Ser Val
305                 310                 315

<210> SEQ ID NO 17
<211> LENGTH: 3054
<212> TYPE: DNA
<213> ORGANISM: homo sapiens

<400> SEQUENCE: 17
attggctgag gccgatacca cgcgccccga tacccggcgc aggagccacc tccctgagcc      60
ccgcggacca cgcctcagtc cgcctgcgct cctcagcctg acggtccgcc tttcggggct     120
cctcagcctt gtcacccgct cttggttttc cttttctctt catctttggc tcctttgacc     180
actcgaagcc gcgcagcggg ttccagcgga cctcacagca gccccagaag tggtgcgcca     240
agcacagcct ctgctcctcc tggagccggt cgggaactgc tgcctgccgc catcatgtct     300
actgcaaatc ctgaaactcc aaactcaacc atctccagag aggccagcac ccagtcctca     360
tcagctgcaa ccagccaagg ctatatttta ccagaaggca aaatcatgcc aaacactgtt     420
tttgttggag gaattgatgt taggatggat gaaactgaga ttagaagctt ctttgctaga     480
tatggttcag tgaaagaagt gaagataatc actgatcgaa ctggtgtgtc caaaggctat     540
ggatttgttt cattttttaa tgacgtggat gtgcagaaga tagtagaatc acagataaat     600
ttccatggta aaaagctgaa gctgggccct gcaatcagga acaaaatttt atgtgcttat     660
catgtgcagc cacgtccttt ggttttaat catcctcctc caccacagtt tcagaatgtc     720
tggactaatc caaacactga aacttatatg cagcccacaa ccacgatgaa tcctataact     780
cagtatgttc aggcatatcc tacttaccca aattccacag ttcaggtcat cactggatat     840
cagttgcctg tatataatta tcagatgcca ccacagtggc ctgttgggga gcaaaggagc     900
tatgttgtac ctccggctta ttcagctgtt aactaccact gtaatgaagt tgatccagga     960

```
gctgaagttg tgccaaatga atgttcagtt catgaagcta ctccaccctc tggaaatggc    1020
ccacaaaaga aatctgtgga ccgaagcata caaacggtgg tatcttgtct gtttaatcca    1080
gagaacagac tgagaaactc tgttgttact caagatgact acttcaagga taaagagtg     1140 catcactttα gaagaagtcg ggcaatgctt aaatctgttt gatcctcctg gcttatctag    1200
ttacatggga agttgctggt tttgaatatt aagctaaaag gtttccacta ttatagaaat    1260
tctgaatttt ggtaaatcac actcaaactt tgtgtataag ttgtattatt agactctcta    1320
gttttatctt aaactgttct tcattagatg tttatttaga aactggttct gtgttgaaat    1380
atagttgaaa gtaaaaaaat aattgagact gaaagaaact aagatttatc tgcaaggatt    1440
ttttaaaaat tggcatttta agtgtttaaa agcaaatact gattttcaaa aaaatgtttt    1500
taaaaaccta ttttgaaagg tcagaatttt gttggtctga atacaaacat ttcacttctc    1560
caacaagtac ctgtgaacag tacagtattt acagtattga gctttgcatt tatgatttct    1620
ccagaaattt accacaaaag caaaattttt aaaactgcat ttttaatcag tggaactcaa    1680
tatatagtta gctttattga agtcttctta tctaaaccca gcaaaacaga ttcaaagcga    1740
acagtccaat cagtgggtca tatgtttatt caaaatattt tatcttttag ctagaatcca    1800
cacatatata tcctatttga ttagggtagt aattaggata actaaaattc tgggcctaat    1860
tttttaaaga atccaagaca aactaaaactt tactaggtac ataagcttct caatgagtca    1920
ccattcttct tttttgtaaa aacttttttc tttgaaatgc taaacttggc tgtatgtcaa    1980
attgtgcaaa atattggtat taagaatgc tgcaactttt ttatgtctct tagaggttaa    2040
tcagagtatc tgaagggaat tgttttttata aaaacattga aatattagtt acttgctata    2100
aatagattta gtctgttata tttccttttg taaagtaaaa tatgtccaga agagtcaaag    2160
tagttagttt tggttatttc taaaccacaa aagttgttta ataagtatat cttaagaatg    2220
tgctagagtt aaaagttagc attgtttcta gattagctgg tgtcttcatt ttacattgtg    2280
acaaacagct agagcatcag agccctttg ctataccaca gtctttcgtt tccagccttt     2340
gtcactagtc tttgaggagg tttgctccta gaactggtga tataaagaat gaaagtagct    2400
gtatgagcag agcagttcaa gggccaaacc ctgaacggt agcaatggga tataatacct      2460
ttctaaggga aaaagttgta tcagtaccat ttgatctgcc atggacatga gtttaaagcg    2520
gctttctggc ccttcttttca gtgacttctt ccctaaaatg tagaaattct aacttaatgt   2580
agttactgtg agccatatta ctagtgcccc ctagggtcta taattcctta aaattttcat    2640
tctgaatctg aaggagagag tcttttaact ttagaattcc caagagggct ttattacacc    2700
tcagaaattg aaagcactat gaatttgtcc atttaaaaat gatctgtagt ttttttggtg    2760
ctataacatt ctgacacata tcattctgtg attaaatctc cagcttacta taatgatat    2820 ctatattcta aagagctact tctaattatt ccaatatgac cttaaggaaa gtaagggaa     2880 taaattttg tctttgttgg agtgaagcat ttaaagagt aagggtaaaa aagataaagt      2940
cctgaacctt tcaaaatgga aaattaattc taaacttaga aatatgcttc tgcctattgc    3000
tgatactgtc tttgcataca tgaataaaaa taaagttttt tcttcaaaa aaaa           3054
```

<210> SEQ ID NO 18
<211> LENGTH: 295
<212> TYPE: PRT
<213> ORGANISM: homo sapiens

<400> SEQUENCE: 18

```
Met Ser Thr Ala Asn Pro Glu Thr Pro Asn Ser Thr Ile Ser Arg Glu
1               5                   10                  15
Ala Ser Thr Gln Ser Ser Ser Ala Ala Thr Ser Gln Gly Tyr Ile Leu
            20                  25                  30
Pro Glu Gly Lys Ile Met Pro Asn Thr Val Phe Val Gly Gly Ile Asp
        35                  40                  45
Val Arg Met Asp Glu Thr Glu Ile Arg Ser Phe Phe Ala Arg Tyr Gly
    50                  55                  60
Ser Val Lys Glu Val Lys Ile Ile Thr Asp Arg Thr Gly Val Ser Lys
65                  70                  75                  80
Gly Tyr Gly Phe Val Ser Phe Phe Asn Asp Val Asp Val Gln Lys Ile
                85                  90                  95
Val Glu Ser Gln Ile Asn Phe His Gly Lys Lys Leu Lys Leu Gly Pro
            100                 105                 110
Ala Ile Arg Lys Gln Asn Leu Cys Ala Tyr His Val Gln Pro Arg Pro
        115                 120                 125
Leu Val Phe Asn His Pro Pro Pro Gln Phe Gln Asn Val Trp Thr
    130                 135                 140
Asn Pro Asn Thr Glu Thr Tyr Met Gln Pro Thr Thr Thr Met Asn Pro
145                 150                 155                 160
Ile Thr Gln Tyr Val Gln Ala Tyr Pro Thr Tyr Pro Asn Ser Pro Val
                165                 170                 175
Gln Val Ile Thr Gly Tyr Gln Leu Pro Val Tyr Asn Tyr Gln Met Pro
            180                 185                 190
Pro Gln Trp Pro Val Gly Glu Gln Arg Ser Tyr Val Val Pro Pro Ala
        195                 200                 205
Tyr Ser Ala Val Asn Tyr His Cys Asn Glu Val Asp Pro Gly Ala Glu
    210                 215                 220
Val Val Pro Asn Glu Cys Ser Val His Glu Ala Thr Pro Pro Ser Gly
225                 230                 235                 240
Asn Gly Pro Gln Lys Lys Ser Val Asp Arg Ser Ile Gln Thr Val Val
                245                 250                 255
Ser Cys Leu Phe Asn Pro Glu Asn Arg Leu Arg Asn Ser Val Val Thr
            260                 265                 270
Gln Asp Asp Tyr Phe Lys Asp Lys Arg Val His His Phe Arg Arg Ser
        275                 280                 285
Arg Ala Met Leu Lys Ser Val
    290                 295
```

<210> SEQ ID NO 19
<211> LENGTH: 2779
<212> TYPE: DNA
<213> ORGANISM: homo sapiens

<400> SEQUENCE: 19

```
gaggcgacgc agtccgcttc tccccacccg ccaggtggca ggttcagggc cggggtccga      60
gcctgcttcc ctgcagctgc cacagccacc ctcgccgcca gggggcgaga gtcccaggca     120
ggacaagcag cgctgctgcc ttggcgtgaa ggtggtttca aactttaggc ttcttttccc     180
taccccgcgt ctctgaagag cagagaggaa gatggaaacc gagtccgggc cgcaaacatc     240
aaaccagatg caaacagatt cattatctcc atccctaat cctgtgtcac ctgtgccttt      300
gaataaccca acaagtgccc caagatatgg aacagtgatc cctaatcgca tctttgtagg     360
aggaattgat tttaagacaa acgaaagtga tttaagaaaa tttttttccc agtatgggtc     420
```

```
tgtgaaagaa gtgaagattg taaatgacag agctggagta tccaaagggt atggtttcgt    480
cacttttgaa acacaagaag atgcacaaaa aattttacaa gaggctgaaa aacttaatta    540
taaggataag aagctgaaca ttggtccagc aataagaaaa caacaagtag ggatccctcg    600
ttctagtata atgccagcag ctggaacaat gtatctaaca acttcaactg gatatcctta    660
tacttaccat aatggtgttg cttatttttca tactccagag gtaacttcgg tcccaccgcc    720
ttggccttca cgttctgtat gtagctcccc tgtgatggta gctcagccca tttatcagca    780
acctgcatat cactaccagg ccaccacaca gtatttacca ggacagtggc agtggagtgt    840
tcctcagcct tctgcctctt ctgctccatt cttatacctg caaccttctg aggttattta    900
tcaaccagtg gaaattgcac aggatggtgg atgtgttcct cctccactgt ctctgatgga    960
aacttcagtt ccagagcctt attctgatca tggagttcaa gcaacatatc accaggttta   1020
tgctccaagt gccatcacta tgcctgcgcc tgtgatgcag cctgagccaa ttaaaacagt   1080
gtggagcatt cattattaag acaattgggc agctctattc cagctcaact gatttcttgt   1140
ccaatgatcc ttgcgtggcc gagatccagc ttcaacgaac cagctagaag ctgcccgttg   1200
tgaaacttag tgttagttaa tacctcacca tactcagtta ttccactata agctgtctaa   1260
atttgatgaa atttgctttt tcagctgttc tacaaaatta tttaggtaga tgtggcatgt   1320
tggttttta tgtgctaacc taactgtaat gaccttttct acaacatgtt ttatccattc   1380
cataaataat aaccacattg gaatagtga ggtgtctttt attttctctg ctttgtgtta    1440
ttttttctta tcaaacaatt agatgttatg tttcatatta tttgatattt attttcatat   1500
ttaggataag aatcattttt aattataata cttttaatac tttcatatat tttacaacag   1560
tatactattt aatattaatg acaattctat ttttgctttg ctgttttgtc atttaatatg   1620
cttttgtcta atttttaatt catttattac tgttactcct tatttaattt tgcgtctgcc   1680
atggttttca gaatctgaat agtatttata cttctttttt ataacatttt ccaaatatta   1740
gaaataccat caacatgatc agtattcttg ccttttcatg taatttgact atattaaatt   1800
ttttctccag tgtttgagac aatattgaaa tcttcctata acataattta tttggtatca   1860
aattttataa aatatggatc caccttttgga attttgataa aagggttcat ctctgacatg   1920
atcccataac actgactgaa attccaccaa attactgttc tttgaatgct ttaatcctta   1980
aacctttct tctgatatgc aaccaatata ttcaattata tatgtgatta atttttaaaa   2040
ggacaattgt tttcataaaa tgcaaaacta tttttttacac caaaggaaaa ttttagattc   2100
tgattctaaa tccgattttt actataaaat tggaaaatag atgggagggg tgtcattcat   2160
tgttcaaaag gtacagaaca aatcatagg gttttaaatc tctaaaattt ctacagtagt   2220
acaggaaata ttcctctttta cattcatttg cagttctttc actgacctcc taattttagg   2280
tggagggggc aggggagcc ataaaagttg gtattaccct aataaatcta tctcttttcct   2340
ccctgtttc aaccccacat gtattccatg ctcagcagca gcagcagaaa tagtaggata   2400
tagatcacaa aggttttct ggtgagtcaa ataggggtgtt ttcttttgaa actgtaatga   2460
atatgtttgc cagtcaaatg gcttcatgag aacagtagaa ccttatgaat gtatactagc   2520
atacaaggat ctcaaataca ttaattattc tcagttttag gaatgtaaat agattaagtc   2580
ccacaatgaa atttcagaag ttttttgttct gtaagtaaaa aattactaac cactgatgtt   2640
caagattttc ttttaatagc actatccttg agaaccaaaa agtttatgtt tgatttttca   2700
aatgttaaac aagatgctaa acaaatcctg gactgttaat aaaaattaat tatgtattat   2760
tggataagga attttaaaa                                                2779
```

<210> SEQ ID NO 20
<211> LENGTH: 295
<212> TYPE: PRT
<213> ORGANISM: homo sapiens

<400> SEQUENCE: 20

Met Glu Thr Glu Ser Gly Pro Gln Thr Ser Asn Gln Met Gln Thr Asp
1               5                   10                  15

Ser Leu Ser Pro Ser Pro Asn Pro Val Ser Pro Val Pro Leu Asn Asn
            20                  25                  30

Pro Thr Ser Ala Pro Arg Tyr Gly Thr Val Ile Pro Asn Arg Ile Phe
        35                  40                  45

Val Gly Gly Ile Asp Phe Lys Thr Asn Glu Ser Asp Leu Arg Lys Phe
50                  55                  60

Phe Ser Gln Tyr Gly Ser Val Lys Glu Val Lys Ile Val Asn Asp Arg
65                  70                  75                  80

Ala Gly Val Ser Lys Gly Tyr Gly Phe Val Thr Phe Glu Thr Gln Glu
                85                  90                  95

Asp Ala Gln Lys Ile Leu Gln Glu Ala Glu Lys Leu Asn Tyr Lys Asp
            100                 105                 110

Lys Lys Leu Asn Ile Gly Pro Ala Ile Arg Lys Gln Gln Val Gly Ile
        115                 120                 125

Pro Arg Ser Ser Ile Met Pro Ala Ala Gly Thr Met Tyr Leu Thr Thr
130                 135                 140

Ser Thr Gly Tyr Pro Tyr Thr Tyr His Asn Gly Val Ala Tyr Phe His
145                 150                 155                 160

Thr Pro Glu Val Thr Ser Val Pro Pro Trp Pro Ser Arg Ser Val
                165                 170                 175

Cys Ser Ser Pro Val Met Val Ala Gln Pro Ile Tyr Gln Gln Pro Ala
            180                 185                 190

Tyr His Tyr Gln Ala Thr Thr Gln Tyr Leu Pro Gly Gln Trp Gln Trp
        195                 200                 205

Ser Val Pro Gln Pro Ser Ala Ser Ser Ala Pro Phe Leu Tyr Leu Gln
210                 215                 220

Pro Ser Glu Val Ile Tyr Gln Pro Val Glu Ile Ala Gln Asp Gly Gly
225                 230                 235                 240

Cys Val Pro Pro Pro Leu Ser Leu Met Glu Thr Ser Val Pro Glu Pro
                245                 250                 255

Tyr Ser Asp His Gly Val Gln Ala Thr Tyr His Gln Val Tyr Ala Pro
            260                 265                 270

Ser Ala Ile Thr Met Pro Ala Pro Val Met Gln Pro Glu Pro Ile Lys
        275                 280                 285

Thr Val Trp Ser Ile His Tyr
        290                 295

<210> SEQ ID NO 21
<211> LENGTH: 2842
<212> TYPE: DNA
<213> ORGANISM: homo sapiens

<400> SEQUENCE: 21
aatcagggag cgccgcgcga gggtggggac cagctgcgca cgaggccagc ggcggggtcg      60
ctgccgttga ggcttcccgc cactgctgct ggcggatttg tggggcaaaa tttctcgctg     120
gctagccttc ttttccctcc cgcactttgg tggggagggg gtggatcctc gtttcggtgc     180

```
ccaagttcac gatgacccga gagaactcga ggaagttgtc gccgcggcca tttccccag      240 tgccgcaact tgctggcctt ggaggggag gagcgccgag gcagtgactg cgacgcaaac      300
atcaaaccag atgcaaacag attcattatc tccatcccct aatcctgtgt cacctgtgcc      360
tttgaataac ccaacaagtg ccccaagata tggaacagtg atccctaatc gcatctttgt      420
aggaggaatt gattttaaga caaacgaaag tgatttaaga aaattttttt cccagtatgg      480
gtctgtgaaa gaagtgaaga ttgtaaatga cagagctgga gtatccaaag ggtatggttt      540
cgtcactttt gaaacacaag aagatgcaca aaaaatttta caagaggctg aaaaacttaa      600
ttataaggat aagaagctga acattggtcc agcaataaga aaacaacaag tagggatccc      660
tcgttctagt ataatgccag cagctggaac aatgtatcta acaacttcaa ctggatatcc      720
ttatacttac cataatggtg ttgcttattt tcatactcca gaggtaactt cggtcccacc      780
gccttggcct tcacgttctg tatgtagctc ccctgtgatg gtagctcagc ccatttatca      840
gcaacctgca tatcactacc aggccaccac acagtattta ccaggacagt ggcagtggag      900
tgttcctcag ccttctgcct cttctgctcc attcttatac ctgcaacctt ctgaggttat      960
ttatcaacca gtggaaattg cacaggatgg tggatgtgtt cctcctccac tgtctctgat      1020
ggaaacttca gttccagagc cttattctga tcatggagtt caagcaacat atcaccaggt      1080
ttatgctcca agtgccatca ctatgcctgc gcctgtgatg cagcctgagc caattaaaac      1140
agtgtggagc attcattatt aagacaattg ggcagctcta ttccagctca actgatttct      1200
tgtccaatga tccttgcgtg gccgagatcc agcttcaacg aaccagctag aagctgcccg      1260
ttgtgaaact tagtgttagt taatacctca ccatactcag ttattccact ataagctgtc      1320
taaatttgat gaaatttgct ttttcagctg ttctacaaaa ttatttaggt agatgtggca      1380
tgttggtttt ttatgtgcta acctaactgt aatgaccttt tctacaacat gttttatcca      1440
ttccataaat aataaccaca ttgggaatag tgaggtgtct tttatttttct ctgctttgtg      1500 ttatttttc ttatcaaaca attagatgtt atgtttcata ttatttgata tttattttca      1560
tatttaggat aagaatcatt tttaattata atacttttaa tactttcata tattttacaa      1620
cagtatacta tttaatatta atgacaattc tattttttgct ttgctgtttt gtcatttaat      1680
atgcttttgt ctaattttta attcatttat tactgttact ccttatttaa ttttgcgtct      1740
gccatggttt tcagaatctg aatagtattt atacttcttt tttataacat tttccaaata      1800
ttagaaatac catcaacatg atcagtattc ttgccttttc atgtaatttg actatattaa      1860
attttttctc cagtgtttga gacaatattg aaatcttcct ataacataat ttatttggta      1920 tcaaattta taaaatatgg atccacctt ggaattttga taaagggtt catctctgac      1980 atgatcccat aacactgact gaaattccac caaattactg ttctttgaat gctttaatcc      2040
ttaaaccttt tcttctgata tgcaaccaat atattcaatt atatatgtga ttaatttta      2100 aaaggacaat tgttttcata aaatgcaaaa ctatttttta caccaaagga aaattttaga      2160
ttctgattct aaatccgatt tttactataa aattggaaaa tagatgggag gggtgtcatt      2220
cattgttcaa aagtacaga acaaatcata ggggttttta atctctaaaa tttctacagt      2280
agtacaggaa atattcctct ttacattcat ttgcagttcc ttcactgacc tcctaatttt      2340
aggtggaggg ggcagggga gccataaaag ttggtattac cctaataaat ctatctcttt      2400
cctcccctgt ttcaacccca catgtattcc atgctcagca gcagcagcag aaatagtagg      2460
atatagatca caaaggtttt tctggtgagt caaatagggt gttttctttt gaaactgtaa      2520
```

-continued

```
tgaatatgtt tgccagtcaa atggcttcat gagaacagta gaaccttatg aatgtatact    2580
agcatacaag gatctcaaat acattaatta ttctcagttt taggaatgta aatagattaa    2640
gtcccacaat gaaatttcag aagttttgt tctgtaagta aaaaattact aaccactgat     2700
gttcaagatt ttctttaat agcactatcc ttgagaacca aaaagtttat gttttgattt     2760
tcaaatgtta aacaagatgc taaacaaatc ctggactgtt aataaaaatt aattatgtat    2820
tattggataa ggaattttaa aa                                              2842
```

<210> SEQ ID NO 22
<211> LENGTH: 283
<212> TYPE: PRT
<213> ORGANISM: homo sapiens

<400> SEQUENCE: 22

```
Met Gln Thr Asp Ser Leu Ser Pro Ser Pro Asn Pro Val Ser Pro Val
1               5                   10                  15

Pro Leu Asn Asn Pro Thr Ser Ala Pro Arg Tyr Gly Thr Val Ile Pro
            20                  25                  30

Asn Arg Ile Phe Val Gly Gly Ile Asp Phe Lys Thr Asn Glu Ser Asp
        35                  40                  45

Leu Arg Lys Phe Phe Ser Gln Tyr Gly Ser Val Lys Glu Val Lys Ile
    50                  55                  60

Val Asn Asp Arg Ala Gly Val Ser Lys Gly Tyr Gly Phe Val Thr Phe
65                  70                  75                  80

Glu Thr Gln Glu Asp Ala Gln Lys Ile Leu Gln Glu Ala Glu Lys Leu
                85                  90                  95

Asn Tyr Lys Asp Lys Lys Leu Asn Ile Gly Pro Ala Ile Arg Lys Gln
            100                 105                 110

Gln Val Gly Ile Pro Arg Ser Ser Ile Met Pro Ala Ala Gly Thr Met
        115                 120                 125

Tyr Leu Thr Thr Ser Thr Gly Tyr Pro Tyr Thr Tyr His Asn Gly Val
    130                 135                 140

Ala Tyr Phe His Thr Pro Glu Val Thr Ser Val Pro Pro Pro Trp Pro
145                 150                 155                 160

Ser Arg Ser Val Cys Ser Ser Pro Val Met Val Ala Gln Pro Ile Tyr
                165                 170                 175

Gln Gln Pro Ala Tyr His Tyr Gln Ala Thr Thr Gln Tyr Leu Pro Gly
            180                 185                 190

Gln Trp Gln Trp Ser Val Pro Gln Pro Ser Ala Ser Ser Ala Pro Phe
        195                 200                 205

Leu Tyr Leu Gln Pro Ser Glu Val Ile Tyr Gln Pro Val Glu Ile Ala
    210                 215                 220

Gln Asp Gly Gly Cys Val Pro Pro Leu Ser Leu Met Glu Thr Ser
225                 230                 235                 240

Val Pro Glu Pro Tyr Ser Asp His Gly Val Gln Ala Thr Tyr His Gln
                245                 250                 255

Val Tyr Ala Pro Ser Ala Ile Thr Met Pro Ala Pro Val Met Gln Pro
            260                 265                 270

Glu Pro Ile Lys Thr Val Trp Ser Ile His Tyr
        275                 280
```

<210> SEQ ID NO 23
<211> LENGTH: 2880
<212> TYPE: DNA
<213> ORGANISM: homo sapiens

<400> SEQUENCE: 23

```
acctgacgca gtgggcgtct tgcacgtgca gccgtttaag tcgcgtgggc gcctgcgagg      60
gcttgggaga gcaagccgcg gagagaactt gaagccacca tgggagatga agattgggaa     120
gcagaaatca accctcatat gtcttcctat gttcccatat ttgagaagga taggtattct     180
ggagaaaatg gagacaattt taacaggact ccagcttcat catcagaaat ggatgatgga     240
ccttctcgaa gagatcattt catgaaaagt ggatttgcct ctgggcggaa ttttggaaac     300
agagatgctg gtgagtgtaa taagcgagat aatacatcca caatgggtgg ttttggagtt     360
ggaaagagtt ttggaaacag aggttttttca aacagcaggt ttgaagatgg tgatagctct     420
ggtttctgga gagagtctag taatgactgc gaagataatc caacacggaa cagagggttt     480
tccaagagag gcggctatcg agatggaaat aattcagaag cttcagggcc atacagaaga     540
ggtggaagag gtagtttccg aggttgccgt ggaggatttg gtctaggaag tccaaataat     600
gacttagacc cagacgaatg tatgcagcgc actggtggcc ttttggttc tagaagacca     660
gtattaagtg gcacaggtaa tggtgatact tctcaaagca gaagtggcag tggaagtgaa     720
cgaggtggtt acaaaggttt aaatgaagaa gtaataacag gctctggaaa gaattcttgg     780
aagtcagaag cagaaggagg agaaagtagt gatactcaag gaccaaaagt gacctacata     840
cccccctcctc cacctgagga tgaggactcc atctttgcac attatcagac aggcataaac     900
ttcgacaaat acgacactat tcttgtggaa gtgtctggac atgatgcacc accagcaatt     960
ctgacttttg aagaagctaa tctctgtcag acactgaata caacattgc taaagctggt    1020
tatactaagc ttactcctgt gcaaaaatac agtattccta tcatacttgc aggacgagat    1080
ttgatggctt gcgctcaaac agggtctggg aagactgcgg cttttctcct accaattttg    1140
gctcatatga tgcatgatgg aataactgcc agtcgttta aagagttgca ggaaccagag    1200
tgtattattg tagcaccaac tcgagaattg gtcaaccaga tttatttgga agccagaaaa    1260
ttttctttg ggacttgtgt aagagctgtt gttatatatg ggggaaccca gctgggacat    1320
tcaattcgac aaatagtaca aggctgtaat atattatgtg ctactcctgg aagactgatg    1380
gatatcatag gcaaagaaaa gattggtctc aaacagatca aatacttagt tttggatgaa    1440
gctgatcgca tgttggatat gggttttggt ccagaaatga agaagttaat ttcttgccca    1500
ggaatgccat caaaggaaca cgccaaaacc cttatgttca gtgcaacttt tccagaggaa    1560
attcaaaggt tggctgcaga gttttaaag tcaaattatc tgtttgttgc tgttggacaa    1620
gtgggtggag catgtagaga tgttcagcag accgttctcc aagttggcca gttctcaaaa    1680
agagaaaagc tcgttgaaat tctgcgaaac atagggatg aaagaactat ggtctttgtt    1740
gaaactaaga aaaagcaga ttttattgca acttttcttt gtcaagaaaa aatatcaact    1800
acaagtattc atggtgatcg ggaacagaga gagcgggagc aagctcttgg agattttcgc    1860
tttgaaaagt gcccagttct tgttgctact tcagtagctg ccagagggct ggatattgaa    1920
aatgtgcaac atgttatcaa ttttgatctt ccttctacca ttgatgaata tgttcatcga    1980
attgggcgta ctggtcgttg tgggaatact ggcagagcaa tttcctttttt tgatcttgaa    2040
tcggataacc atttagcaca gcctctagta aaagtattga cagatgctca acaggatgtt    2100
cctgcatggt tggaagaaat tgcctttagt acatacattc ctggcttcag tggtagtaca    2160
agaggaaacg tgtttgcatc agttgatacc agaaagggca agagcacttt gaacacagct    2220
gggttttctt cttcacaagc tcccaatcca gtagatgatg agtcatggga ttaaagccaa    2280
```

```
aacatccttc aagtctgtgg ttttgatgca gagaagaaaa tagttttgat ttttgagttt    2340
ttaacagaag tataaaactt aacattctca tagctcctgt ccttgtattc tcactcctac    2400
acttaaaaaa aaaatcctta ctgactagtt atgtgagatg ctaaaactta caacattgca    2460
gttactgata caaatggtgt taactgggaa tattaaagca ttctaaatgt ctttcttatt    2520
tctggtatat tctttagggg gcttagacat gtttaatgtt taaatgccaa gtcttactat    2580
agtgtttatt gatcttataa aacaagcaaa taggatatga tacacttttg gttaaaaatt    2640
actgggtctc atttttactt gagtctttaa aacagtagtg tgtcactata atgtgataat    2700
ctttaagaga aagtagaata cttaagcctt tcaaagtgat tttgattttt agatcatcag    2760
atgtatgatg aaaatggtta aatgtttgtg atgggagctc tgtactcaat ggcataacaa    2820
tgtttatttt tataatatac aatctttcct tgaaataaag gatgaaacac ttttccctta    2880
```

<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 24
ggatggatga aactgagatt a                                              21

<210> SEQ ID NO 25
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 25
gcatatccta cttacccaaa t                                              21

<210> SEQ ID NO 26
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 26
gccaaatgaa tgttcagttc a                                              21

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
gcagaagata gtagaatcac a                                              21

<210> SEQ ID NO 28
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 28
ggatatcagt tgcctgtata t                                              21

<210> SEQ ID NO 29
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 29
ggtggtatct tgtctgttta a                                              21

<210> SEQ ID NO 30
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 30
ggtatcttgt ctgtttaatc c                                              21

<210> SEQ ID NO 31
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 31
gcaaatcctg agactccaaa c                                              21

<210> SEQ ID NO 32
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 32
ggaagctgct ttggtagata c                                              21

<210> SEQ ID NO 33
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 33
gccacgtcct ttggtagtta a                                              21

<210> SEQ ID NO 34
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 34
gcatttcctg cttatccaaa t                                              21

<210> SEQ ID NO 35
<211> LENGTH: 21
<212> TYPE: DNA
<213> ORGANISM: Artificial Sequence
<220> FEATURE:

<223> OTHER INFORMATION: synthetic oligonucleotide

<400> SEQUENCE: 35
gcatttcctg cttatccaag t                                              21

<210> SEQ ID NO 36
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 36
gcatctttgt aggaggaatt g                                              21

<210> SEQ ID NO 37
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 37
ggatccctcg ttctagtata a                                              21

<210> SEQ ID NO 38
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 38
gctggaacaa tgtatctaac a                                              21

<210> SEQ ID NO 39
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 39
gcaaccttct gaggttattt a                                              21

<210> SEQ ID NO 40
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 40
gctccaagtg ccatcactat g                                              21

<210> SEQ ID NO 41
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 41
gcatatccaa catatccaaa t                                              21

```
<210> SEQ ID NO 42
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 42
gcagaaaatc gtcgagtcac a                                              21
```

INDUCTION OF GERM CELLS FROM PLURIPOTENT CELLS

GOVERNMENT RIGHTS

This invention was made with Government support under contract HD047721 awarded by the National Institutes of Health. The Government has certain rights in the invention.

FIELD OF THE INVENTION

Methods and compositions for promoting germ cell differentiation from pluripotent cells, and for identifying agents that modulate germ cell differentiation.

BACKGROUND OF THE INVENTION

Infertility is a common heath problem that affects 10-15% of reproductive-age couples. A major cause of infertility is the production of few or no germ cells. However, today's treatments for infertility are largely ineffective in cases in which infertility is due to few or no germ cells. Little is known about the genes that regulate the production of germ cells or the factors that contribute to the block in differentiation of germ cells in infertile individuals. The elucidation of pathways and factors involved in germ cell differentiation, and the identification of agents that promote germ cell development and differentiation, is therefore of clinical and research interest. The present invention addresses these issues.

SUMMARY OF THE INVENTION

Methods are provided for producing germ cells from pluripotent cells by contacting a population of pluripotent cells with an effective dose of at least one agent that promotes germ cell differentiation. In some embodiments of the invention, the pluripotent cells are embryonic stem cells. In some embodiments, the pluripotent cells are induced pluripotent stem cells. In some embodiments, the germ cells are primordial germ cells. In certain embodiments, the at least one agent is a DAZL polypeptide or a nucleic acid that encodes a DAZL polypeptide, or a BOULE polypeptide or a nucleic acid that encodes a BOULE polypeptide, which agents are shown herein to increase the differentiation of pluripotent cells to the primordial germ cell stage of differentiation. In some embodiments, the germ cells are late-stage germ cells, including, without limitation, cells within the oocyte and sperm lineages. In certain embodiments, the at least one agent is a DAZL, DAZ or BOULE polypeptide or a nucleic acid that encodes a DAZL, DAZ or BOULE polypeptide, which agents are shown herein to increase the differentiation of pluripotent cells to late-stage germ cells.

Also provided are methods of enriching for a composition of primordial germ cells. In this aspect of the invention, a population of cultured pluripotent cells is selected for expression of a reporter construct that is selectively active in primordial germ cells. In some embodiments of the invention, the expression of a detectable marker in the reporter construct is directed by the VASA promoter. In some embodiments, the pluripotent cells are embryonic stem cells. In some embodiments, the pluripotent cells are induced pluripotent stem cells.

Also provided are methods for producing late stage germ cells from primordial germ cells. A population of cells comprising primordial germ cells is contacted with an effective dose of at least one agent that promotes late state germ cell differentiation. In some embodiments, the population of cells comprising primordial germ cells is in vivo. In some embodiments, the population of cells comprising primordial germ cells is ex vivo. In some embodiments the population of cells comprising primordial germ cells is a composition of primordial germ cells as prepared by methods of the invention. In some embodiments, the at least one agent is a DAZL, DAZ or BOULE polypeptide or a nucleic acid that encodes a DAZL, DAZ or BOULE polypeptide.

Also provided are methods for screening one or more agents for activity in modulating germ cell differentiation from pluripotent cells. In this aspect of the invention, a first population of pluripotent cells is contacted with a candidate agent. The characteristics of the contacted cells are then compared with the characteristics of a second population of pluripotent cells that have not been contacted with the agent, wherein differences in the characteristics between the first population and the second population indicate that the candidate agent modulates germ cell differentiation. In some embodiments, the pluripotent cells are contacted with a reporter construct that is selectively active in germ cells prior to contacting with the candidate agent, and detection of the detectable marker in the reporter construct is indicative of the presence of germ cells. In some embodiments, the pluripotent cells are embryonic stem cells. In some embodiments, the pluripotent cells are induced pluripotent stem cells. In some embodiments, the germ cells are primordial germ cells. In some embodiments, the germ cells are late-stage germ cells.

Also provided are methods for screening one or more agents for activity in modulating late-stage germ cell differentiation from primordial germ cells. In this aspect of the invention, a first population of primordial germ cells is contacted with a candidate agent. The characteristics of the contacted cells are then compared with the characteristics of a second population of primordial germ cells that have not been contacted with the agent, wherein differences in the characteristics between the first population and the second population indicate that the candidate agent modulates late-stage germ cell differentiation. In some embodiments, the primordial germ cells are provided by the method of enrichment described herein.

These and other objects, advantages, and features of the invention will become apparent to those persons skilled in the art upon reading the details of the subject methods and compositions as more fully described below.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 13a).

FIG. 19. Percentage of cells in each category of SCP3 staining as a function of different combinations of overexpressing vectors. 200 nuclei were counted per each sample. P.: Punctate, E.: Elongated, N.S.: no staining. Same data set were used to make the graphs in FIG. 4c.

DETAILED DESCRIPTION OF THE INVENTION

Figure 1:
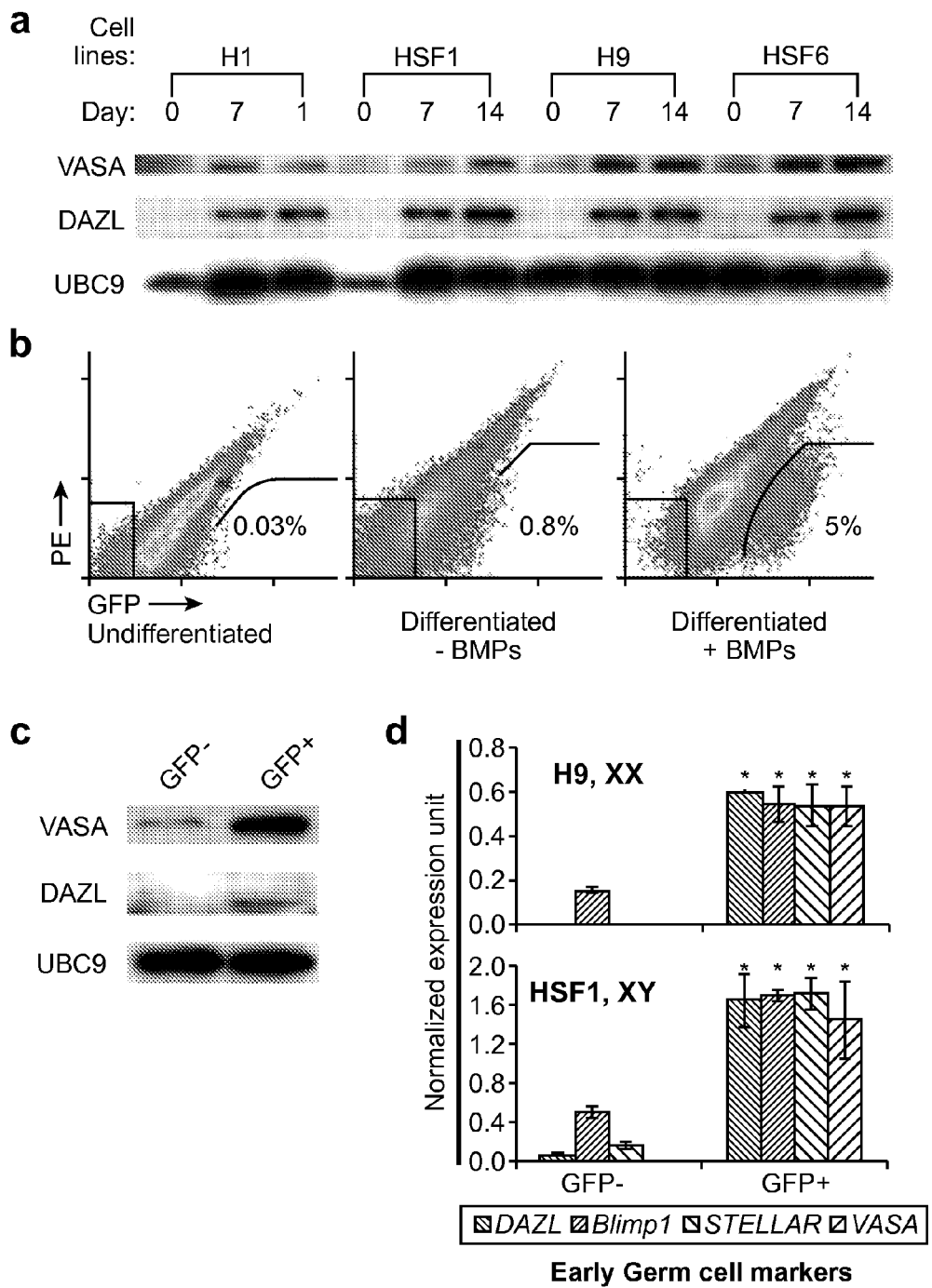
FIG. 1. Enrichment of human germ cells by BMPs and VASA-GFP reporter. a, Western blot analysis of human ES cells after differentiation with BMPs at 7 and 14 days. Equal amounts of cell lysates were loaded in each lane. UBC9 was used as a loading control. b, FACS analysis of GFP populations. c, Western blot analysis of VASA and DAZL after FACS. d, Expression of early germ-cell markers via qPCR Taqman probes. A total of 20,000 GFP+ and GFP− cells (day 7 of differentiation with BMPs) were subjected to qPCR analysis. Error bars indicate standard deviation; asterisk, significant difference by t-test (P<0.05), n=2.

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a DAZL peptide" includes a plurality of such polypeptides, and reference to "the primordial germ cell" includes reference to one or more primordial germ cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Methods are provided for producing germ cells from pluripotent cells, and for screening one or more agents for activity in modulating germ cell differentiation. Also provided are methods for enriching for a particular population of germ cell, namely the primordial germ cell.

Germ Cells.

A germ cell is a progenitor cell that will give rise to the gametes of an organism, that is, sperm and egg.

One example of a germ cell is a primordial germ cell (PGC). A PGC is a diploid cell of the germ cell lineage that has the capacity to self-renew as well as differentiate into gametes. PGCs are derived in the yolk sac of the embryo, and migrate through the mesentery of the gut to take up residence in the gonadal ridge, the anlage for the mature gonads. Characteristics of primordial germ cells include their expression of the germ-cell specific genes VASA/DDX4, DAZL, PRDM1/BLIMP1, and DPPA3/STELLA; the hypomethylated state of their genomic DNA both globally and specifically at imprinted loci including H19, PEG1/MEST, SNRPN, and KCNQ; and their ability to give rise to haploid germ cells under certain culture conditions and embryonic germ (EG) cells under others. EG cells are dense, multilayered colonies of cells that express SSEA-1, SSEA-3, SSEA-4, TRA1-60, TRA1-81, and alkaline phosphatase, that are capable of self-renewal, and that can be further cultured to give rise to embryoid bodies comprising derivatives of all three primary germ layers—endoderm, mesoderm and ectoderm (Geijsen, N. et al. (2004) Nature 427: 148-154; West, J. A. et al. (2009) Nature 460: 909-913). As demonstrated herein, PGCs may be derived in vitro from a population of pluripotent cells, for example, embryonic stem cells or induced pluripotent stem cells.

Another example of a germ cell is a "late-stage germ cell". A late-stage germ cell is any cell of the germ cell lineage that is more differentiated than a primordial germ cell. In other words, a late-stage germ cell is a cell that has already passed through the primordial germ cell stage. An example of a late-stage germ cell would be a cell that has entered meioisis, for example a spermatocyte or oocyte.

Late-stage germ cells may express one or more genes associated with meiosis, including γH2AX (an indicator of meiotic recombination) and SCP3 (an indicator of synaptonemal complex formation in meiotic prophase 1). Late-stage germ cells may have a DNA content of 1N, that is, a haploid DNA content. Late-stage germ cells may demonstrate increased methylation of genomic imprinting loci relative to their primordial germ cell ancestor, and may demonstrate differential methylation of these loci relative to their pluripotent, e.g. ES cell or iPS cell, ancestor. Late stage germ cell may express mature gamete markers, for example TEKT1 and ACR, which mark the spermatid to spermatazoan stages of male gamete differentiation; such markers will be known to one of ordinary skill in the art.

Pluripotent Cells.

A pluripotent cell is any cell having the ability to 1) self-renew, and 2) differentiate into multiple types of cells in an organism.

One example of a pluripotent cell is an embryonic stem (ES) cell. ES cells are derived from the inner cell mass of a blastocyst and can be cultured over a long period of time while maintaining the ability to differentiate into ectoderm, mesoderm, or endoderm tissues in a living organism. In culture, ES cells typically grow as flat colonies with large nucleo-cytoplasmic ratios, defined borders and prominent nuclei. In addition, ES cells express SSEA-3, SSEA-4, TRA-1-60, TRA-1-81, and Alkaline Phosphatase, but not SSEA-1. ES cells are capable of forming teratomas. Examples of methods of generating and characterizing ES cells may be found at U.S. Pat. No. 7,029,913, U.S. Pat. No. 5,843,780, and U.S. Pat. No. 6,200,806, all of which are incorporated herein by reference.

Another example of a pluripotent cell is an induced pluripotent stem cell (iPS cell, or iPSC). Like ES cells, iPS cells can be cultured over a long period of time while maintaining the ability to differentiate into ectoderm, mesoderm, or endoderm tissues in a living organism. iPS cells also have an ES cell-like morphology, growing as flat colonies with large nucleo-cytoplasmic ratios, defined borders and prominent nuclei. Like ES cells, iPS cells express one or more key pluripotency markers known by one of ordinary skill in the art, including but not limited to SSEA-3, SSEA-4, TRA-1-60, TRA-1-81, and Alkaline Phosphatase; other markers include Sox2, Oct3/4, Nanog, TRA-1-60, TRA-1-81, TDGF 1, Dnmt3b, FoxD3, GDF3, Cyp26a1, TERT, and zfp42. And like ES cells, iPS cells are capable of forming teratomas. However, in contrast to ES cells, iPS cells are derived from differentiated somatic cells, that is, cells that had a narrower, more defined potential and that in the absence of experimental manipulation could not give rise to all types of cells in the organism. Examples of methods of generating and characterizing iPS cells may be found in US Application No. 20090047263; US Application No. 20090068742 and U.S. Application No. 61/276,112, which are incorporated herein by reference.

Agents that Modulate Germ Cell Differentiation.

An agent that modulates germ cell differentiation is an agent that alters the number of germ cells that differentiate in culture, or the rate at which the germ cells differentiate in culture, relative to the number or rate of germ cells that differentiate in culture in the absence of the agent. Agents that modulate germ cell differentiation may promote, i.e. induce, enhance, or increase, differentiation or they may inhibit, i.e. prevent, suppress, or decrease, differentiation. An agent that modulates germ cell differentiation is one that modulates the quantity/rate of germ cells differentiating by about 1.5-fold, by about 2-fold, by about 2.5-fold, by about 3-fold, by 4-fold, by about 5-fold, by about 10-fold, by about 20-fold, by about 50-fold, by about 100-fold.

Agents suitable for modulating germ cell differentiation in the present invention include small molecule compounds. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992). Small molecule compounds can be provided directly to the medium in which the cells are being cultured, for example as a solution in DMSO or other solvent.

Agents suitable for modulating germ cell differentiation in the present invention also include nucleic acids, for example, nucleic acids that encode siRNA, shRNA or antisense molecules, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc.

Vectors may be provided directly to the subject cells. In other words, the pluripotent cells are contacted with vectors comprising the nucleic acid of interest such that the vectors are taken up by the cells. Methods for contacting cells with nucleic acid vectors, such as electroporation, calcium chloride transfection, and lipofection, are well known in the art.

Alternatively, the nucleic acid of interest may be provided to the subject cells via a virus. In other words, the pluripotent cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) *Mol. Cell. Biol.* 5:431-437); PA317 (Miller et al. (1986) *Mol. Cell. Biol.* 6:2895-2902); GRIP (Danos et al. (1988) *PNAS* 85:6460-6464). Retroviruses packaged with xenotropic envelope protein, e.g. AKR env, are capable of infecting most mammalian cell types, except murine cells. The appropriate packaging cell line may be used to ensure that the subject CD33+ differentiated somatic cells are targeted by the packaged viral particles. Methods of introducing the retroviral vectors comprising the nucleic acid encoding the reprogramming factors into packaging cell lines and of collecting the viral particles that are generated by the packaging lines are well known in the art.

Vectors used for providing nucleic acid of interest to the subject cells will typically comprise suitable promoters for driving the expression, that is, transcriptional activation, of the nucleic acid of interest. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc Agents suitable for modulating germ cell differentiation in the present invention also include polypeptides. Typically, such a polypeptide will comprise the polypeptide sequences of interest fused to a polypeptide permeant domain. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24): 13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The polypeptide sequence of interest may optionally also be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

The polypeptide of interest may be generated in a cell based system using methods known in the art. In such cases, a nucleic acid (e.g., cDNA or genomic DNA) encoding the polypeptide is inserted into a replicable vector for expression. Many such vectors are available. The vector components generally include, but are not limited to, one or more of the following: an origin of replication, one or more marker genes, an enhancer element, a promoter, and a transcription termination sequence. The polypeptide of interest may be produced recombinantly not only directly, but also as a fusion polypeptide with a heterologous polypeptide, e.g. a polypeptide having a specific cleavage site at the N-terminus of the mature protein or polypeptide. Expression vectors usually contain a selection gene, also termed a selectable marker. This gene encodes a protein necessary for the survival or growth of transformed host cells grown in a selective culture medium. Either way, cells comprising the expression vector are grown under conditions that provide for expression of the desired polypeptide, which is then extracted from the cell lysate by conventional methods. Optionally the polypeptide(s) are purified prior to use.

Alternatively, the polypeptide of interest may be generated in a cell-free system, for example by the methods taught in U.S. Application Ser. No. 61/271,000, which is incorporated herein by reference.

The polypeptide may be provided to the subject cells by standard protein transduction methods. In some cases, the protein transduction method includes contacting cells with a composition containing a carrier agent and the purified polypeptide. Examples of suitable carrier agents and methods for their use include, but are not limited to, commercially available reagents such as Chariot™ (Active Motif, Inc., Carlsbad, Calif.) described in U.S. Pat. No. 6,841,535; Bioport® (Gene Therapy Systems, Inc., San Diego, Calif.), GenomeONE (Cosmo Bio Co., Ltd., Tokyo, Japan), and ProteoJuice™ (Novagen, Madison, Wis.), or nanoparticle protein transduction reagents as described in, e.g., U.S. patent application Ser. No. 10/138,593.

Polypeptide agents may be provided to the subject cells individually or in combination. If provided in combination, they may be provided simultaneously either individually or as a single composition, that is, as a premixed composition, of polypeptide agents; alternatively, the polypeptide agents may be added to the subject cells sequentially at different times, at an effective dose. Dose optimization is readily performed by one of skill in the art. The effective dose in a tissue culture setting may be at least about 1 ng/ml, 10 ng/ml, 100 ng/ml, 1 µg/ml, 10 µg/ml, 100 µg/ml or more, as empirically determined. In some embodiments, cells are incubated in the presence of a polypeptide agent for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours. In some embodiments, protein transduction of cells is repeated with a frequency of about every day to about every 4 days, e.g., every 1.5 days, every 2 days, every 3 days, or any other frequency from about every day to about every four days with the same or different polypeptide agents. Typically, the polypeptide agents are provided to the subject cells once, and the cells are allowed to incubate with the polypeptide agents for 16-24 hours, after which time the media is replaced with fresh media and the cells are cultured further, or the polypeptide agents are provided to the subject cells twice, with two 16-24 hour incubations with polypeptide agents following each provision, after which the media is replaced with fresh media and the cells are cultured further.

Another example of polypeptide agents suitable for modulating germ cell differentiation are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured.

Agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The terms "individual," "subject," "host," and "patient," are used interchangeably herein and refer to any mammalian subject for whom diagnosis, treatment, or therapy is desired, particularly humans.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

Inducing Germ Cell Differentiation

Methods are provided for producing germ cells from pluripotent cells by culturing a population of pluripotent cells in the presence of at least one agent that promotes germ cell differentiation.

Pluripotent cells of interest to the present invention are any cells that have the ability to differentiate into multiple types of cells in an organism, for example, ES cells and iPS cells. They may be obtained from any mammalian species, e.g. human, primate, equine, bovine, porcine, canine, feline, etc, and from any stage of life, e.g. embryonic, neonatal, a juvenile or adult. They may be female or male; that is, XX or XY. They may be previously frozen or freshly prepared. Typically, the cells have been cultured, i.e. passaged in vitro prior to use in the present invention, typically as adherent cultures on inactivate feeder layers, e.g. irradiated mouse embryonic fibroblasts, or an extracellular matrix protein coating, typically in a commercially available medium such as KnockOut DMEM, DMEM-F12, or Iscoves Modified Dulbecco's Medium that has been supplemented with serum or serum substitute, amino acids, and growth factors.

In the methods of the present invention, pluripotent cells are contacted with at least one agent that promotes germ cell differentiation. An agent that promotes germ cell differentiation is an agent that induces, enhances, or otherwise increases the quantity/number of germ cells that differentiate in culture and/or the rate at which the germ cells differentiate in culture relative to germ cell differentiation under the same culture conditions but in the absence of the agent. For example, in some cases in the art, pluripotent cells are induced to develop into germ cells by growing the cells in media comprising Bone Morphogen Proteins (BMPs) -4, -7 and -8b (see, for example, Zhao, G. Q. (2003) Genesis 35: 43-56; see also the Examples provided herein); an agent that promotes germ cell differentiation in these cases would be an agent that induces, enhances, or otherwise increases the quantity or rate of germ cell differentiation in media comprising these BMPs relative to the quantity or rate of germ cell differentiation that would be observed in media comprising these BMPs but in the absence of the agent. An agent that promotes germ cell differentiation is one that increases the quantity/rate of germ cells differentiation by about 1.5-fold, by about 2-fold, by about 2.5-fold, by about 3-fold, by about 4-fold, by about 5-fold, by about 10-fold, by about 20-fold, by about 50-fold, by about 100-fold. For example, in a population in which 5% of the pluripotent cells give rise to germ cells, the addition of an agent that induces germ cell differentiation will result in about 7%, about 10%, about 12%, about 15%, about 20%, about 50%, about 100% of the cells in the culture differentiating into germ cells.

Of particular interest to the invention are polypeptides of the DAZ family and polynucleotides that encode them. Polypeptides of the DAZ family include DAZ polypeptides, DAZL polypeptides, and BOULE polypeptides.

DAZ, or Deleted in Azoospermia 1, polypeptides are polypeptides encoded by DAZ genes. DAZ genes are found on the Y chromosome. Four DAZ genes exist in humans: DAZ1, the sequence of which may be found at GenBank Accession No NM_004081 (SEQ ID NO:1 and NO:2); DAZ2, the sequence of which may be found at GenBank Accession No NM_020363 (isoform 1, SEQ ID NO:3 and SEQ ID NO:4), NM_001005785 (isoform 2, SEQ ID NO:5 and SEQ ID NO:6), and NM_001005786 (isoform 3, SEQ ID NO: 7 and SEQ ID NO:8); DAZ3, the sequence of which may be found at GenBank Accession No. NM_020364 (SEQ ID NO:9 and SEQ ID NO:10); and DAZ4, the sequence of which may be found at GenBank Accession Nos. NM_001005375 (isoform 1, SEQ ID NO:11 and SEQ ID NO:12) and NM_020420.2 (isoform 2, SEQ ID NO:13 and SEQ ID NO:14). As used herein, a DAZ polypeptide is a polypeptide that comprises an amino acid sequence that is at least about 70% identical to the amino acid sequence of a human DAZ1, human DAZ2, human DAZ3, or human DAZ4, as described by the SEQ ID NOs provided above. DAZ polypeptides, e.g. those that are at least 70%, 75%, 80%, 85%, 90%, 91%, 92%, 95%, 97%, 99%, or 100% identical to SEQ ID NO:2, 4, 6, 8, 10, 12, or 14, and the nucleic acids that encode them find use as agents that promote germ cell differentiation, more particularly late-stage germ cell differentiation, in the present invention.

DAZL, or Deleted in Azoospermia-Like, polypeptides are polypeptides that are encoded by the DAZL gene. The DAZL gene is an autosomal gene. A DAZL polypeptide is a polypeptide comprising an amino acid sequence that is at least 70% identical to the amino acid sequence of human DAZL, also known as DAZH, DAZL1, DAZLA, and SPGYLA, the sequence of which may be found at GenBank Accession No. NM_001190811 (isoform 1, SEQ ID NO:15 and SEQ ID NO:16) and NM_001351 (isoform 2, SEQ ID NO:17 and SEQ ID NO:18). DAZL polypeptides, i.e. polypeptides that are at least 70%, 75%, 80%, 85%, 90%, 91%, 92%, 95%, 97%, 99%, or 100% identical to the sequence provided in SEQ ID NO:16 or 18, and the nucleic acids that encode them find use as agents that promote primordial germ cell differentiation and late-stage germ cell differentiation in the present invention.

BOULE (BOLL, bol, boule-like) polypeptides are polypeptides comprising an amino acid sequence that is at least 70% identical to the amino acid sequence of human BOULE, the sequence of which may be found at GenBank Accession Nos. NM_197970 (isoform 1, SEQ ID NO:19 and SEQ ID NO:20) and NM_033030 (isoform 2, SEQ ID NO:21 and SEQ ID NO:22). BOLL polypeptides, i.e. those that are at least 70%, 75%, 80%, 85%, 90%, 91%, 92%, 95%, 97%, 99%, or 100% identical to the sequence provided in SEQ ID NO:20 or SEQ ID NO:22, and the nucleic acids that encode them find use as agents that promote primordial germ cell differentiation and late-stage germ cell differentiation in the present invention.

Concurrent with and/or subsequent to contacting the pluripotent cells with the at least one agent, the pluripotent cells are cultured under conditions that are permissive for the differentiation of germ cells. In some embodiments, the conditions may also induce/promote the differentiation of germ cells. Culturing conditions that are permissive for and/or promote differentiation of germ cells from pluripotent cells are well known in the art; any such conditions may be used herein. For example, pluripotent cells may be grown as adherent cultures on matrigel or other extracellular matrix protein-type coating for culture dishes, for 7-14 days in a commercially available medium, e.g. knockout DMEM, that has been supplemented with serum and chemicals, e.g. 20% fetal bovine serum, 1 mM L-glutamine, 0.1 mM nonessential amino acids, and 0.1 mM 2-mercaptoethanol. Often, the cultures are also supplemented with a growth factor, such as 50 ng/ml recombinant human BMP4, BMP7 and/or BMP8b.

Germ cells that are produced from pluripotent cells by the described method find use in a number of basic research and clinical applications. For example, the germ cells may be studied to better understand the biology of germ cells. The nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions. The germ cells themselves may be analyzed, for example for the expression of genes, for example to better characterize differentiated germ cells. The germ cells may be replated and cultured under conditions known in the art to induce the development of embryonic germ cells or of later stage germ cells, e.g. spermatocytes or oocytes, for example, to study the biology of these cell types.

Likewise, germ cells that are produced from pluripotent cells by the described method find use in a number of clinical applications. For example, the cells may be isolated for use in ex vivo or in vitro fertilization. Optionally, genes may be introduced into the pluripotent cells prior to performing the method or into the differentiated germ cells that are produced after performing the method, for example, to replace genes having a loss of function mutation, provide marker genes, etc., as for gene therapy. Alternatively or additionally, vectors may be introduced that express antisense mRNA or ribozymes so as to block expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the germ cells, e.g. electroporation, calcium precipitated DNA, fusion, transfection, lipofection, infection and the like, as discussed above. The particular manner in which the DNA is introduced is not critical to the practice of the invention.

To prove that one has genetically modified the germ cells, various techniques may be employed. For example, the genome of cells of a differentiated germ cell clone may be restricted and used with or without amplification. The polymerase chain reaction; gel electrophoresis; restriction analysis; Southern, Northern, and Western blots; sequencing; or the like, may all be employed. Additionally, various tests in vitro and in vivo may be employed to ensure that the pluripotent capability of the cells has been maintained. For example, the cells may be cultured by methods known in the art to induce the formation of embryonic germ cells, which may be assayed to ensure that the cells are capable of maturation to all of the lineages while maintaining the ability to express the introduced DNA.

The germ cells produced by the above methods may be used for reconstituting or supplementing differentiating or differentiated germ cells in a recipient. Alternatively, the germ cells may be differentiated into gametes in vitro and used to fertilize eggs or be fertilized by sperm by methods of in vitro fertilization commonly employed in the art.

Kits may be provided, where the kit will comprise reagents that are sufficient to promote the differentiation of germ cells as described herein. A combination of interest may include one or more agents of the present invention that promote germ cell differentiation, and may further include pluripotent cells or primordial germ cells. Kits may also include tubes, buffers, etc., and instructions for use.

Compositions of Primordial Germ Cells

Also provided are methods of enriching for a composition of primordial germ cells (PGCs), wherein a population of pluripotent cells is contacted with a reporter construct that is active in primordial germ cells, the contacted pluripotent cells are cultured under conditions sufficient to promote PGC differentiation; and the cells that express the detectable marker are selected to provide a selected cell population of PGCs.

The report construct is preferably a polynucleotide composition comprising a detectable marker under the control of a promoter sequence that is selectively active in primordial germ cells. Promoters are untranslated sequences located upstream (5') to the start codon of a structural gene (generally within about 100 to 1000 bp) that control the transcription and translation of particular nucleic acid sequence to which they are operably linked. A promoter sequence that is selectively active in primordial germ cells is a sequence that activates the expression of a particular nucleic acid sequence only in the primordial germ cells of the culture. In other words, the only cells in the culture that will transcribe the nucleic acid sequence operably linked to the promoter will be PGCs. One example of a promoter sequence useful in the polynucleotide composition of the subject invention is the promoter sequence for the VASA gene. The VASA gene (also called DDX4; GenBank Accession Nos. NM_001136034 and NM_001142549.1) is located on chromosome 5, nucleotides chr5:55,033,845-55,112,973, as described by, for example, the UC Santa Cruz genome browser, located on the world wide web at genome.ucsc.edu. The regulatory domain, or promoter, for VASA that is sufficient for use as a promoter in the subject polynucleotide composition comprises the nucleotide sequence that spans the first about 2 kB, about the first 2.5 kb, about the first 3 kB, about the first 5 kB of sequence that is immediately 5' to the VASA coding sequence as it is described in GenBank Accession No. NM_024414 (SEQ ID NO:23).

Detectable markers suitable for use in the polynucleotide composition are nucleic acid sequences that encode any polypeptide that can be detected without killing the cell. For example, the detectable marker may be a fluorescent or colored protein, e.g. GFP, dsRED; or a cell surface protein that can be detected with a monoclonal antibody; or a protein that produces a detectable byproduct.

Pluripotent cells that are contacted with the aforementioned polynucleotide composition are cultured under conditions sufficient to promote PGC differentiation. Examples of such conditions may be found in the Examples section provided below and in the art; they typically include the addition of Bone Morphogen Proteins (BMPs) to the culture medium.

Following culturing, the cells that express the detectable marker are selected. It will be understood by those of skill in the art that the stated expression levels reflect detectable amounts of the marker protein. A cell that is negative for staining (the level of binding of a marker specific reagent is not detectably different from an isotype matched control) may still express minor amounts of the marker. And while it is commonplace in the art to refer to cells as "positive" or "negative" for a particular marker, actual expression levels are a quantitative trait. The number of molecules expressed by the cell can vary by several logs, yet still be characterized as "positive".

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but not as intense as the most brightly staining cells normally found in the population. An alternative control may utilize a substrate having a defined density of marker on its surface, for example a fabricated bead or cell line, which provides the positive control for intensity.

If the detectable marker is a cell surface protein, the marked cells may be separated from the complex mixture or heterogeneous culture of cells by affinity separation techniques using affinity reagents such as antibodies that are specific for the cell surface protein. Techniques for affinity separation may include magnetic separation using magnetic beads coated with an affinity reagent, affinity chromatography, cytotoxic agents joined to an affinity reagent or used in conjunction with an affinity reagent, e.g. complement and cytotoxins, and "panning" with an affinity reagent attached to a solid matrix, eg. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Such techniques as fluorescence activated cell sorting may also be used to separate the marked cells from the complex mixture or heterogeneous culture of cells if the detectable marker is an intracellular marker, e.g. a fluorescent protein, e.g. GFP, FRP, dsRED. Any technique may be employed which is not unduly detrimental to the viability of the selected cells.

Compositions that are highly enriched for primordial germ cells are achieved in this manner. The subject population of primoridial germ cells will be 80% or more of the cell composition, about 85% or more of the cell composition, about 90% or more of the cell composition, about 95% or more of the cell composition, and will preferably be about 95% or more of the cell composition. In other words, at least about 80% of the cells, more usually at least 90% and more usually 95% or more of the cells of the enriched cell population will be primordial germ cells. The cells of the subject population will also express higher levels of the genes VASA and DAZL than the cells that express no or low levels of the detectable marker from which they were separated. Additionally, the genomic DNA of the subject cells will be hypomethylated relative the genomic DNA of the cells from which they were separated. This composition may then be used in screening methods such as the screening method described below.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

The enriched cell population may be used immediately. Alternatively, the enriched cell population may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The subject primordial germ cell population may be cultured in vitro under various culture conditions as known in the art. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

The subject primordial germ cells have many applications in modern biotechnology and molecular biology. They are useful in the production of transgenic animals, where embryonic germ (EG) cells derived from PGCs may be used in much the same manner as embryonic stem (ES) cells (see, e.g., Labosky et al., (1994) Development 120:3197-3204). Moreover, they are useful in the study of fetal development, and of the provision of pluripotent stem cells for tissue regeneration in the therapy of degenerative diseases and repopulation of damaged tissue following trauma. The primordial germ cells themselves may be analyzed, for example for the expression of genes, for example to better characterize the subject cells. The primordial germ cells may be replated and cultured under conditions known in the art to induce the development of embryonic germ cells or of later stage germ cells, e.g. spermatocytes or oocytes, for example to study the biology of these other cell types. The primordial germ cells may be used as a tool for screening agents for activity in modulating the differentiation of these other cell types, as described further below.

Screening Assays

Also provided are methods for screening one or more agents for activity in modulating germ cell differentiation. The culture system and compositions described herein provide a useful system to screen candidate agents for activity in modulating germ cell differentiation e.g. by adding a candidate agent to the culture system and assaying for changes in the quantity and/or rate of germ cell differentiation. In screening assays for biologically active agents, a first population of pluripotent cells is contacted with a candidate agent. The characteristics of the contacted cells are then compared with the characteristics of a second population of pluripotent cells that have not been contacted with the agent, wherein differences in the characteristics between the first population and the second population indicate that the candidate agent modulates germ cell differentiation. Prior to contacting the first population of pluripotent cells with the candidate agent, the first population and second population of pluripotent cells are substantially the same. Typically, the first population of pluripotent cells, i.e. the population that was contacted with agent, will be cultured either concurrently with being contacted or subsequent to being contacted under conditions that are permissive for or promote/induce germ cell differentiation. In such cases, the second population of pluripotent cells, i.e. the population that was not contacted with agent, will likewise be cultured under conditions that are substantially the same.

An agent that modulates germ cell differentiation is an agent that modulates, or alters, or affects, the number of germs cells that differentiate in culture or the rate at which the germ cells differentiate in culture relative to the number or rate of germ cells that differentiate in the absence of the agent. Agents that modulate germ cell differentiation may promote, i.e. induce, enhance, or increase, differentiation, or they may inhibit, i.e. prevent, attenuate, or decrease, differentiation. For example, as discussed above, an agent that promotes germ cell differentiation is an agent that induces, enhances, or otherwise increases the quantity/number of germ cells that differentiate in culture and/or the rate at which the germ cells differentiate in culture relative to germ cell differentiation under the same culture conditions but in the absence of the agent. Reciprocally, an agent that inhibits germ cell differentiation prevents, attenuates or decreases the quantity/number of germ cells that differentiate in culture and/or the rate at which the germ cells differentiate in culture relative to germ cell differentiation under the same culture conditions but in the absence of the agent. An agent that modulates germ cell differentiation is one that modulates the quantity/rate of germ cells differentiation by about 1.5-fold, by about 2-fold, by about 2.5-fold, by about 3-fold, by 4-fold, by about 10-fold, by about 20-fold, by about 50-fold, by about 100-fold. As discussed above, candidate agents that may modulate germ cell differentiation include small molecule compounds, nucleic acids, and polypeptides.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype. Positive controls of interest include those genes and polypeptides identified herein as affecting germ cell differentiation.

Characteristics, or parameters, that might be assessed as being reflective of an agent's activity are typically quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Some examples of characteristics, or parameters, that might be assessed include the number of cells that differentiated into germ cells in each population, the genes that are expressed by the cells of the populations, the methylation state of the genomic DNA of the cells of the populations, and/or the ability of the cells of the populations to give rise to embryonic germ cell populations.

Various methods can be utilized for assessing the characteristics of the cell populations after contact with the candidate agent(s). For measuring the amount of a molecule, e.g. a protein, that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). In some embodiments of the invention, the pluripotent cells are contacted with a polynucleotide comprising a detectable marker under control of a promoter that is selectively active in primordial germ cells prior to culturing in the presence of the candidate agent, which may be used to quantify the number of cells in the population that differentiation into primordial germ cells or isolate the primordial germ cells for better assessing their characteristics.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications that might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials and Methods

VASA-GFP Reporter, Transduction and FACS.

2.5 kb of human VASA upstream of the first codon was cloned into pENTR 5'-TOPO. EGFP was fused 1 kb downstream of the last codon of human VASA, and cloned into pENTR/D-TOPO. Cloned plasmids were recombined (Suter, D. M. et al. (2006) Stem Cells 24, 615-623) to create pLVGV. Lentiviral supernatant was produced, human ES cells were transduced overnight on matrigel in conditioned medium and subsequently selected with geneticin (200 ng ml$^{-1}$) for 7 days. Selected human ES cells were differentiated for the times indicated and harvested by brief treatment with collagenase IV and then TrypLEExpress (Invitrogen). The cell suspension was prepared in differentiation medium for FACS with a MoFlow or BD cell sorter.

Human ES Cell Lines and Adherent Differentiation.

Four human ES cell lines were used in this study: HSF1 (XY), HSF6 (XX), H1 (XY) and H9 (XX). Undifferentiated cultures of human ES cells were maintained on irradiated MEFs as previously described in Kee, K. et al (2006) Stem Cells Dev. 15: 831-837. Briefly, all cultures were grown at 37° C. with 5% $CO_2$ in knockout serum replacer (KSR) plus bFGF medium (knockout DMEM, supplemented with 20% knockout serum replacer, 1 mM L-glutamine, 0.1 mM nonessential amino acids, 0.1 mM 2-mercaptoethanol, and 4 ng ml$^{-1}$ recombinant human bFGF (bFGF, R&D systems)). To adherently differentiate human ES cells on matrigel, about 5×10⁴ human ES cells (less than 50% confluency of a six-well plate) were treated with collagenase type IV (1 mg/ml) for 10 min, scraped with a 5 ml plastic pipette, and transferred with fresh KSR+bFGF media to an identical well coated with matrigel. Conditioned media (KSR+bFGF media collected after overnight incubation on irradiated MEFs) was used to maintain the undifferentiated cells whenever drug selection (geneticin at 200 μg ml$^{-1}$, and zeocin and blasticidin at 2 μg ml$^{-1}$) was required. Differentiation began upon aspiration of KSR+bFGF media or conditioned media, washed once with PBS without Ca$^{2+}$ and Mg$^{2+}$, and replaced with differentiation media (knockout DMEM supplemented with 20% fetal bovine serum, 1 mM L-glutamine, 0.1 mM nonessential amino acids, 0.1 mM 2-mercaptoethanol and 50 ng ml$^{-1}$ recombinant human BMP4, BMP7 and BMP8b (R&D systems). Differentiation media was changed after 7 days of incubation if longer differentiation was necessary.

Western Blot Analysis.

To collect the adherently differentiated cells, cells were washed with 3 ml cold PBS without Ca$^{2+}$ and Mg$^{2+}$, then scraped from the plate in 1 ml PBS plus 2× protease inhibitors (Complete Mini, Roche) and transferred immediately to a 1.5-ml tube on ice. The PBS cell suspension was then spun at 5,000 r.p.m. in a microcentrifuge for 3 min and the supernatant was discarded. The cell pellet was resuspended with 200 ul RIPA buffer (50 mM Tris, 150 mM NaCl, 0.5% sodium deoxycholate, 1% NP-40, 0.1% SDS, pH 8) plus 2× protease inhibitors (Complete Mini, Roche). The cell pellet suspension was pipetted rigorously at least 10 times, then vortexed for 30 sec. The suspension was again spun down for 3 min at the same speed. The supernatant was measured for protein concentration and denatured at a 1:1 ratio with 2× Laemmli buffer at 95° C. for 5 min, then loaded onto either a 10% or 12% SDS-PAGE gel. The SDS-PAGE gels were run at 150 V for 1 h and transferred to a PVDF membrane for 1 h at 100 V in CAPS buffer (10 mM CAPS, 10% methanol, pH 11). Transferred blots were blocked in 5% non-fat milk for 1 h at room temperature. The blot was subjected to 1 h of primary antibody incubation (1:500 for anti-VASA (Abcam), 1:500 for anti-DAZL-150 (Reijo, R. A. et al. (2000) Biol. Reprod. 63, 1490-1496), 1:1,000 for anti-V5 (Abcam), 1:10,000 for anti-UBC9 (Abcam) or 1:10,000 for anti-GAPDH (Abcam)), followed by two quick rinses and three washes for 5 min in TBST (TBS, pH 7.4 with 0.1% Tween-20). Secondary antibody (1:10,000 anti-rabbit-HRP conjugated (Amersham)) incubation had the same duration and washes. ECL+ (Amersham) was used to chemiluminescently detect the HRP signal on film.

Quantitative PCR on mRNA Expression and Statistical Analysis.

Total RNA was collected using the RNeasy system (Qiagen) or PicoPure RNA isolation (Arcturus) and cDNA was prepared with SuperScript III Reverse Transcriptase (Invitrogen) according to manufacturer's protocols. Quantitative PCR was conducted with Taqman probes (Applied Biosystems) using the Fluidigm System (Biomark). Gene expression is normalized to a set of housekeeping genes (GAPDH, RPLP0, centrin, CTNNB1, ACTB) and calculated according to geNorm program (Vandesompele, J. et al. (2002) Genome Biol. 3 RESEARCH0034) for GFP– versus GFP+ cells. Gene expressions of the replated cells, fetal liver cDNA (Clontech), and overexpressed cells were normalized again to either the expression of GFP+ cells or control cells carrying empty p2k7, and the normalized expression value is therefore fold of change. Statistical analysis was calculated using Student's t-test or one-way ANOVA by Prism 5.0 program.

DNA Methylation Analysis.

VASA-GFP+, VASA-GFP– and 1N populations were collected by FACS; adult skin fibroblast, H9 and HSF1 were collected from trypsinized cell suspensions; replated GFP+ cells were collected by colony picking under dissection microscope (pooled of five colonies). Genomic DNA was extracted using the ZR Genomic DNA II kit (Zymo Research) or QIAamp DNA Mini kit (Qiagen). For bisulphite sequencing analysis of H19 locus, 100 ng of genomic DNA was processed using the Qiagen Epitect Bisulfite Kit (Qiagen) according to protocol. 1 μl of bisulphite-treated genomic DNA was PCR amplified at the H19 locus using primers as previously described Clark, A. T. et al. (2004) Hum. Mol. Genet. 13: 727-739). The resultant product was gel-extracted using the Qiaquick gel extraction kit (Qiagen) and cloned into the TOPO TA vector (Invitrogen). At least 20 clones were sequenced using ABI BigDye v3.1 dye terminator sequencing chemistry (Applied Biosystems) and ABI PRISM 3730xl capillary DNA analyser for sequence analysis. Quantitative DNA methylation analysis using methylation-sensitive/dependent restriction assay was carried out according to a previous study (Kee, K., (2006) Stem Cells Dev. 15, 831-837). Briefly, ~50-200 ng of each genomic DNA sample was divided equally for control (with buffers), methylation-sensitive (NotI, HhaI and HpaII; New England Biolabs) and methylation-dependent (McrBC; New England Biolabs) restriction digestions. 1/30 of the digested genomic DNA was then used as the input for qPCR reaction (ABI Power SYB master mix) using specific primers for the differentially methylated regions (DMRs) of H19 (Kerjean, A. et al. (2000) Hum. Mol. Genet. 9, 2183-2187), PEG1 (Kerjean, A. et al. (2000) Hum. Mol. Genet. 9, 2183-2187), (SNRPN Rugg-Gunn, P. J. et al. (2005) Nature Genet. 37, 585-587) and KCNQ (Rugg-Gunn, P. J. et al. (2005) Nature Genet. 37, 585-587) respectively, and triplicates were ran for each reaction. Percentage of hypermethylation was calculated as previously reported (Oakes, C. C. (2006) Epigenetics 1, 146-152), and the average percentages with lower standard deviation were chosen between methylation-sensitive and methylation-dependent restriction reactions.

Alkaline Phosphatase Assay.

Cells grown on MEFs were subjected to alkaline phosphatase staining using Vector Red Alkaline Phosphatase Substrate Kit I (Vector Laboratories) according to manufacturer's protocols.

shRNA Vectors and Overexpression Vectors.

All shRNAs targeting human DAZL, DAZ and BOULE were constructed using the Block-iT inducible H1 lentiviral system (Invitrogen). All shRNAs were first introduced into pENTR/H1/TO vectors and transferred into pLenti4/BLOCK-iT-DEST destination vectors (see below for sequence information). When shRNA was tested in 293FT cells for its efficacy of silencing, transient transfection without selection was carried out and cell lysate was collected after 24 h. After specific shRNA was chosen, viral supernatant was prepared as described for pLVGV. Subsequently, the viral supernatant was used to transduce human ES cells on matrigel as described above, except with zeocin selection (2 μg/ml) for 3 days for stable integration of the shRNA vector into human ES cells. Overexpression vectors were constructed by inserting the EF1μ, promoter, and DAZL, DAZ2 or BOULE cDNA into the p2k7$_{bias}$ vectors, selected with blasticidin (2 μg ml$^{-1}$) in culture for 3 days to ensure stable integration and subjected for each differentiation experiment. shRNA sequences were:

| shRNA | sequence | SEQ ID NO: |
|---|---|---|
| shDAZL1 | 5'-GGATGGATGAAACTGAGATTA-3' | 24 |
| shDAZL2 | 5'-GCATATCCTACTTACCCAAAT-3' | 25 |
| shDAZL3 | 5'-GCCAAATGAATGTTCAGTTCA-3' | 26 |
| shDAZL4 | 5'-GCAGAAGATAGTAGAATCACA-3' | 27 |
| shDAZL5 | 5'-GGATATCAGTTGCCTGTATAT-3' | 28 |
| shDAZL6 | 5'-GGTGGTATCTTGTCTGTTTAA-3' | 29 |
| shDAZL7 | 5'-GGTATCTTGTCTGTTTAATCC-3' | 30 |
| shDAZ1 | 5'-GCAAATCCTGAGACTCCAAAC-3' | 31 |
| shDAZ2 | 5'-GGAAGCTGCTTTGGTAGATAC-3' | 32 |
| shDAZ3 | 5'-GCCACGTCCTTTGGTAGTTAA-3' | 33 |
| shDAZ4 | 5'-GCATTTCCTGCTTATCCAAAT-3' | 34 |
| shDAZ5 | 5'-GCATTTCCTGCTTATCCAAGT-3' | 35 |
| shBOULE1 | 5'-GCATCTTTGTAGGAGGAATTG-3' | 36 |
| shBOULE2 | 5'-GGATCCCTCGTTCTAGTATAA-3' | 37 |
| shBOULE3 | 5'-GCTGGAACAATGTATCTAACA-3' | 38 |
| shBOULE4 | 5'-GCAACCTTCTGAGGTTATTTA-3' | 39 |
| shBOULE5 | 5'-GCTCCAAGTGCCATCACTATG-3' | 40 |

VASA and OCT4 Whole-Cell Staining and 5-Methylcytosine Nuclei Staining.

Cell suspensions from FACS were collected onto a glass slide with a Cytospin (Thermo Scientific) at 800 r.p.m. for 5 min followed by a wash in PBS, and fixed with 4% paraformaldehyde/PBS for 15 min. For VASA and OCT4 staining, slides were blocked in 1% BSA/0.1% Tween-20/PBS for 1 h, followed by overnight incubation with primary antibody (1:500 for anti-VASA (Abcam), 1:200 anti-OCT4 (Santa Cruz)). Slides were then rinsed twice and washed three times, 5 min with 0.1% Tween-20/PBS (PBST). Secondary antibody, anti-rabbit-594 (Invitrogen) was incubated for 1 h at room temperature on the slides followed by the same washes. The slides were then mounted with Prolong Antifade with DAPI (Molecular Probes). For 5mC staining, fixed cells were incubated with 1% Triton X-100 for 1 h, washed with PBST twice for 5 min. Denaturation of DNA was carried out by treating cells with 4 M HCl/0.1% Triton X-100 for 10 min and immediately neutralized with 100 mM Tris/HCl (pH 8.5) for 30 min. Slides were blocked in 1% BSA/0.1% Tween-20/PBS at 4° C. overnight. This was then stained with antibody against 5-methylcytosine (Genway) at a concentration of 1:100 in blocking buffer for 4 h at room temperature. The slides were washed, incubated with secondary antibody, and mounted the same as described above.

Meiotic spreads, SCP3 and γH2AX staining.

Meiotic spreads were carried out as described previously (Gonsalves, J. et al. (2004) Hum. Mol. Genet. 13, 2875-2883) with some modifications. Briefly, differentiated human ES cells were prepared as single cells as for FACS analysis. Cells were lysed by a hypotonic solution and dropped on glass slides freshly submerged in 1% PFA and 0.15% Triton X-100. Slides were incubated overnight at 4° C. until the suspension was semi-dry. Slides were treated with 0.04% photoflo for 5 min and blocked with 4% goat serum. Rabbit anti-SCP3 (1:1,000, Novus) and mouse-anti-γH2AX (1:200, Abcam) were incubated for 3 h at room temperature. Washes, secondary antibody incubation (1:1,000, anti-rabbit 594 and anti-mouse 488 (Molecular Probe)) and mounting are the same as described above.

FACS Analysis for DNA Content.

Single cell suspensions were prepared as described above. Fixing and staining of the DNA was conducted as described previously (Darzynkiewicz, Z. & Juan, G. (2001) Curr. Protoc. Cytom. Ch. 7, Unit 75). Briefly, cells were fixed in 70% ethanol for 1 h at room temperature, followed by incubation in 0.5 ml staining solution (0.1% Triton X-100 in PBS, 0.2 mg ml$^{-1}$ RNaseA, 0.02 mg/ml propidium iodide) then transferred to a FACS tube and incubated at 37° C. for about 15 min or more. The cell suspension in the staining solution was subjected to FACS analysis.

FISH of FACS Cells.

1N, 2N and 4N cells were collected by cytospin as described above after the DNA content FACS. Slides were fixed with Carnoy's fixative (1:3 of acetic acid:methanol) 5 min, air dried in chemical hood, dehydrated through an ice cold ethanol series (70%, 80%, 100% ethanol, 2 min each), and air dried for 5 min. FISH probe (against chromosome 16, Vysis) was directly denatured on slides at 85° C. and hybridized at 37° C. overnight. Slides were washed with 2×SSC once, followed by 0.1% SDS in 2×SSC (pre-warm) at 50° C., 5 min, and mounted as described above.

Acrosin Staining.

The FACS-collected 1N population was cytospun onto glass slides, washed once with PBS, and fixed with 4% paraformaldehyde/PBS for 15 min. Fixed cells were then incubated with 1% Triton X-100 for 15 min, washed twice with 0.1% Tween-20/PBS for 5 min. Slides were blocked with 4% goat serum for 1 h at room temperature, then stained with antibody against acrosin (Santa Cruz) diluted 1:50 in blocking buffer for 4 h at room temperature. Slides were rinsed twice and washed three times with PBST, for 5 min. The secondary antibody used was anti-rabbit-Cy5 (Molecular Probes) at 1:1,000 for 1 h at room temperature, followed by the same washes, mounting as described above.

Cloning and Silencing of DAZ1-4.

cDNA clones of DAZ1-4 (NCBI accession numbers: DAZ1, BC11492; DAZ2, NM_020363; DAZ3, BC113005; DAZ4, BC047480) were obtained from ATCC, PCR amplified, cloned into pENTR-D-TOPO vector, and subsequently cloned into pLenti4/TO/V5-DEST (Invitrogen). Expression of these cDNAs resulted in ~42 kDa, 63 kDa, 50 kDa and 44 kDa proteins, respectively, on western blot detected by mouse anti-DAZ1 antibody (Abcam). Co-transfection of the overexpression vector and shDAZ4 at the ratio of 1:1 and 1:2 into 293FT cells was carried out and all the lysates were collected after 24 h and loaded equally onto 10% SDS-PAGE gel.

Replating of VASA-GFP$^+$ Cells.

VASA-GFP– and VASA-GFP+ cells were collected in ice-cold KSR media without bFGF (knockout DMEM, supplemented with 20% knockout serum replacer, 1 mM L-glutamine, 0.1 mM nonessential amino acids, 0.1 mM 2-mercaptoethanol). Immediately after FACS collection, cells were distributed into wells plated with inactivated MEFs containing KSR media. Approximately 20,000 cells were distributed into each well of a 6-well plate. Culture was then grown at 37° C. with 5% CO$_2$. Media was changed every 3 days. Colonies usually appeared after 7 days and at 1/5,000 survival rate. Colonies expanded much slower than human ES cell colonies and harvested when colony size was about 200 μm for various assays.

Results

Figure 5:
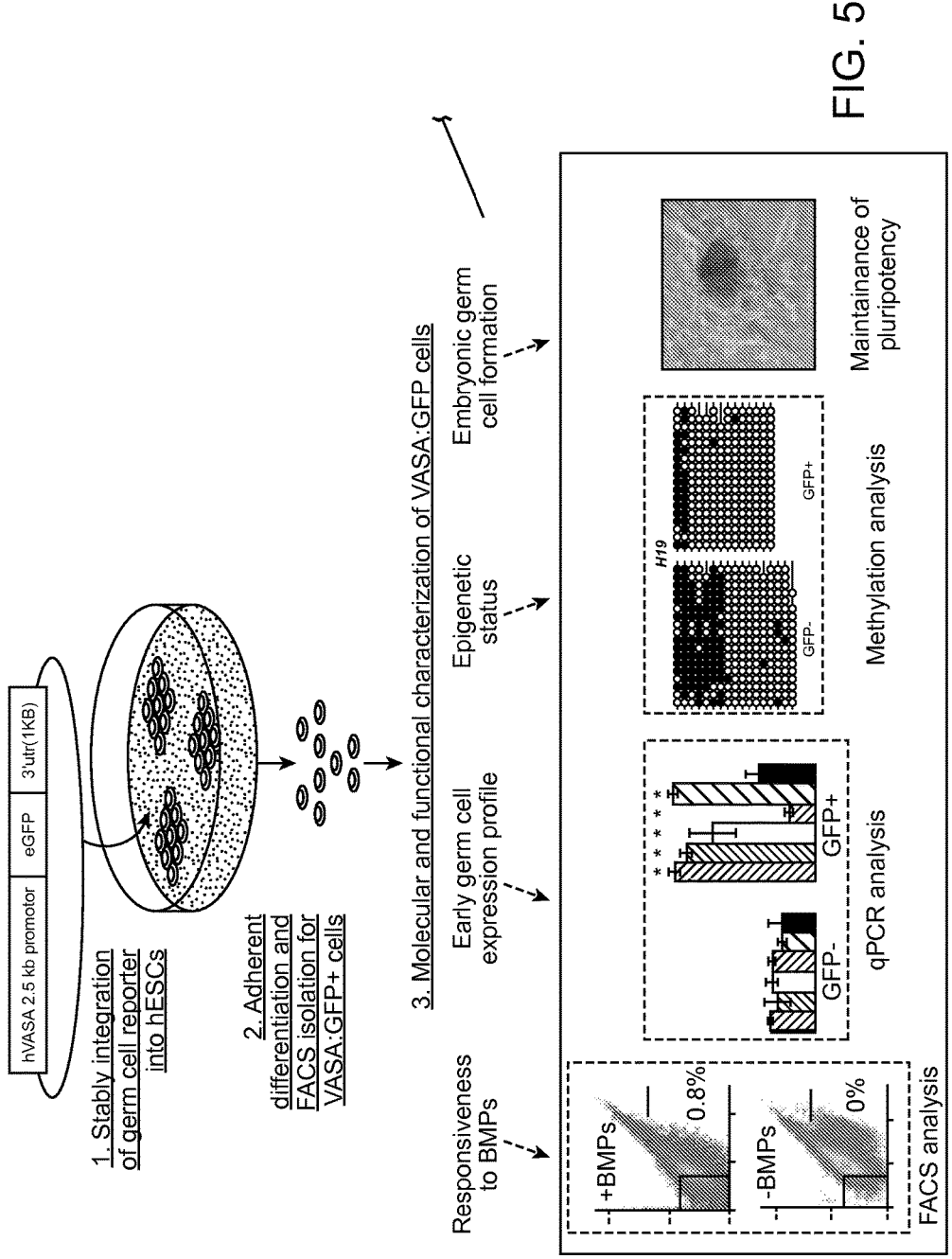
FIG. 5. Experimental overview of system to probe landmark events and genetic requirements for human germ cell formation and differentiation. A germ cell reporter (VASA:GFP) was created and stably integrated into hESCs. Adherent differentiation was developed to achieve efficient recovery of early germ cells for FACS isolation and characterization. Multiple molecular and functional assays were conducted to characterize GFP+ cells after FACS isolation, including quantitative analysis of GFP+ by FACS under various culturing condition to examine the responsiveness of hESCs to BMPs, expression analysis using more than 25 qPCR probes, methylation of genomic DNA by three independent analysis, and ability to propagate EG cells. Results confirmed identity of GFP+ cells as primordial germ cells. The utility for direct human genetic studies of germ cell formation and differentiation was demonstrated by silencing and overexpressing members of the germ cell specific DAZ gene family. Combinations of multiple functional and cellular assays demonstrated that formation of GFP+ cells was modulated by one of the DAZ gene family members, DAZL. The functional role of DAZ and BOULE in contrast was further revealed in promoting germ cell into meiosis and haploid formation.
Figure 5:
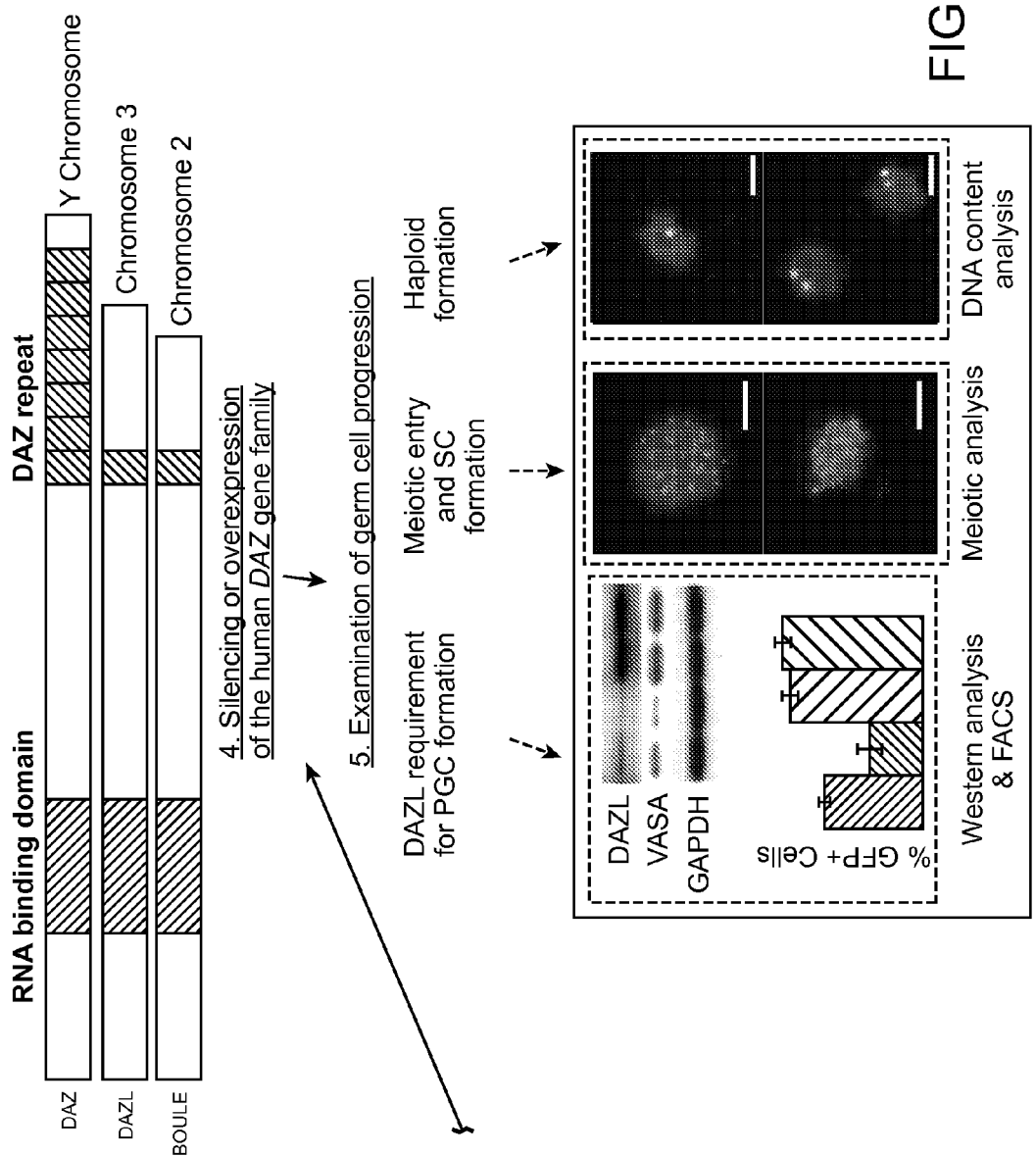
Figure 6:
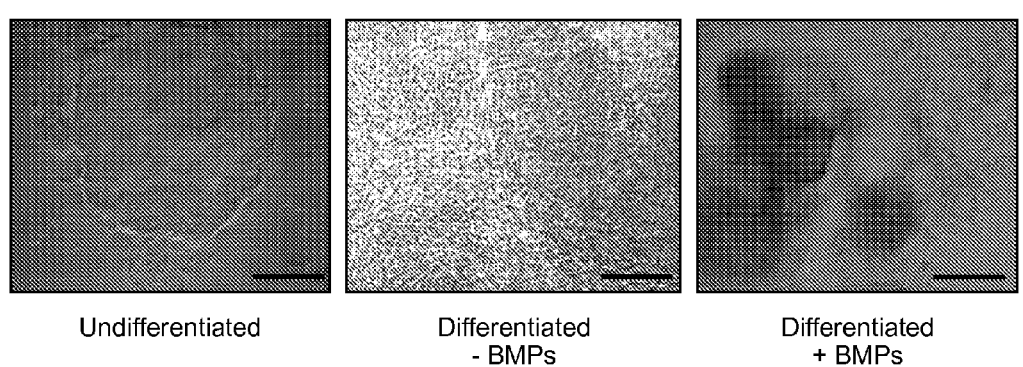
FIG. 6. Phase contrast pictures showing an hESC colony on matrigel before and after differentiation with or without BMPs. After 7 days of differentiation with BMPs, cells on matrigel appear confluent, compact and morphologically distinct from the undifferentiated colony. In contrast, cells differentiated without BMPs appear as monolayers and more homogenous. Scale bar is 500 micron.
Figure 7:
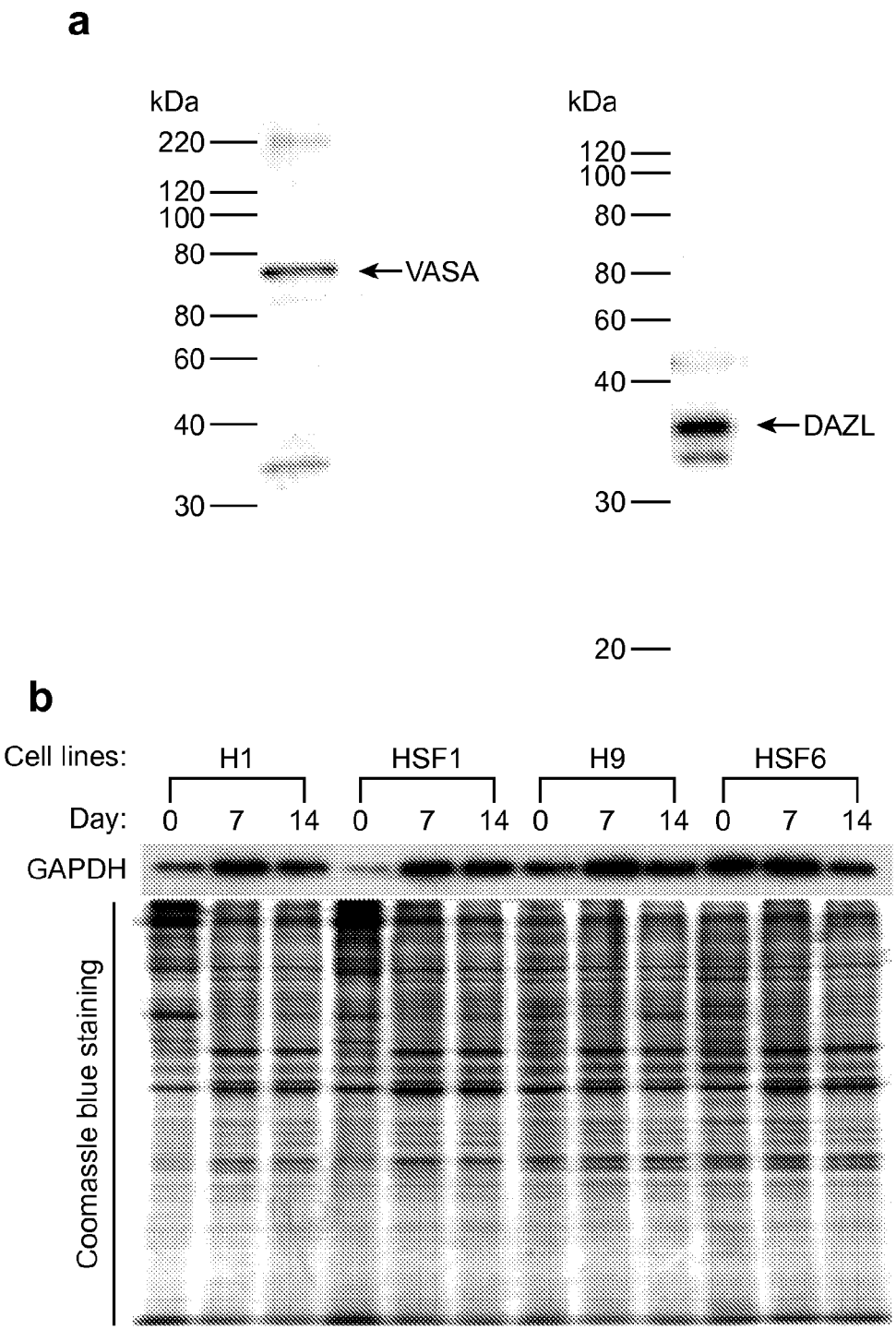
FIG. 7. Western analysis of VASA and DAZL proteins with hESC differentiation. a, Western analysis of VASA and DAZL from the cell lysates of a 14 day differentiated sample with BMPs. Polyclonal VASA and DAZL antibody detected a prominent ~79 kDa band and ~35 kDa band, respectively. b, GAPDH expression and Coomassie Blue staining of protein gel with the four hESC lines at three time points. Similar to UBC9 shown on FIG. 1a, protein expression of housekeeping marker GAPDH was lower in H1 and HSF1 in undifferentiated hESCs. This may reflect previous observations that expression of these housekeeping genes vary in different hESC lines or may reflect legitimate sex-specific differences. Lower panel is Coomassie Blue staining of the samples indicating equal amount of loading but slightly different expression patterns at various time points.

Historically, human germ-cell differentiation has been intractable to direct analysis; yet, infertility is unusually common in both men and women, with genetic requirements that differ from those of other commonly studied species. Here, we sought to develop a system for direct experimental examination of landmark events and genetic requirements in human germ-cell formation, maintenance of pluripotency, epigenetic reprogramming and progression through meiosis (FIG. 5). Although previous studies had demonstrated that bone morphogenetic proteins (BMPs) promote differentiation of human embryonic stem (ES) cells to germ cells in embryoid bodies, the process was inefficient. Thus, we explored adherent differentiation of human ES cells and observed the induction of a variety of morphological changes (FIG. 6). Furthermore, differentiation was accompanied by increased expression of the germ-cell-specific proteins VASA and DAZL in all human ES cell lines tested (two female (XX) and two male (XY) lines from four independent derivations; FIG. 1a and FIG. 7).

Figure 8:
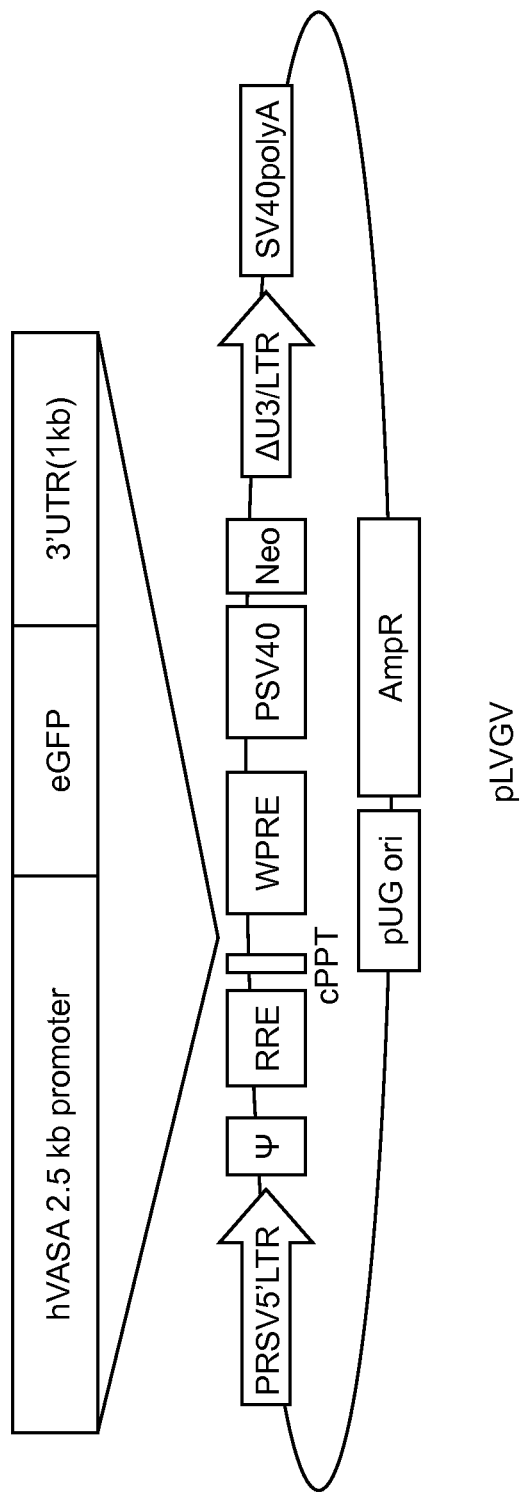
FIG. 8. Simplified diagram of the lentiviral VASA:GFP reporter construct, pLVGV. The reporter construct contains 2.5 kb of promoter sequence 5-prime to the human VASA open reading frame (ORF) to direct expression of eGFP (enhanced Green Fluorescent Protein) expression, followed by 1 kb of 3-prime untranslated region inserted into p2k7 lentiviral vector.
Figure 9:
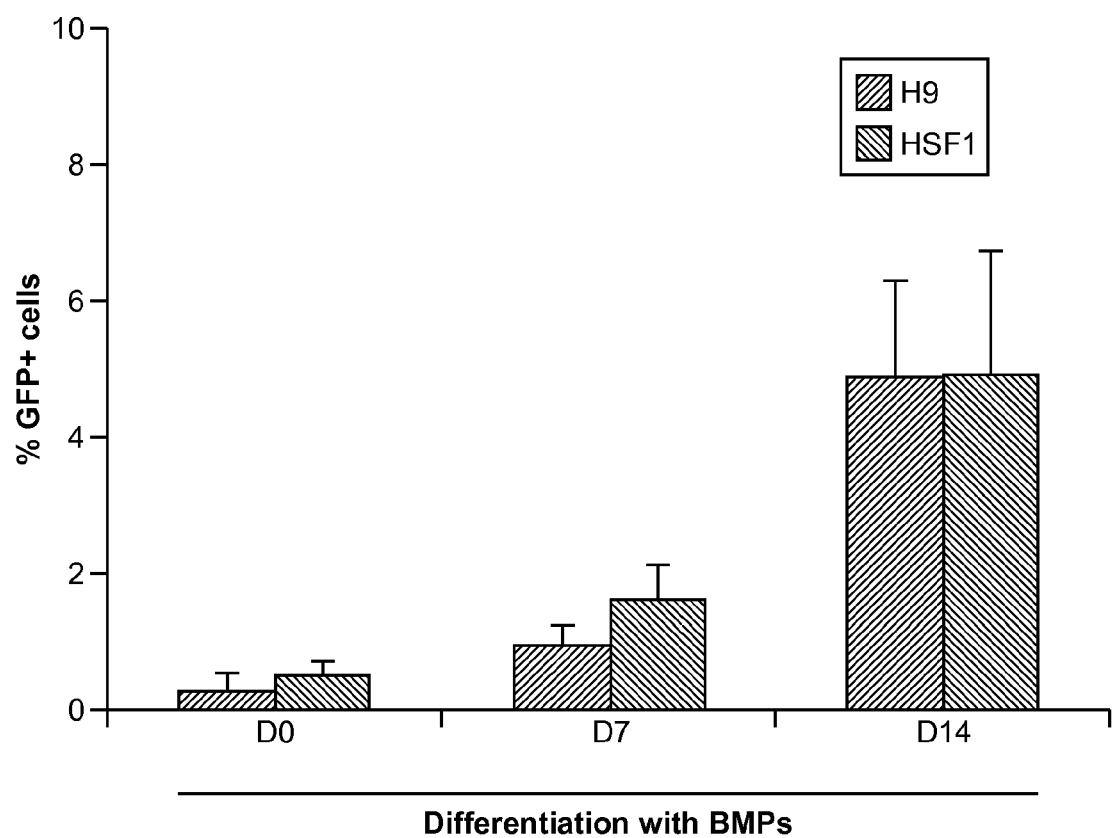
FIG. 9. Average percentages of VASA:GFP+ cells in female and male lines at three timepoints. Three independent cultures of H9 (XX) and HSF1 (XY) after 0, 7 and 14 days of differentiation with BMPs show similar levels of increase in the GFP+ population in both sexes (error bars are standard deviation, sd).

On the basis of these data and previous studies indicating that VASA is germ-cell specific, we constructed a VASA reporter to purify germ cells from the complex cell mixture resulting from human ES cell differentiation (FIG. 8). We introduced the reporter into undifferentiated human ES cells, and then following differentiation, isolated GFP+ cells (putative primordial germ cells (PGCs)) via fluorescence-activated cell sorting (FACS) (FIG. 1b). We observed that both XY- and XX-bearing human ES cells reproducibly gave rise to a GFP+ population after 7 and 14 days of differentiation, and that the percentage of GFP+ cells reached approximately 5% with addition of BMPs (FIG. 9). Protein analysis confirmed that the GFP+ cells are enriched for endogenous VASA and DAZL proteins (FIG. 1c). VASA protein was localized specifically to the cytoplasm of the GFP+ cells and was not detected in GFP− cells (FIG. 10a). Further analysis showed that, as expected, OCT4 protein was expressed most highly in undifferentiated human ES cells but also in both GFP+ and GFP− populations at lower levels due to differentiation (FIG. 10b).

Figure 11:
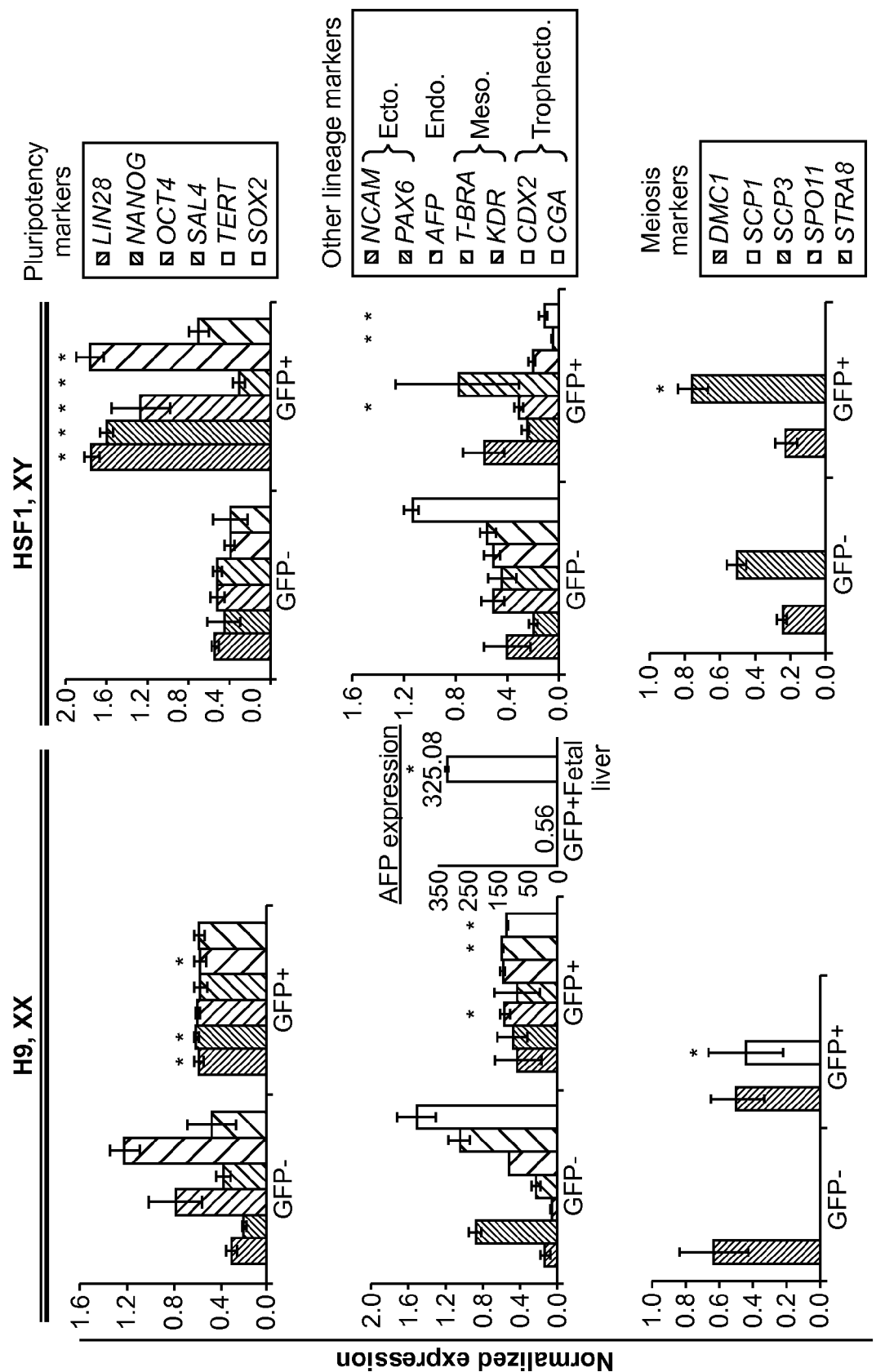
FIG. 11. Expression profiles of GFP− versus GFP+ population from H9 and HSF1 differentiated hESCs. Expression of LIN28, NANOG, OCT4 and TERT was higher in either H9 or HSF1 GFP+ cells, consistent with previous studies demonstrating the expressions of these genes was enriched in early germ cells. Among all somatic lineage markers, only AFP expression was found to be significantly higher in H9 GFP+ cells. However, it was much lower (<325 folds) than fetal liver. In addition, only SCP3 expression was slightly higher in GFP+ cells but four other meiosis markers were either not detected or not significantly higher in GFP+ cells. Hence, the marker analysis depicted GFP+ cells as early germ cells. Error bar=standard deviation; asterisk=significant difference by t-test (p<0.05), n=2.
Figure 12:
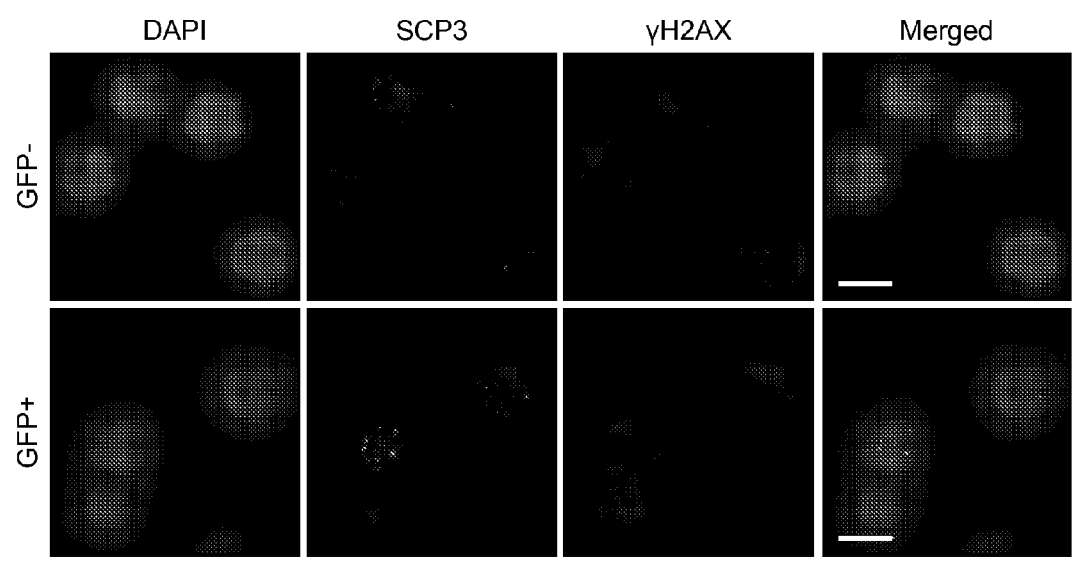
FIG. 12. Meiosis marker detection in FACS-isolated cells. No SCP3 or γH2AX staining was detected in GFP− cells and only a few foci of SCP3 were detected in GFP+ cells. Although slightly higher SCP3 RNA transcript was detected in GFP+ cells, 4 other meiosis markers were either not detected or not significantly higher in GFP+ cells. Taken together with the SCP3 and γH2AX immunostainings shown here, GFP+ cells most likely had not entered into meiotic prophase I. All cells were cytospun and fixed on slides for immunostaining. Scale bar is 10 micron.

Gene expression profiling was carried out on the GFP+ and GFP− populations. Early germ-cell markers such as DAZL, PRDM1 (also called BLIMP1), DPPA3 (also called STELLA) and VASA (also known as DDX4) were significantly enriched in the GFP+ populations (FIG. 1d), whereas those typically expressed during later stages of germ-cell differentiation were either not detected or not enriched, with the exception of low levels of synaptonemal complex protein 3 (SCP3) in the GFP+ population (FIG. 11). γH2AX and SCP3 immunostaining was used to examine meiotic progression throughout our experiments; γH2AX is an indicator of meiotic recombination based on binding to double-strand breaks and SCP3 is indicative of synaptonemal complex formation in meiotic prophase I. When the cells were stained for SCP3 and γH2AX, we observed that the GFP+ cells showed only low levels of scattered, punctate SCP3 staining in rare cells and there was no staining of γH2AX (FIG. 12). These results indicated that the GFP+ cells are probably at a pre-meiotic stage. We also observed that GFP+ cells were enriched for expression of a subset of pluripotency genes—LIN28, NANOG, OCT4 (also called POU5F1) and TERT—consistent with previous reports of their expression in human germ cells.

Figure 2:
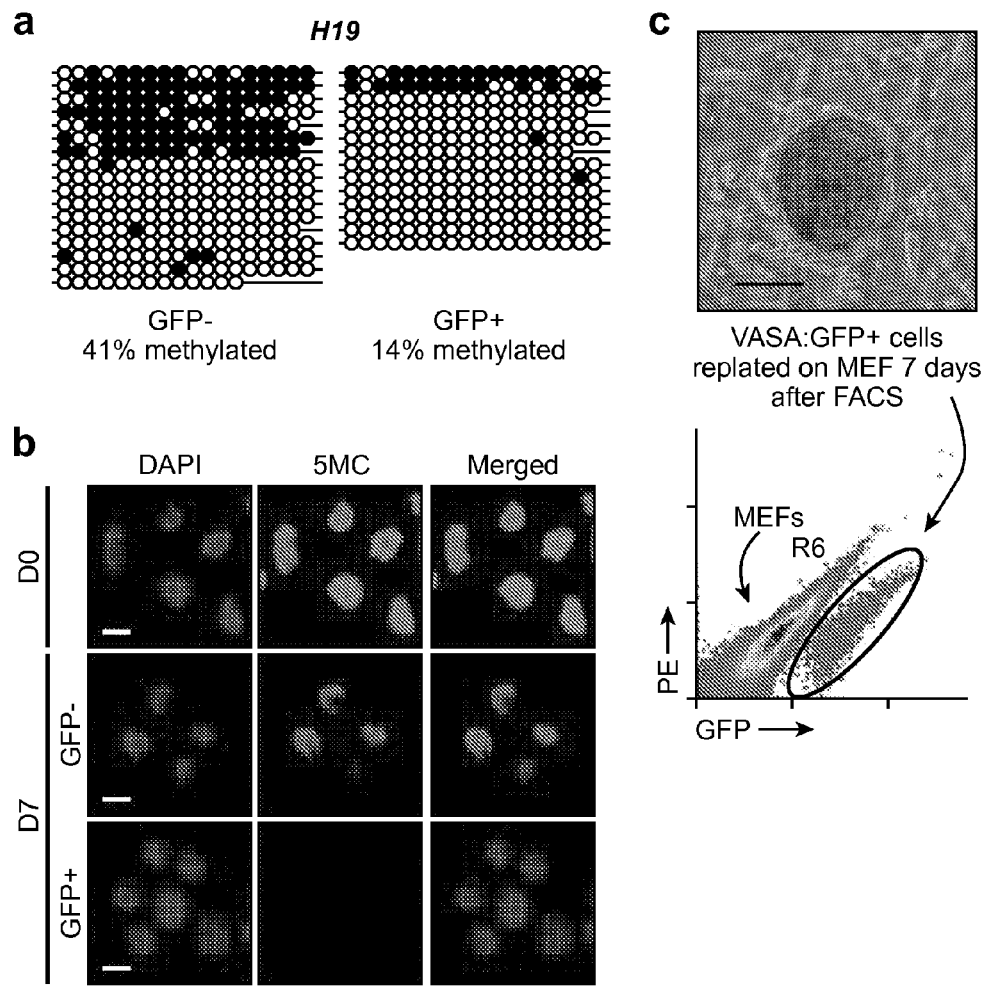
FIG. 2. Germ-cell properties of VASA-GFP+ cells. a, The GFP+ population was hypomethylated at the H19 locus. b, 5-methylcytosine staining of the VASA-GFP+ population to detect global methylation. Cells were immunostained using monoclonal 5-methylcytosine antibody. Images are taken at the same exposure time to show different levels of staining. c, Phase contrast pictures showing representative colony from GFP+ cells after 7 days of replating. No colonies were observed from plating of the GFP− population. FACS plot demonstrates that GFP+ cells maintained GFP expression after 7 days of replating on mouse embryonic fibroblasts (MEFs). Scale bars, 100 microns in c.
Figure 10:
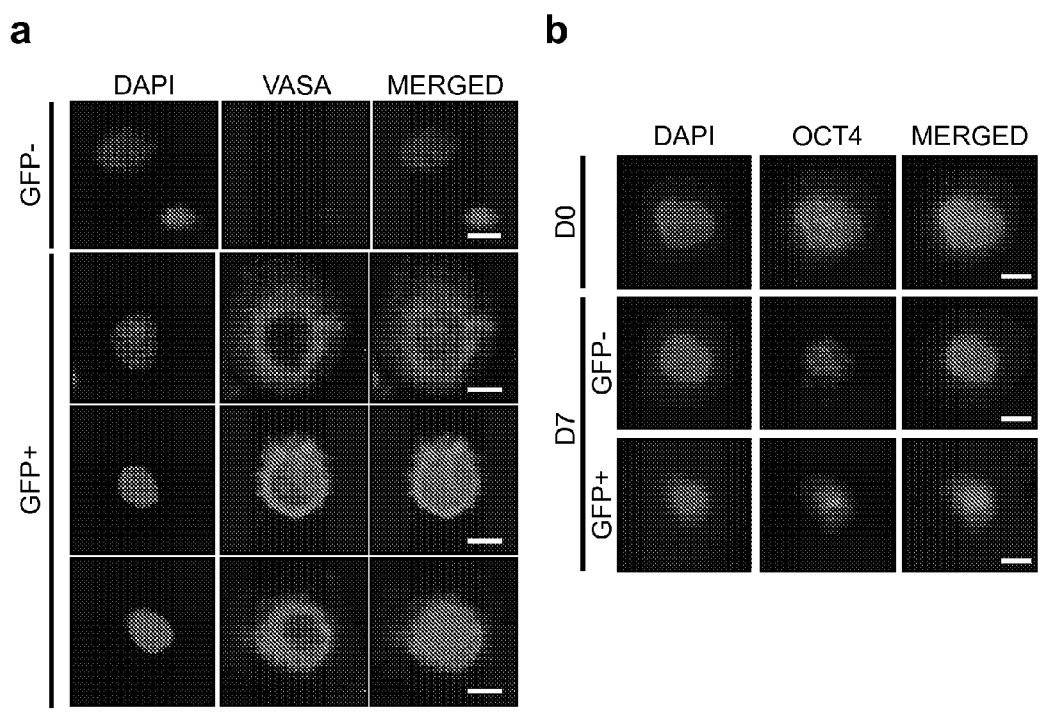
FIG. 10. VASA and OCT4 staining of FACS-isolated cells. a, VASA immunostaining of GFP− and GFP+ cells from Day 7 FACS-isolated samples. b, OCT4 immunostaining of Day 0 undifferentiated hESCs and Day 7 FACS-isolated cells. No VASA was detected in GFP− cells whereas VASA localized to cytoplasm of GFP+ cells. b, Punctate OCT4 staining was detected in nuclei of all three populations of cells but undifferentiated hESCs showed the strongest staining of OCT4. All cells were cytospun and fixed on slides for immunostaining. Scale bar is 10 micron.
Figure 13:
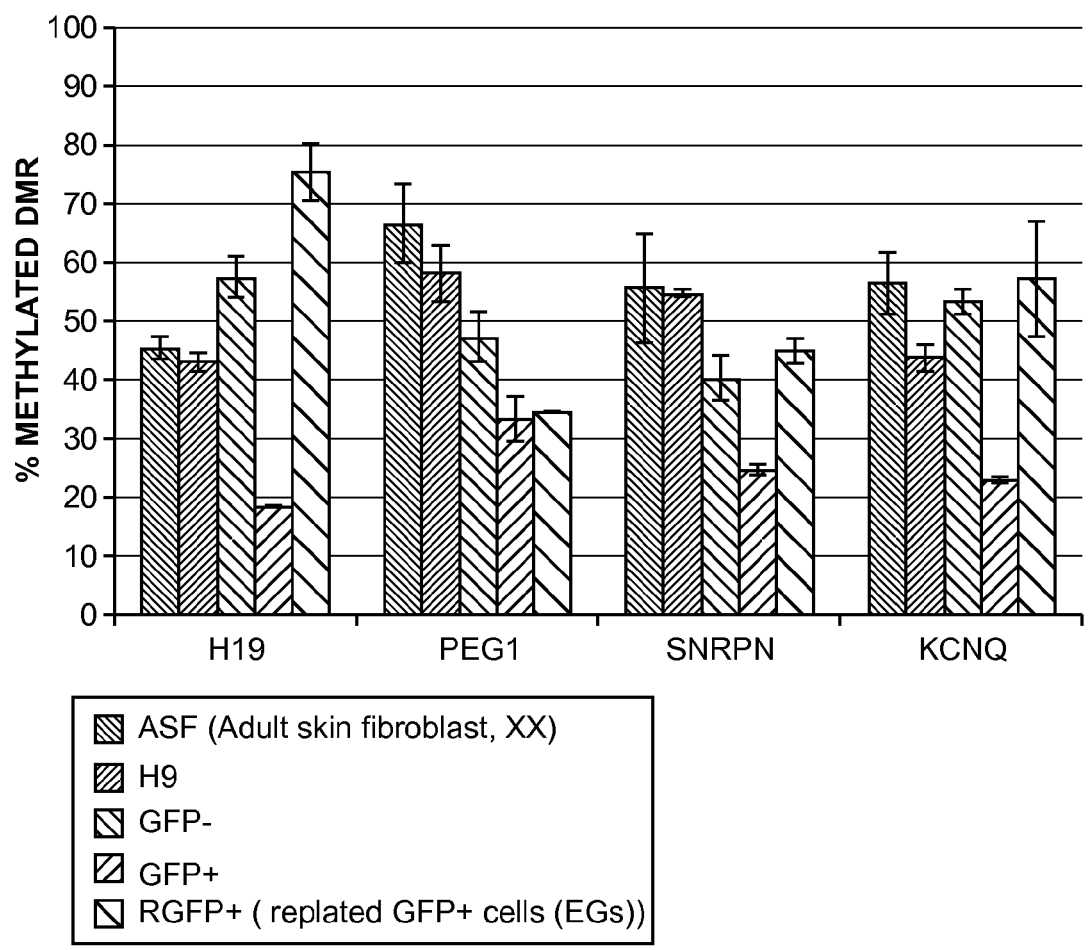
FIG. 13. Methylation status of various XX bearing cells at four imprinted DMRs. Genomic DNA of adult skin fibroblast (ASF), undifferentiated hESCs H9, GFP−, GFP+, and replated GFP+(RGFP) cells were subjected to methylation sensitive and dependent enzyme digestions. qPCR was carried out to measure the methylation level at DMRs of H19 (paternal imprinted), PEG1, SNRPN, and KCNQ (maternal imprinted) loci. Table shows the results of statistical tests for all samples and loci. GFP+ cells were hypomethylated at all four loci, consistent with bisulfite sequencing analysis and 5MC staining shown in FIG. 2. RGFP+ (EG) cells had increased methylation at DMRs of H19, SNRPN and KCNQ relative to freshly-isolated GFP+ cells, suggesting that prolonged culturing changed the methylation status of GFP+ cells. Error bar=standard deviation; asterisk=significant difference by Newman-Keuls test ($p<0.05$), n=3.

Epigenetic reprogramming is diagnostic of germ-cell differentiation (see, e.g. the methods of Hajkova, P. et al. (2002) Mech. Dev. 117: 15-23, which are incorporated herein by reference). Thus, we characterized erasure of methylation (hypomethylation) globally and at the differentially methylated regions (DMRs) of imprinted loci. We found that the H19 locus was hypomethylated in GFP+ cells relative to GFP− cells (FIG. 2a). Results from other imprinted loci (PEG1 (also called MEST), SNRPN, KCNQ) confirmed that the GFP+ cells also showed significantly lower levels of methylation at these DMRs relative to other cell types (FIG. 13, and Table 1 below). Furthermore, examination of global DNA methylation levels (5-methylcytosine (5mC); FIG. 2b) provided strong evidence that the VASA-GFP+ population is in the process of erasing methylation globally. Identity of the populations of GFP− and GFP+ cells was verified by staining for VASA and OCT4 (FIG. 10).

TABLE 1

GFP+ cells show significantly lower levels of methylation at DMRs H19, PEG1, SNRPN, and KCNQ relative to other cell types.

| XX Newman-Keuls Test | Mean Diff | q | Significant? P < 0.05? | Summary |
|---|---|---|---|---|
| H19 LOCUS | | | | |
| GFP+ vs RGFP+ | −57.18 | 25.36 | Yes | *** |
| GFP+ vs GFP− | −38.96 | 19.32 | Yes | *** |
| GFP+ vs ASF | −27.13 | 13.45 | Yes | *** |
| GFP+ vs H9 | −24.57 | 12.18 | Yes | *** |
| H9 vs RGFP+ | −32.61 | 14.46 | Yes | *** |
| H9 vs GFP− | −14.39 | 7.137 | Yes | ** |
| H9 vs ASF | −2.558 | 1.268 | No | ns |
| ASF vs RGFP+ | −30.05 | 13.33 | Yes | *** |
| ASF vs GFP− | −11.84 | 5.869 | Yes | ** |
| GFP− vs RGFP+ | −18.22 | 8.08 | Yes | *** |
| PEG1 LOCUS | | | | |
| GFP+ vs ASF | −33.13 | 12.3 | Yes | *** |
| GFP+ vs H9 | −24.67 | 9.159 | Yes | *** |
| GFP+ vs GFP− | −13.81 | 5.129 | Yes | * |
| GFP+ vs RGFP+ | −1.078 | 0.358 | No | ns |
| RGFP+ vs ASF | −32.05 | 10.64 | Yes | *** |
| RGFP+ vs H9 | −23.59 | 7.834 | Yes | *** |
| RGFP+ vs GFP− | −12.73 | 4.229 | Yes | * |
| GFP− vs ASF | −19.31 | 7.172 | Yes | ** |
| GFP− vs H9 | −10.85 | 4.031 | Yes | * |
| H9 vs ASF | −6.46 | 3.141 | No | ns |
| SNRPN LOCUS | | | | |
| GFP+ vs ASF | −34.04 | 6.685 | Yes | ** |
| GFP+ vs H9 | −24.83 | 4.877 | Yes | * |
| GFP+ vs RGFP+ | −15.17 | 2.664 | No | ns |
| GFP+ vs GFP− | −7.999 | . . . | No | ns |
| GFP− vs ASF | −26.04 | 5.114 | Yes | * |
| GFP− vs H9 | −16.83 | 3.306 | No | ns |
| GFP− vs RGFP+ | −7.169 | . . . | No | ns |
| RGFP+ vs ASF | −16.87 | 3.315 | No | ns |
| RGFP+ vs H9 | −9.663 | . . . | No | ns |
| H9 vs ASF | −9.209 | . . . | No | ns |
| KCNQ LOCUC | | | | |
| GFP+ vs RGFP+ | −32.86 | 8.47 | Yes | ** |
| GFP+ vs ASF | −32.14 | 9.26 | Yes | *** |
| GFP+ vs GFP− | −29.01 | 8.358 | Yes | *** |
| GFP+ vs H9 | −24.45 | 7.044 | Yes | *** |
| H9 vs RGFP+ | −8.417 | 2.169 | No | ns |
| H9 vs ASF | −7.691 | . . . | No | ns |
| H9 vs GFP− | −4.559 | . . . | No | ns |
| GFP− vs RGFP+ | −3.858 | . . . | No | ns |
| GFP− vs ASF | −3.132 | . . . | No | ns |
| ASF vs RGFP+ | −0.7262 | . . . | No | ns |

Figure 14:
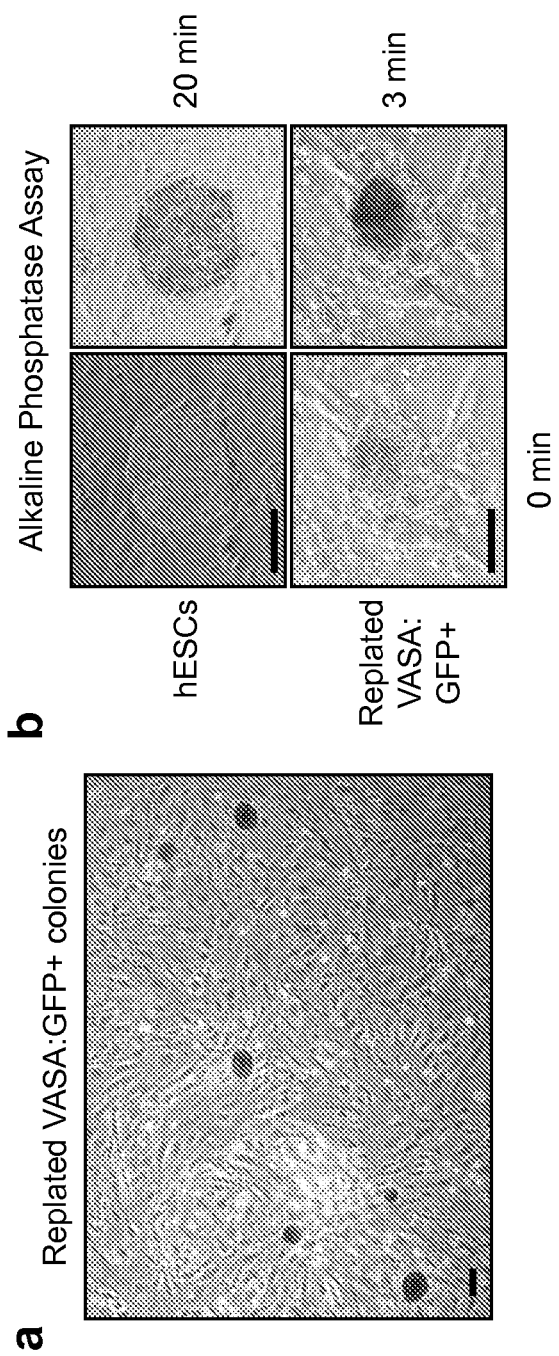
FIG. 14. Phase contrast images showing multiple colonies and alkaline phosphatase (AP) activity of the VASA:GFP+ replated colonies. a, Multiple colonies arise after 7 days of replating VASA:GFP+ cells onto inactivated MEFs. b, Clustered colony shows stronger AP activity after 3 min of staining than an undifferentiated hESC colony stained for 20 min. Scale bar indicates 100 micron in a and b.
Figure 15:
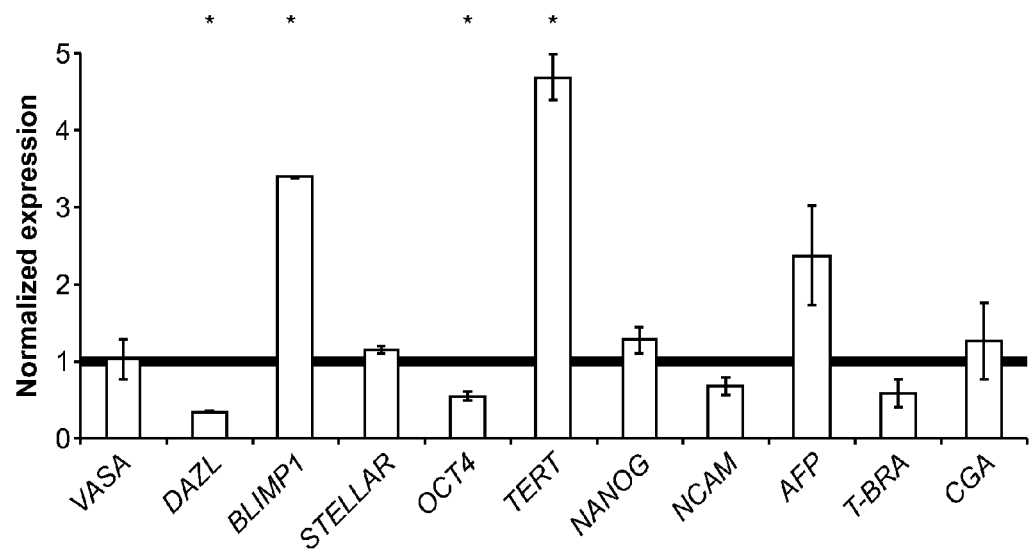
FIG. 15. Expression profiles of the replated VASA:GFP+ cells. Expression was normalized first to 4 housekeeping genes and to corresponding expressions of freshly isolated VASA:GFP+ cells without replating. Asterisk indicates a significant difference in expression to freshly isolated VASA:GFP+ cells at $p<0.05$, n=2.

PGCs possess the ability to establish embryonic germ-cell lines with diagnostic gene expression and morphology (see, e.g., the methods of Geijsen, N. et al. (2004) Nature 427: 148-154, and West, J. A. et al. (2009) Nature 460: 909-913, the disclosures of which are incorporated herein by reference). Thus, we tested whether GFP+ cells form embryonic germ lines on inactivated feeder cells in media lacking the growth factor basic fibroblast growth factor (bFGF). We found that the GFP+ cells gave rise to colonies that resembled embryonic germ cells after 7 days (FIG. 2c and FIG. 14a), whereas the GFP− cells did not give rise to any colonies. Similar to embryonic germ cells, replated GFP+ cells had intense alkaline phosphatase activity (FIG. 14b) and remained GFP+ after extensive culture (FIG. 2c). Gene expression profiles of replated cells (after 20 days) were similar to those of freshly isolated GFP+ cells, with a few exceptions (FIG. 15). We noted, however, that DMRs of replated cells had significantly more methylation after replating (FIG. 13). This is similar to previous reports with human ES cells (Rugg-Gunn, P. J. et al. (2005) Nature Genet. 37: 585-587) but had not been examined in human embryonic germ cells.

Figure 3:
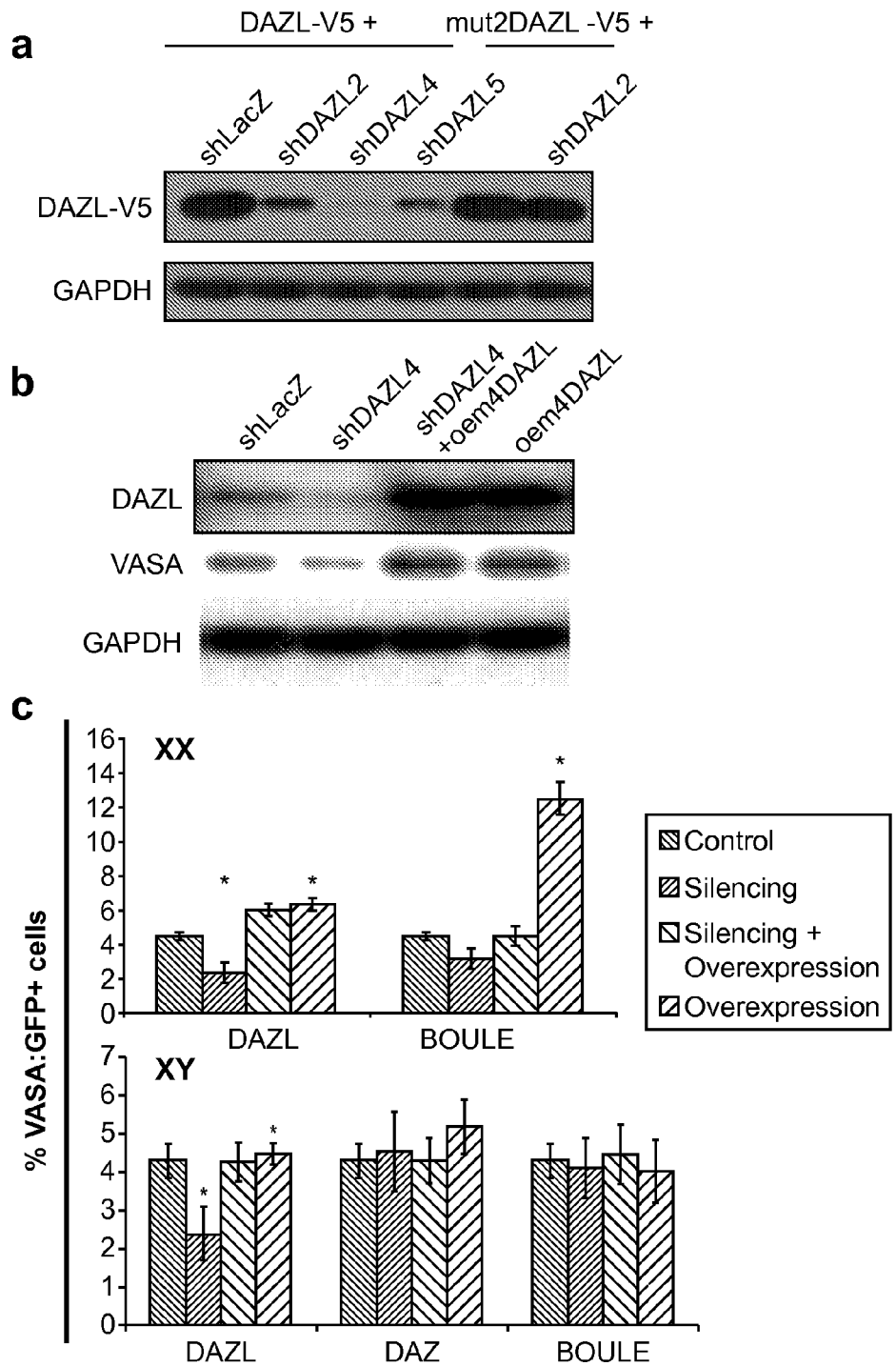
FIG. 3. Silencing of DAZ family members and germ-cell numbers. a, Western blot analysis of DAZL polypeptide fused to a V5 epitope tag (DAZL-V5) silenced by independent shDAZL constructs. DAZL-V5 was co-transfected with control (shLacZ) or shDAZL constructs in 293T cells. Mut2DAZL fused to the V5 tag (Mut2DAZL-V5) was resistant to shDAZL2. b, Western blot analysis of DAZL and VASA after silencing with shDAZL4 or rescue with over-expressed mutant 4DAZL (oem4DAZL) in human ES cells (H9). c, FACS results using H9 (XX line) and HSF1 (XY line) for silencing of DAZL, BOULE and DAZ. Error bars indicate standard deviation; asterisk, significant difference in percentage of VASA-GFP+ cells by one-way analysis of variance (ANOVA; P<0.05), n=2 (averages from two independently differentiated samples at 14 days).
Figure 16:
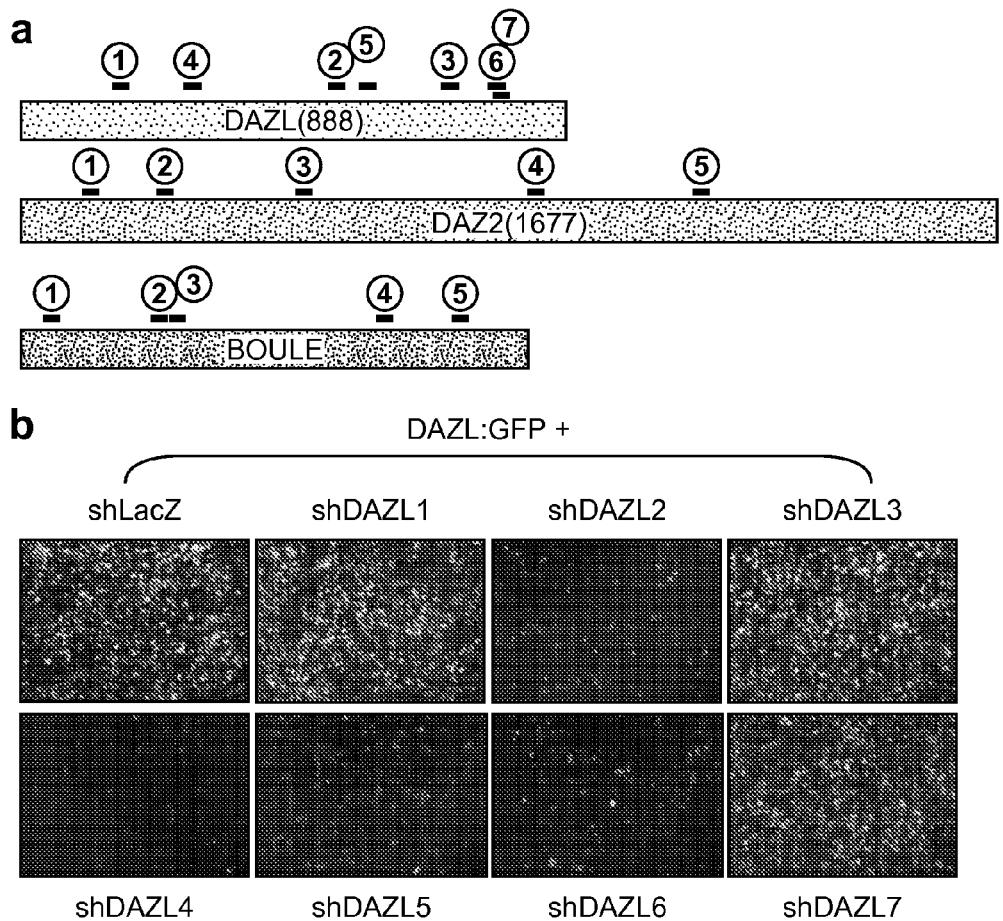
FIG. 16. Silencing of DAZ gene family members. a, shRNA target sites at DAZL, DAZ2, and BOULE. b, Silencing of DAZL:GFP by different shDAZLs. We identified 3 shRNAs which significantly reduced DAZL:GFP fusion protein expression when cotransfected in 293T cells. Initial screening of shDAZL1-3 showed that shDAZL2 (SEQ ID NO:22) was most effective, but additional screening of shDAZL4-7 identified shDAZL4 (SEQ ID NO:24) as the most effective silencer for DAZL. c, Synonymous mutations for shDAZL2 and shDAZL4. Changing 3-4 nucleotide sequences within shDAZL2 (mut2DAZL2, SEQ ID NO:41) and shDAZL4 (mutDAZL4, SEQ ID NO:42) targeting regions imparted resistance to silencing, as shown (FIG. 3.
Figure 17:
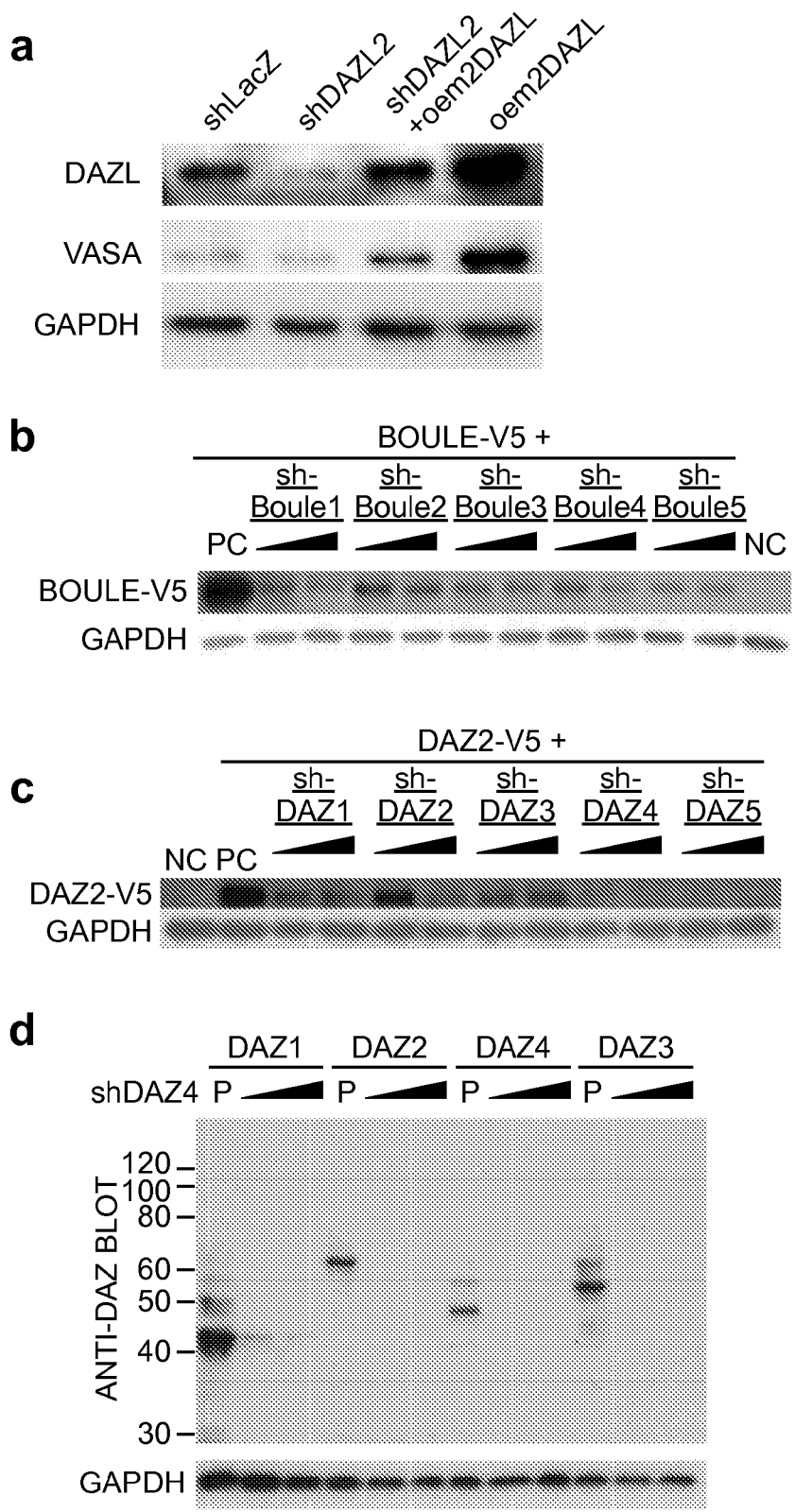
FIG. 17. Silencing of DAZL, DAZ and BOULE. a, Silencing of DAZL and VASA by shDAZL2 in hESCs. DAZL and VASA expression was reduced when shDAZL2 was expressed and rescued by overexpression of mut2DAZL. Similar to mut4DAZL (FIG. 3b), mut2DAZL elevated VASA expression in hESCs. b, Western analysis of BOULE silencing vectors. BOULE-V5 was cotransfected with control or 5 unique shBOULEs in 293T cells. PC was positive control with shLacZ vectors and NC was negative control without BOULE-V5 or silencing vectors. Two levels of silencing vectors were added to show the silencing effect is dependent on the level of transfected silencing vector. c, Western analysis of DAZ2 by silencing vectors. Same experimental design was used as in b. Four shRNAs (shDAZ1-4) were identified as being able to target all four copies of DAZ based on sequence comparisons, and another shRNA, shDAZ5, was identified as targeting DAZ2 only. When the five shDAZs were cotranfected with DAZ2-V5, shDAZ1, shDAZ3, shDAZ4 and shDAZ5 significantly decreased protein level of DAZ2-V5. d, Silencing of DAZ1-4 by shDAZ4 in 293FT cells. In the case of DAZ, there are four copies of the DAZ genes on the human Y chromosomes with highly-conserved sequences. Western analysis shows that all four DAZ proteins were silenced by shDAZ4.

Because gene expression, immunostaining, epigenetic status and the ability to give rise to colonies resembling embryonic germ cells strongly suggested that the GFP+ cells are PGCs, we next examined genetic requirements for formation and differentiation of human PGCs. We focused on the human DAZ gene family which contains three members: four human DAZ genes which are commonly deleted from the Y chromosome of infertile men who lack germ cells, and autosomal DAZL and BOULE homologues which are conserved from invertebrates to humans. We first silenced expression of the autosomal DAZL gene by short hairpin RNA (shRNA) technology (FIG. 16a, b) and observed reduced protein levels with three silencing constructs (FIG. 3a); specificity of silencing was confirmed with synonymous mutations (FIG. 16c). Changing just three nucleotides in the DAZL shRNA (shDAZL) targeting region created a mutated DAZL-V5 resistant to silencing (FIG. 3a). When human ES cells were stably integrated with DAZL silencing vectors and differentiated for 14 days with BMPs, expression of DAZL and VASA was significantly reduced in cells carrying two of the four shDAZL constructs, shDAZL4 and shDAZL2 (FIG. 3b and FIG. 17a). Overexpression of the mutated DAZL that was resistant to silencing resulted in rescue as observed by elevated DAZL and VASA protein expression. Notably, overexpression of DAZL alone elevated endogenous VASA levels relative to controls, indicating that VASA is regulated by DAZL.

Figure 18:
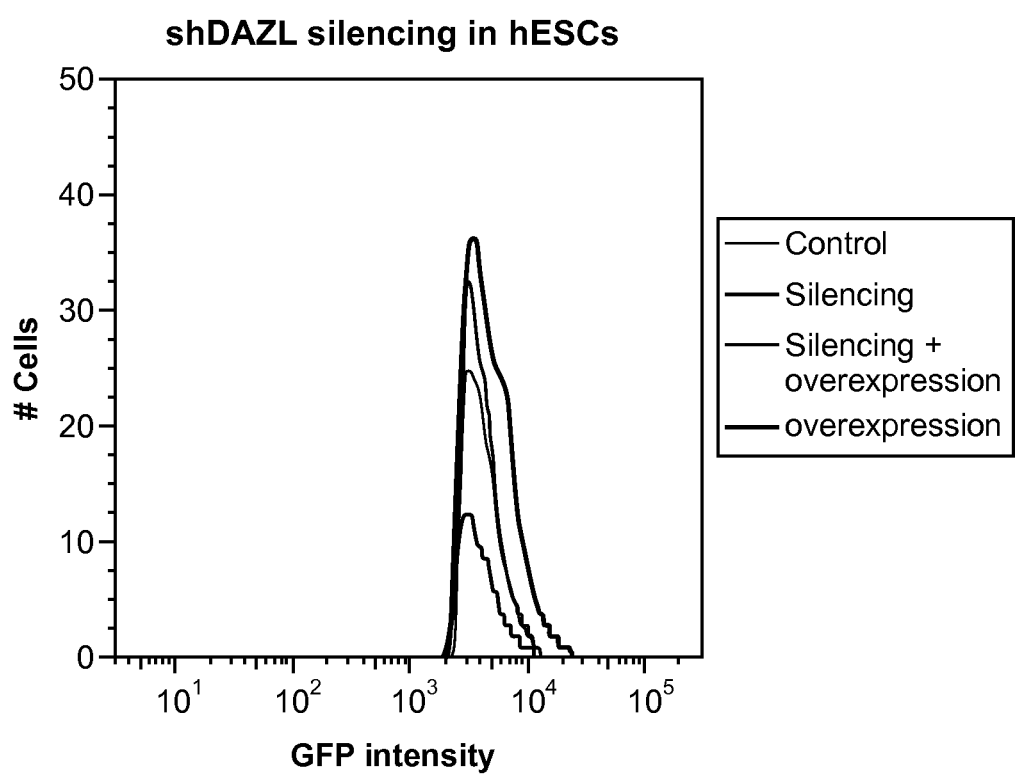
FIG. 18. VASA:GFP+ cells were reduced by shDAZL4 and rescued by overexpression of mut4DAZL. Histogram of FACS results with silencing of DAZL in H9 cells carrying the VASA:GFP reporter. >10,000 cells of each treatment were analyzed and compared.

To examine whether silencing of BOULE or DAZ affects PGC differentiation, we identified multiple shBOULE and shDAZ constructs that significantly reduced expression of BOULE and DAZ, respectively (FIG. 17b, c). We introduced the silencing constructs into human ES cells carrying the VASA-GFP reporter with individual shRNAs: shDAZL and shBOULE separately into H9 (XX), and shDAZL, shBOULE and shDAZ into HSF1 (XY). Corresponding target genes were also co-transduced to rescue silencing effects. We observed that the VASA-GFP$^+$ population was reduced to almost half by silencing DAZL in both XX and XY lines (FIG. 3c and FIG. 18; statistically significant in XX and marginal in XY cells). In contrast, silencing of BOULE reduced the GFP$^+$ population slightly in the XX line but not in the XY line, and the number of GFP$^+$ cells was unaffected when DAZ was silenced. Finally, overexpression of BOULE alone increased the VASA-GFP$^+$ population to nearly 12% in XX but not in XY cells, suggesting that BOULE has a more important role in directing human female PGC differentiation than male. Overexpression of combinations of DAZL, BOULE and DAZ did not result in synergistic enhancement of PGC formation.

Figure 4:
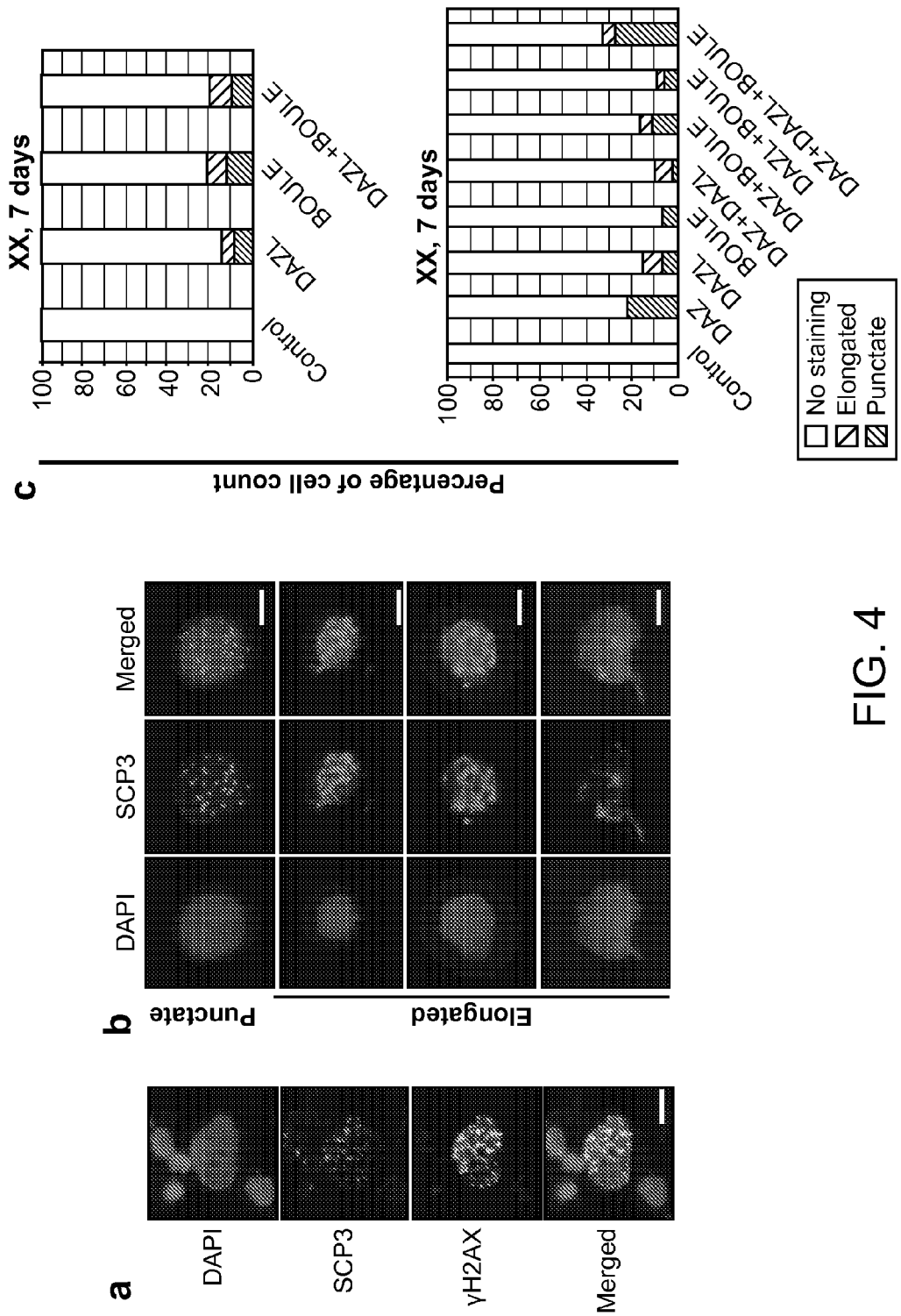
FIG. 4. Overexpression of DAZL, DAZ and BOULE induces meiotic progression and haploid formation. a, Meiotic spread from day 7 differentiated cells; immunofluorescence staining with SCP3 and γH2AX is shown. b, Meiotic cells overexpressing DAZ family proteins and stained for SCP3. c, Percentage of cells showing punctate or elongated SCP3 staining at day 7. A total of 200 meiotic spreads were counted and categorized for each sample. All scale bars, 10 microns. d, FACS of DNA content of human semen and cells overexpressing DAZL, DAZ and BOULE. e, Fluorescent in situ hybridization of chromosome 16 in cells sorted as 1N, 2N, 4N. f, Acrosin staining of 1N population from human semen and HSF1 with three overexpression vectors. All cells were from whole cultures without GFP FACS.
Figure 4:
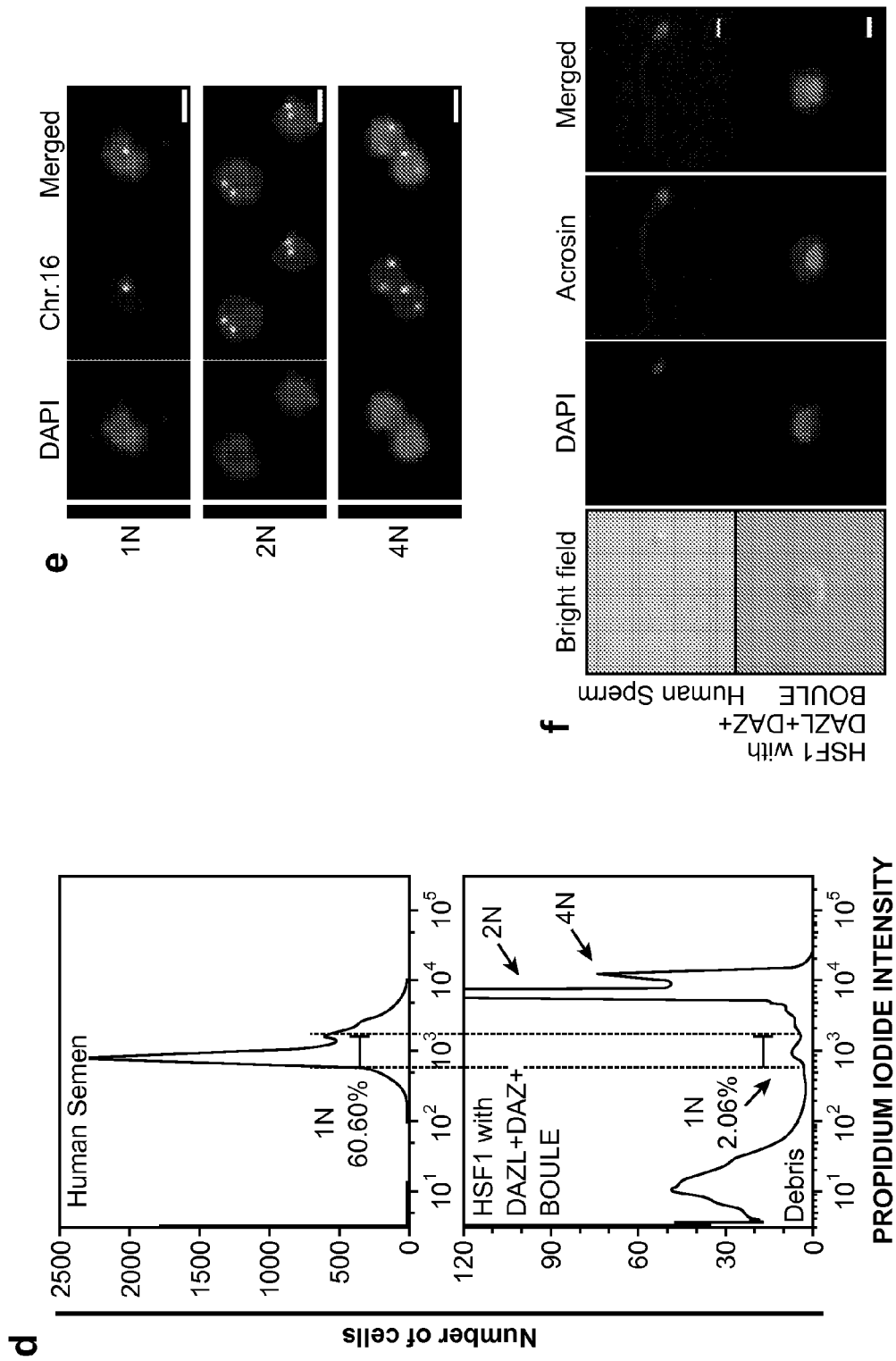

The data above suggested that overexpression of DAZL, and BOULE (in XX lines), promotes PGC formation. We next examined if overexpression of these genes promotes germ-cell differentiation beyond the PGC stage. Thus, combinations of vectors that overexpressed DAZ gene family members were introduced into XX and XY human ES cells. Human ES cells were differentiated for 7 days in the absence of BMPs (to test whether internal factors alone can induce late germ-cell differentiation) and examined for meiotic progression. The majority of nuclei from differentiated human ES cells showed no obvious γH2AX staining (including nuclei that did not enter meiosis and those that might have completed meiosis) (FIG. 4a). When γH2AX was detected in the nuclei, it was accompanied by more than ten punctate SCP3 foci, indicating that the nuclei had entered meiotic prophase I. Elongated SCP3 localization with different intensities and lengths was also detected but was not accompanied by γH2AX staining (FIG. 4b). This staining pattern probably corresponds to that of synaptonemal complexes at zygotene, pachytene or diplotene stages. To quantify synaptonemal complex formation, we categorized SCP3 staining as punctate or elongated, and counted the percentage of nuclei in each category and those negative for SCP3. Overexpression of DAZL, BOULE, or a combination of both gave similar results at day 7 in the XX line (FIG. 4c). In XY cells, overexpression of DAZ, DAZL and BOULE resulted in the highest percentage of cells with SCP3 staining (FIG. 4c and FIG. 19). Indeed, overexpression of DAZ alone gave rise to more than 20% of cells with punctate SCP3, much more than DAZL or BOULE alone. We infer that overexpression of DAZL or BOULE was sufficient to induce elongated synaptonemal complex formation in the XY line, but the addition of DAZ provided the highest level of synaptonemal complex formation.

Figure 20:
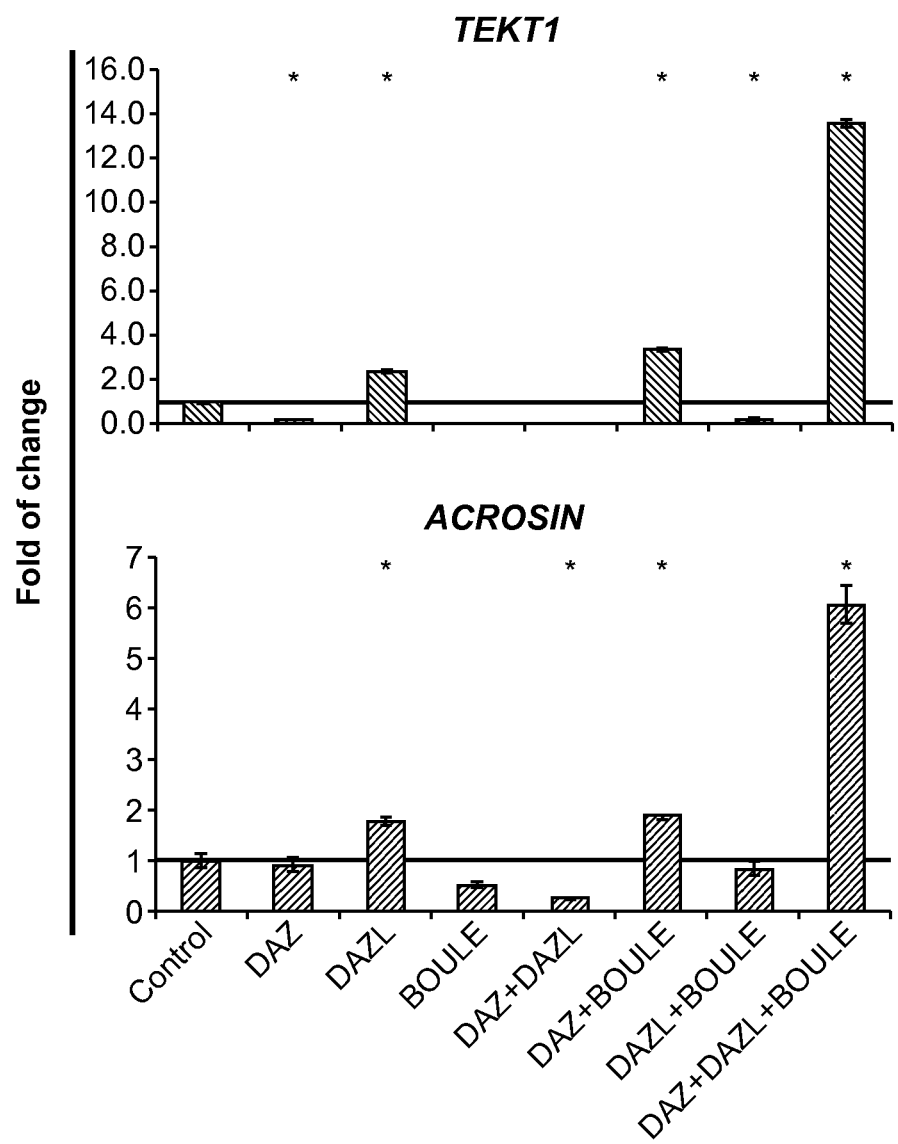
FIG. 20. Expression of TEKT1 and ACROSIN in the XY line with overexpression of different factors. Differentiated hESCs (Day 14) without BMPs and without FACS were subjected to RNA extraction and qPCR analysis. Expression was normalized to 4 housekeeping genes followed by normalization to control (carrying empty overexpression vector). Asterisk indicates significant difference compared to control sample at $p<0.05$. Overexpression of DAZ, DAZL, and BOULE together induced the highest TEKT1 and ACROSIN expression, consistent with the DNA content and ACROSIN immunostaining results shown on FIG. 4d, f. The high percentage of meiotic cells at both Days 7 and 14 indicates clearly that meiotic progression is not synchronized. Moreover, ACROSIN and TEKT1 expression was only enriched in the cells at Day 14, but not at Day 7 (data not shown). Thus, at other days, such as Days 8 or 9, cells are unlikely to have completed meiosis to form 1N cells. Error bar=standard deviation; asterisk=significant difference from control cells by one-way ANOVA test ($p<0.05$), n=2.
Figure 21:
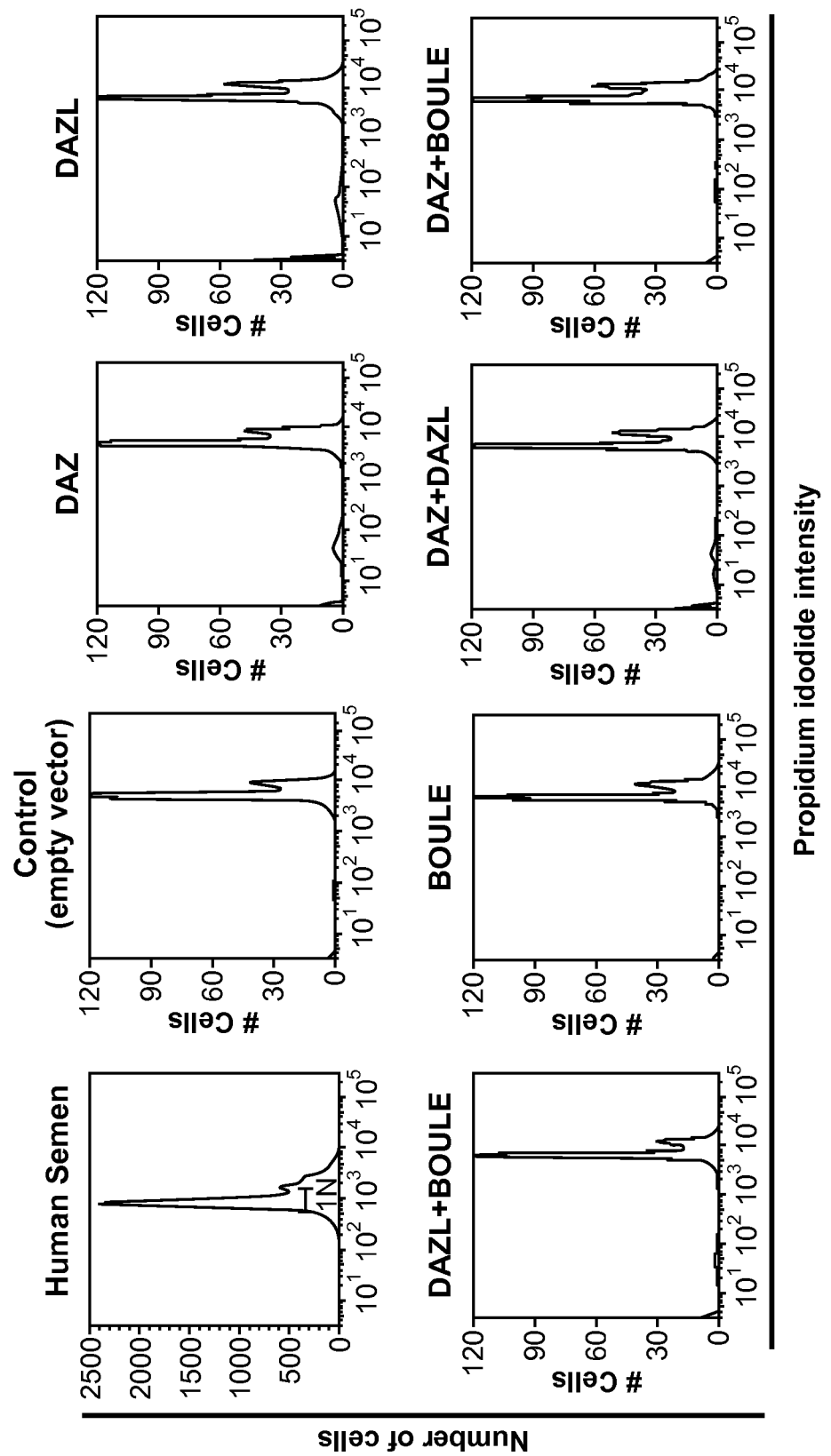
FIG. 21. DNA content (FACS) of human semen and control cells. Control hESCs carrying empty overexpression vector and different combinations of DAZ, DAZL, and BOULE. No specific population of 1N cells was detected at the scale setting at which the 1N sperm was detected by using human semen sample. In contrast, a small but significant peak/population was detected in cells with overexpression of DAZ, DAZL, and BOULE together (FIG. 4d).
Figure 22:
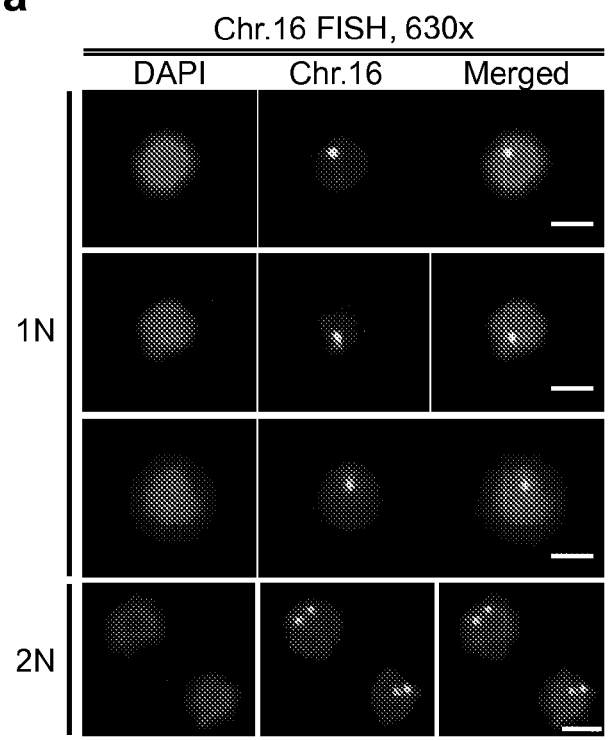
FIG. 22. Additional FISH staining and ACROSIN immunostaining at high resolution. a, Fluorescent in situ hybridization (FISH) with probe against chromosome 16 in the sorted 1N cells and 2N cells. FACS-isolated cells were cytospun onto slides and fixed for FISH analysis. Denaturation of samples at 85° C. is required before specific DNA probe can bind to target chromosome sequence, in this analysis, autosomal chromosome 16. b, ACROSIN staining of the FACS-isolated 1N cells and control cells without any overexpression factors. Independent cell sample was used for this staining because denaturation step in FISH would denature ACROSIN making immunodetection of the antigen difficult. Scale bar is 10 micron.
Figure 22:
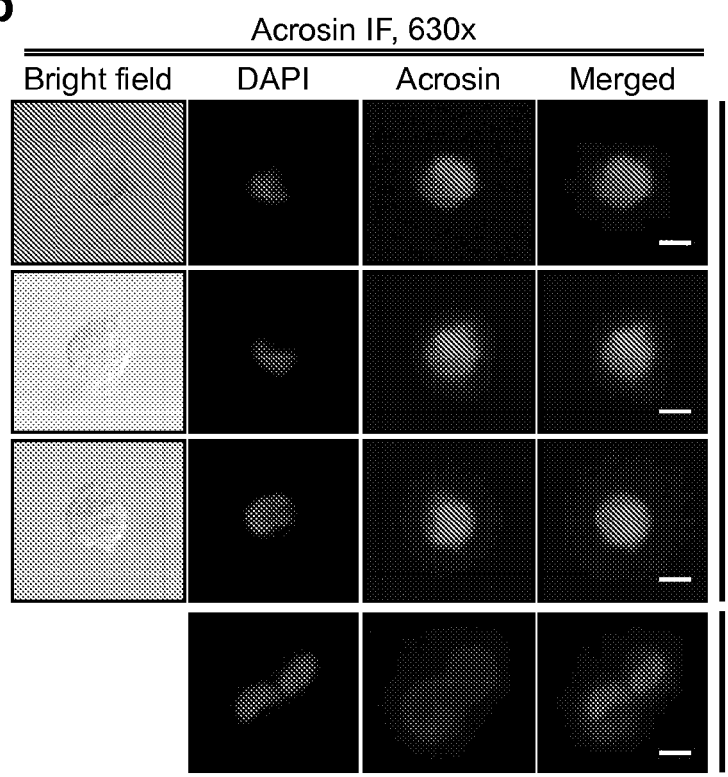
Figure 23:
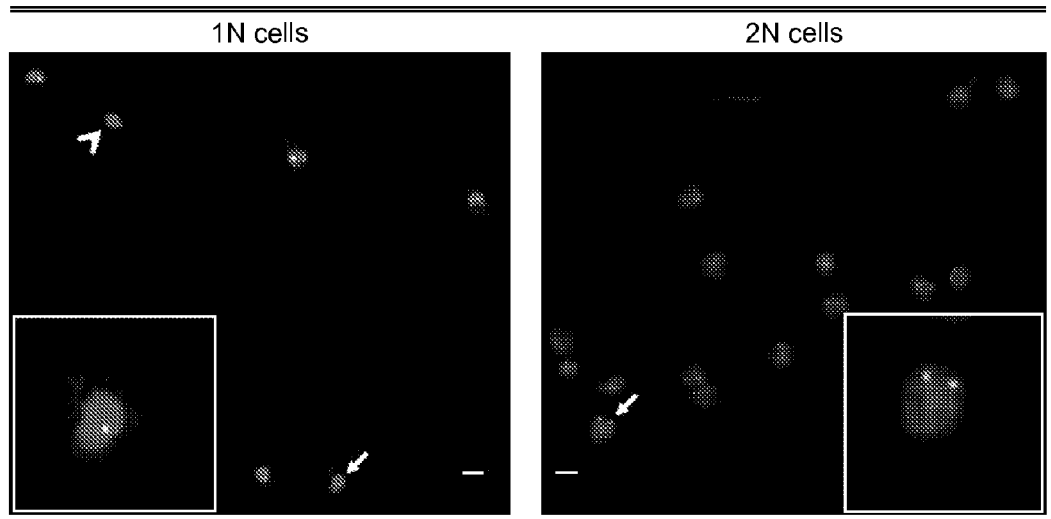
FIG. 23. Whole population FISH analysis of 1N and 2N cells with quantification of purity. All cells were FACS-isolated and cytospun onto slides before FISH procedures. Insets depict the cells labeled with arrows. The FACS profile is shown on the lower left and the purity quantification is shown on the lower right. 89 out of 100 cells had single focus of chromosome 16 probe, indicating single copy of chromosome 16. 11 out of 100 cells of the 1N FACS-isolated cells had two chromosome 16 (for example, the cell labeled with arrowhead at the upper left hand corner of the 1N cells image), suggesting incomplete detection of propidium iodide of 2N cells during FACS isolation or inherent chromosome aneuploidy of these cells. 2N cells had 100 out of 100 cells with 2 chromosome 16, indicating high purity of this population. Scale bar is 10 micron.
Figure 23:
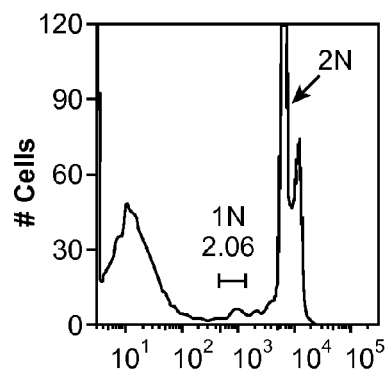
Figure 24:
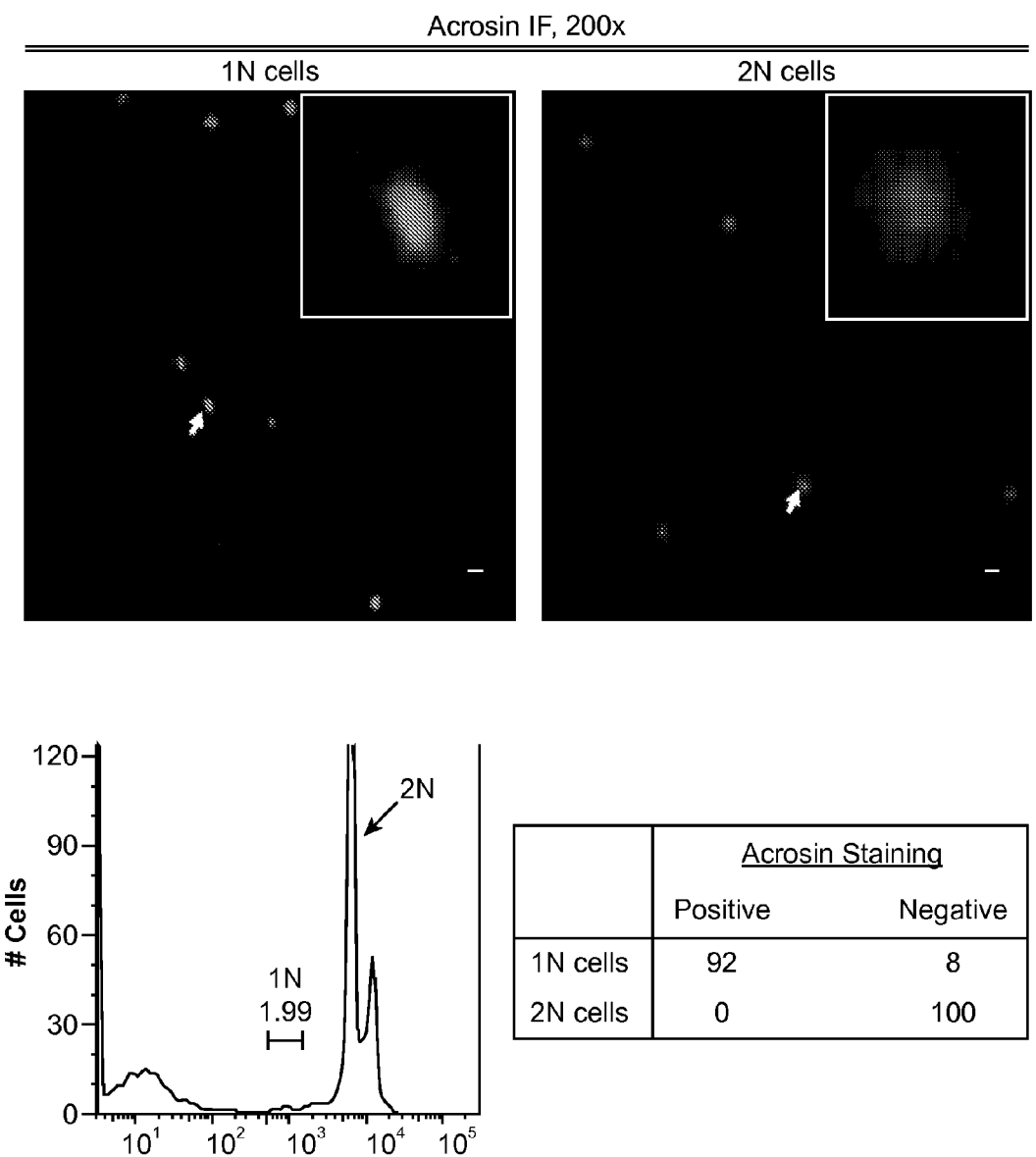
FIG. 24. Whole population ACROSIN analysis of 1N and 2N cells with quantification of purity. All cells were FACS-isolated and cytospun onto slide before immunostaining procedures. Insets depict the cells labeled with arrows. The FACS profile is shown on the lower left and the purity quantification is shown on the lower right. 92 out of 100 of 1N cells had strong ACROSIN staining and 8 cells had low or no detectable level of ACROSIN staining. In contrast, 2N cells showed no ACROSIN staining in all cells. Hence, 1N cells are strongly correlated with ACROSIN staining, supporting the FISH results that these cells are haploid cells and expressing spermatid/sperm marker, ACROSIN.
Figure 25:
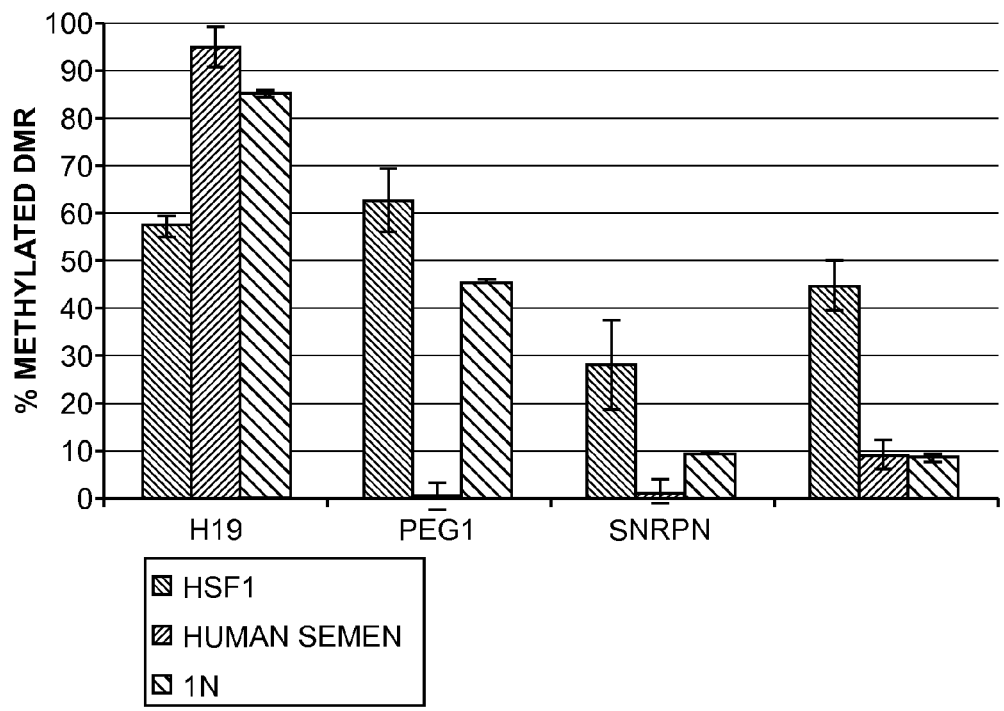
FIG. 25. Methylation status of various XY bearing cells at four imprinted differentially methylated regions (DMRs). Genomic DNA of undifferentiated HSF1, human semen and 1N FACS-isolated cells was subjected to methylation sensitive and dependent enzyme digestions. qPCR was carried out to measure the methylation level at DMRs of H19 (paternal imprinted) and PEG1, SNRPN, KCNQ (maternal imprinted) loci. Lower panel shows DNA content profile of the 1N cells used in this analysis. 1N cells had similar profiles as human semen at H19, SNRPN and KCNQ, but not PEG1. Both 1N cells and human semen showed expected imprinted pattern at H19, SNPRN and KCNQ, i.e., hypomethylated at the maternal loci and hypermethylated at paternal locus. The difference at PEG1 suggested incomplete erasure of the 1N cells possibly caused by in vitro differentiation. Error bar=standard deviation; asterisk=significant difference by Newman-Keuls test ($p<0.05$), n=3. See also Table 2 in the Examples section below, which shows results of statistical tests for all samples and loci.
Figure 25:
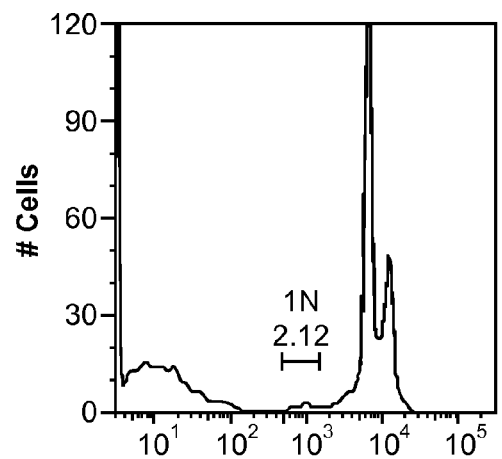
Figure 26:
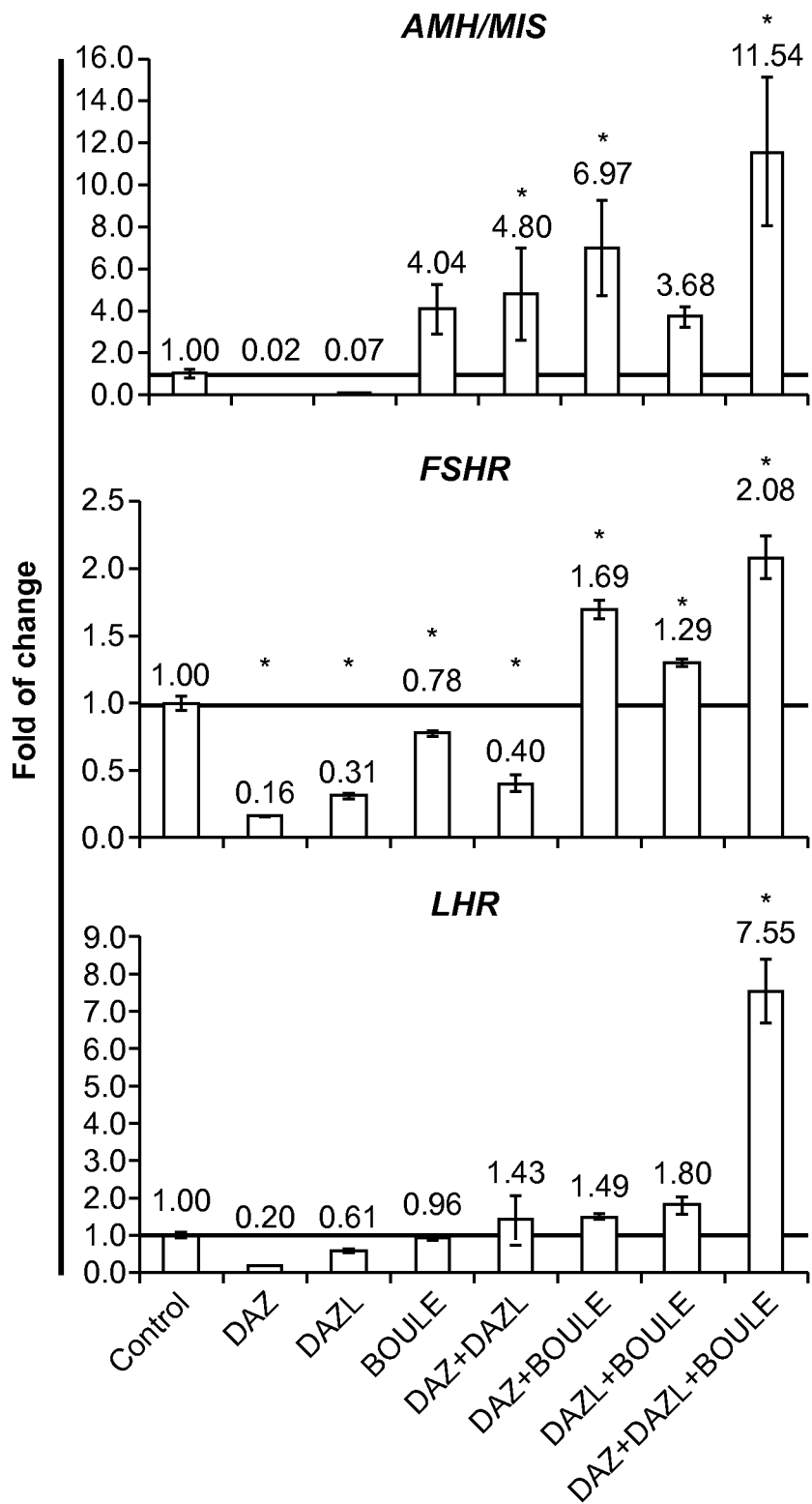
FIG. 26. Expression of Sertoli and Leydig cell markers in the XY line with different overexpression factors. Day 14 differentiated hESCs (without BMPs) were subjected to RNA extraction and qPCR analysis. Expression was normalized to 4 housekeeping genes followed by normalization to control (carrying empty overexpression vector). Asterisk indicates significant difference compared to control sample at $p<0.05$. Overexpression of DAZ, DAZL, and BOULE together was associated with the highest AMH/MIS, FSHR, LHR, SOX9 expression, suggesting the presence of Sertoli and Leydig cells in the differentiated hESC cultures. All cells are collected from whole differentiated culture without FACS for GFP+ cells. Error bar=standard deviation; asterisk=significant difference from control cells by one-way ANOVA test ($p<0.05$), n=3.
Figure 26:
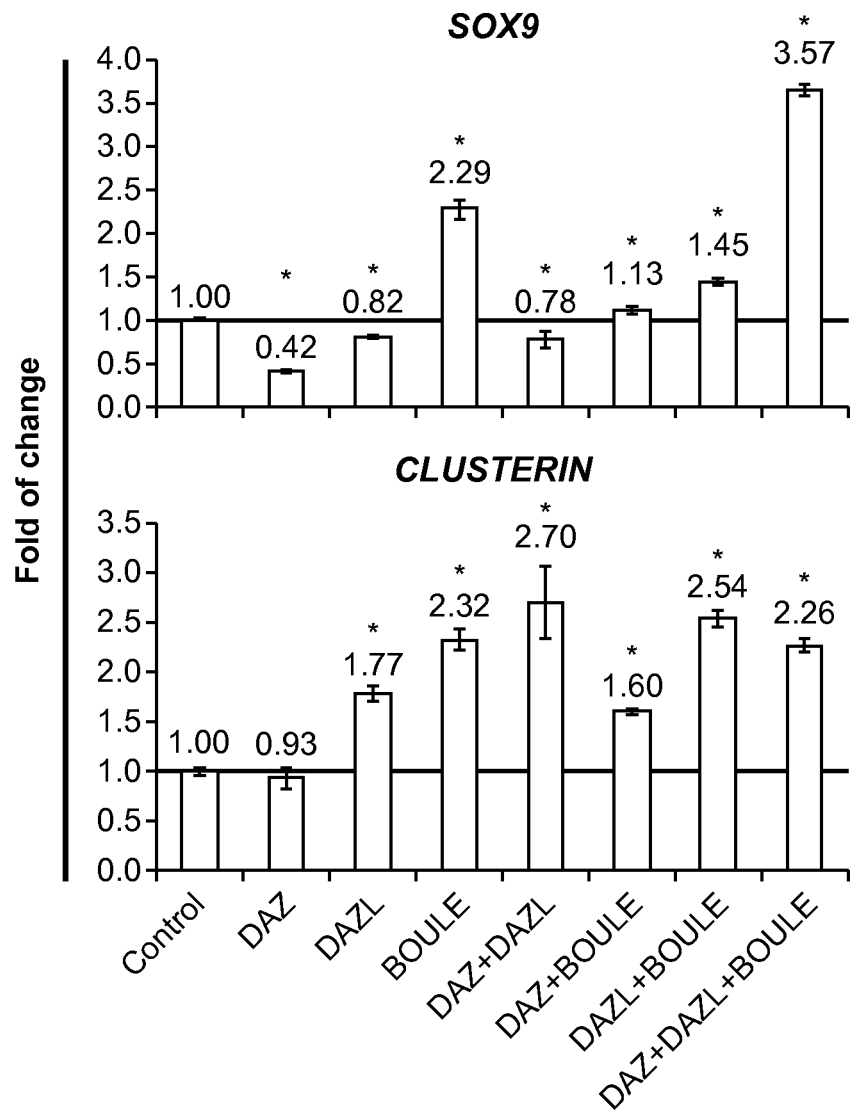

We next determined if haploid cells were produced. We found that messenger RNA expression of the mature sperm markers TEKT1 and acrosin (ACR) was highly elevated in cells that overexpressed all three family members at day 14 (FIG. 20), suggesting potential formation of haploid gametes. Moreover, when cells were sorted by DNA content (using parameters developed to sort 1N cells from a human semen sample obtained from the Stanford IVF Clinic), ~2% of cells had 1N content on day 14 after overexpression of DAZL, BOULE and DAZ. No corresponding haploid cells were isolated from control cells that lacked overexpression of DAZ gene family members (FIG. 4d and FIG. 21). DNA content was confirmed by fluorescent in situ hybridization (FISH) using a probe for chromosome 16. As expected, sorted 1N cells possessed a single chromosome 16, whereas 2N and 4N cells carried 2 and 4 chromosomes, respectively (FIG. 4e, FIG. 22a and FIG. 23). In addition, most 1N cells also expressed the mature sperm protein ACR, which is present from spermatid to spermatozoan stage (FIG. 4f, FIG. 22b and FIG. 24). In contrast, 2N cells differentiated in the same culture were negative for ACR. We also observed that the H19 DMR was hypermethylated in 1N cells, whereas, SNRPN and KCNQ DMRs were hypomethylated with patterns similar to those detected in human semen (FIG. 25, and Table 2, below). Finally, we observed that expression of the genes AMH (also called MIS), FSHR, LHCGR (also called LHR) and SOX9 was greater in cultures that produced the highest number of germ cells (overexpressed DAZ, DAZL and BOULE proteins; in whole culture without FACS), indicating increased numbers of Sertoli and Leydig cells in the same differentiated cultures to support maturation of male germ cells (FIG. 26).

TABLE 2

Methylation status of various XY bearing cells at four imprinted differentially methylated regions (DMRs); results of statistical tests for all samples and loci.

| XY Newman-Keuls Test | Mean Diff. | q | Significant? P < 0.05? | Summary |
|---|---|---|---|---|
| H19 LOCUS | | | | |
| HSF1 vs HS | −37.7 | 9.958 | Yes | ** |
| HSF1 vs 1N | −23.37 | 6.173 | Yes | ** |
| 1N vs HS | −14.33 | 3.785 | Yes | * |
| PEG1 LOCUS | | | | |
| HS vs HSF1 | −62.06 | 44.8 | Yes | *** |
| HS vs 1N | −44.97 | 32.45 | Yes | *** |
| 1N vs HSF1 | −17.09 | 12.34 | Yes | *** |
| SNRPN LOCUS | | | | |
| HS vs HSF1 | −26.52 | 5.179 | Yes | * |
| HS vs 1N | −16.83 | 3.287 | No | ns |
| 1N vs HSF1 | −9.692 | 1.893 | No | ns |
| KCNQ LOCUS | | | | |
| 1N vs HSF1 | −36.14 | 24.11 | Yes | *** |
| 1N vs HS | −0.689 | 0.4598 | No | ns |
| HS vs HSF1 | −35.45 | 26.44 | Yes | *** |

Our results indicate that human germ cells can be differentiated and isolated from pluripotent human ES cells and that they possess the ability to enter and progress through meiosis. Moreover, we observed that members of the human DAZ gene family that encode translational regulators modulate both germ-cell formation and differentiation. The human DAZL and BOULE genes function in PGC formation, whereas DAZ, DAZL and BOULE function to promote germ-cell progression to meiosis and formation of haploid germ cells that resemble round spermatids in cellular and molecular characteristics.

Example 2

Materials and Methods

Cell culture. Human ESCs H9 (XX) and HSF1 (XY), human fetal derived iPSC line iPS(IMR90) (XX) and human adult derived iPSC line iHUF4 (XY; lentiviral transfection with OCT3/4, SOX2, KLF4 and C-MYC) were used in the experiments. Human ES cells and iPS cells were maintained on irradiated mouse embryonic fibroblasts (MEFs) in KoDMEM culture medium for ES cells and DMEM/F12 for iPS cells supplemented with 20% KnockOut serum replacer, 2 mM L-glutamine, 0.1 mM nonessential amino acids, 10 ng/ml basic FGF (all from Invitrogen, Carlsbad, Calif.) and 0.1 mM 2-mercaptoethanol (Millipore, Billerrica, Mass.). Cells were passaged onto fresh MEFs every 3-5 days using 1 mg/ml Collagenase IV (Invitrogen). The feeder-free culture was maintained on matrigel (BD Biosciences, Bedford, Mass.) coated plates with culture medium conditioned on MEFs for 24 hours. Cells were differentiated on matrigel coated plates with differentiation medium, KoDMEM supplemented with 20% fetal bovine serum (Hyclone Laboratories, Logan, Utah), 2 mM L-Glutamine, 0.1 mM nonessential amino acids, 0.1 mM 2-mercaptoethanol and 50 ng/ml BMP-4, BMP-7 and BMP-8b (R&D systems, Minneapolis, Minn.).

Immunostaining of Fixed Cells.

Undifferentiated cells and cells differentiated for 7 or 14 days were fixed with 4% paraformaldehyde (USB corporation, Cleveland, Ohio) for 15 min and washed 3×5 min with PBS (Invitrogen). Cells were then permeabilized with 0.3% Triton X-100 (Sigma Aldrich) in PBS for 30 min and blocked with 4% chicken serum (Sigma Aldrich) in PBS for 30 min. Rabbit polyclonal anti-VASA primary antibody (Abcam, Cambridge, England) was used with 1:200 dilution and incubated overnight at +4° C. Cells were washed 3×5 min with 0.1% Tween-20 (Sigma Aldrich) in PBS. Chicken anti-rabbit Alexa 488 secondary antibody (Invitrogen) was used with a dilution of 1:300 and incubated for 1 h at room temperature. Cells were washed again 3×5 min with 0.1% Tween-20 in PBS and 1 ng of DAPI (Sigma Aldrich) was added to the cells. The amount of VASA positive cells was quantified of counting an average of 2,500 cells for each sample group.

Western Analysis.

Adherent cell cultures were incubated with TrypLE (Invitrogen) for 10 minutes and collected by scraping. Cells were washed twice with PBS and resuspended with RIPA buffer (Sigma) plus 2× protease inhibitors (Complete Mini, Roche). Sample tubes were rocked for 20 min and centrifuge for 20 min with 13,000 rpm at +4° C. Supernatant was measured for protein concentration and denatured at a 1:1 ratio with 2× Laemmli buffer at 95° C. for 5 min, then loaded onto 10% SDS-PAGE gel. The gels were run at 150 volts for 70 min (DAZL) or 85 min (VASA) and transferred to a PVDF membrane for one hour at 100 volts in CAPS buffer (10 mM CAPS, 10% methanol, pH 11). Transferred blots were blocked in 5% non-fat milk for one hour at room temperature. The blot was incubated overnight at +4° C. with primary antibody (1:500 for anti-VASA (Abcam), 1:500 for anti-DAZL-1 50 (prepared by the lab), 1:10,000 for anti-GAPDH (Abcam)), followed by 2 rinses and 3×5 min washes in TBST (TBS, pH7.5, with 0.1% Tween 20). Secondary antibody (1:10,000 anti-rabbit-HRP conjugated (Amersham) was incubated for 1 hour with the same washes. ECL+(Amersham) was used to detect the HRP signal on film.

Gene Expression Analysis.

Total RNA was prepared as described in the RNeasy Mini Kit (Qiagen, Valencia, Calif.) with on-column DNase I digestion. About 1 µg total RNA from each sample was used for random primed reverse transcription, which was carried out as described in the product protocol (SuperScript™ III First-Strand Synthesis System for RT-PCR, Invitrogen). 1.25 µl of the cDNA was pre-amplified using 96 different 0.2× Taqman assays (Applied Biosystems, Carlsbad, Calif.) as primers in a reaction; 5 µl 2× buffer (from CellsDirect™ One-Step qRT-PCR kit, Invitrogen), 2.5 µl Taqman assay mix, 0.25 µl TE buffer, 1 µl Platinum Taq (Invitrogen) and 1.25 µl cDNA. Reactions were completed using a PCR reaction of 95° C. for 10 min and 14 cycles of 95° C. for 15 s and 60° C. for 4 min. The preamplified cDNA was diluted 1:2 with TE buffer and used for the Biomark 96.96 gene expression chip (Fluidigm). Transcription levels were determined in triplicate reactions and normalized to two housekeeping genes (GAPDH and RPLPO) chosen based on their stability by the qBasePlus software (Biogazelle, Zulte, Belgium). ΔΔCt values were calculated with the formula $2^{-(\Delta\Delta Ct)}$.

Meiotic Spreads.

Cells were collected and resuspended to 500 µl of hypoextraction buffer (30 mM Tris (Sigma Aldrich), 50 mM Sucrose (Sigma Aldrich), 17 mM Citric acid (Sigma Aldrich), 5 mM EDTA (Invitrogen), 2 tablets of Complete Mini, pH 8.2). Solution was incubated 30 min on ice and spun down. The cell pellet was resuspended in 20 µl of hypoextraction buffer and 60 µl of 100 mM sucrose. Solution was dropped on a slide that was dipped into 1% PFA and 0.15% TritonX-100 and then incubated overnight at +4° C. The slide was washed with PBS and incubated 5 min with 0.04% photoflo (KODAK, Hertfordshire, England) followed by blocking 60 min with 4% goat serum in 1% BSA, 0.1 Tween-20 in PBS. Rabbit polyclonal anti-SCP3 primary antibody (Novus Biologicals, Littleton, Colo.) was used at 1:1,000 dilution and mouse polyclonal anti-CENP-A antibody was used at 1:500 dilution and incubated for 3 hours at room temperature. Slide was washed with 1% BSA+0.1% Tween-20 in PBS and goat anti-rabbit Alexa 594 and goat anti-mouse Alexa 488 secondary antibodies (Invitrogen) were applied in 1:1,000 dilution and incubated 1 hour at room temperature. The slide was washed and ProLong Gold antifade reagent with DAPI (Invitrogen) was applied.

Overexpression of DAZL, BOULE and DAZ.

Cells on matrigel were transduced with lentiviral overexpression vectors for DAZL, BOULE and in addition DAZ for XY cell lines (see Example 1) supplemented with polybrene (Sigma Aldrich) to a final concentration of 8 µg/ml. The transduction was done overnight at 37° C. using ⅓ DAZL, ⅓ of BOULE and ⅓ of DAZ overexpression viral supernatant or conditioned medium. Cells were selected in conditioned medium with 2 µg/ml blasticidin (Invitrogen) for 3 days, after which the differentiation was started with the differentiation medium described above.

Statistical Analysis.

For the quantification of VASA immunostaining, Chi square test was used to compare all four cell lines within each group, undifferentiated cells, differentiated for 7 days and differentiated for 14 days. Significance was accepted at $p<0.01$. The statistical analysis of gene expression data was performed with one-way ANOVA, followed by the Bonferroni posttest. All four cell lines were compared within each time group, undifferentiated, 4 days differentiated, 7 days differentiated and 14 days differentiated cells for each gene separately. Significance was accepted at $p<0.01$.

Results

Mammalian somatic cells can be reprogrammed to a fate similar to embryonic stem cells via the introduction of a small set of transcription factors (see, e.g., Yu, J. & Thomson, J (2008) *Genes Dev* 22: 1987-1997; Maherali, N. et al. (2007) *Cell Stem Cells* 1: 55-70; Wernig, M. et al. (2007) *Nature* 448: 318-325; Park, I. et al. (2008) *Nature* 451: 141-146; Takahashi, K. & Yamanaka, S (2006) *Cell* 126: 663-676; Takahashi, K. et al. (2007) *Cell* 131: 861-872; and Takahashi, K. et al. (2007) *Nature Protoc* 2: 3081-3089). Initially, the derivation of induced pluripotent stem cells (iPSCs) from mouse embryonic and adult fibroblast cultures was demonstrated via introduction of retroviral constructs that encode Oct3/4, Sox2, c-Myc and Klf4. Subsequently, the derivation of human iPSCs from both fetal and adult fibroblasts was demonstrated via introduction of the same four factors or an alternate combination of OCT3/4, SOX2, LIN28, and NANOG (see, e.g., Takahashi, K. et al. (2007) *Cell* 131: 861-872; Yu, J. et al. (2007) *Science* 318:1917-1920). Regardless of the gene combination, the human iPSCs were remarkably similar to human embryonic stem cells (hESCs) in their morphology, culture and proliferation, gene expression, and ability to differentiate to mesoderm, endoderm and ectoderm both in vitro and in vivo in teratoma assays. However, the potential of human iPSCs derived from both fetal and adult somatic cells to differentiate to germ cells has not been documented. At best, a recent report suggested that iPSCs derived from fetal cells may differentiate to primordial germ cells; however, no evidence of functional entry into meiosis, a diagnostic property of germ cells, was provided. Thus, in this study, we assessed the potential of a human adult-derived iPSC line (iHUF4; karyotype 46:XY) and a previously-derived human fetal iPSC line, iPS(IMR90) (karyotype 46:XX), to differentiate to both germ cells and somatic cells relative to hESCs (H9; karyotype 46:XX and HSF1; karyotype 46:XY). The ability to reprogram human adult somatic cells to an embryonic state capable of differentiating to immature and mature germ cells may provide the platform for many basic studies and potential clinical applications related to germ cell depletion.

Figure 27:
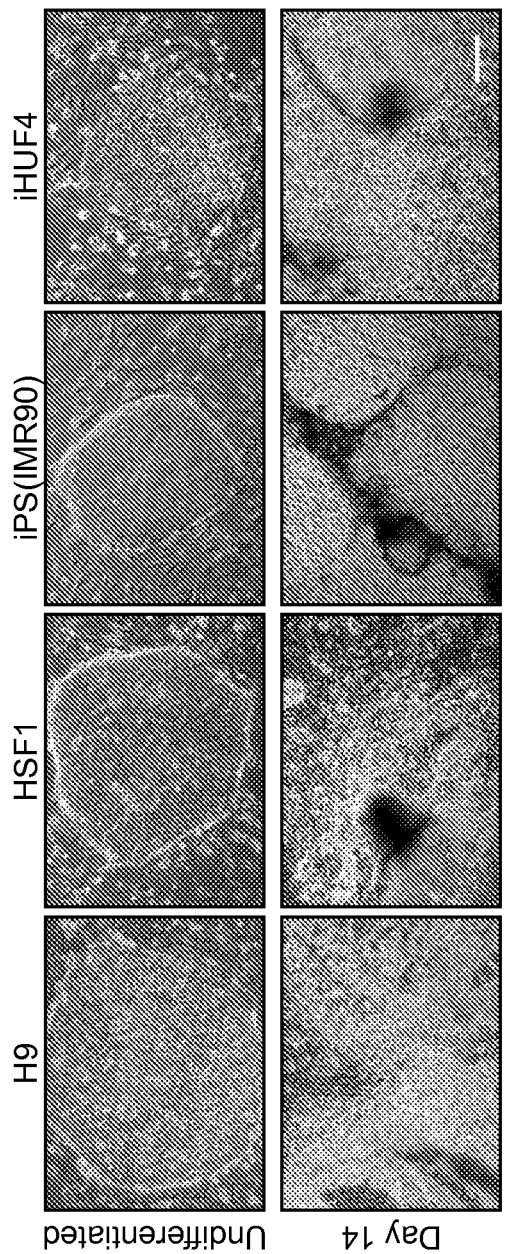
FIG. 27. Morphology of undifferentiated cell colonies and cells differentiated as adherent culture. H9, HSF1, iPS (IMR90) and iHUF4 undifferentiated cells were routinely cultured on MEFs. Cells were differentiated as adherent cultures with media supplement with BMPs. After 14 days of differentiation, cultures appeared confluent, with cell morphology distinct from the undifferentiated cells for all the cell lines. Scale bar 200 μm.
Figure 28:
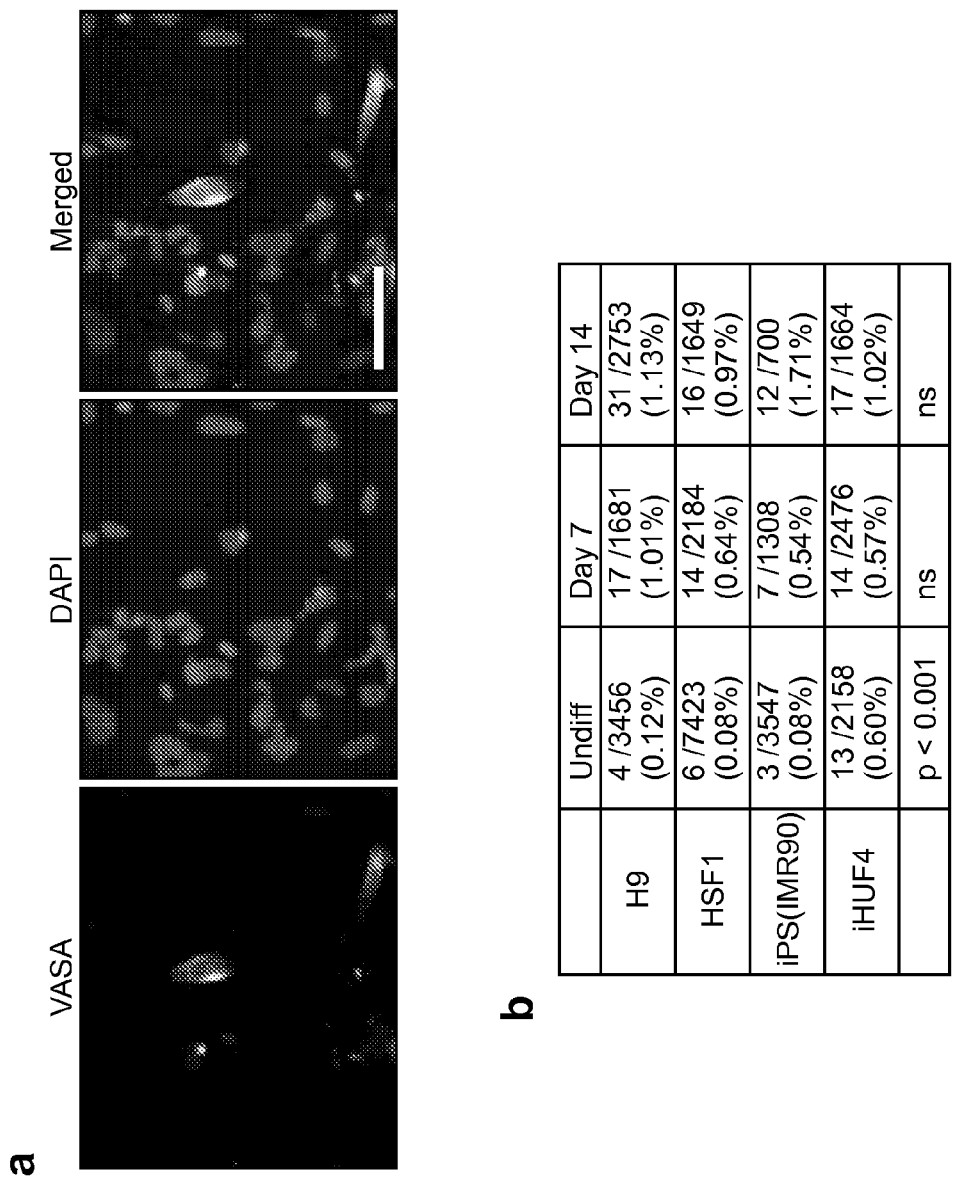
FIG. 28. hESCs and iPSCs differentiate to primordial germ cells shown by immunostaining and Western analysis. (a) Cytoplasmic VASA staining was observed for all cell lines. Representative images are shown. (b) Cells with VASA staining were quantified for all four cell lines for undifferentiated cells and cells differentiated for 7 and 14 days. (c) Western analysis of VASA and DAZL protein expression for undifferentiated and differentiated hESCs and iPSCs. GAPDH is shown as a loading control and 293T cells are negative controls. Two independently differentiated samples are shown for each time point for all cell lines. Scale bar 100 μm (a).
Figure 28:
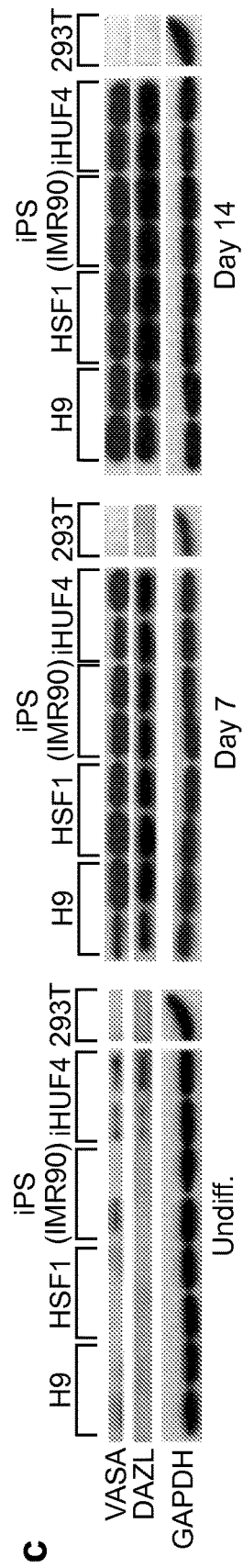
Figure 31:
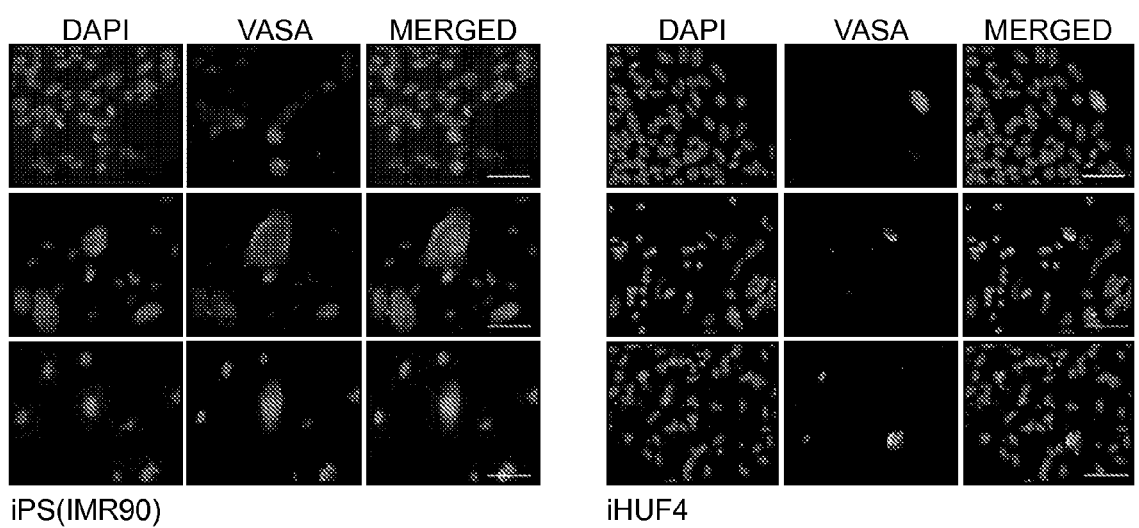
FIG. 31. Immunohistochemistry for the presence of VASA protein in iPSCs. Scale bar 100 μm.

Human ESCs can be differentiated to primordial germ cells in the presence of bone morphogenetic proteins (BMPs) -4, -7 and -8b. Using feeder-free adherent differentiation in the presence of BMPs, we differentiated the iPSC lines, iHUF4 and iPS(IMR90), and the hESC lines H9 and HSF1 for 7 and 14 days. We observed that all cell lines maintained similar colony morphology in routine culture: after 14 days of differentiation, culture wells were confluent and cells of all lines acquired a morphology distinct from undifferentiated cells (FIG. 27). Cells were assayed by immunostaining for the presence of VASA protein. VASA (DDX4) is a putative RNA helicase specifically expressed in germ cells and conserved in diverse species from fruit flies to humans. The cells with clear and bright cytoplasmic VASA staining were identified and counted. We observed the presence of a subset of cells positive for VASA protein in all cell lines, with the highest percentage of VASA positive cells after 14 days of differentiation (1.71%; FIG. 28*a-b* and FIG. 31). We noted that 0.60% VASA positive cells in undifferentiated iHUF4 cells was significantly higher relative to all other undifferentiated cell lines (0.12%, 0.08%, 0.08%), at a level similar to cells differentiated for 7 days (1.01%, 0.64%, 0.54%; FIG. 28*b*). Results were confirmed by Western analysis of VASA protein and the germ cell-specific DAZL (Deleted in AZoospermia-Like) protein in cell lysates; in both cases, we observed increased expression of both VASA and DAZL proteins with differentiation (FIG. 28*c*). In addition, we detected a low level of VASA and DAZL protein expression in undifferentiated iHUF4 cells, as well as in one sample of the undifferentiated iPS(IMR90) cells, confirming the presence of a subpopulation of cells expressing germ cell markers even in the undifferentiated state.

Figure 29:
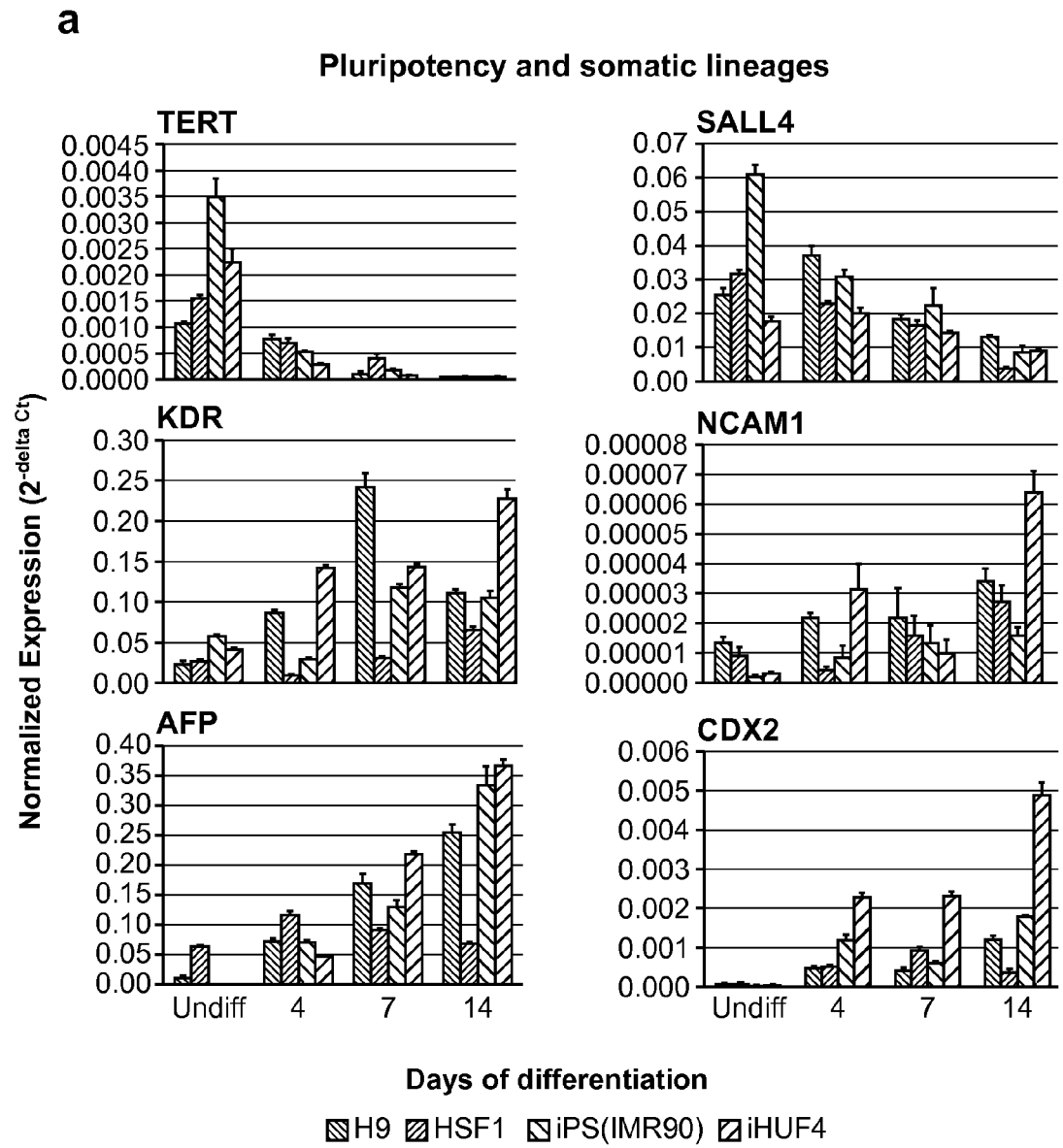
FIG. 29. Gene expression of undifferentiated cells and cells differentiated for 4, 7, or 14 days. (a) Decreased expression of pluripotency markers, TERT and SALL4, is indicative of differentiation, which is further shown by the increased expression levels of KDR (mesodermal marker), NCAM1 (ectodermal marker), AFP (endodermal marker) and CDX2 (trophectodermal marker). (b) Early germ cell markers, VASA, IFITM1, STELLAR, NANOS3, PRDM1A and PLAP have low levels of expression in all cells lines. Values are normalized to expression levels of housekeeping genes, GAPDH and RPLPO, error bars indicate SD between technical replicates.
Figure 29:
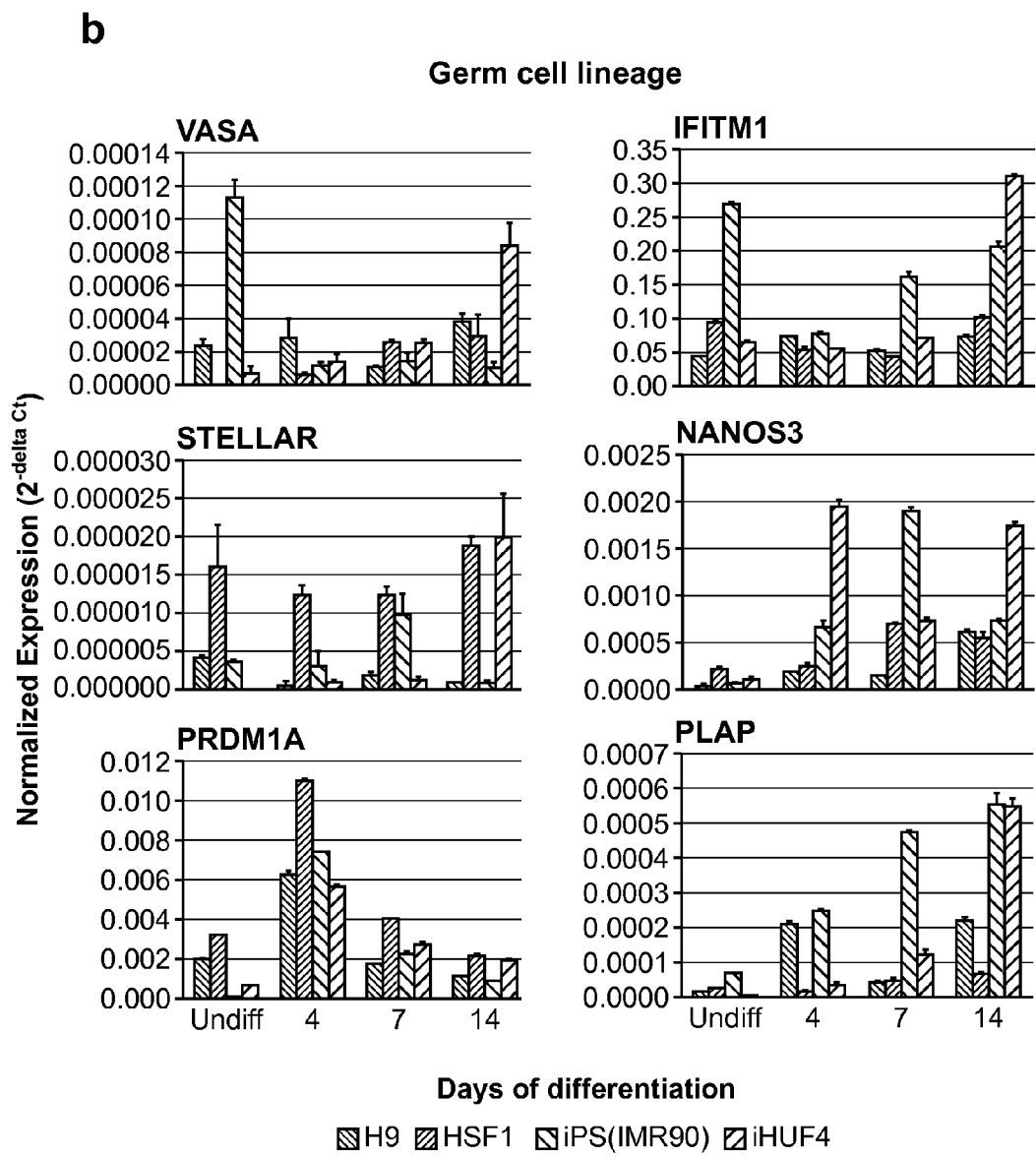
Figure 32:
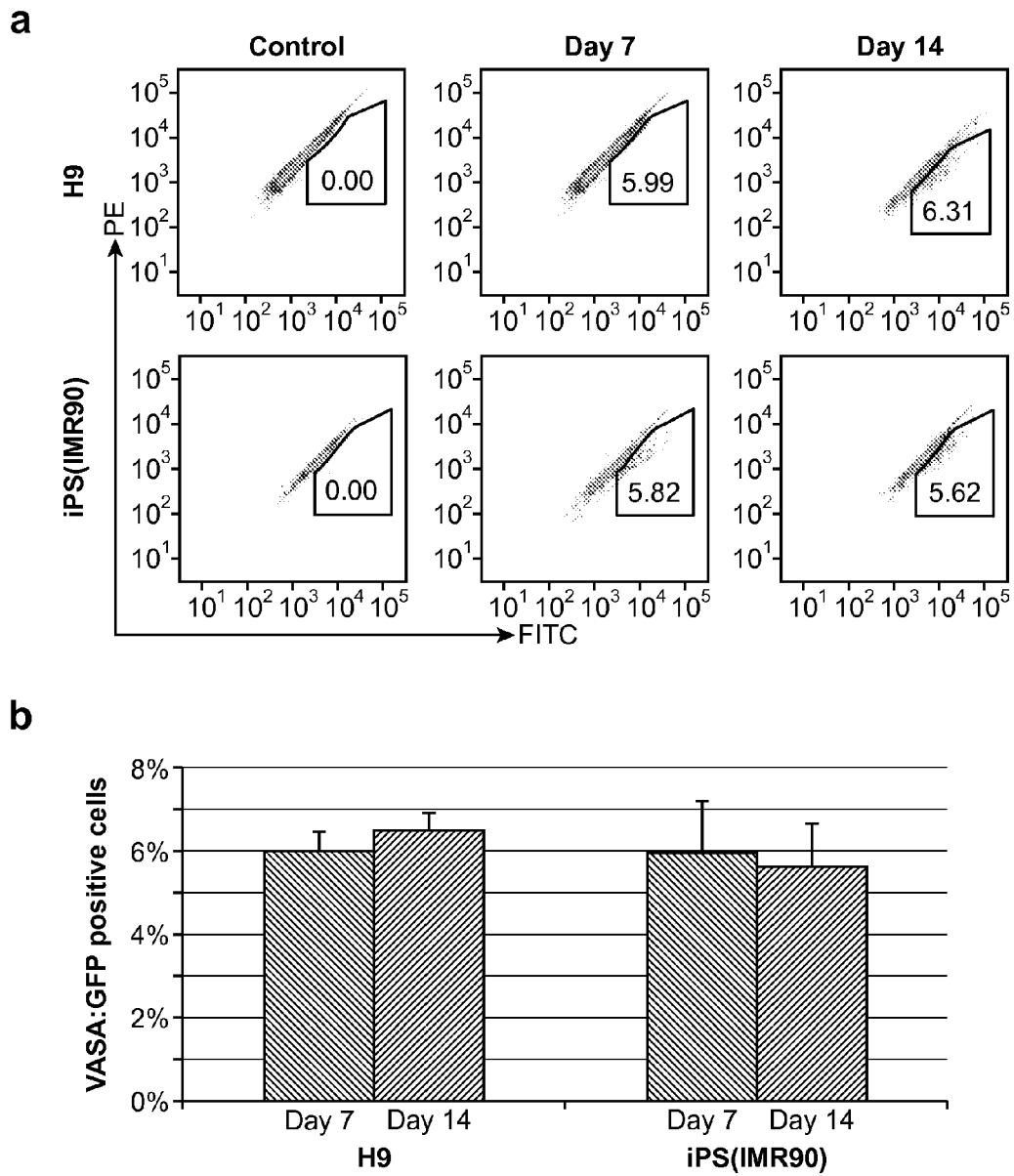
FIG. 32. The iPS(IMR90) and H9 cells were transfected with a lentiviral vector carrying eGFP gene under VASA promoter. Cells were differentiated for 7 and 14 days and the percentage of GFP positive cells was analyzed by FACS. a) Non-transfected, differentiated cells were used as a control for FACS gating, PE parameter was used to assist with the gating. Representative samples are shown for both cell lines. b) The percentage of VASA positive cells after 7 and 14 days of differentiation. Error bars indicate variation between three independently differentiated samples.

To further assess the differentiation potential of both iPSCs and hESCs, we assayed gene expression after 0, 4, 7 and 14 days of differentiation by quantitative RT-PCR. We observed that the expression of endogenous pluripotency markers such as TERT (telomerase reverse transcriptase) and SALL4 (sal-like 4) decreased with similar kinetics with differentiation of all cell lines, although the baseline expression of these genes was significantly higher in the undifferentiated iPS (IMR90) cell line relative to other cell lines (FIG. 29*a* and Table 3, below). As expected, we observed that the expression of the exogenous transcription factors (derived from viral vectors) including NANOG, LIN28 and OCT3/4 (POU5F) was significantly higher in undifferentiated iPSCs compared to hESCs (FIG. 32 and Table 4 below). Although the expression of these factors decreased with differentiation, the levels of NANOG in iPS(IMR90) cells and OCT3/4 and C-MYC in iHUF4 cells remained significantly higher than levels in other cell lines. Upon differentiation, all cell lines expressed markers of the mesoderm (Kinase insert domain receptor, KDR), ectoderm (Neural cell adhesion molecule 1, NCAM1) and endoderm (Alpha-fetoprotein, AFP) lineages, as well as trophectoderm (Caudal type homeobox transcription factor 2, CDX2) indicating their broad differentiation potential (FIG. 29 and Table 3).

TABLE 3

Statistical analysis of gene expression of TERT, SAL4, KDR, NCAM1, AFP, and CDX2 as illustrated in FIG. 29a. One-way ANOVA followed by Bonferroni posttest was performed to each time point and gene separately, comparing the 4 different cell lines. Significance was accepted as $p < 0.01$.

| Bonferroni's Multiple Comparison Test | Mean Diff. | t | Significant? $P < 00.01$? | Summary | 99% CI of diff |
|---|---|---|---|---|---|
| TERT | | | | | |
| H9 Undiff vs HSF1 Undiff | −0.0004631 | 2.445 | No | ns | −0.001342 to 0.0004156 |
| H9 Undiff vs IMR90 Undiff | −0.002408 | 12.71 | Yes | *** | −0.003286 to −0.001529 |
| H9 Undiff vs HUF4 Undiff | −0.001158 | 5.114 | Yes | ** | −0.002037 to −0.0002792 |
| HSF1 Undiff vs IMR90 Undiff | −0.001945 | 10.27 | Yes | *** | −0.002823 to −0.001066 |
| HSF1 Undiff vs HUF4 Undiff | −0.0006948 | 3.669 | No | * | −0.001573 to 0.0001839 |
| IMR90 Undiff vs HUF4 Undiff | 0.001250 | 7 | Yes | ** | 0.0003712 to 0.002129 |
| H9 D4 vs HSF1 D4 | 0.00005889 | 1.310 | No | ns | −0.0001491 to 0.0002665 |
| H9 D4 vs IMR90 D4 | 0.0002353 | 5.263 | Yes | ** | 0.00002746 to 0.0004431 |
| H9 D4 vs HUF4 D4 | 0.0004972 | 11.10 | Yes | *** | 0.0002894 to 0.0007050 |
| HSF1 D4 vs IMR90 D4 | 0.0001766 | 3.943 | No | * | −0.00003123 to 0.0003844 |
| HSF1 D4 vs HUF4 D4 | 0.0004385 | 9.790 | Yes | *** | 0.0002307 to 0.0006463 |
| IMR90 D4 vs HUF4 D4 | 0.0002619 | 5.847 | Yes | ** | 0.00005407 to 0.0004697 |
| H9 D7 vs HSF1 D7 | −0.0002933 | 10.61 | Yes | *** | −0.0004215 to −0.0001650 |
| H9 D7 vs IMR90 D7 | −0.00006479 | 2.344 | No | ns | −0.0001930 to 0.00006344 |
| H9 D7 vs HUF4 D7 | 0.00003275 | 1.185 | No | ns | −0.00009549 to 0.0001610 |
| HSF1 D7 vs IMR90 D7 | 0.0002285 | 8.266 | Yes | *** | 0.0001002 to 0.0003567 |
| HSF1 D7 vs HUF4 D7 | 0.0003260 | 11.80 | Yes | *** | 0.0001978 to 0.0004542 |
| IMR90 D7 vs HUF4 D7 | 0.00009754 | 3.529 | No | * | −0.00003070 to 0.0002258 |
| H9 D14 vs HSF1 D14 | −0.000009564 | 0.9807 | No | ns | −0.00005481 to 0.00003569 |
| H9 D14 vs IMR90 D14 | 0.00001143 | 1.172 | No | ns | −0.00003382 to 0.00005668 |
| H9 D14 vs HUF4 D14 | −0.00001365 | 1.400 | No | ns | −0.00005890 to 0.00003160 |
| HSF1 D14 vs IMR90 D14 | 0.00002100 | 2.153 | No | ns | −0.00002425 to 0.00005625 |
| HSF1 D14 vs HUF4 D14 | −0.000004085 | 0.4188 | No | ns | −0.00004934 to 0.00004117 |
| IMR90 D14 vs HUF4 D14 | −0.00002508 | 2.572 | No | ns | −0.00007033 to 0.00002017 |
| SAL4 | | | | | |
| H9 Undiff vs HSF1 Undiff | −0.006005 | 3.930 | No | * | −0.01310 to 0.001085 |
| H9 Undiff vs IMR90 Undiff | −0.03549 | 23.22 | Yes | *** | −0.04259 to −0.02840 |
| H9 Undiff vs HUF4 Undiff | 0.008011 | 5.241 | Yes | ** | 0.0009196 to 0.01510 |
| HSF1 Undiff vs IMR90 Undiff | −0.02949 | 19.29 | Yes | *** | −0.03658 to −0.02240 |
| HSF1 Undiff vs HUF4 Undiff | 0.01402 | 9.171 | Yes | *** | 0.006925 to 0.02111 |
| IMR90 Undiff vs HUF4 Undiff | 0.0435 | 28.47 | Yes | *** | 0.03641 to 0.05060 |
| H9 D4 vs HSF1 D4 | 0.0143 | 8.888 | Yes | *** | 0.006834 to 0.02176 |
| H9 D4 vs IMR90 D4 | 0.006542 | 4.067 | No | * | −0.0009208 to 0.01400 |
| H9 D4 vs HUF4 D4 | 0.01724 | 10.72 | Yes | *** | 0.009778 to 0.02470 |
| HSF1 D4 vs IMR90 D4 | −0.007754 | 4.821 | Yes | ** | −0.01522 to −0.0002915 |
| HSF1 D4 vs HUF4 D4 | 0.002945 | 1.831 | No | ns | −0.004518 to 0.01041 |
| IMR90 D4 vs HUF4 D4 | 0.0107 | 6.652 | Yes | *** | 0.003236 to 0.01816 |
| H9 D7 vs HSF1 D7 | 0.002017 | 0.8530 | No | ns | −0.008956 to 0.01299 |
| H9 D7 vs IMR90 D7 | −0.003910 | 1.653 | No | ns | −0.01488 to 0.007063 |
| H9 D7 vs HUF4 D7 | 0.004388 | 1.855 | No | ns | −0.005585 to 0.01536 |
| HSF1 D7 vs IMR90 D7 | −0.005928 | 2.506 | No | ns | −0.01690 to 0.005046 |
| HSF1 D7 vs HUF4 D7 | 0.002371 | 1.002 | No | ns | −0.008602 to 0.01334 |
| IMR90 D7 vs HUF4 D7 | 0.008298 | 3.509 | No | * | −0002675 to 0.01927 |
| H9 D14 vs HSF1 D14 | 0.009137 | 9.356 | Yes | *** | 0.004606 to 0.01367 |
| H9 D14 vs IMR90 D14 | 0.004902 | 5.019 | Yes | ** | 0.0003707 to 0.009433 |
| H9 D14 vs HUF4 D14 | 0.004299 | 4.402 | No | * | −0.0002325 to 0.008830 |
| HSF1 D14 vs IMR90 D14 | −0.004235 | 4.336 | No | * | −0.008766 to 0.0002964 |
| HSF1 D14 vs HUF4 D14 | −0.004838 | 4.954 | Yes | ** | −0.009369 to −0.0003068 |
| IMR90 D14 vs HUF4 D14 | −0.0006032 | 0.618 | No | ns | −0.005134 to 0.003928 |
| KDR | | | | | |
| H9 Undiff vs HSF1 Undiff | −0.002926 | 1.561 | No | ns | −0.01163 to 0.005774 |
| H9 Undiff vs IMR90 Undiff | −0.03369 | 17.97 | Yes | *** | −0.04239 to −0.02499 |
| H9 Undiff vs HUF4 Undiff | −0.01780 | 9.494 | Yes | *** | −0.02650 to −0.009102 |
| HSF1 Undiff vs IMR90 Undiff | −0.30760 | 16.40 | Yes | *** | −0.03946 to −0.02206 |
| HSF1 Undiff vs HUF4 Undiff | −0.01488 | 7.934 | Yes | *** | −0.02358 to −0.006176 |
| IMR90 Undiff vs HUF4 Undiff | 0.01588 | 8.471 | Yes | *** | 0.007164 to 0.02458 |
| H9 D4 vs HSF1 D4 | 0.07659 | 32.14 | Yes | *** | 0.06553 to 0.08765 |
| H9 D4 vs IMR90 D4 | 0.05750 | 24.13 | Yes | *** | 0.04645 to 0.06856 |
| H9 D4 vs HUF4 D4 | −0.05364 | 22.51 | Yes | *** | −0.06470 to −0.04258 |
| HSF1 D4 vs IMR90 D4 | −0.01909 | 8.009 | Yes | *** | −0.03015 to −0.008030 |
| HSF1 D4 vs HUF4 D4 | −0.1302 | 54.64 | Yes | *** | −0.1413 to −0.1192 |
| IMR90 D4 vs HUF4 D4 | −0.1111 | 46.63 | Yes | *** | −0.1222 to −0.1001 |
| H9 D7 vs HSF1 D7 | 0.2106 | 29.69 | Yes | *** | 0.1776 to 0.2435 |
| H9 D7 vs IMR90 D7 | 0.1250 | 17.63 | Yes | *** | 0.09213 to 0.1579 |
| H9 D7 vs HUF4 D7 | 0.09929 | 14.00 | Yes | *** | 0.06638 to 0.1322 |

TABLE 3-continued

Statistical analysis of gene expression of TERT, SAL4, KDR, NCAM1, AFP, and CDX2 as illustrated in FIG. 29a. One-way ANOVA followed by Bonferroni posttest was performed to each time point and gene separately, comparing the 4 different cell lines. Significance was accepted as $p < 0.01$.

| Bonferroni's Multiple Comparison Test | Mean Diff. | t | Significant? $P < 00.01$? | Summary | 99% CI of diff |
|---|---|---|---|---|---|
| HSF1 D7 vs IMR90 D7 | −0.08552 | 12.06 | Yes | *** | −0.1184 to −0.05262 |
| HSF1 D7 vs HUF4 D7 | −0.1113 | 15.69 | Yes | *** | −0.1442 to −0.07838 |
| IMR90 D7 vs HUF4 D7 | −0.02574 | 3.630 | No | * | −0.05865 to 0.007161 |
| H9 D14 vs HSF1 D14 | 0.04675 | 7.362 | Yes | *** | 0.01729 to 0.07621 |
| H9 D14 vs IMR90 D14 | 0.006920 | 1.090 | No | ns | −0.02254 to 0.03638 |
| H9 D14 vs HUF4 D14 | −0.1156 | 18.20 | Yes | *** | −0.1450 to −0.08611 |
| HSF1 D14 vs IMR90 D14 | −0.03983 | 6.273 | Yes | ** | −0.06929 to −0.01037 |
| HSF1 D14 vs HUF4 D14 | −0.1623 | 25.56 | Yes | *** | −0.1918 to −0.1329 |
| IMR90 D14 vs HUF4 D14 | −0.1225 | 19.29 | Yes | *** | −0.1520 to −0.09303 |
| NCAM1 | | | | | |
| H9 Undiff vs HSF1 Undiff | 0.000004301 | 3.006 | No | ns | −0.000002338 to 0.00001094 |
| H9 Undiff vs IMR90 Undiff | 0.00001147 | 8.015 | Yes | *** | 0.000004830 to 0.00001811 |
| H9 Undiff vs HUF4 Undiff | 0.00001061 | 7.418 | Yes | *** | 0.000003975 to 0.00001725 |
| HSF1 Undiff vs IMR90 Undiff | 0.000007168 | 5.009 | Yes | ** | 0.0000005283 to 0.00001381 |
| HSF1 Undiff vs HUF4 Undiff | 0.000006313 | 4.412 | No | * | −0.0000003264 to 0.00001295 |
| IMR90 Undiff vs HUF4 Undiff | −0.0000008547 | 0.5973 | No | ns | −0.000007494 to 0.000005785 |
| H9 D4 vs HSF1 D4 | 0.00001785 | 4.437 | No | * | −0.0000008161 to 0.00003652 |
| H9 D4 vs IMR90 D4 | 0.00001338 | 3.325 | No | ns | −0.000005288 to 0.00003205 |
| H9 D4 vs HUF4 D4 | −0.000009114 | 2.265 | No | ns | −0.00002776 to 0.00009553 |
| HSF1 D4 vs IMR90 D4 | −0.000004472 | 1.111 | No | ns | −0.00002314 to 0.00001420 |
| HSF1 D4 vs HUF4 D4 | −0.00002696 | 6.702 | Yes | *** | −0.00004563 to −0.000008298 |
| IMR90 D4 vs HUF4 D4 | −0.00002249 | 5.591 | Yes | ** | −0.00004116 to −0.000003826 |
| H9 D7 vs HSF1 D7 | 0.000006377 | 1.128 | No | ns | −0.00001985 to 0.00003261 |
| H9 D7 vs IMR90 D7 | 0.000008616 | 1.524 | No | ns | −0.00001761 to 0.00003484 |
| H9 D7 vs HUF4 D7 | 0.00001195 | 2.114 | No | ns | −0.00001428 to 0.00003818 |
| HSF1 D7 vs IMR90 D7 | 0.000002239 | 0.3960 | No | ns | −0.00002399 to 0.00002847 |
| HSF1 D7 vs HUF4 D7 | 0.000005571 | 0.9655 | No | ns | −0.00002066 to 0.00003180 |
| IMR90 D7 vs HUF4 D7 | 0.000003332 | 0.5895 | No | ns | −0.00002290 to 0.00002956 |
| H9 D14 vs HSF1 D14 | 0.000006822 | 1.560 | No | ns | −0.00001346 to 0.00002710 |
| H9 D14 vs IMR90 D14 | 0.00001803 | 4.125 | No | * | −0.000002251 to 0.00003832 |
| H9 D14 vs HUF4 D14 | −0.000029970 | 8.865 | Yes | *** | −0.00005026 to −0.000009683 |
| HSF1 D14 vs IMR90 D14 | 0.00001121 | 2.564 | No | ns | −0.000009072 to 0.00003149 |
| HSF1 D14 vs HUF4 D14 | −0.00003679 | 8.415 | Yes | *** | −0.00005707 to −0.00001650 |
| IMR90 D14 vs HUF4 D14 | −0.00004800 | 10.98 | Yes | *** | −0.00006828 to −0.00002772 |
| AFP | | | | | |
| H9 Undiff vs HSF1 Undiff | −0.05274 | 81.23 | Yes | *** | −0.05575 to −0.04972 |
| H9 Undiff vs IMR90 Undiff | 0.01135 | 17.48 | Yes | *** | 0.008334 to 0.01436 |
| H9 Undiff vs HUF4 Undiff | 0.001132 | 17.44 | Yes | *** | 0.008307 to 0.01433 |
| HSF1 Undiff vs IMR90 Undiff | 0.06408 | 98.71 | Yes | *** | 0.06107 to 0.06710 |
| HSF1 Undiff vs HUF4 Undiff | 0.06406 | 98.67 | Yes | *** | 0.06104 to 0.06707 |
| IMR90 Undiff vs HUF4 Undiff | −0.00002709 | 0.04173 | No | ns | −0.003039 to 0.002985 |
| H9 D4 vs HSF1 D4 | −0.04204 | 11.92 | Yes | *** | −0.05841 to −0.02567 |
| H9 D4 vs IMR90 D4 | 0.002416 | 0.6646 | No | ns | −0.01395 to 0.01879 |
| H9 D4 vs HUF4 D4 | 0.02717 | 7.699 | Yes | *** | 0.01079 to 0.04354 |
| HSF1 D4 vs IMR90 D4 | 0.04446 | 12.60 | Yes | *** | 0.02809 to 0.06063 |
| HSF1 D4 vs HUF4 D4 | 0.06920 | 19.61 | Yes | *** | 0.05283 to 0.08558 |
| IMR90 D4 vs HUF4 D4 | 0.02475 | 7.015 | Yes | *** | 0.008379 to 0.04112 |
| H9 D7 vs HSF1 D7 | 0.07765 | 8.889 | Yes | *** | 0.03712 to 0.1182 |
| H9 D7 vs IMR90 D7 | 0.03988 | 4.565 | No | * | −0.0006553 to 0.08042 |
| H9 D7 vs HUF4 D7 | −0.04842 | 5.543 | Yes | ** | −0.08896 to −0.007888 |
| HSF1 D7 vs IMR90 D7 | −0.03777 | 4.324 | No | * | −0.07831 to 0.002761 |
| HSF1 D7 vs HUF4 D7 | −0.1261 | 14.43 | Yes | *** | −0.1656 to −0.08554 |
| IMR90 D7 vs HUF4 D7 | −0.0883 | 10.11 | Yes | *** | −0.1288 to −0.04777 |
| H9 D14 vs HSF1 D14 | 0.1860 | 12.59 | Yes | *** | 0.1174 to 0.2545 |
| H9 D14 vs IMR90 D14 | −0.07867 | 5.325 | Yes | ** | −0.1472 to −0.01012 |
| H9 D14 vs HUF4 D14 | −0.1112 | 7.530 | Yes | *** | −0.1798 to −0.04270 |
| HSF1 D14 vs IMR90 D14 | −0.2646 | 17.91 | Yes | *** | −0.3332 to −0.1961 |
| HSF1 D14 vs HUF4 D14 | −0.2972 | 20.12 | Yes | *** | −0.3657 to −0.2287 |
| IMR90 D14 vs HUF4 D14 | −0.03258 | 2.205 | No | ns | −0.1011 to 0.03596 |

TABLE 3-continued

Statistical analysis of gene expression of TERT, SAL4, KDR, NCAM1, AFP, and CDX2 as illustrated in FIG. 29a. One-way ANOVA followed by Bonferroni posttest was performed to each time point and gene separately, comparing the 4 different cell lines. Significance was accepted as p < 0.01.

| Bonferroni's Multiple Comparison Test | Mean Diff. | t | Significant? P < 00.01? | Summary | 99% CI of diff |
|---|---|---|---|---|---|
| CDX2 | | | | | |
| H9 Undiff vs HSF1 Undiff | 0.000001281 | 0.1093 | No | ns | −0.00005307 to 0.00005563 |
| H9 Undiff vs IMR90 Undiff | 0.00006349 | 5.420 | Yes | ** | 0.000009140 to 0.0001178 |
| H9 Undiff vs HUF4 Undiff | 0.00005411 | 4.619 | No | * | −0.0000002429 to 0.0001085 |
| HSF1 Undiff vs IMR90 Undiff | 0.00006221 | 5.311 | Yes | ** | 0.000007859 to 0.0001166 |
| HSF1 Undiff vs HUF4 Undiff | 0.00005283 | 4.510 | No | * | −0.000001524 to 0.0001072 |
| IMR90 Undiff vs HUF4 Undiff | −0.000009383 | 0.8009 | No | ns | −0.00006374 to 0.00004497 |
| H9 D4 vs HSF1 D4 | −0.00002758 | 0.3752 | No | ns | −0.0003686 to 0.0003135 |
| H9 D4 vs IMR90 D4 | −0.0007074 | 9.624 | Yes | *** | −0.001048 to −0.0003664 |
| H9 D4 vs HUF4 D4 | −0.001789 | 24.34 | Yes | *** | −0.002131 to −0.001448 |
| HSF1 D4 vs IMR90 D4 | −0.0006799 | 9.249 | Yes | *** | −0.001021 to −0.0003388 |
| HSF1 D4 vs HUF4 D4 | −0.001762 | 23.97 | Yes | *** | −0.002103 to −0.001421 |
| IMR90 D4 vs HUF4 D4 | −0.001082 | 14.72 | Yes | *** | −0.001423 to −0.0007410 |
| H9 D7 vs HSF1 D7 | −0.0005085 | 7.303 | Yes | *** | −0.0008318 to −0.0001855 |
| H9 D7 vs IMR90 D7 | −0.0001843 | 2.646 | No | ns | −0.0005074 to 0.0001389 |
| H9 D7 vs HUF4 D7 | −0.001913 | 27.46 | Yes | *** | −0.002236 to −0.001589 |
| HSF1 D7 vs IMR90 D7 | 0.0003243 | 4.657 | Yes | ** | 0.000001197 to 0.0006475 |
| HSF1 D7 vs HUF4 D7 | −0.001404 | 20.16 | Yes | *** | −0.001727 to −0.001081 |
| IMR90 D7 vs HUF4 D7 | −0.001728 | 24.82 | Yes | *** | −0.002051 to −0.001405 |
| H9 D14 vs HSF1 D14 | 0.0008138 | 5.540 | Yes | ** | 0.0001322 to 0.001495 |
| H9 D14 vs IMR90 D14 | −0.0005875 | 4.000 | No | * | −0.001269 to 0.00009406 |
| H9 D14 vs HUF4 D14 | −0.003701 | 25.19 | Yes | *** | −0.004382 to −0.003019 |
| HSF1 D14 vs IMR90 D14 | −0.001401 | 9.639 | Yes | *** | −0.002083 to −0.0007197 |
| HSF1 D14 vs HUF4 D14 | −0.004514 | 30.73 | Yes | *** | −0.005196 to −0.003833 |
| IMR90 D14 vs HUF4 D14 | −0.003113 | 21.19 | Yes | *** | −0.003795 to −0.002431 |

TABLE 4

Figure 33:
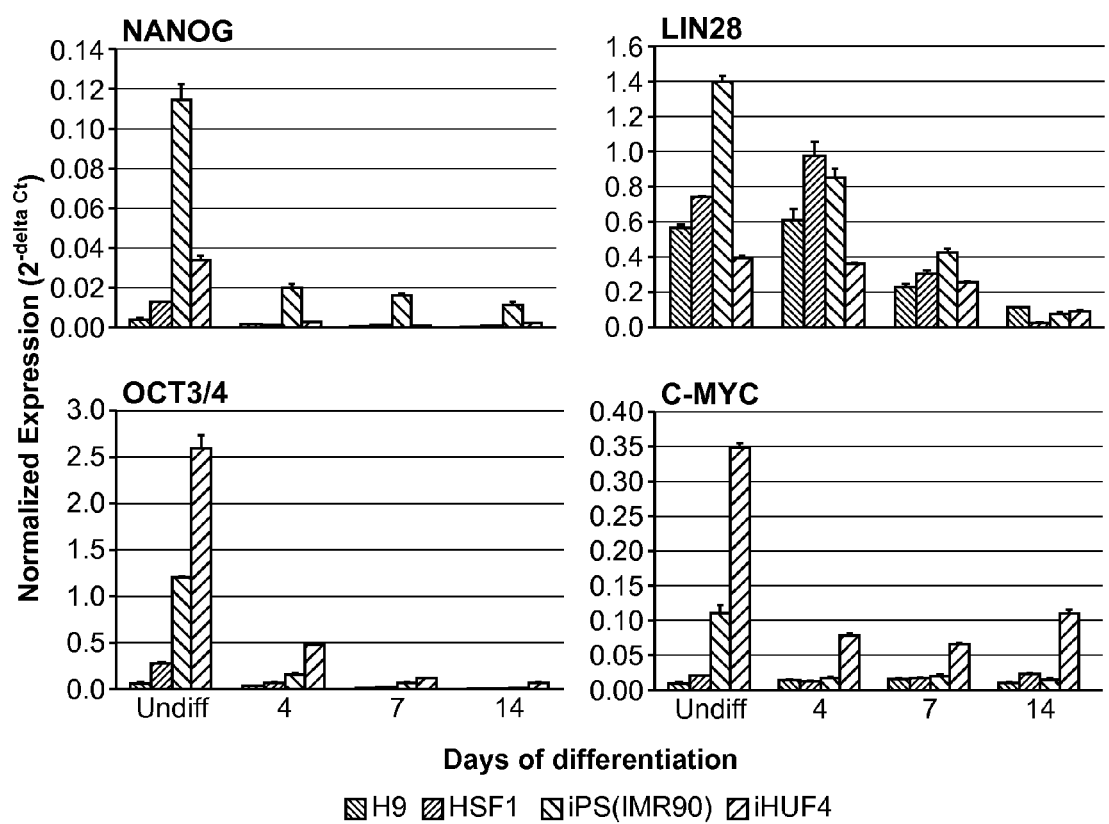
FIG. 33. Expression of exogenous pluripotency markers (derived from viral vectors). NANOG, LIN28 and OCT3/4 were used for iPS(IMR90) derivation and OCT3/4 and C-MYC for iHUF4. Values are normalized to expression levels of housekeeping genes, GAPDH and RPLPO, error bars indicate standard deviation between technical replicates.

Statistical analysis of gene expression of NANOG, LIN28, OCT3/4 and C-MYC as illustrated in FIG. 33. One-way ANOVA followed by Bonferroni posttest was performed to each time point and gene separately, comparing the 4 different cell lines. Significance was accepted as p < 0.01.

| Bonferroni's Multiple Comparison Test | Mean Diff | t | Significant? P < 00.01? | Summary | 99% CI of diff |
|---|---|---|---|---|---|
| NANOG | | | | | |
| H9 Undiff vs HSF1 Undiff | −0.009070 | 2.673 | No | ns | −0.02481 to 0.006672 |
| H9 Undiff vs IMR90 Undiff | −0.1105 | 32.56 | Yes | *** | −0.1262 to −0.09474 |
| H9 Undiff vs HUF4 Undiff | −0.02948 | 8.690 | Yes | *** | −0.04522 to −0.01374 |
| HSF1 Undiff vs IMR90 Undiff | −0.1014 | 29.89 | Yes | *** | −0.1172 to −0.8567 |
| HSF1 Undiff vs HUF4 Undiff | −0.02041 | 6.017 | Yes | ** | −0.03615 to −0.004671 |
| IMR90 Undiff vs HUF4 Undiff | 0.08100 | 23.87 | Yes | *** | 0.06526 to 0.09674 |
| H9 D4 vs HSF1 D4 | 0.0005102 | 0.7691 | No | ns | −0.02567 to 0.003588 |
| H9 D4 vs IMR90 D4 | −0.01864 | 28.10 | Yes | *** | −0.02172 to −0.01555 |
| H9 D4 vs HUF4 D4 | −0.001144 | 1.725 | No | ns | −0.004222 to 0.001934 |
| HSF1 D4 vs IMR90 D4 | −0.01915 | 28.87 | Yes | *** | −0.02223 to −0.01607 |
| HSF1 D4 vs HUF4 D4 | −0.001654 | 2.494 | No | ns | −0.004732 to 0.001424 |
| IMR90 D4 vs HUF4 D4 | 0.01749 | 26.37 | Yes | *** | 0.01442 to 0.02057 |
| H9 D7 vs HSF1 D7 | −0.0008306 | 1.784 | No | ns | −0.002991 to 0.001329 |
| H9 D7 vs IMR90 D7 | −0.01569 | 33.71 | Yes | *** | −0.01785 to −0.01353 |
| H9 D7 vs HUF4 D7 | −0.0005324 | 1.144 | No | ns | −0.002692 to 0.001628 |
| HSF1 D7 vs IMR90 D7 | −0.01486 | 31.92 | Yes | *** | −0.01702 to −0.01270 |
| HSF1 D7 vs HUF4 D7 | 0.0002983 | 0.6407 | No | ns | −0.001862 to 0.002458 |
| IMR90 D7 vs HUF4 D7 | 0.01516 | 32.56 | Yes | *** | 0.01300 to 0.01732 |
| H9 D14 vs HSF1 D14 | −0.0001619 | 0.1767 | No | ns | −0.004413 to 0.004089 |
| H9 D14 vs IMR90 D14 | −0.01043 | 11.38 | Yes | *** | −0.01458 to −0.006179 |
| H9 D14 vs HUF4 D14 | −0.001910 | 2.085 | No | ns | −0.006161 to 0.002340 |
| HSF1 D14 vs IMR90 D14 | −0.01027 | 11.21 | Yes | *** | −0.01452 to −0.006017 |
| HSF1 D14 vs HUF4 D14 | −0.001749 | 1.909 | No | ns | −0.006000 to 0.002502 |
| IMR90 D14 vs HUF4 D14 | 0.00852 | 9.299 | Yes | *** | 0.004269 to 0.01277 |

TABLE 4-continued

Statistical analysis of gene expression of NANOG, LIN28, OCT3/4 and C-MYC as illustrated in FIG. 33. One-way ANOVA followed by Bonferroni posttest was performed to each time point and gene separately, comparing the 4 different cell lines. Significance was accepted as p < 0.01.

| Bonferroni's Multiple Comparison Test | Mean Diff | t | Significant? P < 00.01? | Summary | 99% CI of diff |
|---|---|---|---|---|---|
| LIN28 | | | | | |
| H9 Undiff vs HSF1 Undiff | −0.1756 | 11.36 | Yes | *** | −0.2473 to −0.1039 |
| H9 Undiff vs IMR90 Undiff | −0.8386 | 54.23 | Yes | *** | −0.9103 to −0.7668 |
| H9 Undiff vs HUF4 Undiff | 0.1727 | 11.17 | Yes | *** | 0.1009 to 0.2444 |
| HSF1 Undiff vs IMR90 Undiff | −0.6630 | 42.88 | Yes | *** | −0.7347 to −0.5912 |
| HSF1 Undiff vs HUF4 Undiff | 0.3483 | 22.52 | Yes | *** | 0.2765 to 0.4200 |
| IMR90 Undiff vs HUF4 Undiff | 1.011 | 55.40 | Yes | *** | 0.9395 to 1.083 |
| H9 D4 vs HSF1 D4 | −0.3669 | 7.770 | Yes | *** | −0.5860 to −0.1478 |
| H9 D4 vs IMR90 D4 | −0.2392 | 5.065 | Yes | ** | −0.4583 to −0.02010 |
| H9 D4 vs HUF4 D4 | 0.2498 | 5.289 | Yes | ** | 0.03064 to 0.4689 |
| HSF1 D4 vs IMR90 D4 | 0.1277 | 2.704 | No | ns | −0.09140 to 0.3468 |
| HSF1 D4 vs HUF4 D4 | 0.6167 | 13.06 | Yes | *** | 0.3976 to 0.8358 |
| IMR90 D4 vs HUF4 D4 | 0.4890 | 10.35 | Yes | *** | 0.2699 to 0.7081 |
| H9 D7 vs HSF1 D7 | −0.07529 | 5.494 | Yes | ** | −0.1389 to −0.01171 |
| H9 D7 vs IMR90 D7 | −0.1945 | 14.19 | Yes | *** | −0.2581 to −0.1309 |
| H9 D7 vs HUF4 D7 | −0.01999 | 1.458 | No | ns | −0.08357 to 0.04360 |
| HSF1 D7 vs IMR90 D7 | −0.1192 | 8.699 | Yes | *** | −0.1828 to −0.05563 |
| HSF1 D7 vs HUF4 D7 | 0.05530 | 4.036 | No | * | −0.008279 to 0.1189 |
| IMR90 D7 vs HUF4 D7 | 0.1745 | 12.74 | Yes | *** | 0.1109 to 0.2381 |
| H9 D14 vs HSF1 D14 | 0.08666 | 21.44 | Yes | *** | 0.06791 to 0.1054 |
| H9 D14 vs IMR90 D14 | 0.03736 | 9.242 | Yes | *** | 0.01860 to 0.05611 |
| H9 D14 vs HUF4 D14 | 0.02248 | 5.562 | Yes | ** | 0.003729 to 0.04124 |
| HSF1 D14 vs IMR90 D14 | −0.04930 | 12.20 | Yes | *** | −0.06806 to −0.03055 |
| HSF1 D14 vs HUF4 D14 | −0.06418 | 15.88 | Yes | *** | −0.08293 to −0.04542 |
| IMR90 D14 vs HUF4 D14 | −0.01487 | 3.680 | No | * | −0.03363 to 0.003879 |
| OCT3/4 | | | | | |
| H9 Undiff vs HSF1 Undiff | −0.2167 | 3.849 | No | * | −0.4779 to 0.04451 |
| H9 Undiff vs IMR90 Undiff | −1.143 | 20.30 | Yes | *** | −1.404 to −0.8814 |
| H9 Undiff vs HUF4 Undiff | −2.535 | 45.03 | Yes | *** | −2.796 to 2.274 |
| HSF1 Undiff vs IMR90 Undiff | −0.9259 | 16.45 | Yes | *** | −1.187 to −0.6647 |
| HSF1 Undiff vs HUF4 Undiff | −2.319 | 41.18 | Yes | *** | −2.560 to −2.057 |
| IMR90 Undiff vs HUF4 Undiff | −1.393 | 24.74 | Yes | *** | −1.664 to −1.131 |
| H9 D4 vs HSF1 D4 | −0.04095 | 7.816 | Yes | *** | −0.06526 to −0.01664 |
| H9 D4 vs IMR90 D4 | −0.1404 | 26.80 | Yes | *** | −0.1647 to −0.1161 |
| H9 D4 vs HUF4 D4 | −0.4601 | 87.82 | Yes | *** | −0.4844 to −0.4358 |
| HSF1 D4 vs IMR90 D4 | −0.09945 | 18.98 | Yes | *** | −0.1238 to −0.07515 |
| HSF1 D4 vs HUF4 D4 | −0.4192 | 80.00 | Yes | *** | −0.4435 to −0.3949 |
| IMR90 D4 vs HUF4 D4 | −0.3197 | 61.02 | Yes | *** | −0.3440 to −0.2954 |
| H9 D7 vs HSF1 D7 | −0.01167 | 3.379 | No | ns | −0.02770 to 0.004356 |
| H9 D7 vs IMR90 D7 | −0.05429 | 15.72 | Yes | *** | −0.07032 to −0.03826 |
| H9 D7 vs HUF4 D7 | −0.1159 | 33.54 | Yes | *** | −0.1319 to −0.09983 |
| HSF1 D7 vs IMR90 D7 | −0.04262 | 12.34 | Yes | *** | −0.05865 to −0.026559 |
| HSF1 D7 vs HUF4 D7 | −0.1042 | 30.16 | Yes | *** | 0.12021 −0.08816 |
| IMR90 D7 vs HUF4 D7 | −0.06156 | 17.82 | Yes | *** | −0.07759 to −0.04554 |
| H9 D14 vs HSF1 D14 | −0.001152 | 0.8223 | No | ns | −0.00765010 0.005347 |
| H9 D14 vs IMR90 D14 | −0.003307 | 2.361 | No | ns | −0.009805 to 0.003192 |
| H9 D14 vs HUF4 D14 | −0.05744 | 41.01 | Yes | *** | −0.06394 to −0.06094 |
| HSF1 D14 vs IMR90 D14 | −0.002155 | 1.539 | No | ns | −0.008653 to 0.004343 |
| HSF1 D14 vs HUF4 D14 | −0.05629 | 40.19 | Yes | *** | −0.06276 to −0.04979 |
| IMR90 D14 vs HUF4 D14 | −0.05413 | 38.65 | Yes | *** | −0.06063 to −0.04763 |
| C-MYC | | | | | |
| H9 Undiff vs HSF1 Undiff | −0.01175 | 2.431 | No | ns | −0.03418 to 0.01068 |
| H9 Undiff vs IMR90 Undiff | −0.1022 | 21.14 | Yes | *** | −0.1246 to −0.07976 |
| H9 Undiff vs HUF4 Undiff | −0.3366 | 70.05 | Yes | *** | −0.3610 to −0.3161 |
| HSF1 Undiff vs IMR90 Undiff | −0.09044 | 18.71 | Yes | *** | −0.1129 to −0.06801 |
| HSF1 Undiff vs HUF4 Undiff | −0.3268 | 67.62 | Yes | *** | −0.3492 to −0.3044 |
| IMR90 Undiff vs HUF4 Undiff | −0.2364 | 48.90 | Yes | *** | −0.2588 to −0.2139 |
| H9 D4 vs HSF1 D4 | 0.001958 | 1.544 | No | ns | −0.003927 to 0.007844 |
| H9 D4 vs IMR90 D4 | −0.003659 | 2.885 | No | ns | −0.009544 to 0.002226 |
| H9 D4 vs HUF4 D4 | −0.06498 | 51.23 | Yes | *** | −0.07087 to −0.05910 |

TABLE 4-continued

Statistical analysis of gene expression of NANOG, LIN28, OCT3/4 and C-MYC as illustrated in FIG. 33. One-way ANOVA followed by Bonferroni posttest was performed to each time point and gene separately, comparing the 4 different cell lines. Significance was accepted as p < 0.01.

| Bonferroni's Multiple Comparison Test | Mean Diff | t | Significant? P < 00.01? | Summary | 99% CI of diff |
|---|---|---|---|---|---|
| HSF1 D4 vs IMR90 D4 | −0.005617 | 4.429 | No | * | −0.0150 to 0.0002679 |
| HSF1 D4 vs HUF4 D4 | −0.06694 | 52.77 | Yes | *** | −0.07282 to −00.06105 |
| IMR90 D4 vs HUF4 D4 | −0.06132 | 48.34 | Yes | *** | −0.06721 to −0.05544 |
| H9 D7 vs HSF1 D7 | −0.001832 | 1.312 | No | ns | −0.008314 to 0.004549 |
| H9 D7 vs IMR90 D7 | −0.005038 | 3.606 | No | * | −0.01152 to 0.001444 |
| H9 D7 vs HUF4 D7 | 0.05090 | 36.43 | Yes | *** | −0.05738 to −0.04442 |
| HSF1 D7 vs IMR90 D7 | −0.003206 | 2.295 | No | ns | −0.009687 to 0.0003276 |
| HSF1 D7 vs HUF4 D7 | −0.04907 | 35.12 | Yes | *** | −0.05555 to −0.04258 |
| IMR90 D7 vs HUF4 D7 | −0.04586 | 32.83 | Yes | *** | −0.05234 to −0.03938 |
| H9 D14 vs HSF1 D14 | −0.01424 | 5.766 | Yes | *** | −0.02569 to −0.002781 |
| H9 D14 vs IMR90 D14 | −0.004935 | 1.999 | No | ns | −0.01639 to 0.006519 |
| H9 D14 vs HUF4 D14 | −0.1002 | 40.59 | Yes | *** | −0.1116 to −0.08874 |
| HSF1 D14 vs IMR90 D14 | 0.009301 | 3.768 | No | * | −0.002153 to 0.02075 |
| HSF1 D14 vs HUF4 D14 | −0.08596 | 34.82 | Yes | *** | −0.09741 to −0.07450 |
| IMR90 D14 vs HUF4 D14 | −0.09526 | 38.59 | Yes | *** | −0.1067 to −0.08381 |

We next examined the expression of germ cell specific genes in iPSCs relative to hESCs. In the undifferentiated state, iPS(IMR90) cells had increased expression of germ cell markers with a significant increase in expression of VASA, IFITM1 and PLAP relative to the other cell lines. At day 7 of differentiation, the expression of IFITM1 (Interferon induced transmembrane protein 1), NANOS3 and PLAP (placental alkaline phosphatase) was significantly higher in the iPS(IMR90) cells relative to other cell lines; iHUF4 cells also had significantly higher expression of PLAP compared to hESCs (FIG. 29b and Table 5, below). Subsequently, at day 14 of differentiation, both iPS(IMR90) and iHUF4 cells had significantly higher expression of IFITM1 and PLAP relative to hESCs and iHUF4 had a significantly higher expression of NANOS3 compared to all cell lines, as well. Similar expression of most of the somatic cell markers and higher expression of germ cell genes and/or proteins in the undifferentiated iPSCs suggest that the observed increase in expression of germ cell specific markers is specific to the iPSCs.

TABLE 5

Statistical analysis of gene expression of VASA, IFITM1, STELLAR, NANOS3, PRDM1A, and PLAP in FIG. 29b. One-way ANOVA followed by Bonferroni posttest was performed to each time point and gene separately, comparing the 4 different cell lines. Significance was accepted as p < 0.01.

| Bonferroni's Multiple Comparison Test | Mean Diff | t | Significant? P < 00.01? | Summary | 99% CI of diff |
|---|---|---|---|---|---|
| VASA | | | | | |
| H9 Undiff vs HSF1 Undiff | 0.00002402 | 3.992 | No | ns | −0.00002128 to 0.00006931 |
| H9 Undiff vs IMR90 Undiff | −0.00008979 | 14.92 | Yes | *** | −0.0001551 to −0.00004449 |
| H9 Undiff vs HUF4 Undiff | 0.00001700 | 2.826 | No | ns | −0.00002829 to 0.00006230 |
| HSF1 Undiff vs IMR90 Undiff | −0.0001138 | 18.92 | Yes | *** | −0.0001591 to −0.00006551 |
| HSF1 Undiff vs HUF4 Undiff | −0.000007011 | 1.165 | No | ns | −0.00005231 to 0.00003828 |
| IMR90 Undiff vs HUF4 Undiff | 0.0001068 | 17.75 | Yes | *** | 0.00006150 to 0.0001521 |
| H9 D4 vs HSF1 D4 | 0.00002258 | 3.334 | No | ns | −0.00002641 to 0.00007357 |
| H9 D4 vs IMR90 D4 | 0.00001703 | 2.515 | No | ns | −0.00003395 to 0.00006802 |
| H9 D4 vs HUF4 D4 | 0.00001441 | 2.128 | No | ns | −0.00003657 to 0.00006540 |
| HSF1 D4 vs IMR90 D4 | −0.000005545 | 0.8187 | No | ns | −0.00005653 to 0.00004544 |
| HSF1 D4 vs HUF4 D4 | −0.000005153 | 1.205 | No | ns | −0.00005915 to 0.00004282 |
| IMR90 D4 vs HUF4 D4 | −0.000002618 | 0.3866 | No | ns | −0.00005361 to 0.00004837 |
| H9 D7 vs HSF1 D7 | −0.00001560 | 5.179 | No | * | −0.00003829 to 0.00000707 |
| H9 D7 vs IMR90 D7 | −0.000003312 | 1.099 | No | ns | −0.00002599 to 0.00001937 |
| H9 D7 vs HUF4 D7 | −0.00001502 | 4.959 | No | * | −0.00003770 to 0.000007651 |
| HSF1 D7 vs IMR90 D7 | 0.00001229 | 4.050 | No | ns | −0.00001039 to 0.00003497 |
| HSF1 D7 vs HUF4 D7 | 0.0000005828 | 0.1934 | No | ns | −0.00002210 to 0.00002327 |
| IMR90 D7 vs HUF4 D7 | −0.00001171 | 3.555 | No | ns | −0.00003439 to 0.00001097 |
| H9 D14 vs HSF1 D14 | 0.000008955 | 0.8903 | No | ns | −0.00005577 to 0.00008458 |
| H9 D14 vs IMR90 D14 | 0.00002816 | 2.800 | No | ns | −0.00004756 to 0.0001039 |
| H9 D14 vs HUF4 D14 | −0.00004600 | 4.573 | No | ns | −0.0001217 to 0.00002972 |
| HSF1 D14 vs IMR90 D14 | 0.00001920 | 1.909 | No | ns | −0.00005652 to 0.00009493 |
| HSF1 D14 vs HUF4 D14 | −0.00005496 | 5.454 | No | * | −0.0001307 to 0.00002077 |
| IMR90 D14 vs HUF4 D14 | −0.00007416 | 7.373 | No | * | −0.0001499 to 0.000001565 |

TABLE 5-continued

Statistical analysis of gene expression of VASA, IFITM1, STELLAR, NANOS3,
PRDM1A, and PLAP in FIG. 29b. One-way ANOVA followed by Bonferroni posttest was
performed to each time point and gene separately, comparing the 4 different cell lines.
Significance was accepted as p < 0.01.

| Bonferroni's Multiple Comparison Test | Mean Diff | t | Significant? P < 00.01? | Summary | 99% CI of diff |
|---|---|---|---|---|---|
| IFITM1 | | | | | |
| H9 Undiff vs HSF1 Undiff | −0.04955 | 26.970 | Yes | *** | −0.06339 to −0.03572 |
| H9 Undiff vs IMR90 Undiff | −0.2240 | 121.9 | Yes | *** | −0.2379 to −0.2102 |
| H9 Undiff vs HUF4 Undiff | −0.02004 | 10.91 | Yes | ** | −0.03388 to −0.008210 |
| HSF1 Undiff vs IMR90 Undiff | −0.1745 | 94.95 | Yes | *** | −0.1583 to −0.1607 |
| HSF1 Undiff vs HUF4 Undiff | 0.02961 | 16.05 | Yes | *** | 0.01568 to 0.04334 |
| IMR90 Undiff vs HUF4 Undiff | 0.2040 | 111.0 | Yes | *** | 0.1902 to 0.2178 |
| H9 D4 vs HSF1 D4 | 0.01895 | 10.37 | Yes | ** | 0.005188 to 0.03271 |
| H9 D4 vs IMR90 D4 | −0.003787 | 2.072 | No | ns | −0.01755 to 0.009973 |
| H9 D4 vs HUF4 D4 | 0.01926 | 10.54 | Yes | ** | 0.005497 to 0.03302 |
| HSF1 D4 vs IMR90 D4 | −0.02273 | 12.44 | Yes | ** | −0.03649 to −0.008975 |
| HSF1 D4 vs HUF4 D4 | 0.0003089 | 0.1690 | No | ns | −0.01345 to 0.01407 |
| IMR90 D4 vs HUF4 D4 | 0.02304 | 12.51 | Yes | ** | 0.009283 to 0.03880 |
| H9 D7 vs HSF1 D7 | 0.006648 | 1.468 | No | ns | −0.02699 to 0.04029 |
| H9 D7 vs IMR90 D7 | −0.1101 | 24.63 | Yes | *** | 0.1437 to −0.07643 |
| H9 D7 vs HUF4 D7 | −0.02055 | 4.666 | No | ns | −0.05449 to 0.01279 |
| HSF1 D7 vs IMR90 D7 | −0.1167 | 28.12 | Yes | *** | −0.1504 to −0.08308 |
| HSF1 D7 vs HUF4 D7 | −0.02750 | 6.164 | No | * | −0.06114 to 0.006142 |
| IMR90 D7 vs HUF4 D7 | 0.08922 | 19.97 | Yes | *** | 0.05558 to 0.1229 |
| H9 D14 vs HSF1 D14 | −0.03021 | 7.953 | Yes | ** | −0.05881 to −0.001611 |
| H9 D14 vs IMR90 D14 | −0.1334 | 35.13 | Yes | *** | −0.1620 to −0.1048 |
| H9 D14 vs HUF4 D14 | −0.2382 | 62.72 | Yes | *** | −0.2555 to −0.2095 |
| HSF1 D14 vs IMR90 D14 | −0.1032 | 27.18 | Yes | *** | −0.1318 to −0.07483 |
| HSF1 D14 vs HUF4 D14 | −0.2080 | 54.77 | Yes | *** | −0.2356 to −0.1794 |
| IMR90 D14 vs HUF4 D14 | −0.1048 | 27.59 | Yes | *** | −0.1334 to −0.07620 |
| STELLAR | | | | | |
| H9 Undiff vs HSF1 Undiff | −0.00001185 | 4.325 | No | ns | −0.00003249 to 0.000008782 |
| H9 Undiff vs IMR90 Undiff | 0.0000005791 | 0.2113 | No | ns | −0.00002006 to 0.00002122 |
| H9 Undiff vs HUF4 Undiff | 0.000004105 | 1.498 | No | ns | −0.00001653 to 0.00002474 |
| HSF1 Undiff vs IMR90 Undiff | 0.00001243 | 4.536 | No | ns | −0.000008203 to 0.00003307 |
| HSF1 Undiff vs HUF4 Undiff | 0.00001595 | 5.822 | No | * | −0.000004677 to 0.00003660 |
| IMR90 Undiff vs HUF4 Undiff | 0.000003526 | 1.266 | No | ns | −0.00001711 to 00.00002416 |
| H9 D4 vs HSF1 D4 | −0.00001183 | 9.958 | Yes | ** | −0.00002077 to −0.000002886 |
| H9 D4 vs IMR90 D4 | −0.000002450 | 2.062 | No | ns | −0.00001139 to 0.000006493 |
| H9 D4 vs HUF4 D4 | −0.0000002955 | 0.2513 | No | ns | −0.000009242 to 0.000008845 |
| HSF1 D4 vs IMR90 D4 | 0.000009379 | 7.896 | Yes | ** | 0.0000004364 to 0.00001832 |
| HSF1 D4 vs HUF4 D4 | 0.00001153 | 9.707 | Yes | ** | 0.000002587 to 0.00002047 |
| IMR90 D4 vs HUF4 D4 | 0.000002151 | 1.811 | No | ns | −0.000005792 to 0.00001109 |
| H9 D7 vs HSF1 D7 | −0.00001050 | 5.901 | No | * | −0.00002196 to 0.0000009550 |
| H9 D7 vs IMR90 D7 | −0.000007904 | 5.194 | No | * | −0.00001936 to 0.000003554 |
| H9 D7 vs HUF4 D7 | 0.0000005421 | 0.3562 | No | ns | −0.00001092 to 0.00001200 |
| HSF1 D7 vs IMR90 D7 | 0.000002599 | 1.708 | No | ns | −0.000008859 to 0.00001406 |
| HSF1 D7 vs HUF4 D7 | 0.00001104 | 7.257 | No | * | −0.0000004129 to 0.00002250 |
| IMR90 D7 vs HUF4 D7 | 0.000008446 | 5.550 | No | * | −0.000003012 to 0.00001990 |
| H9 D14 vs HSF1 D14 | −0.00001783 | 6.075 | No | * | −0.00003992 to 0.000004267 |
| H9 D14 vs IMR90 D14 | 1.455E−08 | 0.004959 | No | ns | −0.00002208 to 0.00002211 |
| H9 D14 vs HUF4 D14 | −0.00001891 | 6.442 | No | * | −0.00004100 to 0.000003190 |
| HSF1 D14 vs IMR90 D14 | 0.00001764 | 6.060 | No | * | −0.000004253 to 0.00003994 |
| HSF1 D14 vs HUF4 D14 | −0.000001078 | 0.3673 | No | ns | −0.00002317 to 0.00002102 |
| IMR90 D14 vs HUF4 D14 | −0.00001892 | 6.447 | No | * | −0.00004102 to 0.000003175 |
| NANOS3 | | | | | |
| H9 Undiff vs HSF1 Undiff | −0.0001854 | 18.02 | Yes | *** | −0.0002542 to −0.0001085 |
| H9 Undiff vs IMR90 Undiff | −0.00003576 | 3.457 | No | ns | −0.0001136 to 0.00004212 |
| H9 Undiff vs HUF4 Undiff | −0.00008028 | 7.751 | Yes | ** | −0.0001582 to −0.000002405 |
| HSF1 Undiff vs IMR90 Undiff | 0.0001506 | 14.56 | Yes | *** | 0.00007272 to 0.0002285 |
| HSF1 Undiff vs HUF4 Undiff | 0.0001061 | 10.25 | Yes | ** | 0.00002820 to 0.0001840 |
| IMR90 Undiff vs HUF4 Undiff | −0.00004452 | 4.304 | No | ns | −0.0001224 to 0.00003336 |
| H9 D4 vs HSF1 D4 | −0.00006512 | 1.239 | No | ns | −0.0004610 to 0.00003307 |
| H9 D4 vs IMR90 D4 | −0.0004726 | 8.990 | Yes | ** | −0.0008685 to −0.00007681 |
| H9 D4 vs HUF4 D4 | −0.001757 | 33.43 | Yes | *** | −0.002153 to −0.0001362 |
| HSF1 D4 vs IMR90 D4 | −0.0004075 | 7.751 | Yes | ** | −0.0008034 to −0.00001169 |

TABLE 5-continued

Statistical analysis of gene expression of VASA, IFITM1, STELLAR, NANOS3, PRDM1A, and PLAP in FIG. 29b. One-way ANOVA followed by Bonferroni posttest was performed to each time point and gene separately, comparing the 4 different cell lines. Significance was accepted as p < 0.01.

| Bonferroni's Multiple Comparison Test | Mean Diff | t | Significant? P < 00.01? | Summary | 99% CI of diff |
|---|---|---|---|---|---|
| HSF1 D4 vs HUF4 D4 | −0.001692 | 32.19 | Yes | *** | −0.002088 to −0.001296 |
| IMR90 D4 vs HUF4 D4 | −0.001285 | 24.44 | Yes | *** | −0.001681 to −0.0008890 |
| H9 D7 vs HSF1 D7 | −0.0005576 | 22.39 | Yes | *** | −0.0007451 to −0.0003701 |
| H9 D7 vs IMR90 D7 | −0.001743 | 70.01 | Yes | *** | −0.001931 to −0.001555 |
| H9 D7 vs HUF4 D7 | −0.0005885 | 23.56 | Yes | *** | −0.0007741 to −0.0003991 |
| HSF1 D7 vs IMR90 D7 | −0.001186 | 47.62 | Yes | *** | −0.001373 to −0.0009954 |
| HSF1 D7 vs HUF4 D7 | −0.00002900 | 1.165 | No | ns | −0.0002165 to 0.0001555 |
| IMR90 D7 vs HUF4 D7 | 0.001157 | 48.46 | Yes | *** | 0.0009694 to 0.001344 |
| H9 D14 vs HSF1 D14 | 0.00006151 | 1.753 | No | ns | −0.0002030 to 0.0003262 |
| H9 D14 vs IMR90 D14 | −0.0001109 | 3.155 | No | ns | −0.0003755 to 0.0001537 |
| H9 D14 vs HUF4 D14 | −0.001123 | 31.97 | Yes | *** | −0.001388 to −0.0008588 |
| HSF1 D14 vs IMR90 D14 | −0.0001725 | 4.909 | No | * | −0.0004371 to 0.00009208 |
| HSF1 D14 vs HUF4 D14 | −0.001185 | 33.72 | Yes | *** | −0.001450 to −0.0009205 |
| IMR90 D14 vs HUF4 D14 | −0.001013 | 28.81 | Yes | *** | −0.001277 to −0.0007480 |
| PRDM1A | | | | | |
| H9 Undiff vs HSF1 Undiff | −0.0012260 | 69.54 | Yes | *** | −0.001359 to −0.001093 |
| H9 Undiff vs IMR90 Undiff | 0.0018900 | 107.2 | Yes | *** | 0.001758 to 0.002023 |
| H9 Undiff vs HUF4 Undiff | 0.0013590 | 77.09 | Yes | *** | 0.001226 to 0.001492 |
| HSF1 Undiff vs IMR90 Undiff | 0.003116 | 176.8 | Yes | *** | 0.002964 to 0.003249 |
| HSF1 Undiff vs HUF4 Undiff | 0.002585 | 146.6 | Yes | *** | 0.002453 to 0.002718 |
| IMR90 Undiff vs HUF4 Undiff | −0.0005311 | 30.12 | Yes | *** | −0.0006636 to −0.0003954 |
| H9 D4 vs HSF1 D4 | −0.004819 | 44.26 | Yes | *** | −0.005638 to −0.003999 |
| H9 D4 vs IMR90 D4 | −0.001169 | 10.92 | Yes | ** | −0.002009 to −0.0003697 |
| H9 D4 vs HUF4 D4 | 0.0005582 | 5.127 | No | * | −0.0002614 to 0.001378 |
| HSF1 D4 vs IMR90 D4 | 0.003630 | 33.34 | Yes | *** | 0.002810 to 0.004449 |
| HSF1 D4 vs HUF4 D4 | 0.005377 | 49.39 | Yes | *** | 0.004557 to 0.005197 |
| IMR90 D4 vs HUF4 D4 | 0.001747 | 16.05 | Yes | *** | 0.0009279 to 0.002567 |
| H9 D7 vs HSF1 D7 | −0.0022279 | 20.58 | Yes | *** | −0.003108 to −0.001449 |
| H9 D7 vs IMR90 D7 | −0.0005312 | 4.621 | No | ns | −0.001361 to 0.0002984 |
| H9 D7 vs HUF4 D7 | −0.0009543 | 8.660 | Yes | ** | −0.001784 to −0.0001247 |
| HSF1 D7 vs IMR90 D7 | 0.001748 | 15.55 | Yes | *** | 0.0009150 to 0.002577 |
| HSF1 D7 vs HUF4 D7 | 0.001326 | 12.02 | Yes | ** | 0.0004949 to 0.002154 |
| IMR90 D7 vs HUF4 D7 | −0.0004231 | 3.839 | No | ns | −0.001253 to 0.0004065 |
| H9 D14 vs HSF1 D14 | −0.001082 | 27.87 | Yes | *** | −0.001374 to −0.0007895 |
| H9 D14 vs IMR90 D14 | 0.0002030 | 5.229 | No | * | −0.00008925 to 0.0004952 |
| H9 D14 vs HUF4 D14 | −0.0008769 | 22.59 | Yes | *** | −0.0001169 to −0.0005847 |
| HSF1 D14 vs IMR90 D14 | 0.001285 | 33.10 | Yes | *** | 0.0009925 to 0.001577 |
| HSF1 D14 vs HUF4 D14 | 0 0002049 | 5.278 | No | * | −0.00008735 to 0.0004971 |
| IMR90 D14 vs HUF4 D14 | −0.001060 | 27.82 | Yes | *** | −0.001372 to −0.0007877 |
| PLAP | | | | | |
| H9 Undiff vs HSF1 Undiff | −0.000009707 | 12.04 | Yes | ** | −0.00001577 to −0.00003640 |
| H9 Undiff vs IMR90 Undiff | −0.00005417 | 67.22 | Yes | *** | −0.00006024 to −0.00004811 |
| H9 Undiff vs HUF4 Undiff | 0.00001139 | 14.13 | Yes | *** | 0.000005320 to 0.00001746 |
| HSF1 Undiff vs IMR90 Undiff | −0.00004447 | 55.17 | Yes | *** | −0.00005053 to −0.00003840 |
| HSF1 Undiff vs HUF4 Undiff | 0.00002110 | 26.17 | Yes | *** | 0.00001503 to 0.00002716 |
| IMR90 Undiff vs HUF4 Undiff | 0.00005555 | 81.35 | Yes | *** | 0.0005949 to 0.00007183 |
| H9 D4 vs HSF1 D4 | 0.0001937 | 34.75 | Yes | *** | 0.0001517 to 0.0002357 |
| H9 D4 vs IMR90 D4 | −0.00003811 | 8.839 | No | * | −0.00008007 to 0.000003848 |
| H9 D4 vs HUF4 D4 | 0.0001733 | 31.10 | Yes | *** | 0.0001314 to 0.0002153 |
| HSF1 D4 vs IMR90 D4 | −0.0002318 | 41.59 | Yes | *** | −0.0002738 to −0.0001899 |
| HSF1 D4 vs HUF4 D4 | −0.00002039 | 3.659 | No | ns | −0.00006235 to 0.00002157 |
| IMR90 D4 vs HUF4 D4 | 0.0002114 | 37.94 | Yes | *** | 0.0001695 to 0.0002534 |
| H9 D7 vs HSF1 D7 | −0.000005556 | 0.6630 | No | ns | −0.00007236 to 0.00006065 |
| H9 D7 vs IMR90 D7 | −0.0004316 | 48.86 | Yes | *** | −0.00004981 to 0.00003651 |
| H9 D7 vs HUF4 D7 | −0.00008028 | 9.089 | Yes | ** | −0.0001468 to −0.0001378 |
| HSF1 D7 vs IMR90 D7 | −0.0004257 | 46.20 | Yes | *** | −0.0004923 to −0.000003592 |
| HSF1 D7 vs HUF4 D7 | −0.00007443 | 8.426 | Yes | ** | −0.0001409 to −0.0007925 |
| IMR90 D7 vs HUF4 D7 | 0.0003513 | 39.77 | Yes | *** | 0.0002848 to 0.000004178 |
| H9 D14 vs HSF1 D14 | 0.0001547 | 7.433 | No | * | 0.0001982 to 0.0003114 |
| H9 D14 vs IMR90 D14 | −0.0003324 | 15.97 | Yes | *** | −0.000004891 to 0.0001757 |
| H9 D14 vs HUF4 D14 | −0.0003293 | 15.82 | Yes | *** | −0.0004850 to −0.0001726 |
| HSF1 D14 vs IMR90 D14 | −0.0004871 | 23.41 | Yes | *** | −0.0006438 to −0.0003305 |
| HSF1 D14 vs HUF4 D14 | −0.0004840 | 23.25 | Yes | *** | −0.0006407 to −0.0003273 |
| IMR90 D14 vs HUF4 D14 | 0.000003150 | 0.1513 | No | ns | −0.0001535 to −0.0001598 |

Figure 30:
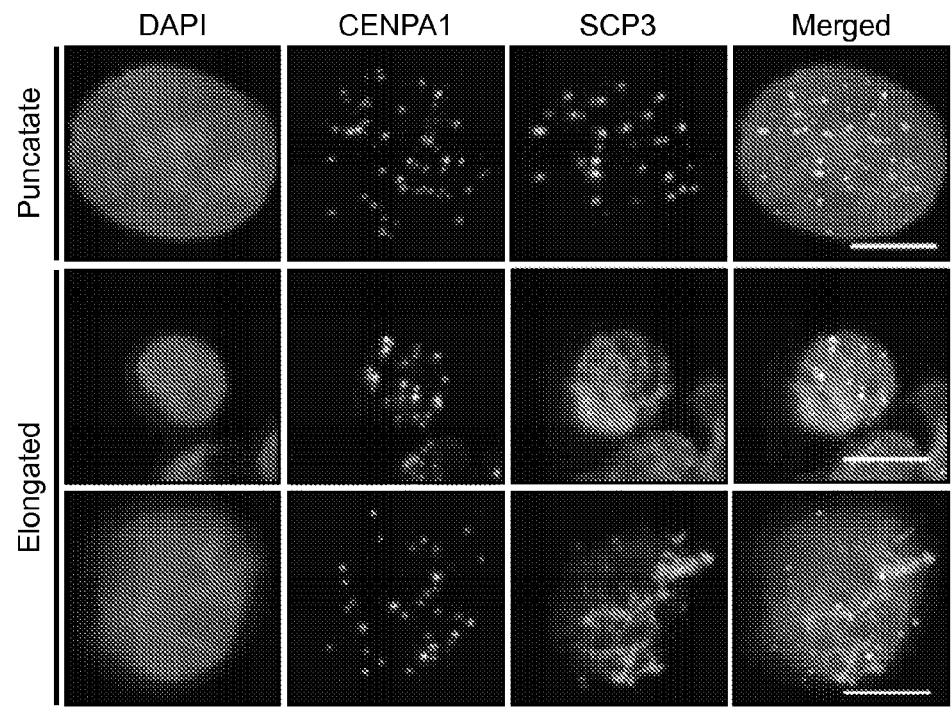
FIG. 30. Meiotic progression of hESCs and iPSCs. The cells were transfected with constructs that encode human DAZL and BOULE (and DAZ for the XY cell lines HSF1 and iHUF4) and differentiated as adherent feeder-free cultures with medium supplemented with BMPs. Undifferentiated cells were not transfected. (a) Meiotic spreads demonstrated by SCP3 (red) and CENP-A (green) immunostaining. Representative images for are shown for undifferentiated and differentiated cells; the undifferentiated H9 cell represents punctate staining pattern, iPS(IMR90) and iHUF4 cells represent elongated SCP3 staining. (b) Meiotic spreads from H9, HSF1, iPS(IMR90) and iHUF4 cell lines at different time points were classified to punctate or elongated staining patterns and quantified by counting 200 cells of each sample. Scale bar 10 μm (a).
Figure 30:
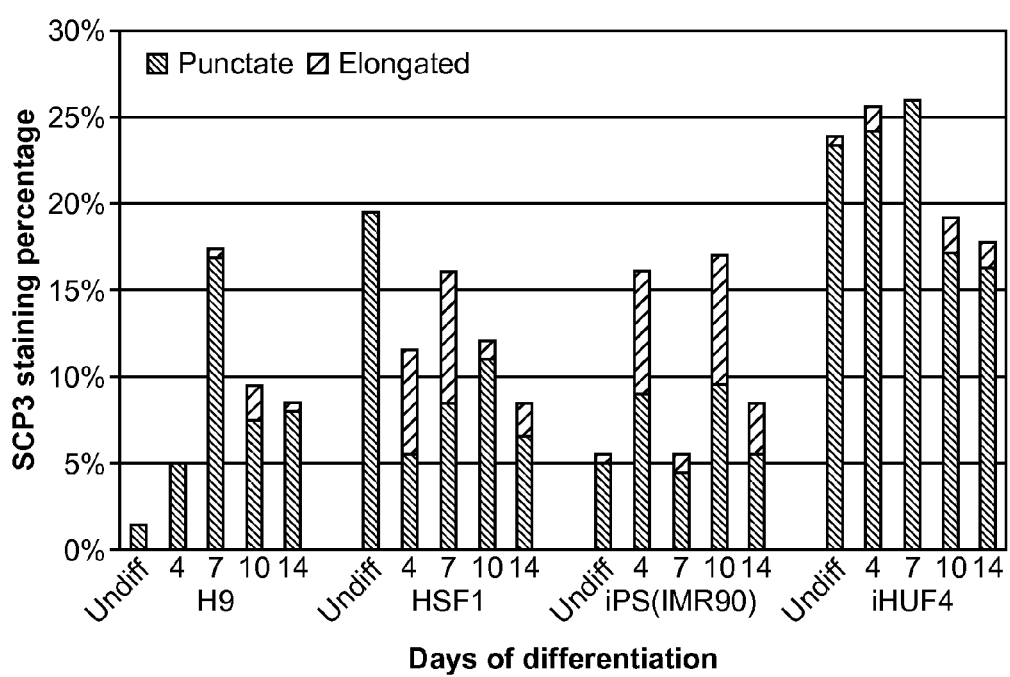

To further assess the ability of iPSCs to differentiate to germ cells, we investigated the potential of iPSCs to initiate and/or progress through meiosis in response to the overexpression of genes in the DAZ gene family, as previously reported for hESCs (see Example 1, herein). For this purpose, we overexpressed DAZL and BOULE in XX bearing lines and DAZL, BOULE and a Y chromosome-specific DAZ in XY bearing lines, and examined the number and stage of differentiated meiotic cells formed (Gonsalves, J. et al. (2004) *Hum Mol Genet* 13: 2875-2883). Cells were coimmunostained with an antibody to synaptonemal complex protein 3 (SCP3, a component of the synaptonemal complex (SC) in meiotic prophase I) and with an antibody to centromeric protein A (CENP-A, a component of the centromere). We observed that the majority of the cells did not have detectable SCP3 staining, indicating either that the cells had not entered meiosis or had already completed meiosis; however, a small subpopulation of cells had either punctate SCP3 staining, indicating that the cells had entered meiotic prophase I, or elongated SCP3 staining, a pattern corresponding to zygotene, pachytene, or diplotene stages of prophase I (FIG. 30a and FIG. 33). The SCP3 staining overlapped with CENP-A and DAPI staining, indicating colocalization to meiotic chromosomes. We observed the presence of elongated SCP3 staining in undifferentiated iPS(IMR90) and iHUF4 cells; in contrast, there were no elongated structures observed in undifferentiated hESCs, further indicating the existence of a germ cell population in undifferentiated iPSCs (FIG. 30b and Table 6, below). The iHUF4 cells had the highest percentage of meiotic cells at all time points compared to other cell lines (iHUF4 Undiff. 23.9%, D4 25.6%, D7 26%, D10 19.1%, D14 17.7%), whereas iPS(IMR90) cell line had the highest percentage of cells with elongated SCP3 staining combining all time points (19%).

TABLE 6

Meiotic progression of iPSCs and ESCs. Data table for FIG. 30b.

|  |  | Punctate | Elongated | TOTAL |
|---|---|---|---|---|
| H9 | Undiff. | 1.5% | 0.0% | 1.5% |
|  | D4 | 5.0% | 0.0% | 5.0% |
|  | D7 | 16.9% | 0.5% | 17.4% |
|  | D10 | 7.5% | 2.0% | 9.5% |
|  | D14 | 8.0% | 0.5% | 8.5% |
| HSF1 | Undiff. | 19.5% | 0.0% | 19.5% |
|  | D4 | 5.5% | 6.0% | 11.5% |
|  | D7 | 8.5% | 7.5% | 16.0% |
|  | D10 | 11.0% | 1.0% | 12.0% |
|  | D14 | 6.5% | 2.0% | 8.5% |
| iPS(IMR90) | Undiff. | 5.0% | 0.5% | 5.5% |
|  | D4 | 9.0% | 7.0% | 16.0% |
|  | D7 | 4.5% | 1.0% | 5.5% |
|  | D10 | 9.5% | 7.5% | 17.0% |
|  | D14 | 5.5% | 3.0% | 8.5% |
| iHUF4 | Undiff. | 23.4% | 0.5% | 23.9% |
|  | D4 | 24.1% | 1.5% | 25.6% |
|  | D7 | 26.0% | 0.0% | 26.0% |
|  | D10 | 17.2% | 2.0% | 19.1% |
|  | D14 | 16.3% | 1.5% | 17.7% |

In conclusion, we note that human fetal and adult iPSCs can differentiate to germ cells in a manner similar to hESCs. In addition, we observed that, like hESCs, germ cells differentiated from iPSCs entered meiosis, a functional marker of germ cell formation and differentiation, when DAZ family proteins were overexpressed. The primary difference between iPSCs and hESCs that we noted here was that iPSCs possess a subpopulation of cells with characteristics of germ cells even in the undifferentiated state. Indeed, undifferentiated iPSCs derived from adult somatic cells (iHUF4) has a higher percentage of cells positive for VASA protein, increased expression of both VASA and DAZL proteins by Western Blot analysis, and increased expression of SCP3 protein in elongated complexes indicative of meiosis, relative to hESCs.

The presence of a subpopulation of germ cells in the undifferentiated iPSCs may be a consequence of the high gene expression of pluripotency factors such as OCT3/4. Studies demonstrate that OCT3/4 expression is restricted to pluripotent cells, including germ cells, and that it is required for primordial germ cell survival. Previously, increased expression of OCT3/4 (of less than 2-fold) has been associated with distinct changes in cell fate in both mESCs and hESCs; however, effects on germ cell formation were not investigated.

Finally, we note that a major cause of infertility is the production of few or no germ cells. Nonetheless, today's treatments for infertility are largely ineffective for those with few or no germ cells. We envision that the production of germ cells from iPSCs may enable direct screening and assay of genes and/or chemicals that may promote germ cell survival or demise and may contribute to new strategies for the diagnosis and treatment of infertility, a common heath problem that affects 10-15% of reproductive-age couples.

Example 3

Polycyclic aromatic hydrocarbons (PAHs) are one of the most common components of air pollution and are formed during the incomplete burning of organic substances (coal, oil, tobacco, meat); they enter the environment mainly as exhaust from automobiles, residential wood burning or forest fires, or secondhand cigarette smoke. Numerous studies have linked PAH exposure to tumorigenicity, reproductive failure, and differentiational birth defects in laboratory animals. Consistent with this, epidemiological studies have linked human PAH exposure to lowered reproductive capacity, pulmonary disease, tumorigenicity, birth defects and behavioral abnormalities. However, although animal and epidemiological studies indicate adverse outcomes in association with PAH exposure, tools to directly assay adverse outcomes of PAH exposure during differentiation of particular human cell lineages have not been available.

A series of studies in mice have demonstrated that oocytes and fetal germ cells in mice are susceptible to exposure to PAHs. Moreover, studies indicate that PAH-mediated oocyte destruction could be prevented by inactivation of the apoptotic gene, Bax and depended on the aromatic hydrocarbon receptor (AHR) to activate Bax expression. More recently, mouse fetal germ cells were also shown to apoptose in response to incubation with PAHs; however, fetal germ cell toxicity could be prevented by the selective AHR antagonist, α-napthoflavone (ANF). Taken together, these studies indicate that PAH exposure can severely reduce the number of oocytes and developing fetal germ cells in mammals. Here, we addressed whether differentiation of hESCs to the germ cell lineage, which ultimately gives rise to mature eggs and/or sperm, was altered in the presence of PAHs and/or PAH inhibitors.

Materials and Methods hESC Differentiation and Treatment

A federally approved hESC line (H9, XX) was maintained and differentiated as previously described (see methods of Kee, K., et al. (2006) *Stem Cells & Differentiation* 15: 831-837, the disclosure of which is incorporated herein).

Briefly, adherent differentiation began upon the addition of differentiation media containing 20% FBS (Hyclone) and supplemented with Bone Morphogenetic Proteins (BMPs) -4, -7, and -8b (R&D) reconstituted in 4 mM HCl/0.1% BSA and used at 50 ng/ml. DMBA (Sigma), ANF (Sigma) and DMBA-DHD(MRI) were dissolved in DMSO at a 1:1000 dilution before adding to the media to the indicated final concentrations.

RT-PCR/qPCR Analysis by Fluidigm

Figure 35:
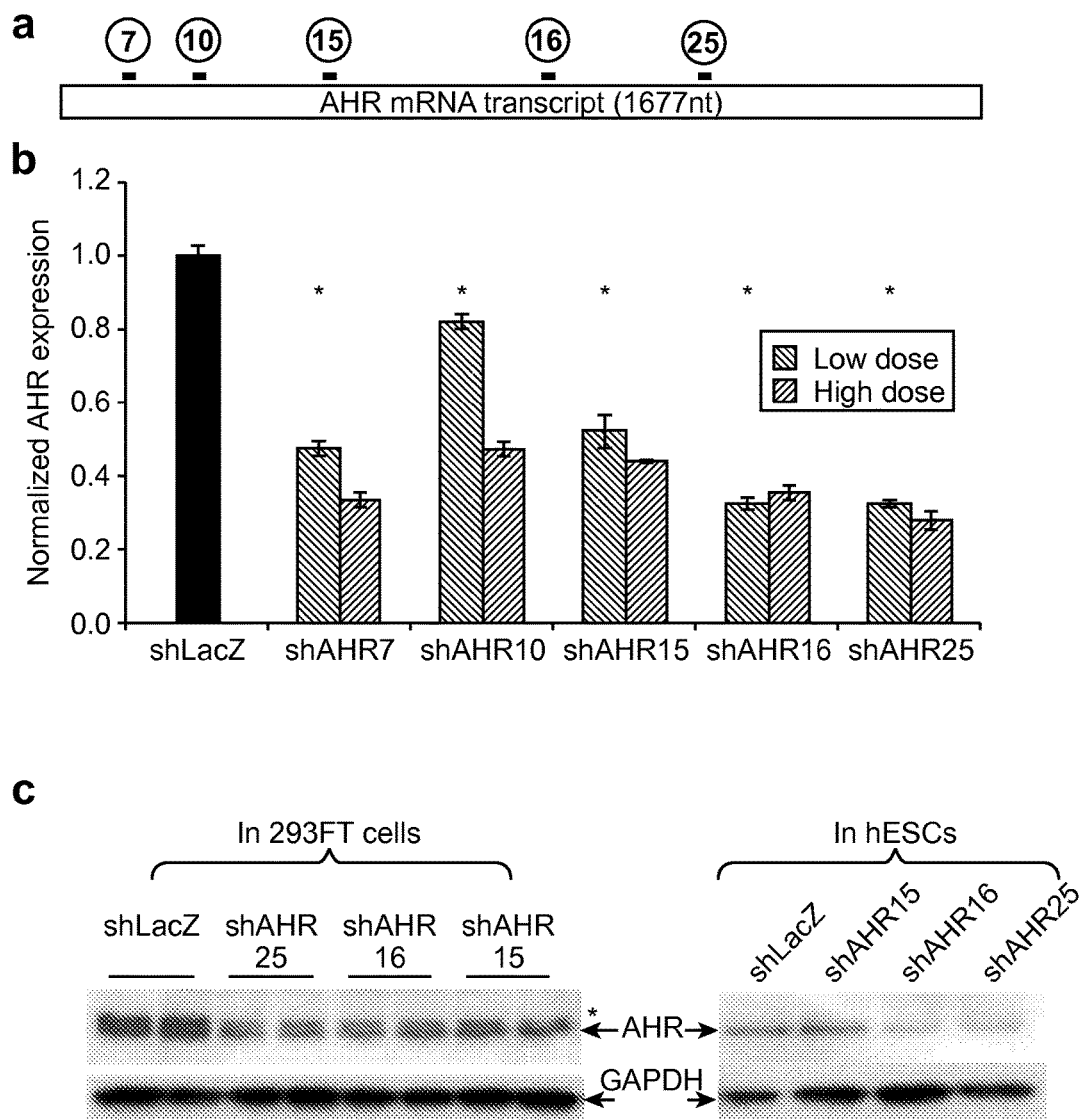
FIG. 35. AHR is silenced in 293FT cells and hESCs. (A) Location of shRNA targeting sequences on the messenger RNA transcript of AHR. (B) Normalized AHR expressions in 293FT cells with control silencing vector, shLacZ, and five shAHR targeting different regions of AHR exons. Two amounts of shAHR, 0.5 and 1 μg, were transfected into 293FT, and qPCR of AHR gene expressions were measured after 24 h. One-microgram shLacZ transfection was used as control and for normalization. Asterisk indicates averages from three independent samples, significantly different from respective controls by one-way ANOVA analysis; p<0.05. (C) Western analysis of AHR in 293FT and hESCs. Upper panels are Western blots against AHR in 293FT cells and hESCs, and lower panels are Western blots of GAPDH as loading controls of the same samples. Asterisk indicates second band, which may be a posttranslationally modified form of AHR in 293FT cells.

Total RNA was extracted using the RNeasy kit (Qiagen) and cDNA prepared with SuperScriptIII (Invitrogen) according to the manufacturer's protocols using 1 µg RNA. The cDNA was subjected to a pre-amplification using 1.25 µl out of 20 µl total cDNA, 1 µl Platinum Taq (Invitrogen), 5 µl CellsDirect 2× Reaction Buffer and 2.5 µl 0.2× Taqman (Applied Biosystem) probe mix. PCR cycle program for pre-amplification is: 95° C., 10 minutes; 95° C., 15 seconds and 60° C., 4 minutes for 14 cycles. Assays and samples are prepared according to the Fluidigm protocol and run on a 48×48 chip. BioMark (Fluidigm) program was used to obtain delta Ct value before imported into Excel file sheet to calculate delta-delta Ct value=$2^{\wedge}(Ct_{Gene}-Ct_{Housekeeping\ genes})$. The delta-delta Ct value is then normalized to the control of each experiment to obtain the final normalized expression level. All delta-delta Ct values were calculated using four housekeeping genes (GAPDH, CTNNB1, ACTS, CENTRIN) except in experiment in FIG. 35, which only used GAPDH as housekeeping gene in a regular qPCR reaction in 7300 Real Time PCR System (Applied Biosystems).

Western Analysis of Human AHR.

Cells were collected in pre-chilled PBS with Complete Mini Protease Inhibitor (Roche) followed by centrifugation for 3 minutes at 5000 rpm in microcentrifuge at 4° C. Supernatant was removed and the pellet resuspended in 200 µl RIPA buffer and stored at −80° C. Samples were thawed and centrifuged again before the supernatant was subjected to BCA protein concentration measurement (Pierce). 35 µg protein was loaded on an 8% SDS-PAGE gel and transferred onto PVDF membrane for 1 hour at 100V in CAPS buffer (10 mM CAPS, 20% methanol, pH 11). The membrane was blocked overnight in 5% nonfat milk at 4° C. Mouse monoclonal antibody to AHR (Abcam) was diluted to 1:1000 in 5% nonfat milk, followed by goat anti-mouse secondary-HRP (Zymed) at 1:20,000. Illuminated signal was detected using the ECL Plus System (Amersham).

shRNA Vectors and Preparation of Lentivirus.

shRNA was used to target AHR by the BLOCK-IT™ Inducible H1 Lentiviral RNAi System (Invitrogen). Double stranded oligos were generated, ligated into the pENTR vector and transfected into 293FT cells for initial screening. After 24 hours, RNA was harvested using the RNeasy kit and cDNA generated using SuperScriptIII with 1 µg total RNA input. The destination lentiviral vector was generated by recombining the pENTR vector with the pLenti4/BLOCK-it-DEST vector via the Gateway technology according to the manufacturer's protocol. Lentiviral supernatant carrying the pLenti4/BLOCK-it-DEST-shAHR vector was generated by co-transfection with 10 µg of each vector with 10 µg Vsvg and 15 µg Δ8.9 into 293FT cells grow on T175 plates. Supernatant was harvested after three days and either used immediately for transduction of hESCs or frozen at −80° C. until further usage. hESCs prepared for transduction were plated to 50% confluency on matrigel coated plates. Polybrene was added to the lentivirus supernatant for a final concentration of 8 µg/ml. 0.5 ml of the mixture was incubated with hESCs in a well of 6 well plate for 6 hours at 37° C. before adding 2.5 ml conditioned media (hESCs media incubated overnight with irradiated MEFs). hESCs were incubated overnight before being washed 2× with PBS and replacing with new conditioned media. The next day, Zeocin was added at 2 µg/ml final concentration to new conditioned media and the transduced hESCs were selected for 3 days before beginning differentiation as described above.

FACS Analysis and Caspase 3/7 Assay.

Single cell suspensions were prepared by incubating differentiated hESCs in Collagenase Type IV (1 mg/ml) for ten minutes, followed by ten minutes in TrypLE (Invitrogen). Cell pellet was resuspended in 0.5 ml differentiated media and passed through a 40 µm strainer. Cell suspensions were then subjected to FACS analysis with BD FACSAria system (BD). Cells were sorted for either VASA:GFP+ or VASA:GFP−. 1000 cells of each group were collected in 100 µl PBS and mixed with 100 µl of Caspase-Glo 3/7 reagent according to manufacturer protocol (Promega). Luminescence was measured after 1 hour of incubation at room temperature with Fluostar Optima (BMG).

Results

Figure 34:
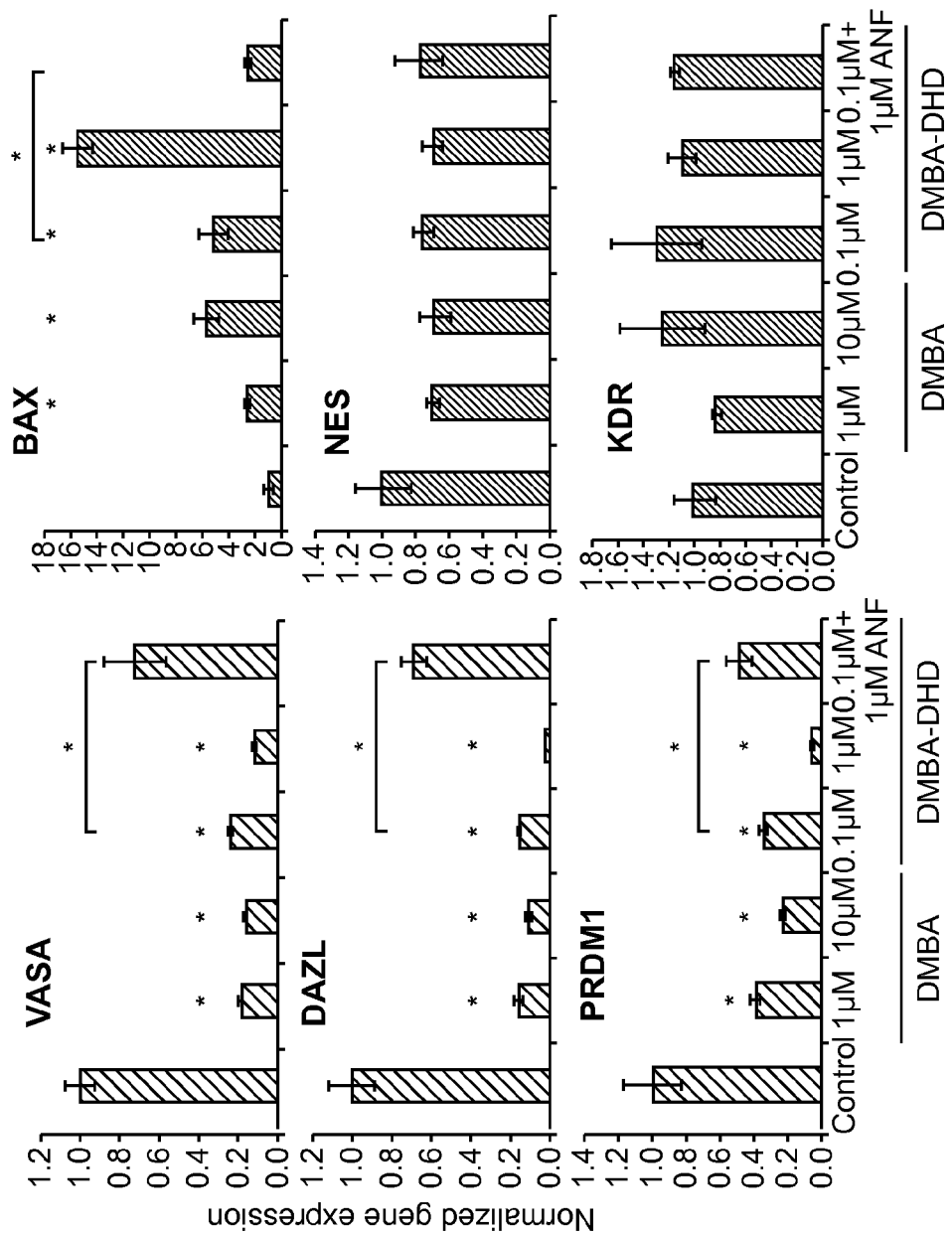
FIG. 34. Expression of early germ cell genes is reduced in the presence of PAHs. Normalized gene expressions of VASA, DAZL, PRDM1, BAX, NES, KDR in differentiated hESCs induced by BMPs to germ cells. Controls are differentiated cells treated only with the solvent, DMSO. DMBA, DMBA-DHD, and ANF were dissolved in DMSO before addition to the differentiating cells. Gene expression was measured by quantitative PCR and normalized first to 4 housekeeping genes (GAPDH, CTNNB1, ACTB, CENTRIN), followed by normalization to the controls. Error bars are standard deviations from duplicates or triplicates.
Figure 38:
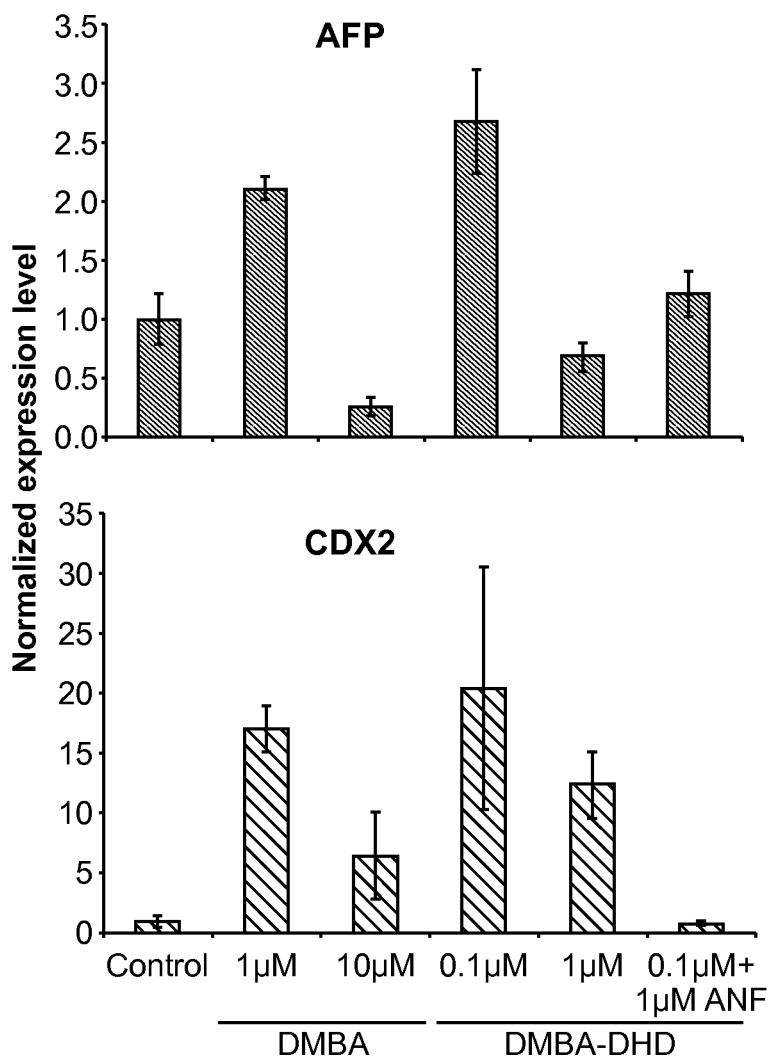
FIG. 38. Normalized gene expression of AFP and CDX2 in differentiated hESCs cultured with BMPs in the presence of DMVA or DMBA-DHD or control (no DMBA or DMBA-DHD). Sample, treatments and qPCR analysis are described in FIG. 34.

To examine the effect of PAH exposure on human germ cell differentiation, we tested whether the prototypical PAH, 9,10-dimethylbenz[a]anthracene (DMBA), or its metabolite, DMBA-3,4-dihydrodiol (DMBA-DHD), affected germ cell differentiation from hESCs. Our previous studies indicated that expression of human germ cell specific genes, including VASA and DAZL, is induced by culture with Bone Morphogenetic Protein (BMP)-4, -7, and -8b. Addition of either DMBA or DMBA-DHD at the concentrations used previously in mouse studies reduced the expression of the early germ cell specific genes VASA, DAZL, and PRDM1 (BLIMP1) (FIG. 34). Expression of VASA and DAZL decreased to ~0.2 to 0.02 of control levels, with a lesser effect observed for PRDM1 (0.4 to 0.06 of control). Consistent with previous studies in mice in which DMBA-DHD was more potent than DMBA, we observed a comparable decrease in germ cell gene expression with 0.1 µM DMBA-DHD and with 1 µM DMBA, and observed that 1 µM DMBA-DHD was more potent than 10 µM DMBA, indicating that DMBA-DHD is at least one log more potent than DMBA as measured by the decrease in germ cell specific gene expression (FIG. 34; FIG. 38). Concurrent with analysis of germ cell specific gene expression, we also analyzed expression of the apoptotic gene, BAX and the lineage markers NES (ectoderm), KDR (mesoderm), AFP (endoderm) and CDX2 (trophectoderm). We observed expression of BAX increased 5- to 20-fold with addition of DMBA and DMBA-DHD, respectively. When the antagonist of AHR, ANF, was added with DMBA-DHD, BAX expression decreased while the expression of the germ cell lineage markers VASA, DAZL, and PRDM1 increased relative to DMBA-DHD addition alone. Although the rescue by ANF did not restore germ cell expression to the same level as controls, the partial rescue strongly suggested that DMBA-DHD acted through the AHR pathway. In contrast, we noted that both DMBA and DMBA-DHD did not significantly alter expression of the two somatic gene markers KDR (mesodermal marker) and NES (ectodermal marker) and moreover, no rescue by ANF was observed. Finally we noted that both AFP and CDX2 expression was not reproducibly reduced, or rescued by ANF, indicating that formation of these lineages may occur via complex pathways that modulate toxicity of PAH derivatives (FIG. 38). Taken together, these observations indicate that PAH addition to differentiating hESCs resulted in a specific decrease in expression of germ cell specific genes that are diagnostic of primordial germ cells.

To test if the decreased germ cell gene expression was mediated through the AHR signaling pathway, we constructed short hairpin RNAs to silence AHR expression. By disrupting the essential component of the apoptosis pathway, we expected that the adverse effect of PAH addition to differentiating human germ cell cultures would be alleviated. Five targeting sequences (shAHR) were chosen, subcloned and tested in 293FT cells for their silencing effect on AHR. Quantitative PCR (qPCR) measurement of AHR transcript levels indicated significant reduction by all shAHRs (FIG. 35a) with reductions to approximately 0.8 to 0.3 fold of the control (a silencing vector carrying LacZ targeting sequence). shAHR25 showed the greatest silencing effect, followed by shAHR16, shAHR7, shAHR15, and lastly, shAHR10. We recombined shAHR15, 16, and 25 into our destination vectors and examined silencing further by Western analysis in both 293FT cells and hESCs (FIG. 35b). We noted that Western analysis with lysates of 293FT resulted in detection of two prominent bands that migrated to the expected size of AHR, ~95 kDa (kilodaltons), whereas only one protein band was detected in the lysates of hESCs. We observed that a reduction in both the upper and lower bands occurred in 293FT cells and were similarly reduced by all three shAHRs, indicating that both bands represent legitimate isoforms of AHR, likely to be differentially post-translationally modified in AHR in 293FT cells. More importantly, shAHR16 and shAHR25 both reduced AHR protein levels in hESCs more than shAHR15 and the control, shLacZ, consistent with the qPCR analysis of AHR transcript in 293FT cells.

We then proceeded to examine the effect of silencing AHR on human germ cell differentiation from hESCs in the presence of DMBA-DHD (FIG. 36A) and observed that expression of AHR was reduced to approximately 50% when shAHR25 was transduced into hESCs and cells were differentiated for 14 days with BMPs. VASA expression was significantly elevated (rescued) when AHR was silenced in the presence of DMBA-DHD. Expression of DAZL and PRDM1 were also rescued by shAHR, but to a lesser extent.

Figure 36:
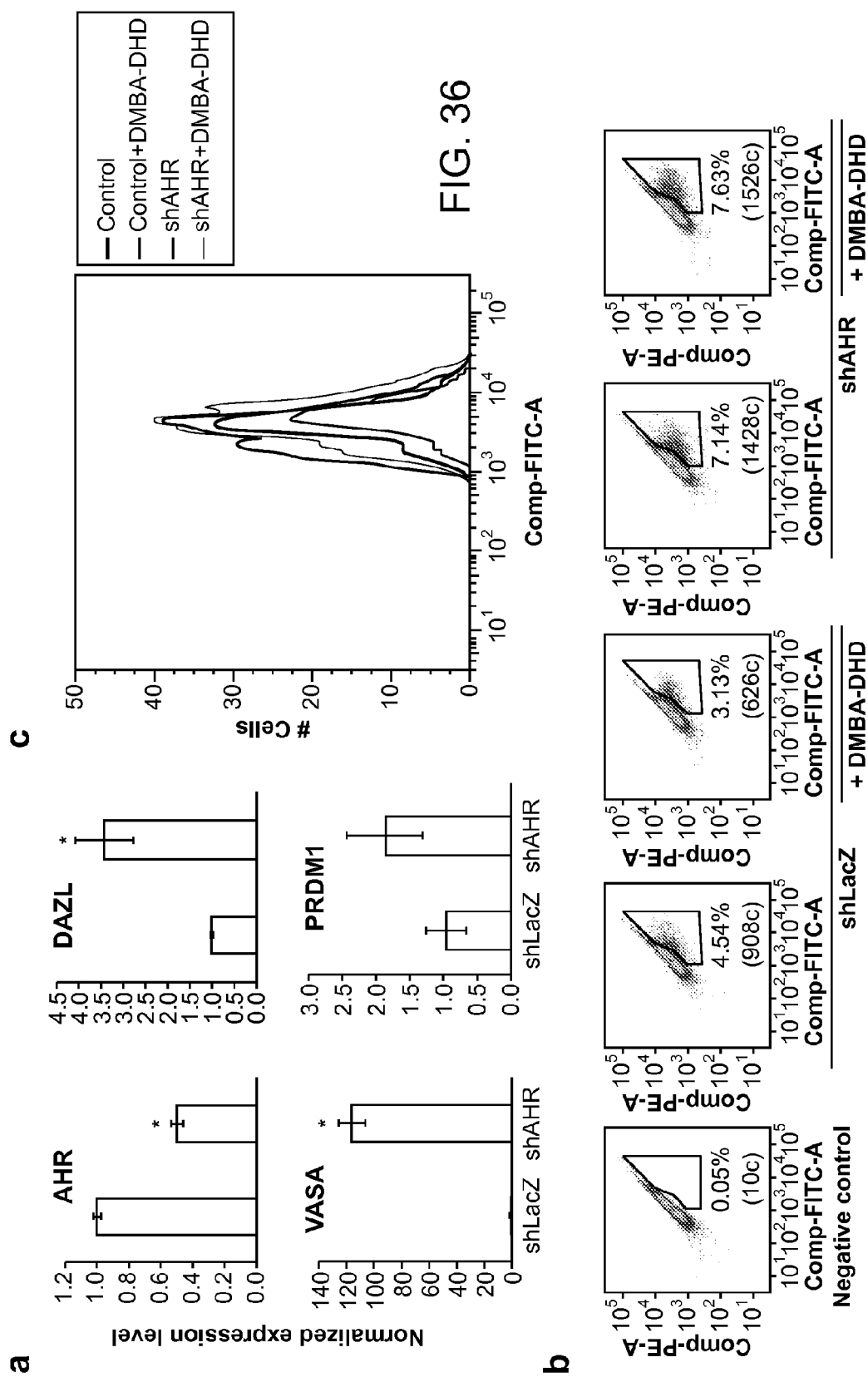
FIG. 36. Silencing of AHR specifically rescues VASA: GFP cells. (A) Gene expressions of AHR, DAZL, VASA, and PRDM1 in differentiated hESCs treated with 0.1 µM DMBA-DHD carrying either control silencing vector shLacZ or shAHR25. (B) FACS plots of differentiated hESCs carrying VASA:GFP reporter. Percentages of GFP positive cells are indicated on each plot of 20,000 cells, with the number of VASA:GFP+ in parenthesis. Negative control is hESCs without VASA:GFP reporter. shLacZ or shAHR25 was transduced into hESCs with or without 1 µM DMBA-DHD. (C) Histogram plot of the VASA:GFP positive populations from (B) comparing intensities and number of cells in 20,000 sorted cells.

To further examine the effects of DMBA-DHD and shAHR at the cellular level in terms of germ cell numbers, we used a VASA:GFP reporter system to harvest human PGCs and quantify differentiation. For this purpose, hESCs were transduced with the VASA:GFP reporter and selected for stable integration. Silencing vectors against AHR or the control, LacZ, were introduced into the hESCs and the cells were differentiated in the presence or absence of DMBA-DHD. In FACS (fluorescence activated cell sorting), the majority of differentiated control hESCs reside on the diagonal axis of the FACS plots when the PE and FITC channels were used to isolate VASA:GFP cells (FIG. 36b), likely due to auto-fluorescence of these cells. In hESCs carrying the VASA:GFP reporter, a population of cells also resided on the FITC side of the plot when differentiated and was designated as the VASA:GFP+ cells. Extensive characterization has demonstrated that this population has properties of PGCs, including diagnostic gene expression, methylation status at the imprinted loci and genome-wide, and alkaline phosphatase activity. We observed that approximately 4.5% of cells were VASA:GFP+ PGCs after 14 days of BMP induction in cells carrying the control vector, shLacZ, without DMBA-DHD treatment (FIG. 3B,C). When hESC cultures were treated with DMBA-DHD, the percentage of VASA:GFP+ PGCs was reduced to 3.1% (the difference in terms of real numbers of PGCs was approximately 908 PGCs out of 20,000 differentiated hESCs in the control versus 626 PGCs in the DMBA-DHD treated group). In contrast, cells carrying shAHR25 showed 7.6% and 7.1% of VASA:GFP+ cells with or without addition of DMBA-DHD. Thus, shAHR not only rescued the reduction of VASA:GFP+ population, but elevated the level of VASA:GFP+ compared to the control cells. These results mirror those that reported an elevated number of primordial oocytes in Ahr knockout mice, again highlighting the AHR pathway as the major apoptotic pathway of mammalian germ cells. As further illustrated, a direct comparison of the number of VASA:GFP+ cells in all four treatment groups, demonstrates a significant reduction of VASA:GFP+ at the same GFP+ intensity in the DMBA-DHD treated shLacZ group but not in the shAHR groups (FIG. 36C).

Figure 37:
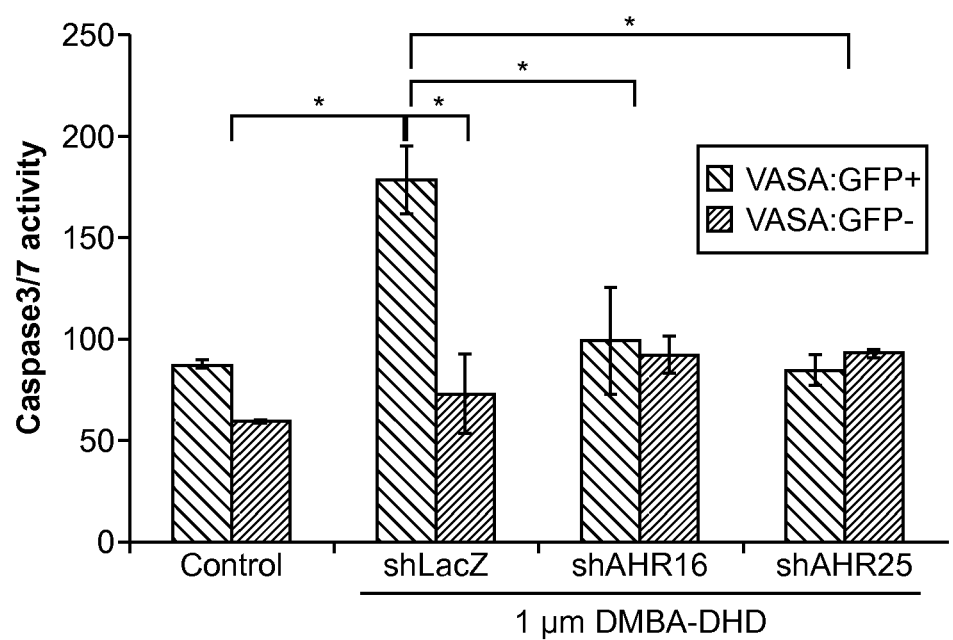
FIG. 37. Caspase 3/7 activity in germ cells is specifically reduced by silencing of AHR. Apoptosis assay measuring Caspase 3/7 activity in FACS cells. Caspase 3/7 activity is triplicate readings of luminescence unit of 1000 sorted cells. Error bars are standard deviations. Control is hESCs treated with DMSO and differentiated with BMPs. hESCs carrying shLacZ, shAHR16, or shAHR25 were treated with 1 µM DMBA-DHD and differentiated the same way as control.

Finally, we sought to determine whether the adverse effect of PAH exposure was specific to human germ cell differentiation, by further analysis of apoptosis in the VASA:GFP+ PGC population versus the VASA:GFP− population (FIG. 37). We observed that apoptosis activity was significantly increased by the addition of DMBA-DHD in the VASA:GFP+ cells but not in the VASA:GFP− cells. Moreover, this increase of apoptotic activity was reduced by silencing of AHR with shAHR16 and shAHR25, confirming that the pathway acted through AHR and was specifically altered in the PGC population.

In summary, these results demonstrate that exposure to PAHs adversely and significantly affects human primordial germ cell differentiation from hESCs. These results also clearly demonstrate that the molecular mechanism underlying reduction in both germ cell specific gene expression and germ cell numbers is linked to AHR and apoptosis of PGCs. Moreover, we noted that increased apoptosis induced by PAHs was specific to PGCs and was not detected in the somatic population. Thus, our analysis demonstrated that the clear detrimental effect of PAHs on hESC differentiation is lineage specific.

Although the reduction in human PGCs was less than two-fold in the presence of DMBA-DHD, this is significant when we consider human female reproductive biology. Even though recent studies suggested that pluripotent stem cells might replenish depleted oocyte populations endowed at birth, independent analysis indicated that replenishment of the mammalian germ cell population in females does not occur under normal physiological conditions. Hence, the consequences of reducing germ cell numbers by 30-50% in humans in vivo would be expected to strongly and negatively impact fertility due to the limited number of available oocytes at birth and the subsequent decline in numbers until menopause in women.

Notably in this study, silencing of AHR allowed us to directly examine the effect of gene dosage and silencing on germ cell formation, which has never been feasible before on a human genome background. Although gene expression was reduced to 50%, we observed a similar requirement for AHR in hESC differentiation as observed in mouse knockout models. Given the extensive retrospective epidemiological data that indicates adverse fetal effects of maternal exposure to PAHs, methods to directly assess lineage-specific human differentiational defects are much needed. These studies suggest that at least in regards to PAH exposure, the hESC system allows robust examination of environmental factors or extrinsic factors on human differentiation, especially the germ cell lineage in early differentiation. This opens the door for large scale toxicological or drug screening studies for basic or clinical reproductive biology.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing human primordial germ cells, the method comprising:
   contacting a population of pluripotent human embryonic stem cells (ES cells) or induced pluripotent stem cells (iPSs) with a DAZL polypeptide or a nucleic acid that encodes a DAZL polypeptide;
   wherein cells of the contacted population of pluripotent cells are induced to become primordial germ cells (PGCs).

2. The method according to claim 1, further comprising contacting the population of pluripotent cells with at least one of: a BOULE polypeptide, a nucleic acid that encodes a BOULE polypeptide, a DAZ polypeptide, and a nucleic acid that encodes a DAZ polypeptide.

3. A method of enriching for a composition of primordial germ cells (PGCs), the method comprising:
   contacting a population of pluripotent cells with a polynucleotide comprising a detectable marker under the control of a promoter that is selectively active in primordial germ cells;
   contacting the polynucleotide-contacted pluripotent cells with a DAZL polypeptide or a nucleic acid that encodes a DAZL polypeptide under conditions sufficient to promote PGC differentiation; and
   selecting for cells that express the detectable marker to provide a selected cell population;
   wherein the cells of the selected cell population are PGCs.

4. The method according to claim 3, wherein the pluripotent cells are embryonic stem cells (ES cells).

5. The method according to claim 3, wherein the pluripotent cells are induced pluripotent stem cells (iPSs).

6. The method according to claim 3, wherein the promoter is a VASA promoter.

7. The method according to claim 3, further comprising the step of:
   contacting the polynucleotide-contacted pluripotent cells with at least one of: a BOULE polypeptide, a nucleic acid that encodes a BOULE polypeptide, a DAZ polypeptide, and a nucleic acid that encodes a DAZ polypeptide.

* * * * *